(12) United States Patent
Baloglu et al.

(10) Patent No.: US 8,981,084 B2
(45) Date of Patent: Mar. 17, 2015

(54) OXADIAZOLE HDAC INHIBITORS

(75) Inventors: Erkan Baloglu, Cambridge, MA (US); Shomir Ghosh, Cambridge, MA (US); Mercedes Lobera, Cambridge, MA (US); Darby Schmidt, Cambridge, MA (US)

(73) Assignee: Tempero Pharmaceuticals, Inc., Cambridge, MA (US)

( * ) Notice: Subject to any disclaimer, the term of this patent is extended or adjusted under 35 U.S.C. 154(b) by 30 days.

(21) Appl. No.: 13/522,070

(22) PCT Filed: Jan. 13, 2011

(86) PCT No.: PCT/US2011/021104
§ 371 (c)(1),
(2), (4) Date: Jul. 13, 2012

(87) PCT Pub. No.: WO2011/088192
PCT Pub. Date: Jul. 21, 2011

(65) Prior Publication Data
US 2012/0289495 A1    Nov. 15, 2012

(51) Int. Cl.
*C07D 413/12* (2006.01)
*C07D 413/14* (2006.01)
*C07D 417/12* (2006.01)
*C07D 417/14* (2006.01)
*C07D 487/08* (2006.01)
*C07D 271/06* (2006.01)
*C07D 409/12* (2006.01)
*C07D 409/14* (2006.01)
*C07D 495/04* (2006.01)

(52) U.S. Cl.
CPC ............ *C07D 487/08* (2013.01); *C07D 271/06* (2013.01); *C07D 409/12* (2013.01); *C07D 409/14* (2013.01); *C07D 413/12* (2013.01); *C07D 413/14* (2013.01); *C07D 417/12* (2013.01); *C07D 417/14* (2013.01); *C07D 495/04* (2013.01)
USPC ........... 540/575; 544/278; 544/295; 544/364; 544/367; 544/369; 544/121; 544/357; 546/194; 546/199; 546/209; 546/269.1; 548/131

(58) Field of Classification Search
None
See application file for complete search history.

(56) References Cited

U.S. PATENT DOCUMENTS

| | | | |
|---|---|---|---|
| 6,552,022 B1 * | 4/2003 | Daugan | 514/252.11 |
| 6,667,398 B2 * | 12/2003 | Dunn et al. | 544/262 |
| 7,799,825 B2 | 9/2010 | Ferrigno et al. | |
| 2009/0048228 A1 | 2/2009 | Attenni et al. | |
| 2009/0076101 A1 | 3/2009 | Ferrigno et al. | |

FOREIGN PATENT DOCUMENTS

| | | |
|---|---|---|
| WO | WO 01/18045 A1 | 3/2001 |
| WO | WO 01/98284 A1 | 12/2001 |
| WO | WO 02/22577 A2 | 3/2002 |
| WO | WO 03/087057 A1 | 10/2003 |
| WO | WO 2005/040152 A1 | 5/2005 |
| WO | WO 2011/088181 A1 | 7/2011 |
| WO | WO 2011/088187 A1 | 7/2011 |
| WO | WO 2013/006408 A1 | 1/2013 |
| WO | WO 2013/008162 A1 | 1/2013 |

OTHER PUBLICATIONS

Narita et al. Chem.Eur.J. pp. 1-14 (2009) (electronic version).*
Lobera, et al. Nature Chemical Biology, 9: 319-328 (2013).
Lobera, et al. Supplementary Information, Nature Chemical Biology, 1-23 (2013). [Nature Chemical Biology: doi:10.1038/nchembio.1223].
Scarpelli, et al. Bioorganic & Medicinal Chemistry Letters, 18: 6078-6082 (2008).
Jones, et al. Bioorganic & Medicinal Chemistry Letters, 18: 3456-3461 (2008).
Muraglia, et al. Bioorganic & Medicinal Chemistry Letters, 18: 6083-6087 (2008).

* cited by examiner

*Primary Examiner* — Emily Bernhardt
(74) *Attorney, Agent, or Firm* — Kathryn A. Lutomski; John Lemanowicz

(57) ABSTRACT

Disclosed are compounds having the formula:

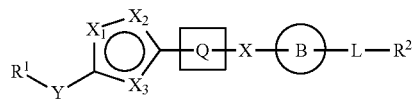

wherein $X_1$, $X_2$, $X_3$, $R^1$, $R^2$, Y, Q, X, B and L are as defined herein, and methods of making and using the same.

7 Claims, No Drawings

OXADIAZOLE HDAC INHIBITORS

This application is a §371 of International Application No. PCT/US2011/021104, filed 13 Jan. 2011, which claims the benefit of U.S. Provisional Application No. 61/294,626, filed 13 Jan. 2010, which is incorporated herein in its entirety.

BACKGROUND OF THE INVENTION

1. Field of the Invention

The present invention relates to compounds that inhibit histone deacetylase (HDAC) enzymes, the preparation of these compounds, the use of these compounds in the treatment of diseases or conditions ameliorated by inhibition of HDAC activity and pharmaceutical compositions comprising these compounds.

2. Background of the Invention

Chromatin organization involves DNA wound around histone octamers that form nucleosomes. Core histones with N-terminal tails extending from compact nucleosomal core particles can be acetylated or deacetylated at epsilon lysine residues affecting histone-DNA and histone-non-histone protein interactions. Histone deacetylases (HDACs) catalyze the deacetylation of histone and non-histone proteins and play an important role in epigenetic regulation. There are currently 18 known HDACs that are organized into three classes: class I HDACs (HDAC1, HDAC2, HDAC3, HDAC8 and HDAC11) are mainly localized to the nucleus; class II HDACs (HDAC4, HDAC5, HDAC6, HDAC7, HDAC9 and HDAC10), which shuttle between the nucleus and the cytoplasm; and class III HDACs (SIRT1-7), whose cellular localization includes various organelles.

Class II HDACs are further characterized as class IIa HDACs and class IIb HDACs.

HDAC9 is class IIa histone deacetylase highly expressed in human Tregs. HDAC9 deficiency: 1) increases Foxp3 expression (and other Treg markers), 2) increases Foxp3 and histone 3 acetylation, 3) increases Foxp3 DNA binding, 4) increases Treg numbers, 5) increases suppressive activity in vitro and in vivo, and 6) ameliorates murine colitis. Tregs which are deficient in HDAC9 induce permanent tolerance of fully mismatched cardiac allografts. In addition, HDAC9 inhibitors maybe useful for treatment of diseases and disorders associated with abnormal cell proliferation, differentiation and survival, e.g breast and prostate tumors.

Preliminary data shows that targeting HDAC7, a class IIa histone deacetylase, enhances Treg suppression in vitro and in vivo. HDAC7 enhances FOXP3+ Treg function and induces long-term allograft survival.

Inhibition of HDAC6, a class IIb HDAC, has been shown to increase Treg suppressive function in vitro along with increased expression of FOXP3 protein and Treg associated genes including CTLA, IL-10, TNR18. HDAC6 inhibition in vivo decreased severity of colitis in the dextran sodium sulphate-induced colitis model and the CD4+CD62L high adoptive transfer model of colitis. In addition, inhibition of HDAC6 with a subtherapeutic dose of rapamycin led to prolonged cardiac allograft survival.

Based on the above evidence, an orally available small molecule selective inhibitor of Class II HDAC activity (more specifically HDAC9 or HDAC7 or HDAC6) is expected to modulate autoimmune diseases through expansion and enhancement of Treg activity.

Inhibition of other Class II HDAC's for example HDAC4 and 5 impair myogenesis by modulating the stability and activity of HDAC-MEF2 complexes and maybe potentially useful for the treatment of muscle and heart diseases including cardiac hypertrophy and heart failure. Also, inhibition of Class II HDAC activity, represents a novel approach for disrupting or intervening in cell cycle regulation.

Class II HDAC inhibitors have therapeutic potential in the study and/or treatment of diseases or conditions ameliorated by modulating HDAC activity (in particular, cell proliferative diseases (such as cancer), diabetes (type I and/or type II diabetes), inflammation, cardiac disease, obesity, stroke, epilepsy, depression, immunological disease or viral or fungal infection.

Many HDAC inhibitors, however, inhibit all HDAC isoforms. It would be advantageous to identify HDAC inhibitors that inhibited one or more but not all HDAC isoforms.

SUMMARY OF THE INVENTION

The invention is directed to novel HDAC inhibitors. Specifically, the invention is directed to a compound according to Formula I:

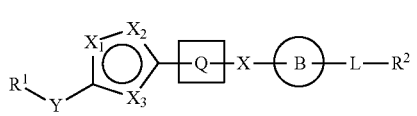

I wherein:

$R^1$ is fluoro($C_1$-$C_4$)alkyl containing at least 2 fluoro atoms;

Y is a bond and $X_1$ is O, N or NH, $X_2$ is N or CH and $X_3$ is N or NH, or Y is —C(O)— and $X_1$ and $X_2$ are CH or N, $X_3$ is O or S, or Y is —O(O)— and $X_1$ is O, $X_2$ is CH or N, and $X_3$ is CH or N;

Q is A-Z or E, wherein:

A is optionally substituted ($C_3$-$C_6$)cycloalkyl, phenyl, naphthyl, 4-7 membered heterocycloalkyl, 5-6 membered heteroaryl, or 9-10 membered heteroaryl, wherein said optionally substituted ($C_3$-$C_6$)cycloalkyl, phenyl, naphthyl, 4-7 membered heterocycloalkyl, 5-6 membered heteroaryl, or 9-10 membered heteroaryl is optionally substituted by 1, 2 or 3 groups independently selected from ($C_1$-$C_4$)alkyl, halogen, cyano, halo($C_1$-$C_4$)alkyl, ($C_1$-$C_4$)alkoxy, halo($C_1$-$C_4$)alkoxy, —$NR^AR^B$ and —(($C_1$-$C_4$)alkyl)$NR^AR^B$; and Z is —C(=O)—, —$SO_2$—, —$NR^XC(=O)$—, —CH($CF_3$)—, —($C_1$-$C_4$)alkyl-; and E is —(($C_1$-$C_6$)alkyl)C(=O)—, —(($C_1$-$C_6$)alkyl)$SO_2$—, —(($C_1$-$C_6$)alkyl)$NR^XC(=O)$—, —CH($CF_3$)—, —(($C_1$-$C_6$)alkyl)CH($CF_3$)—;

X is $NR^X$ or a bond;

B is a phenyl, pyridyl or 4-10 membered heterocycloalkyl containing 1 or 2 heteroatoms independently selected from N, O and S, wherein said phenyl, pyridyl or heterocycloalkyl is optionally substituted by 1, 2 or 3 groups independently selected from ($C_1$-$C_4$)alkyl, halo($C_1$-$C_4$)alkyl, halogen, cyano, aryl($C_1$-$C_4$)alkyl-, ($C_3$-$C_7$)cycloalkyl($C_1$-$C_4$)alkyl-, —($C_1$-$C_4$)$OR^Y$, —$NR^YR^Y$, —($C_1$-$C_4$)$NR^YR^Y$, —C(=O)$OR^Y$, —($C_1$-$C_4$)C(=O)$OR^Y$, —C(=O)$NR^YR^Y$, —($C_1$-$C_4$)C(=O)$NR^YR^Y$, —$NR^YC(=O)R^Y$, —($C_1$-$C_4$)$NR^YC(=O)R^Y$, —$SO_2NR^YR^Y$, —($C_1$-$C_4$)$SO_2NR^YR^Y$, —$NR^YSO_2R^Y$, —($C_1$-$C_4$)$NR^YSO_2R^Y$, —OC(=O)$NR^YR^Y$, —($C_1$-$C_4$)OC(=O)$NR^YR^Y$, —$NR^YC(=O)OR^Y$, —($C_1$-$C_4$)$NR^YC(=O)OR^Y$, —$NR^YC(=O)NR^YR^Y$, and —($C_1$-$C_4$)$NR^YC(=O)NR^YR^Y$, wherein when B is heterocycloalkyl, X and L are attached to different ring atoms;

L is a bond or $(C_1-C_4)$alkyl;

$R^2$ is $(C_1-C_4)$alkyl, —$NR^AR^B$, —$NR^AC(=O)R^B$, —$C(=O)$—$NR^AR^B$, 5-6 membered heteroaryl, 9-10 membered heteroaryl, 3-7 membered heterocycloalkyl, $(C_3-C_6)$ cycloalkyl, phenyl, —C(O)-(5-6 membered heteroaryl), —C(O)-(9-10 membered heteroaryl), —C(O)-(3-7 membered heterocycloalkyl), —C(O)—$((C_3-C_6)$cycloalkyl), or —O(O)-phenyl, wherein any of said 5-6 membered heteroaryl, 9-10 membered heteroaryl, 3-7 membered heterocycloalkyl, $(C_3-C_6)$ cycloalkyl, or phenyl groups is optionally substituted by 1, 2 or 3 groups independently selected from $(C_1-C_4)$alkyl, halo$(C_1-C_4)$alkyl, halogen, cyano, nitro, $(C_1-C_4)$alkoxy, $(C_1-C_4)$ alkylthio-, halo$(C_1-C_4)$alkoxy, $((C_1-C_4)$alkyl$)((C_1-C_4)$alkyl)$N(C_2-C_4)$alkoxy, hydroxyl, —$NR^AR^B$, $((C_1-C_4)$alkyl) $NR^AR^B$, and an optionally substituted 5-6 membered heteroaryl or phenyl group, wherein said optionally substituted heteroaryl or phenyl group is optionally substituted by 1, 2 or 3 groups independently selected from $(C_1-C_4)$alkyl, halogen, cyano, halo$(C_1-C_4)$alkyl, $(C_1-C_4)$alkoxy, halo$(C_1-C_4)$alkoxy, hydroxyl, —$NR^AR^B$ and —$((C_1-C_4)$alkyl)$NR^AR^B$; and wherein:

each $R^A$ and $R^B$ are independently selected from H, $(C_1-C_4)$alkyl, phenyl, 5-6 membered heterocycloalkyl, and 5-6 membered heteroaryl, or $R^A$ and $R^B$ taken together with the atom or atoms through which they are attached form an optionally substituted 4-8 membered heterocyclic ring, optionally containing one additional heteroatom selected from N, O and S;

each $R^X$ is independently selected from H, $(C_1-C_6)$alkyl, or optionally substituted $(C_2-C_6)$alkyl, wherein said optionally substituted $(C_2-C_6)$alkyl is optionally substituted by hydroxyl, cyano, amino, $(C_1-C_4)$alkoxy, $(C_1-C_4)$alkyl)NH—, or $((C_1-C_4)$alkyl$)((C_1-C_4)$alkyl)N—; and each $R^Y$ is independently selected from H, $(C_1-C_4)$alkyl, phenyl, and —$(C_1-C_4)$alkylphenyl;

or a salt thereof, or a salt, particularly a pharmaceutically acceptable salt, thereof, and is further directed to a pharmaceutical composition comprising the compound of Formula I, or a salt thereof, a method of inhibiting HDAC by contacting a HDAC with the compound of Formula I or a salt thereof, and a method of treating a subject having a disease or disorder mediated by inhibition of a HDAC comprising administering the compound of Formula I, or a salt thereof, or a pharmaceutical composition comprising the compound of Formula I, or a salt thereof, to the subject.

In one embodiment, a compound of Formula I excludes the following compounds:

4-[(cyclohexylamino)carbonyl]-3-[[[2-[2-(trifluoromethyl)-1H-imidazol-5-yl]ethyl]amino]carbonyl]-1-(3R)-piperazinecarboxylic acid 1,1-dimethylethyl ester, 4-{4-[4-(2-methylpropyl)phenyl]-1,3-thiazol-2-yl}-1-{[5-(trifluoromethyl)-1,2,4-oxadiazol-3-yl]acetyl}piperidine, 2-[[3-[5-(trifluoromethyl)-1,2,4-oxadiazol-3-yl]phenyl]methyl]-6-(3,4,5-trifluorophenyl)-3(2H)pyridazinone, 3-(1,1-dimethylethyl)-1-ethyl-4,5-dihydro-N-[3-[5-(trifluoromethyl)-1,2,4-oxadiazol-3-yl]phenyl]-1H-pyrazole-5-carboxamide, 1-[[4-ethoxy-3-[5-(trifluoromethyl)-1,2,4-oxadiazol-3-yl] phenyl]sulfonyl]-4-methyl-piperazine, 4-{4-[4-(2-methylpropyl)phenyl]-1,3-thiazol-2-yl}-1-{[3-(trifluoromethyl)-1H-1,2,4-triazol-5-yl]acetyl}piperidine, 4-(4-{4-[(1-methylethyl)oxy]phenyl}-1,3-thiazol-2-yl)-1-{[5-(trifluoromethyl)-1,2,4-oxadiazol-3-yl] acetyl}piperidine, 1-[4-(4-acetyl-2-thiazolyl)-1-piperidinyl]-2-[5-(trifluoromethyl)-1H-1,2,4-triazol-3-yl]-ethanone, 3'-(4-chlorophenyl)-4-cyano-4',5'-dihydro-N-[4-[5-(trifluoromethyl)-1,2,4-oxadiazol-3-yl]phenyl]-[1,4'-bi-1H-pyrazole]-1'-carboxamide, 4-(4-{4-[(1-methylethyl)oxy]phenyl}-1,3-thiazol-2-yl)-1-{[3-(trifluoromethyl)-1H-1,2,4-triazol-5-yl] acetyl}piperidine, N-[[2,3-dihydro-5-[5-(trifluoromethyl)-1,2,4-oxadiazol-3-yl]-7-benzofuranyl]methyl]-2-phenyl-3-piperidinamine, 1-[5-[3-[[3,5-bis(trifluoromethyl)phenyl]methyl]-1,2,4-oxadiazol-5-yl]-2-thienyl]-2,2,2-trifluoro-ethanone, 3-[[[4-(1-methylethyl)phenyl]sulfonyl]methyl]-5-(trifluoromethyl)-,2,4-oxadiazole;

or a salt thereof.

The invention is further directed to a pharmaceutical composition comprising a compound of the invention. The invention is still further directed to methods of inhibiting HDAC enzymes and treatment of conditions associated therewith using a compound of the invention or a pharmaceutical composition comprising a compound of the invention.

DETAILED DESCRIPTION OF THE INVENTION

The alternative definitions for the various groups and substituent groups of Formula I provided throughout the specification are intended to particularly describe each compound species disclosed herein, individually, as well as groups of one or more compound species. The scope of this invention includes any combination of these group and substituent group definitions.

In one embodiment of this invention, $R^1$ is a $(C_1-C_2)$alkyl group containing at least 2 fluoro atoms (groups). In a specific embodiment, $R^1$ is $CHF_2$ or $CF_3$; more specifically, $R^1$ is $CF_3$ In selected embodiments, when Y is a bond, $X_1$, $X_2$, and $X_3$, taken together with the atoms to which they are attached, form an oxadiazolyl ($X_1$ is O, $X_2$ and $X_3$ are N), oxazolyl ($X_1$ is O, $X_2$ is CH, $X_3$ is N), imidazolyl ($X_1$ is N or NH, $X_2$ is CH, $X_3$ is N or NH); or a triazolyl ($X_1$ is N or NH, $X_2$ is N, $X_3$ is N or NH) ring moiety. In specific embodiments, when Y is a bond, $X_1$, $X_2$, and $X_3$, taken together with the atoms to which they are attached form an oxadiazolyl ring moiety.

In selected embodiments, when Y is —C(O)—, $X_1$, $X_2$, and $X_3$, taken together with the atoms to which they are attached, form a thiazolyl ($X_3$ is S, $X_1$ is CH and $X_2$ is N or $X_3$ is S, $X_1$ is N and $X_2$ is CH), oxazolyl ($X_3$ is O, $X_1$ is CH and $X_2$ is N or $X_3$ is O, $X_1$ is N and $X_2$ is CH), thienyl ($X_1$ and $X_2$ are CH, $X_3$ is S) or furanyl ($X_1$ and $X_2$ are CH, $X_3$ is O) ring moiety. In specific embodiments, when Y is —C(O)—, $X_1$, $X_2$, and $X_3$, taken together with the atoms to which they are attached form a thienyl, thiazolyl or oxazolyl ring moiety, more specifically a thienyl moiety.

In selected embodiments, when Y is —C(O)—, $X_1$, $X_2$, and $X_3$, taken together with the atoms to which they are attached, form a furanyl or furyl ($X_1$ is O, $X_2$ and $X_3$ are CH), oxazolyl ($X_1$ is O, $X_2$ is CH, and $X_3$ is N), isoxazolyl ($X_1$ is O, $X_2$ is N, and $X_3$ is CH), or oxadiazolyl ($X_1$ is O, $X_2$ and $X_3$ are N) ring moiety. In specific embodiments, when Y is —C(O)—, $X_1$, $X_2$, and $X_3$, taken together with the atoms to which they are attached form a furanyl (furyl) ring moiety.

The invention is further directed to a compound of Formula (I-a):

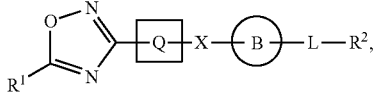
(I-a)

wherein R$^1$, R$^2$, R$^3$, R$^4$, A, Z, n and L are as defined herein.

The invention is still further directed to a compound of Formula (I-b):

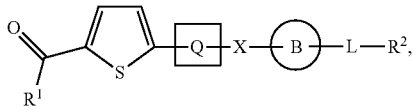
(I-b)

wherein R$^1$, R$^2$, R$^3$, R$^4$, A, Z, n and L are as defined herein.

The invention is further directed to a compound of Formula (I-c), (I-d), or (I-e):

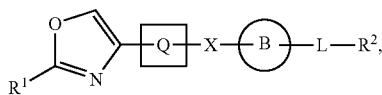
(I-c)

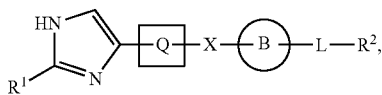
(I-d)

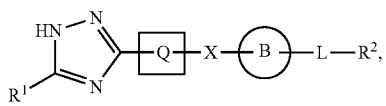
(I-e)

wherein R$^1$, R$^2$, R$^3$, R$^4$, A, Z, n and L are as defined herein.

The invention is still further directed to a compound of Formula (I-f), (I-g), (I-h), (I-i), or (I-j):

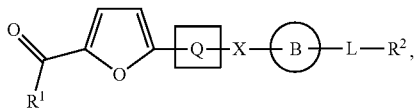
(I-f)

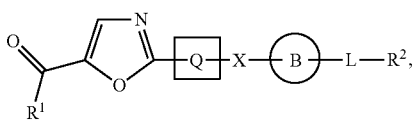
(I-g)

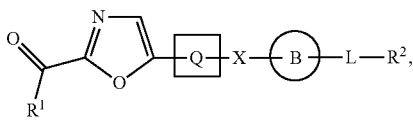
(I-h)

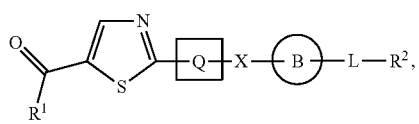
(I-i)

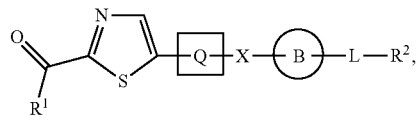
(I-j)

wherein R$^1$, R$^2$, R$^3$, R$^4$, A, Z, n and L are as defined herein.

The invention is still further directed to a compound of Formula (I-k), (I-l), (I-m), or (I-n):

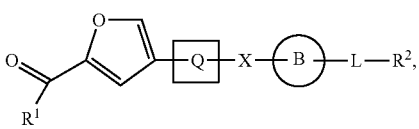
(I-k)

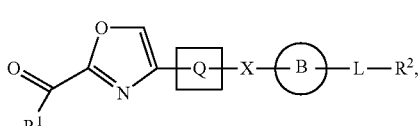
(I-l)

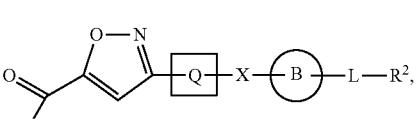
(I-m)

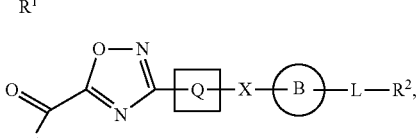
(I-n)

wherein R$^1$, R$^2$, R$^3$, R$^4$, A, n and L are as defined herein.

In another embodiment, the invention is directed to a compound according to Formula I-A:

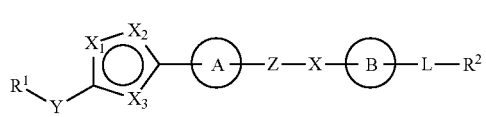
I-A wherein:
R$^1$ is fluoro(C$_1$-C$_4$)alkyl containing at least 2 fluoro atoms;
Y is a bond and X$_1$ is O, N or NH, X$_2$ is N or CH and X$_3$ is N or NH,
or Y is —C(O)— and X$_1$ and X$_2$ are CH or N, X$_3$ is O or S,
or Y is —C(O)— and X$_1$ is O, X$_2$ is CH or N, and X$_3$ is CH or N;
A is optionally substituted (C$_3$-C$_6$)cycloalkyl, phenyl, naphthyl, 4-7 membered heterocycloalkyl, 5-6 membered heteroaryl, or 9-10 membered heteroaryl,
wherein said optionally substituted (C$_3$-C$_6$)cycloalkyl, phenyl, naphthyl, 4-7 membered heterocycloalkyl, 5-6 membered heteroaryl, or 9-10 membered heteroaryl is optionally substituted by 1, 2 or 3 groups independently selected from (C$_1$-C$_4$)alkyl, halogen, cyano, halo(C$_1$-C$_4$)alkyl, (C$_1$-C$_4$)alkoxy, halo(C$_1$-C$_4$)alkoxy, —NR$^A$R$^B$ and —((C$_1$-C$_4$)alkyl)NR$^A$R$^B$;
Z is —C(=O)—, —SO$_2$—, —NR$^X$C(=O)—, —CH(CF$_3$)—, —(C$_1$-C$_4$)alkyl-;
X is NR$^X$ or a bond;

B is a phenyl, pyridyl or 4-10 membered heterocycloalkyl containing 1 or 2 heteroatoms independently selected from N, O and S, wherein said phenyl, pyridyl or heterocycloalkyl is optionally substituted by 1, 2 or 3 groups independently selected from $(C_1-C_4)$alkyl, halo$(C_1-C_4)$alkyl, halogen, cyano, aryl $(C_1-C_4)$alkyl-, $(C_3-C_7)$cycloalkyl$(C_1-C_4)$alkyl-, —$OR^Y$, —$(C_1-C_4)OR^Y$, —$NR^YR^Y$, —$(C_1-C_4)NR^YR^Y$, —$C(=O)OR^Y$, —$(C_1-C_4)C(=O)OR^Y$, —$C(=O)NR^YR^Y$, —$(C_1-C_4)C(=O)NR^YR^Y$, —$NR^YC(=O)R^Y$, —$(C_1-C_4)NR^YC(=O)R^Y$, —$SO_2NR^YR^Y$, —$(C_1-C_4)SO_2NR^YR^Y$, —$NR^YSO_2R^Y$, —$(C_1-C_4)NR^YSO_2R^Y$, —$OC(=O)NR^YR^Y$, —$(C_1-C_4)OC(=O)NR^YR^Y$, —$NR^YC(=O)OR^Y$, —$(C_1-C_4)NR^YC(=O)OR^Y$, —$NR^YC(=O)NR^YR^Y$, and —$(C_1-C_4)NR^YC(=O)NR^YR^Y$, wherein when B is heterocycloalkyl, X and L are attached to different ring atoms;

L is a bond or $(C_1-C_4)$alkyl;

$R^2$ is $(C_1-C_4)$alkyl, —$NR^AR^B$, —$NR^AC(=O)R^B$, —$C(=O)$—$NR^AR^B$, 5-6 membered heteroaryl, 9-10 membered heteroaryl, 3-7 membered heterocycloalkyl, $(C_3-C_6)$cycloalkyl, phenyl, —C(O)-(5-6 membered heteroaryl), —C(O)-(9-10 membered heteroaryl), —C(O)-(3-7 membered heterocycloalkyl), —C(O)—(($C_3-C_6$)cycloalkyl), or —C(O)-phenyl, wherein any of said 5-6 membered heteroaryl, 9-10 membered heteroaryl, 3-7 membered heterocycloalkyl, $(C_3-C_6)$cycloalkyl, or phenyl groups is optionally substituted by 1, 2 or 3 groups independently selected from $(C_1-C_4)$alkyl, halo$(C_1-C_4)$alkyl, halogen, cyano, nitro, $(C_1-C_4)$alkoxy, $(C_1-C_4)$alkylthio-, halo$(C_1-C_4)$alkoxy, $((C_1-C_4)$alkyl$)((C_1-C_4)$alkyl$)N(C_2-C_4)$alkoxy, hydroxyl, —$NR^AR^B$, $((C_1-C_4)$alkyl$)NR^AR^B$, and an optionally substituted 5-6 membered heteroaryl or phenyl group, wherein said optionally substituted heteroaryl or phenyl group is optionally substituted by 1, 2 or 3 groups independently selected from $(C_1-C_4)$alkyl, halogen, cyano, halo$(C_1-C_4)$alkyl, $(C_1-C_4)$alkoxy, halo$(C_1-C_4)$alkoxy, hydroxyl, —$NR^AR^B$ and —$((C_1-C_4)$alkyl$)NR^AR^B$; and wherein:

each $R^A$ and $R^B$ are independently selected from H, $(C_1-C_4)$alkyl, phenyl, 5-6 membered heterocycloalkyl, and 5-6 membered heteroaryl, or $R^A$ and $R^B$ taken together with the atom or atoms through which they are attached form an optionally substituted 4-8 membered heterocyclic ring, optionally containing one additional heteroatom selected from N, O and S;

each $R^X$ is independently selected from H, $(C_1-C_6)$alkyl, or optionally substituted $(C_2-C_6)$alkyl, wherein said optionally substituted $(C_2-C_6)$alkyl is optionally substituted by hydroxyl, cyano, amino, $(C_1-C_4)$alkoxy, $(C_1-C_4)$alkyl)NH—, or $((C_1-C_4)$alkyl$)((C_1-C_4)$alkyl$)$N—; and each $R^Y$ is independently selected from H, $(C_1-C_4)$alkyl, phenyl, and —$(C_1-C_4)$alkylphenyl;

or a salt, particularly a pharmaceutically acceptable salt, thereof.

In another embodiment, the invention is directed to a compound according to Formula I-B

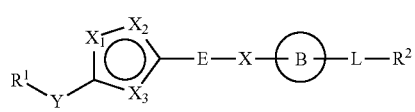

I-B $R^1$ is fluoro$(C_1-C_4)$alkyl containing at least 2 fluoro atoms;

Y is a bond and $X_1$ is O, N or NH, $X_2$ is N or CH and $X_3$ is N or NH, or Y is —C(O)— and $X_1$ and $X_2$ are CH or N, $X_3$ is O or S, or Y is —C(O)— and $X_1$ is O, $X_2$ is CH or N, and $X_3$ is CH or N;

E is —$((C_1-C_6)$alkyl$)C(=O)$—, —$((C_1-C_6)$alkyl$)SO_2$—, —$((C_1-C_6)$alkyl$)NR^XC(=O)$—, —$CH(CF_3)$—, —$((C_1-C_6)$alkyl$)CH(CF_3)$—;

X is $NR^X$ or a bond,

B is a phenyl, pyridyl or 4-10 membered heterocycloalkyl containing 1 or 2 heteroatoms independently selected from N, O and S, wherein said phenyl, pyridyl or heterocycloalkyl is optionally substituted by 1, 2 or 3 groups independently selected from $(C_1-C_4)$alkyl, halo$(C_1-C_4)$alkyl, halogen, cyano, aryl $(C_1-C_4)$alkyl-, $(C_3-C_7)$cycloalkyl$(C_1-C_4)$alkyl-, —$OR^Y$, —$(C_1-C_4)OR^Y$, —$NR^YR^Y$, —$(C_1-C_4)NR^YR^Y$, —$C(=O)OR^Y$, —$(C_1-C_4)C(=O)OR^Y$, —$C(=O)NR^YR^Y$, —$(C_1-C_4)C(=O)NR^YR^Y$, —$NR^YC(=O)R^Y$, —$(C_1-C_4)NR^YC(=O)R^Y$, —$SO_2NR^YR^Y$, —$(C_1-C_4)SO_2NR^YR^Y$, —$NR^YSO_2R^Y$, —$(C_1-C_4)NR^YSO_2R^Y$, —$OC(=O)NR^YR^Y$, —$(C_1-C_4)OC(=O)NR^YR^Y$, —$NR^YC(=O)OR^Y$, —$(C_1-C_4)NR^YC(=O)OR^Y$, —$NR^YC(=O)NR^YR^Y$, and —$(C_1-C_4)NR^YC(=O)NR^YR^Y$, wherein when B is heterocycloalkyl, X and L are attached to different ring atoms;

L is a bond or $(C_1-C_4)$alkyl;

$R^2$ is $(C_1-C_4)$alkyl, —$NR^AR^B$, —$NR^AC(=O)R^B$, —$C(=O)$—$NR^AR^B$, 5-6 membered heteroaryl, 9-10 membered heteroaryl, 3-7 membered heterocycloalkyl, $(C_3-C_6)$cycloalkyl, phenyl, —C(O)-(5-6 membered heteroaryl), —C(O)-(9-10 membered heteroaryl), —C(O)-(3-7 membered heterocycloalkyl), —C(O)—(($C_3-C_6$)cycloalkyl), or —O(O)-phenyl, wherein any of said 5-6 membered heteroaryl, 9-10 membered heteroaryl, 3-7 membered heterocycloalkyl, $(C_3-C_6)$cycloalkyl, or phenyl groups is optionally substituted by 1, 2 or 3 groups independently selected from $(C_1-C_4)$alkyl, halo$(C_1-C_4)$alkyl, halogen, cyano, nitro, $(C_1-C_4)$alkoxy, $(C_1-C_4)$alkylthio-, halo$(C_1-C_4)$alkoxy, $((C_1-C_4)$alkyl$)((C_1-C_4)$alkyl$)N(C_2-C_4)$alkoxy, hydroxyl, —$NR^AR^B$, $((C_1-C_4)$alkyl$)NR^AR^B$, and an optionally substituted 5-6 membered heteroaryl or phenyl group, wherein said optionally substituted heteroaryl or phenyl group is optionally substituted by 1, 2 or 3 groups independently selected from $(C_1-C_4)$alkyl, halogen, cyano, halo$(C_1-C_4)$alkyl, $(C_1-C_4)$alkoxy, halo$(C_1-C_4)$alkoxy, hydroxyl, —$NR^AR^B$ and —$((C_1-C_4)$alkyl$)NR^AR^B$; and wherein:

each $R^A$ and $R^B$ are independently selected from H, $(C_1-C_4)$alkyl, phenyl, 5-6 membered heterocycloalkyl, and 5-6 membered heteroaryl, or $R^A$ and $R^B$ taken together with the atom or atoms through which they are attached form an optionally substituted 4-8 membered heterocyclic ring, optionally containing one additional heteroatom selected from N, O and S;

each $R^X$ is independently selected from H, $(C_1-C_6)$alkyl, or optionally substituted $(C_2-C_6)$alkyl, wherein said optionally substituted $(C_2-C_6)$alkyl is optionally substituted by hydroxyl, cyano, amino, $(C_1-C_4)$alkoxy, $(C_1-C_4)$alkyl)NH—, or $((C_1-C_4)$alkyl$)((C_1-C_4)$alkyl$)$N—; and each $R^Y$ is independently selected from H, $(C_1-C_4)$alkyl, phenyl, and —$(C_1-C_4)$alkylphenyl;

or a salt, particularly a pharmaceutically acceptable salt, thereof.

In another embodiment, the invention is directed to a compound according to Formula I-C:

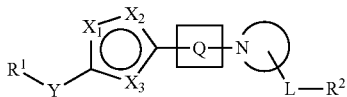

I-C wherein:

R$^1$ is fluoro(C$_1$-C$_4$)alkyl containing at least 2 fluoro atoms;

Y is a bond and X$_1$ is O, N or NH, X$_2$ is N or CH and X$_3$ is N or NH, or Y is —C(O)— and X$_1$ and X$_2$ are CH or N, X$_3$ is O or S, or Y is —C(O)— and X$_1$ is O, X$_2$ is CH or N, and X$_3$ is CH or N;

Q is —CH(CF$_3$)—, -phenyl-C(=O)—, -phenyl-S(O$_2$)—, -phenyl-CH(CF$_3$)—, -phenyl-(C$_1$-C$_4$)alkyl-, -(5-6 membered heteroaryl)-C(=O)—, -(5-6 membered heteroaryl)-SO$_2$—, -(5-6 membered heteroaryl)-CH(CF$_3$)—, -(5-6 membered heteroaryl)-(C$_1$-C$_4$)alkyl-, -(9-10 membered heteroaryl)-C(=O)—, -(9-10 membered heteroaryl)-SO$_2$—, -(9-10 membered heteroaryl)-CH(CF$_3$)—, -(9-10 membered heteroaryl)-(C$_1$-C$_4$)alkyl-, —(C$_3$-C$_6$)cycloalkyl-C(=O)—, —(C$_3$-C$_6$)cycloalkyl-SO$_2$—, —(C$_3$-C$_6$)cycloalkyl-CH(CF$_3$)—, —(C$_3$-C$_6$)cycloalkyl-(C$_1$-C$_4$)alkyl-, —(C$_1$-C$_6$)alkyl-C(=O)—, (C$_1$-C$_6$)alkyl-SO$_2$—, —(C$_1$-C$_6$)alkyl-CH(CF$_3$)—, naphthyl-C(=O)—, -naphthyl-S(O$_2$)—, -naphthyl-CH(CF$_3$)—, -naphthyl-(C$_1$-C$_4$)alkyl-, -(4-7 membered heterocycloalkyl)-C(=O)—, -(4-7 membered heterocycloalkyl)-SO$_2$—, -(4-7 membered heterocycloalkyl)-CH(CF$_3$)—, -(4-7 membered heterocycloalkyl)-(C$_1$-C$_4$)alkyl; wherein any (C$_3$-C$_6$)cycloalkyl, phenyl, naphthyl, 4-7 membered heterocycloalkyl, 5-6 membered heteroaryl, or 9-10 membered heteroaryl moiety is optionally substituted by 1, 2 or 3 groups independently selected from (C$_1$-C$_4$)alkyl, halogen, cyano, halo(C$_1$-C$_4$)alkyl, (C$_1$-C$_4$)alkoxy, halo(C$_1$-C$_4$)alkoxy, —NR$^A$R$^B$ and —((C$_1$-C$_4$)alkyl)NR$^A$R$^B$;

L is a bond or is (C$_1$-C$_4$)alkyl;

R$^2$ is (C$_1$-C$_4$)alkyl, —NR$^A$R$^B$, —(C$_1$-C$_4$)alkyl-NR$^A$R$^B$, —NR$^A$C(=O)R$^B$, —C(=O)—NR$^A$R$^B$, 5-6 membered heteroaryl, 9-10 membered heteroaryl, 3-7 membered heterocycloalkyl, (C$_3$-C$_6$)cycloalkyl, phenyl, —C(O)-(5-6 membered heteroaryl), —C(O)-(9-10 membered heteroaryl), —C(O)-(3-7 membered heterocycloalkyl), —C(O)—((C$_3$-C$_6$)cycloalkyl), or —C(O)-phenyl, wherein any of said 5-6 membered heteroaryl, 9-10 membered heteroaryl, 3-7 membered heterocycloalkyl, (C$_3$-C$_6$)cycloalkyl, or phenyl groups is optionally substituted by 1, 2 or 3 groups independently selected from (C$_1$-C$_4$)alkyl, halo(C$_1$-C$_4$)alkyl, halogen, cyano, nitro, (C$_1$-C$_4$)alkoxy, (C$_1$-C$_4$)alkylthio-, halo(C$_1$-C$_4$)alkoxy, ((C$_1$-C$_4$)alkyl)((C$_1$-C$_4$)alkyl)N(C$_2$-C$_4$)alkoxy, hydroxyl, —NR$^A$R$^B$, ((C$_1$-C$_4$)alkyl)NR$^A$R$^B$, and an optionally substituted 5-6 membered heteroaryl or phenyl group, wherein said optionally substituted heteroaryl or phenyl group is optionally substituted by 1, 2 or 3 groups independently selected from (C$_1$-C$_4$)alkyl, halogen, cyano, halo(C$_1$-C$_4$)alkyl, (C$_1$-C$_4$)alkoxy, halo(C$_1$-C$_4$)alkoxy, hydroxyl, —NR$^A$R$^B$ and —((C$_1$-C$_4$)alkyl)NR$^A$R$^B$; and wherein:

each R$^A$ and R$^B$ are independently selected from H, (C$_1$-C$_4$)alkyl, phenyl, 5-6 membered heterocycloalkyl, and 5-6 membered heteroaryl, or R$^A$ and R$^B$ taken together with the atom or atoms through which they are attached form an optionally substituted 4-8 membered heterocyclic ring, optionally containing one additional heteroatom selected from N, O and S;

is an optionally substituted 4-10 membered heterocyclic ring, optionally containing one additional heteroatom selected from N, O and S, where said 4-10 membered heterocyclic ring is optionally substituted by 1 or 2 groups independently selected from (C$_1$-C$_4$)alkyl, halo(C$_1$-C$_4$)alkyl, halogen, cyano, aryl(C$_1$-C$_4$)alkyl-, (C$_3$-C$_7$)cycloalkyl(C$_1$-C$_4$)alkyl-, —OR$^Y$, —(C$_1$-C$_4$)OR$^Y$, —NR$^Y$R$^Y$, —(C$_1$-C$_4$)NR$^Y$R$^Y$, —C(=O)OR$^Y$, —(C$_1$-C$_4$)C(=O)OR$^Y$, —C(=O)NR$^Y$R$^Y$, —(C$_1$-C$_4$)C(=O)NR$^Y$R$^Y$, —NR$^Y$C(=O)R$^Y$, —(C$_1$-C$_4$)NR$^Y$C(=O)R$^Y$, —SO$_2$NR$^Y$R$^Y$, —(C$_1$-C$_4$)SO$_2$NR$^Y$R$^Y$, —NR$^Y$SO$_2$R$^Y$, —(C$_1$-C$_4$)NR$^Y$SO$_2$R$^Y$, —OC(=O)NR$^Y$R$^Y$, —(C$_1$-C$_4$)OC(=O)NR$^Y$R$^Y$, —NR$^Y$C(=O)OR$^Y$, —(C$_1$-C$_4$)NR$^Y$C(=O)OR$^Y$, —NR$^Y$C(=O)NR$^Y$R$^Y$, and —(C$_1$-C$_4$)NR$^Y$C(=O)NR$^Y$R$^Y$, where each R$^Y$ is independently selected from H and (C$_1$-C$_4$)alkyl, phenyl, and —(C$_1$-C$_4$)alkylphenyl;

or a salt, particularly a pharmaceutically acceptable salt, thereof.

Another embodiment of this invention is a compound of Formula I-C wherein

R$^1$ is —CF$_3$;

Y is a bond and X$_1$ is O, N or NH, X$_2$ is N or CH and X$_3$ is N or NH,

Q is -phenyl-C(=O)—, -phenyl-SO$_2$—, -phenyl-CH(CF$_3$)—, -pyridyl-C(=O)—, -pyridyl-SO$_2$—, -pyridyl-CH(CF$_3$)—, -isoquinolyl-C(=O)—, -isoquinolyl-SO$_2$—, -isoquinolyl-CH(CF$_3$)—, -indazolyl-C(=O)—, -indazolyl-SO$_2$—, -indazolyl-CH(CF$_3$)—, —(C$_3$-C$_6$)cycloalkyl-C(=O)—, —(C$_3$-C$_6$)cycloalkyl-SO$_2$—, —(C$_3$-C$_6$)cycloalkyl-CH(CF$_3$)—, —(C$_1$-C$_8$)alkyl-C(=O)—, —(C$_1$-C$_8$)alkyl-SO$_2$—, or —(C$_1$-C$_8$)alkyl-CH(CF$_3$)—, wherein said phenyl, pyridyl, isoquinolyl, indazolyl, or (C$_3$-C$_6$)cycloalkyl is optionally substituted by chloro, fluoro, cyano, methoxy, methyl, or trifluoromethyl;

L is a bond, methylene, ethylene or propylene;

R$^2$ is —C(=O)NH$_2$, morpholinyl, —CO-morpholinyl, dimethylamino-, diethylamino-, butylaminocarbonyl-, —CO-pyrrolidinyl, —CO-indolyl, phenyl, pyridyl, pyrazinyl, pyrimidinyl, thiazolyl, oxazolyl, 1,3-benzodioxolyl, thienopyrimidinyl, benzo-isothiazolyl, benzimidazolyl, benzimidazolonyl, or indolinyl, where any morpholinyl, pyrrolidinyl, indolyl, phenyl, pyridyl, pyrazinyl, pyrimidinyl, thiazolyl, oxazolyl, 1,3-benzodioxolyl, thienopyrimidinyl, benzo-isothiazolyl, benzimidazolyl, or benzimidazolonyl moiety is optionally substituted with 1 or 2 groups independently selected from (C$_1$-C$_4$)alkyl, halo(C$_1$-C$_4$)alkyl, halogen, cyano, nitro, (C$_1$-C$_4$)alkoxy, (C$_1$-C$_4$)alkylthio-, halo(C$_1$-C$_4$)alkoxy, ((C$_1$-C$_4$)alkyl)((C$_1$-C$_4$)alkyl)N(C$_2$-C$_4$)alkoxy, hydroxyl, NR$^A$R$^B$, ((C$_1$-C$_4$)alkyl)NR$^A$R$^B$, and an optionally substituted 5-6 membered heteroaryl or phenyl group, wherein said optionally substituted heteroaryl or phenyl group is optionally substituted by 1 or 2 groups independently selected from (C$_1$-C$_4$)alkyl, halogen, cyano, halo(C$_1$-C$_4$)alkyl, (C$_1$-C$_4$)alkoxy, and halo(C$_1$-C$_4$)alkoxy;

wherein R$^A$ and R$^B$ are independently selected from H and (C$_1$-C$_4$)alkyl or R$^A$ and R$^B$ taken together with the nitrogen atom to which they are attached form an optionally substituted 4-6 membered heterocyclic ring, optionally containing one additional heteroatom selected from N, O and S;

is an optionally substituted 5 or 6-membered heterocyclic ring, optionally containing one additional nitrogen ring atom, where said 5 or 6-membered heterocyclic ring is optionally substituted by 1 or 2 groups independently selected from $(C_1-C_2)$alkyl, halo$(C_1-C_2)$alkyl, cyano, —$OR^y$, —$(C_1-C_2)OR^y$, —$NR^yR^y$, —$(C_1-C_2)NR^yR^y$, —$C(=O)OR^y$, —$(C_1-C_2)C(=O)OR^y$, —$C(=O)NR^yR^y$, and —$(C_1-C_2)C(=O)NR^yR^y$, where each $R^y$ is independently selected from H and methyl;

or a salt, particularly a pharmaceutically acceptable salt, thereof.

In embodiments of compounds of Formula I-A of this invention, A is a phenyl or pyridyl group optionally substituted by 1-2 groups independently selected from $(C_1-C_4)$alkyl, halogen, cyano, halo$(C_1-C_4)$alkyl, $(C_1-C_4)$alkoxy, halo$(C_1-C_4)$alkoxy, —$NR^AR^A$ and —$((C_1-C_4)$alkyl$)NR^AR^A$. In further embodiments, A is a phenyl or pyridyl group optionally substituted by 1 group selected from methyl, ethyl, fluoro, chloro, trifluoromethyl, methoxy, ethoxy, trifluoromethoxy, cyano, —$NR^AR^B$ and —$((C_1-C_4)$alkyl$)NR^AR^B$, where each $R^A$ and $R^B$ is independently selected from H and methyl. In further embodiments, A is an unsubstituted phenyl or pyridyl group or a phenyl group substituted by an ethyl, fluoro, cyano or methoxy group. In specific embodiments of compounds of Formula I-A, A is an unsubstituted phenyl group.

In another embodiment of compounds of Formulas I and I-A, A is naphthyl, optionally substituted by 1-2 groups independently selected from $(C_1-C_4)$alkyl, halogen, cyano, halo$(C_1-C_4)$alkyl, $(C_1-C_4)$alkoxy, halo$(C_1-C_4)$alkoxy, —$NR^AR^B$ and —$((C_1-C_4)$alkyl$)NR^AR^B$.

In yet another embodiment of compounds of Formulas I and I-A, A is a cyclopropyl, cyclopentyl or cyclohexyl group, optionally substituted by 1-2 groups independently selected from $(C_1-C_4)$alkyl, $(C_1-C_4)$alkoxy, —$NR^AR^B$ and —$((C_1-C_4)$alkyl$)NR^AR^B$. In further embodiments, A is a cyclopropyl, cyclopentyl or cyclohexyl group, optionally substituted by 1-2 groups independently selected from methyl, ethyl, tert-butyl, methoxy, ethoxy, —$NR^AR^B$ and —$((C_1-C_4)$alkyl$)NR^AR^B$, where each $R^A$ and $R^B$ is independently selected from H and methyl.

In further embodiments, A is a 5-6 membered heteroaryl or a 9-10 membered heteroaryl, optionally substituted by 1-2 groups independently selected from $(C_1-C_4)$alkyl, halogen, cyano, halo$(C_1-C_4)$alkyl, $(C_1-C_4)$alkoxy, halo$(C_1-C_4)$alkoxy, —$NR^AR^{AB}$ and —$((C_1-C_4)$alkyl$)NR^AR^B$. In still further embodiments, A is a 5-6 membered heteroaryl or a 9-10 membered heteroaryl optionally substituted by 1 group selected from methyl, ethyl, fluoro, trifluoromethyl, —$NR^AR^B$ and —$((C_1-C_4)$alkyl$)NR^AR^B$, where each $R^A$ and $R^B$ is independently selected from H and methyl, and the 5-6 membered heteroaryl contains 1 ring heteroatom selected form N, O and S and optionally contains 1 additional ring nitrogen atom.

In another embodiment of compounds of Formulas I and I-A, A is a 4-7 membered heterocycloalkyl group optionally substituted by 1-3 groups independently selected from $(C_1-C_4)$alkyl, halogen, cyano, halo$(C_1-C_4)$alkyl, $(C_1-C_4)$alkoxy, halo$(C_1-C_4)$alkoxy, —$NR^AR^B$ and —$((C_1-C_4)$alkyl$)NR^AR^B$.

In another embodiment of compounds of Formulas I and I-A of this invention, Z is —$C(=O)$— or —$NR^XC(=O)$—, particularly —$C(=O)$—. In another embodiment of this invention, Z is —$SO_2$—. In another embodiment of this invention, Z is —$CH(CF_3)$— or —$(C_1-C_4)$alkyl-. In selected embodiments Z is —$NHC(=O)$—. In specific embodiments Z is —$C(=O)$—.

In an embodiment of compounds of Formulas I and I-B of this invention, E is —$((C_1-C_5)$alkyl$)C(=O)$— or —$((C_1-C_5)$alkyl$)NR^XC(=O)$—. In an embodiment, E is —$((C_1-C_4)$alkyl$)C(=O)$— or —$((C_1-C_4)$alkyl$)NR^XC(=O)$—. In another embodiment of this invention, E is —$((C_1-C_5)$alkyl$)SO_2$— or —$((C_1-C_4)$alkyl$)SO_2$—. In another embodiment of this invention, E is —$CH(CF_3)$— or —$((C_1-C_4)$alkyl$)CH(CF_3)$—. In other embodiments, E is -propyl-$C(=O)$— or -pentyl-$C(=O)$—; more specifically, E is —$CH_2CH_2CH_2C(=O)$— or —$CH_2CH_2C(CH_3)_2C(=O)$—.

Further, in embodiments of compounds of Formulas I, I-A and I-B, X is $NR^X$ or a bond, where each $R^X$ is independently selected from H, $(C_1-C_4)$alkyl, or optionally substituted $(C_2-C_4)$alkyl, where the optionally substituted $(C_2-C_4)$alkyl is optionally substituted by hydroxyl, cyano, amino, $(C_1-C_4)$alkoxy, $(C_1-C_4)$alkyl)NH—, or $((C_1-C_4)$alkyl$)((C_1-C_4)$alkyl$)N$—. In another embodiment, each $R^X$ is selected from H, methyl, ethyl, tert-butyl, hydroxyethyl-, methoxymethyl-, cyanoethyl-, N-methylaminoethyl- and dimethylaminoethyl-. In specific embodiments, each $R^X$ is H.

Accordingly, in specific embodiments of the compounds of this invention, the moiety Z—X is —$C(=O)$— or —$C(=O)NH$— and the moiety E-X is —$((C_1-C_5)$alkyl$)C(=O)$— or —$((C_1-C_5)$alkyl$)C(=O)NH$—.

In another embodiment of this invention, B is a phenyl, pyridyl or 4-10 membered heterocycloalkyl containing 1 or 2 heteroatoms independently selected from N, O and S, wherein the phenyl, pyridyl or heterocycloalkyl is optionally substituted by 1 or 2 groups independently selected from $(C_1-C_2)$alkyl, halo$(C_1-C_2)$alkyl, halogen, cyano, aryl$(C_1-C_3)$alkyl-, $(C_3-C_6)$cycloalkyl$(C_1-C_3)$alkyl-, —$OR^Y$, —$(C_1-C_2)OR^Y$, —$NR^YR^Y$, —$(C_1-C_2)NR^YR^Y$, —$C(=O)OR^Y$, —$(C_1-C_2)C(=O)OR^Y$, —$C(=O)NR^YR^Y$, —$(C_1-C_2)C(=O)NR^YR^Y$, —$NR^YC(=O)R^Y$, —$(C_1-C_2)NR^YC(=O)R^Y$, —$SO_2NR^YR^Y$, —$(C_1-C_2)SO_2NR^YR^Y$, —$NR^YSO_2R^Y$, —$(C_1-C_2)NR^YSO_2R^Y$, —$OC(=O)NR^YR^Y$, —$(C_1-C_2)OC(=O)NR^YR^Y$, —$NR^YC(=O)OR^Y$, —$(C_1-C_2)NR^YC(=O)OR^Y$, —$NR^YC(=O)NR^YR^Y$, and —$(C_1-C_2)NR^YC(=O)NR^YR^Y$, where each $R^Y$ is as defined above, and more particularly, where each $R^Y$ is independently selected from H and methyl.

In another embodiment of this invention, B is a phenyl, pyridyl or 4-8 membered heterocycloalkyl containing 1 or 2 heteroatoms independently selected from N, O and S, wherein the phenyl, pyridyl or heterocycloalkyl is optionally substituted as defined above.

In other embodiments, B is a 4, 5, 6 or 7 membered heterocycloalkyl containing 1 or 2 nitrogen atoms, optionally substituted by 1 or 2 groups independently selected from $(C_1-C_2)$alkyl, halo$(C_1-C_2)$alkyl, halogen, cyano, aryl$(C_1-C_3)$alkyl-, $(C_3-C_6)$cycloalkyl$(C_1-C_3)$alkyl-, —$OR^Y$, —$(C_1-C_2)OR^Y$, —$NR^YR^Y$, —$(C_1-C_2)NR^YR^Y$, —$C(=O)OR^Y$, —$(C_1-C_2)C(=O)OR^Y$, —$C(=O)NR^YR^Y$, and —$(C_1-C_2)C(=O)NR^YR^Y$, where each $R^Y$ is independently selected from H and methyl.

In selected embodiments, B is 1,4-diazepanyl, piperazinyl, piperidinyl, pyrrolidinyl, or azetidinyl, optionally substituted by 1 or 2 groups independently selected from methyl, —$CH_2OH$ and —$C(=O)OH$. In specific embodiments, B is 1,4-diazepanyl, piperazinyl or piperidinyl, optionally substituted by 1 or 2 groups independently selected from methyl and —$C(=O)OH$.

In all cases where B is heterocycloalkyl, the bonding arrangement of X—B-L is such that X and L are attached to different ring atoms, that is X and L are not attached to the same ring atom of B.

In another embodiment of this invention, L is a bond or $(C_1-C_3)$alkyl (that is, a $(C_1-C_3)$alkylene linker), specifically, L is a bond or is methyl (methylene), ethyl (ethylene) or propyl (propylene).

In another embodiment of this invention, $R^2$ is $(C_1-C_4)$ alkyl, —$NR^AR^B$, —$NR^AC(=O)R^B$, —$C(=O)$—$NR^AR^B$, where each $R^A$ and $R^B$ are independently selected from H, $(C_1-C_4)$alkyl, phenyl, 5-6 membered heterocycloalkyl, and 5-6 membered heteroaryl, or $R^A$ and $R^B$ taken together with the nitrogen atom to which they are attached form an optionally substituted 4-6 membered heterocyclic ring, optionally containing one additional heteroatom selected from N, O and S.

In another embodiment of this invention, $R^2$ is 5-6 membered heteroaryl, 9-10 membered heteroaryl, 3-7 membered heterocycloalkyl, $(C_3-C_6)$cycloalkyl, phenyl, —C(O)-(5-6 membered heteroaryl), —C(O)-(9-10 membered heteroaryl), —C(O)-(3-7 membered heterocycloalkyl), —C(O)—(($C_3$-$C_6$)cycloalkyl), or —C(O)-phenyl, wherein any of said 5-6 membered heteroaryl, 9-10 membered heteroaryl, 3-7 membered heterocycloalkyl, $(C_3-C_6)$ cycloalkyl, or phenyl groups is optionally substituted by 1 or 2 groups independently selected from $(C_1-C_4)$alkyl, halo$(C_1$-$C_4)$alkyl, halogen, cyano, nitro, $(C_1-C_4)$alkoxy, $(C_1-C_4)$alkylthio-, halo$(C_1-C_4)$alkoxy, $((C_1-C_4)$alkyl$)((C_1-C_4)$alkyl)N $(C_2-C_4)$alkoxy, hydroxyl, —$NR^AR^B$, —$((C_1-C_4)$alkyl) $NR^AR^B$, and an optionally substituted 5-6 membered heteroaryl or phenyl group, wherein said optionally substituted heteroaryl or phenyl group is optionally substituted by 1 or 2 groups independently selected from $(C_1-C_4)$alkyl, halogen, cyano, halo$(C_1-C_4)$alkyl, $(C_1-C_4)$alkoxy, halo$(C_1-C_4)$ alkoxy, hydroxyl, —$NR^AR^B$ and —$((C_1-C_4)$alkyl$)NR^AR^B$; and wherein:

each $R^A$ and $R^B$ are independently selected from H, $(C_1$-$C_4)$alkyl, phenyl, 5-6 membered heterocycloalkyl, and 5-6 membered heteroaryl, or $R^A$ and $R^B$ taken together with the atom or atoms through which they are attached form an optionally substituted 4-6 membered heterocyclic ring, optionally containing one additional heteroatom selected from N, O and S.

In selected embodiments, $R^2$ is —$N(CH_2CH_3)_2$, —$C(=O)$ $NH_2$, —$C(=O)NH(CH_2CH_2CH_2CH_3)$, —$C(=O)$morpholinyl, —$C(=O)$pyrrolidinyl, phenyl, pyridyl, pyrazinyl, pyrimidinyl, thiazolyl, oxazolyl, 1,3-benzodioxolyl, thienopyrimidinyl, benzo-isothiazolyl, 2,3-dihydro-1,4-benzodioxinyl, benzofuranyl, benzimidazolyl, benzimidazolonyl, tetrahydroisoquinolyl, indolinyl or isoindolinyl, where the pyrrolidinyl, phenyl, pyridyl, pyrazinyl, pyrimidinyl, thiazolyl, oxazolyl, 1,3-benzodioxolyl, thienopyrimidinyl, benzo-isothiazolyl, 2,3-dihydro-1,4-benzodioxinyl, benzofuranyl, benzimidazolyl, benzimidazolonyl, tetrahydroisoquinolyl, indolinyl or isoindolinyl moieties are optionally substituted with 1 or 2 groups independently selected from methyl, trifluoromethyl, chloro, fluoro, cyano, methoxy, methylthio-, nitro, phenyl, fluoro-phenyl, and morpholinylpropyl-.

In specific embodiments, $R^2$ is —$N(CH_2CH_3)_2$, —$C(=O)$ $NH_2$, —$C(=O)NH(CH_2CH_2CH_2CH_3)$, —$C(=O)$morpholinyl, —$C(=O)$pyrrolidinyl, phenyl, pyridyl, pyrazinyl, pyrimidinyl, thiazolyl, oxazolyl, 1,3-benzodioxolyl, thienopyrimidinyl, benzo-isothiazolyl, benzimidazolyl, benzimidazolonyl, or indolinyl, where the phenyl, pyridyl, pyrazinyl, pyrimidinyl, thiazolyl, oxazolyl, and benzimidazolonyl are optionally substituted with 1 or 2 groups independently selected from methyl, trifluoromethyl, chloro, fluoro, cyano, methoxy, methylthio-, nitro, fluoro-phenyl, and morpholinylpropyl-.

As used herein, the term "alkyl" represents a saturated, straight or branched hydrocarbon moiety, which may be unsubstituted or substituted by one, or more of the substituents defined herein. Exemplary alkyls include, but are not limited to methyl (Me), ethyl (Et), n-propyl, isopropyl, n-butyl, isobutyl, sec-butyl, t-butyl, n-pentyl, iso-pentyl (3-methyl-butyl), neo-pentyl (2,2-dimethylpropyl), etc. The term "$C_1$-$C_4$" refers to an alkyl containing from 1 to 4 carbon atoms.

When the term "alkyl" is used in combination with other substituent groups, such as "haloalkyl" or "cycloalkyl-alkyl" or "arylalkyl", the term "alkyl" is intended to encompass a divalent straight or branched-chain hydrocarbon radical. For example, "arylalkyl" is intended to mean the radical-alkylaryl, wherein the alkyl moiety thereof is a divalent straight or branched-chain carbon radical and the aryl moiety thereof is as defined herein, and is represented by the bonding arrangement present in a benzyl group (—$CH_2$-phenyl).

In addition, the term "alkyl" may be used to define a divalent substituent, such as a group bonded to two other groups. In this instance, the term "alkyl" is intended to encompass a divalent straight or branched-chain hydrocarbon radical. For example, "pentyl" is intended to represent a pentylene diradical—wherein the pentyl moiety is any one of a divalent straight (—$CH_2CH_2CH_2CH_2CH_2$—) or branched (—$CH_2CH(CH_3)CH_2CH_2$—, —$CH_2CH_2CH(CH_2CH_3)$—, —$CH_2CH_2C(CH_3)_2$—) chain 5-carbon radical.

As used herein, the term "cycloalkyl" refers to a non-aromatic, saturated, cyclic hydrocarbon ring. The term "($C_3$-$C_8$)cycloalkyl" refers to a non-aromatic cyclic hydrocarbon ring having from three to eight ring carbon atoms. Exemplary "($C_3$-$C_8$)cycloalkyl" groups useful in the present invention include cyclopropyl, cyclobutyl, cyclopentyl, cyclohexyl, cycloheptyl, and cyclooctyl.

"Alkoxy" refers to a group containing an alkyl radical attached through an oxygen linking atom. The term "($C_1$-$C_4$) alkoxy" refers to a straight- or branched-chain hydrocarbon radical having at least 1 and up to 4 carbon atoms attached through an oxygen linking atom. Exemplary "($C_1$-$C_4$) alkoxy" groups useful in the present invention include, but are not limited to, methoxy, ethoxy, n-propoxy, isopropoxy, n-butoxy, s-butoxy, and t-butoxy.

"Aryl" represents a group or moiety comprising an aromatic, monovalent monocyclic or bicyclic hydrocarbon radical containing from 6 to 10 carbon ring atoms, which may be unsubstituted or substituted by one or more of the substituents defined herein, and to which may be fused one or more cycloalkyl rings, which may be unsubstituted or substituted by one or more substituents defined herein.

Generally, in the compounds of this invention, aryl is phenyl.

Heterocyclic groups may be heteroaryl or heterocycloalkyl groups. "Heterocycloalkyl" represents a group or moiety comprising a stable, non-aromatic, monovalent monocyclic or bicyclic radical, which is saturated or partially unsaturated, containing 3 to 10 ring atoms, which includes 1 to 4 heteroatoms selected from nitrogen, oxygen and sulfur, and which may be unsubstituted or substituted by one or more of the substituents defined herein. The heterocycloalkyl may be attached by any atom of the monocyclic or bicyclic radical which results in the creation of a stable structure. This term encompasses bicyclic heterocycloalkyl moieties where the rings are joined at two atoms per ring, as exemplified by the bonding arrangement in 2,5-diazabicyclo[2.2.1]heptyl, 2-azabicyclo[2.2.1]heptyl, 2-oxa-5-azabicyclo[2.2.1]heptyl, 7-oxa-2-azabicyclo[2.2.1]heptyl, 2-thia-5-azabicyclo[2.2.1]heptyl, 7-azabicyclo[2.2.1]heptyl, 2,6-diazatricyclo[3.3.1.1³,⁷]decyl, 2-azatricyclo[3.3.1.1³,⁷]decyl, 2,4,9-triazatricyclo[3.3.1.1³,⁷]decyl, 3-azabicyclo[3.2.1]octyl, 2,5-diazabicyclo[2.2.2]octyl, 2-azabicyclo[2.2.2]octyl, 3-azabicyclo[3.2.1]octyl, 8-azabicyclo[3.2.1]octyl, octahydro-1H-pyrrolo[3,2-b]pyridyl group. This term specifically excludes bicyclic heterocycloalkyl moieties where the rings are joined at a single atom per ring (spiro), as exemplified by the bonding arrangement in a 1-oxa-2-azaspiro[4.5]dec-2-en-3-yl group. Illustrative examples of heterocycloalkyls include, but are not limited to, azetidinyl, pyrrolidyl (or pyrrolidinyl), piperidinyl, piperazinyl, morpholinyl, tetrahydro-2H-1,4-thiazinyl, tetrahydrofuryl (or tetrahydrofuranyl), dihydrofuryl, oxazolinyl, thiazolinyl, pyrazolinyl, tetrahydropyranyl, dihydropyranyl, 1,3-dioxolanyl, 1,3-dioxanyl, 1,4-dioxanyl, 1,3-oxathiolanyl, 1,3-oxathianyl, 1,3-dithianyl, azabicylo[3.2.1]octyl, azabicylo[3.3.1]nonyl, azabicylo[4.3.0]nonyl, oxabicylo[2.2.1]heptyl and 1,5,9-triazacyclododecyl.

Generally, in the compounds of this invention, heterocycloalkyl groups are 5-membered and/or 6-membered heterocycloalkyl groups, such as pyrrolidyl (or pyrrolidinyl), tetrahydrofuryl (or tetrahydrofuranyl), tetrahydrothienyl, dihydrofuryl, oxazolinyl, thiazolinyl or pyrazolinyl, piperidyl (or piperidinyl), piperazinyl, morpholinyl, tetrahydropyranyl, dihydropyranyl, 1,3-dioxanyl, tetrahydro-2H-1,4-thiazinyl, 1,4-dioxanyl, 1,3-oxathianyl, and 1,3-dithianyl.

"Heteroaryl" represents a group or moiety comprising an aromatic monovalent monocyclic or bicyclic radical, containing 5 to 10 ring atoms, including 1 to 4 heteroatoms selected from nitrogen, oxygen and sulfur, which may be unsubstituted or substituted by one or more of the substituents defined herein. This term also encompasses bicyclic heterocyclic-aryl compounds containing an aryl ring moiety fused to a heterocycloalkyl ring moiety, containing 5 to 10 ring atoms, including 1 to 4 heteroatoms selected from nitrogen, oxygen and sulfur, which may be unsubstituted or substituted by one or more of the substituents defined herein. Illustrative examples of heteroaryls include, but are not limited to, thienyl, pyrrolyl, imidazolyl, pyrazolyl, furyl (or furanyl), isothiazolyl, furazanyl, isoxazolyl, oxazolyl, oxadiazolyl, thiazolyl, pyridyl (or pyridinyl), pyrazinyl, pyrimidinyl, pyridazinyl, triazinyl, tetrazinyl, triazolyl, tetrazolyl, benzo[b]thienyl, isobenzofuryl, 2,3-dihydrobenzofuryl, chromenyl, chromanyl, indolizinyl, isoindolyl, indolyl, indazolyl, purinyl, isoquinolyl, quinolyl, phthalazinyl, naphthridinyl, quinzolinyl, benzothiazolyl, benzimidazolyl, tetrahydroquinolinyl, cinnolinyl, pteridinyl, isothiazolyl.

Some of the heteroaryl groups present in the compounds of this invention are 5-6 membered monocyclic heteroaryl groups. Selected 5-membered heteroaryl groups contain one nitrogen, oxygen or sulfur ring heteroatom, and optionally contain 1, 2 or 3 additional nitrogen ring atoms. Selected 6-membered heteroaryl groups contain 1, 2, 3 or 4 nitrogen ring heteroatoms. Selected 5- or 6-membered heteroaryl groups include thienyl, pyrrolyl, imidazolyl, pyrazolyl, furyl, isothiazolyl, furazanyl, isoxazolyl, oxazolyl, oxadiazolyl, thiadiazolyl, thiazolyl, triazolyl, and tetrazolyl or pyridyl, pyrazinyl, pyrimidinyl, pyridazinyl, and triazinyl.

Some of the heteroaryl groups present in the compounds of this invention are 9-10 membered bicyclic heteroaryl groups. Selected 9-membered heteroaryl groups contain one nitrogen, oxygen or sulfur ring heteroatom, and optionally contain 1, 2 or 3 additional nitrogen ring atoms. Selected 10-membered heteroaryl groups contain one nitrogen, oxygen or sulfur ring heteroatom, and optionally contain 1, 2, 3 or 4 additional nitrogen ring atoms. Selected 9-10 membered heteroaryl groups include benzo[b]thienyl, isobenzofuryl, 2,3-dihydrobenzofuryl, chromenyl, chromanyl, indolizinyl, isoindolyl, indolyl, indazolyl, purinyl, isoquinolyl, quinolyl, phthalazinyl, naphthridinyl, quinzolinyl, benzothiazolyl, benzimidazolyl, tetrahydroquinolinyl, cinnolinyl, pteridinyl.

The terms "halogen" and "halo" represent chloro, fluoro, bromo or iodo substituents. "Hydroxy" or "hydroxyl" is intended to mean the radical —OH.

The compounds of the invention are only those which are contemplated to be "chemically stable" as will be appreciated by those skilled in the art.

Accordingly, the invention is further directed to a compound according to Formula I, wherein:

A is a phenyl or pyridyl group optionally substituted by 1-2 groups independently selected from $(C_1-C_4)$alkyl, halogen, cyano, halo$(C_1-C_4)$alkyl, $(C_1-C_4)$alkoxy, halo$(C_1-C_4)$alkoxy, —NR$^A$R$^A$ and —(($C_1-C_4$)alkyl)NR$^A$R$^A$;

Z is —C(=O)— or —NR$^X$C(=O)—;

X is NR$^X$ or a bond, where R$^X$ is independently selected from H, $(C_1-C_4)$alkyl, or optionally substituted $(C_2-C_4)$alkyl, where the optionally substituted $(C_2-C_4)$alkyl is optionally substituted by hydroxyl, cyano, amino, $(C_1-C_4)$alkoxy, $(C_1-C_4)$alkyl)NH—, or (($C_1-C_4$)alkyl)(($C_1-C_4$)alkyl)N—;

B is a phenyl, pyridyl or 4-10 membered heterocycloalkyl containing 1 or 2 heteroatoms independently selected from N, O and S, wherein the phenyl, pyridyl or heterocycloalkyl is optionally substituted by 1 or 2 groups independently selected from $(C_1-C_2)$alkyl, halo$(C_1-C_2)$alkyl, halogen, cyano, aryl$(C_1-C_3)$alkyl-, $(C_3-C_6)$cycloalkyl$(C_1-C_3)$alkyl-, —OR$^Y$, —$(C_1-C_2)$OR$^Y$, —NR$^Y$R$^Y$, —$(C_1-C_2)$NR$^Y$R$^Y$, —C(=O)OR$^Y$, —$(C_1-C_2)$C(=O)OR$^Y$, —C(=O)NR$^Y$R$^Y$, —$(C_1-C_2)$C(=O)NR$^Y$R$^Y$, —NR$^Y$C(=O)R$^Y$, —$(C_1-C_2)$NR$^Y$C(=O)R$^Y$, —SO$_2$NR$^Y$R$^Y$, —$(C_1-C_2)$SO$_2$NR$^Y$R$^Y$, —NR$^Y$SO$_2$R$^Y$, —$(C_1-C_2)$NR$^Y$SO$_2$R$^Y$, —OC(=O)NR$^Y$R$^Y$, —$(C_1-C_2)$OC(=O)NR$^Y$R$^Y$, —NR$^Y$C(=O)OR$^Y$, —$(C_1-C_2)$NR$^Y$C(=O)OR$^Y$, —NR$^Y$C(=O)NR$^Y$R$^Y$, and —$(C_1-C_2)$NR$^Y$C(=O)NR$^Y$R$^Y$;

L is a bond or $(C_1-C_3)$alkyl;

R$^2$ is $(C_1-C_4)$alkyl, —NR$^A$R$^B$, —NR$^A$C(=O)R$^B$, —C(=O)—NR$^A$R$^B$, where each R$^A$ and R$^B$ are independently selected from H, $(C_1-C_4)$alkyl, phenyl, 5-6 membered heterocycloalkyl, and 5-6 membered heteroaryl, or R$^A$ and R$^B$ taken together with the nitrogen atom to which they are attached form an optionally substituted 4-6 membered heterocyclic ring, optionally containing one additional heteroatom selected from N, O and S;

or R$^2$ is 5-6 membered heteroaryl, 9-10 membered heteroaryl, 3-7 membered heterocycloalkyl, $(C_3-C_6)$cycloalkyl, phenyl, —C(O)-(5-6 membered heteroaryl), —C(O)-(9-10 membered heteroaryl), —C(O)-(3-7 membered heterocycloalkyl), —C(O)—(($C_3-C_6$)cycloalkyl), or —C(O)-phenyl, wherein any of said 5-6 membered heteroaryl, 9-10 membered heteroaryl, 3-7 membered heterocycloalkyl, $(C_3-C_6)$cycloalkyl, or phenyl groups is optionally substituted by 1 or 2 groups independently selected from $(C_1-C_4)$alkyl, halo$(C_1-C_4)$alkyl, halogen, cyano, nitro, $(C_1-C_4)$alkoxy, $(C_1-C_4)$alkylthio-, halo$(C_1-C_4)$alkoxy, (($C_1-C_4$)alkyl)(($C_1-C_4$)alkyl)N$(C_2-C_4)$alkoxy, hydroxyl, —NR$^A$R$^B$, —(($C_1-C_4$)alkyl)NR$^A$R$^B$, and an optionally substituted 5-6 membered heteroaryl or phenyl group, wherein said optionally substituted heteroaryl or phenyl group is optionally substituted by 1 or 2 groups independently selected from $(C_1-C_4)$alkyl, halogen, cyano, halo($C_1$-$C_4$)alkyl, ($C_1$-$C_4$)alkoxy, halo($C_1$-$C_4$)alkoxy, hydroxyl, —NR$^A$R$^B$ and —(($C_1$-$C_4$)alkyl)NR$^A$R$^B$; and wherein:

each R$^A$ and R$^B$ are independently selected from H, ($C_1$-$C_4$)alkyl, phenyl, 5-6 membered heterocycloalkyl, and 5-6 membered heteroaryl, or R$^A$ and R$^B$ taken together with the atom or atoms through which they are attached form an optionally substituted 4-6 membered heterocyclic ring, optionally containing one additional heteroatom selected from N, O and S;

or a salt, particularly a pharmaceutically acceptable salt, thereof.

The invention is further directed to a compound according to Formula I, wherein:

A is a phenyl or pyridyl group optionally substituted by 1 group selected from methyl, ethyl, fluoro, chloro, trifluoromethyl, methoxy, ethoxy, trifluoromethoxy, cyano, —NR$^A$R$^B$ and —(($C_1$-$C_4$)alkyl)NR$^A$R$^B$, where each R$^A$ and R$^B$ is independently selected from H and methyl;

Z is —C(=O)— or —NR$^X$C(=O)—;

X is NR$^X$ or a bond, where R$^X$ is selected from H, methyl, ethyl, tert-butyl, hydroxyethyl-, methoxymethyl-, cyanoethyl-, N-methylaminoethyl- and dimethylaminoethyl-;

B is a 4, 5, 6 or 7 membered heterocycloalkyl containing 1 or 2 nitrogen atoms, optionally substituted by 1 or 2 groups independently selected from ($C_1$-$C_2$)alkyl, halo($C_1$-$C_2$)alkyl, halogen, cyano, aryl($C_1$-$C_3$)alkyl-, ($C_3$-$C_6$)cycloalkyl($C_1$-$C_3$)alkyl-, —OR$^Y$, —($C_1$-$C_2$)OR$^Y$, —NR$^Y$R$^Y$, —($C_1$-$C_2$)NR$^Y$R$^Y$, —C(=O)OR$^Y$, —($C_1$-$C_2$)C(=O)OR$^Y$, —C(=O)NR$^Y$R$^Y$, and —($C_1$-$C_2$)C(=O)NR$^Y$R$^Y$, where each R$^Y$ is independently selected from H and methyl;

L is a bond or ($C_1$-$C_3$)alkyl;

R$^2$ is —N(CH$_2$CH$_3$)$_2$, —C(=O)NH$_2$, —C(=O)NH(CH$_2$CH$_2$CH$_3$), —C(=O)morpholinyl, —C(=O)pyrrolidinyl, phenyl, pyridyl, pyrazinyl, pyrimidinyl, thiazolyl, oxazolyl, 1,3-benzodioxolyl, thienopyrimidinyl, benzo-isothiazolyl, 2,3-dihydro-1,4-benzodioxinyl, benzofuranyl, benzimidazolyl, benzimidazolonyl, tetrahydroisoquinolyl, indolinyl or isoindolinyl, where the pyrrolidinyl, phenyl, pyridyl, pyrazinyl, pyrimidinyl, thiazolyl, oxazolyl, 1,3-benzodioxolyl, thienopyrimidinyl, benzo-isothiazolyl, 2,3-dihydro-1,4-benzodioxinyl, benzofuranyl, benzimidazolyl, benzimidazolonyl, tetrahydroisoquinolyl, indolinyl or isoindolinyl moieties are optionally substituted with 1 or 2 groups independently selected from methyl, trifluoromethyl, chloro, fluoro, cyano, methoxy, methylthio-, nitro, phenyl, fluoro-phenyl, and morpholinylpropyl-; or a salt, particularly a pharmaceutically acceptable salt, thereof.

The invention is further directed to a compound according to Formula I, wherein:

A is an unsubstituted phenyl or pyridyl group or a phenyl group substituted by an ethyl, fluoro, cyano or methoxy group;

Z is —C(=O)— or —NR$^X$C(=O)—;

X is NR$^X$ or a bond, where R$^X$ is selected from H, methyl, ethyl, tert-butyl, hydroxyethyl-, methoxymethyl-, cyanoethyl-, N-methylaminoethyl- and dimethylaminoethyl-;

B is 1,4-diazepanyl, piperazinyl, piperidinyl, pyrrolidinyl, or azetidinyl, optionally substituted by 1 or 2 groups independently selected from methyl, —CH$_2$OH and —C(=O)OH;

L is a bond or ($C_1$-$C_3$)alkyl;

R$^2$ is —N(CH$_2$CH$_3$)$_2$, —C(=O)NH$_2$, —C(=O)NH(CH$_2$CH$_2$CH$_3$), —C(=O)morpholinyl, —C(=O)pyrrolidinyl, phenyl, pyridyl, pyrazinyl, pyrimidinyl, thiazolyl, oxazolyl, 1,3-benzodioxolyl, thienopyrimidinyl, benzo-isothiazolyl, 2,3-dihydro-1,4-benzodioxinyl, benzofuranyl, benzimidazolyl, benzimidazolonyl, tetrahydroisoquinolyl, indolinyl or isoindolinyl, where the pyrrolidinyl, phenyl, pyridyl, pyrazinyl, pyrimidinyl, thiazolyl, oxazolyl, 1,3-benzodioxolyl, thienopyrimidinyl, benzo-isothiazolyl, 2,3-dihydro-1,4-benzodioxinyl, benzofuranyl, benzimidazolyl, benzimidazolonyl, tetrahydroisoquinolyl, indolinyl or isoindolinyl moieties are optionally substituted with 1 or 2 groups independently selected from methyl, trifluoromethyl, chloro, fluoro, cyano, methoxy, methylthio-, nitro, phenyl, fluoro-phenyl, and morpholinylpropyl-;

or a salt, particularly a pharmaceutically acceptable salt, thereof.

The invention is further directed to a compound according to Formula I, wherein:

A is an unsubstituted phenyl or pyridyl group;

Z is —C(=O)—;

X is NR$^X$ or a bond, where R$^X$ is H;

B is 1,4-diazepanyl, piperazinyl or piperidinyl, optionally substituted by 1 or 2 groups independently selected from methyl and —C(=O)OH;

L is a bond or is methyl (methylene), ethyl (ethylene) or propyl (propylene);

R$^2$ is —N(CH$_2$CH$_3$)$_2$, —C(=O)NH$_2$, —C(=O)NH(CH$_2$CH$_2$CH$_3$), —C(=O)morpholinyl, —C(=O)pyrrolidinyl, phenyl, pyridyl, pyrazinyl, pyrimidinyl, thiazolyl, oxazolyl, 1,3-benzodioxolyl, thienopyrimidinyl, benzo-isothiazolyl, benzimidazolyl, benzimidazolonyl, or indolinyl, where the phenyl, pyridyl, pyrazinyl, pyrimidinyl, thiazolyl, oxazolyl, and benzimidazolonyl are optionally substituted with 1 or 2 groups independently selected from methyl, trifluoromethyl, chloro, fluoro, cyano, methoxy, methylthio-, nitro, 4-fluoro-phenyl, and morpholinylpropyl-;

or a salt, particularly a pharmaceutically acceptable salt, thereof.

The invention is further directed to a compound according to Formula I, wherein:

A is a cyclopropyl, cyclopentyl or cyclohexyl group, optionally substituted by 1-2 groups independently selected from ($C_1$-$C_4$)alkyl, ($C_1$-$C_4$)alkoxy, —NR$^A$R$^B$ and —(($C_1$-$C_4$)alkyl)NR$^A$R$^B$;

Z is —C(=O)—;

X is NR$^X$ or a bond, where R$^X$ is independently selected from H, ($C_1$-$C_4$)alkyl, or optionally substituted ($C_2$-$C_4$)alkyl, where the optionally substituted ($C_2$-$C_4$)alkyl is optionally substituted by hydroxyl, cyano, amino, ($C_1$-$C_4$)alkoxy, (($C_1$-$C_4$)alkyl)NH—, or (($C_1$-$C_4$)alkyl)(($C_1$-$C_4$)alkyl)N—;

B is a phenyl, pyridyl or 4-10 membered heterocycloalkyl containing 1 or 2 heteroatoms independently selected from N, O and S, wherein the phenyl, pyridyl or heterocycloalkyl is optionally substituted by 1 or 2 groups independently selected from ($C_1$-$C_2$)alkyl, halo($C_1$-$C_2$)alkyl, halogen, cyano, aryl($C_1$-$C_3$)alkyl-, ($C_3$-$C_6$)cycloalkyl($C_1$-$C_3$)alkyl-, —OR$^Y$, —($C_1$-$C_2$)OR$^Y$, —NR$^Y$R$^Y$, —($C_1$-$C_2$)NR$^Y$R$^Y$, —C(=O)OR$^Y$, —($C_1$-$C_2$)C(=O)OR$^Y$, —C(=O)NR$^Y$R$^Y$, —($C_1$-$C_2$)C(=O)NR$^Y$R$^Y$, —NR$^Y$C(=O)R$^Y$, —($C_1$-$C_2$)NR$^Y$C(=O)R$^Y$, —SO$_2$NR$^Y$R$^Y$, —($C_1$-$C_2$)SO$_2$NR$^Y$R$^Y$, —NR$^Y$SO$_2$R$^Y$, —($C_1$-$C_2$)NR$^Y$SO$_2$R$^Y$, —OC(=O)NR$^Y$R$^Y$, —($C_1$-$C_2$)OC(=O)NR$^Y$R$^Y$, —NR$^Y$C(=O)OR$^Y$, —($C_1$-$C_2$)NR$^Y$C(=O)OR$^Y$, —NR$^Y$C(=O)NR$^Y$R$^Y$, and —($C_1$-$C_2$)NR$^Y$C(=O)NR$^Y$R$^Y$;

L is a bond or ($C_1$-$C_3$)alkyl;

R$^2$ is ($C_1$-$C_4$)alkyl, —NR$^A$R$^B$, —NR$^A$C(=O)R$^B$, —C(=O)—NR$^A$R$^B$, where each R$^A$ and R$^B$ are independently selected from H, ($C_1$-$C_4$)alkyl, phenyl, 5-6 membered heterocycloalkyl, and 5-6 membered heteroaryl, or R$^A$ and R$^B$ taken together with the nitrogen atom to which they are attached form an optionally substituted 4-6 membered heterocyclic ring, optionally containing one additional heteroatom selected from N, O and S;

or $R^2$ is 5-6 membered heteroaryl, 9-10 membered heteroaryl, 3-7 membered heterocycloalkyl, $(C_3-C_6)$cycloalkyl, phenyl, —C(O)-(5-6 membered heteroaryl), —C(O)-(9-10 membered heteroaryl), —C(O)-(3-7 membered heterocycloalkyl), —C(O)—$((C_3-C_6)$cycloalkyl), or —C(O)-phenyl, wherein any of said 5-6 membered heteroaryl, 9-10 membered heteroaryl, 3-7 membered heterocycloalkyl, $(C_3-C_6)$cycloalkyl, or phenyl groups is optionally substituted by 1 or 2 groups independently selected from $(C_1-C_4)$alkyl, halo$(C_1-C_4)$alkyl, halogen, cyano, nitro, $(C_1-C_4)$alkoxy, $(C_1-C_4)$alkylthio-, halo$(C_1-C_4)$alkoxy, $((C_1-C_4)$alkyl$)((C_1-C_4)$alkyl$)N(C_2-C_4)$alkoxy, hydroxyl, —$NR^AR^B$, —$((C_1-C_4)$alkyl$)NR^AR^B$, and an optionally substituted 5-6 membered heteroaryl or phenyl group, wherein said optionally substituted heteroaryl or phenyl group is optionally substituted by 1 or 2 groups independently selected from $(C_1-C_4)$alkyl, halogen, cyano, halo$(C_1-C_4)$alkyl, $(C_1-C_4)$alkoxy, halo$(C_1-C_4)$alkoxy, hydroxyl, —$NR^AR^B$ and —$((C_1-C_4)$alkyl$)NR^AR^B$; and wherein:

each $R^A$ and $R^B$ are independently selected from H, $(C_1-C_4)$alkyl, phenyl, 5-6 membered heterocycloalkyl, and 5-6 membered heteroaryl, or $R^A$ and $R^B$ taken together with the atom or atoms through which they are attached form an optionally substituted 4-6 membered heterocyclic ring, optionally containing one additional heteroatom selected from N, O and S;

or a salt, particularly a pharmaceutically acceptable salt, thereof.

The invention is further directed to a compound according to Formula I, wherein:

A is a cyclopropyl, cyclopentyl or cyclohexyl group, optionally substituted by 1-2 groups independently selected from methyl, ethyl, tert-butyl, methoxy, ethoxy, —$NR^AR^B$ and —$((C_1-C_4)$alkyl$)NR^AR^B$, where each $R^A$ and $R^B$ is independently selected from H and methyl;

Z is —C(=O)— or —$NR^XC$(=O)—;

X is $NR^X$ or a bond, where $R^X$ is selected from H, methyl, ethyl, tert-butyl, hydroxyethyl-, methoxymethyl-, cyanoethyl-, N-methylaminoethyl- and dimethylaminoethyl-;

B is 1,4-diazepanyl, piperazinyl, piperidinyl, pyrrolidinyl, or azetidinyl, optionally substituted by 1 or 2 groups independently selected from methyl, —$CH_2OH$ and —C(=O)OH;

L is a bond or $(C_1-C_3)$alkyl;

$R^2$ is —$N(CH_2CH_3)_2$, —C(=O)$NH_2$, —C(=O)NH$(CH_2CH_2CH_2CH_3)$, —C(=O)morpholinyl, —C(=O)pyrrolidinyl, phenyl, pyridyl, pyrazinyl, pyrimidinyl, thiazolyl, oxazolyl, 1,3-benzodioxolyl, thienopyrimidinyl, benzoisothiazolyl, 2,3-dihydro-1,4-benzodioxinyl, benzofuranyl, benzimidazolyl, benzimidazolonyl, tetrahydroisoquinolyl, indolinyl or isoindolinyl, where the pyrrolidinyl, phenyl, pyridyl, pyrazinyl, pyrimidinyl, thiazolyl, oxazolyl, 1,3-benzodioxolyl, thienopyrimidinyl, benzo-isothiazolyl, 2,3-dihydro-1,4-benzodioxinyl, benzofuranyl, benzimidazolyl, benzimidazolonyl, tetrahydroisoquinolyl, indolinyl or isoindolinyl moieties are optionally substituted with 1 or 2 groups independently selected from methyl, trifluoromethyl, chloro, fluoro, cyano, methoxy, methylthio-, nitro, phenyl, fluoro-phenyl, and morpholinylpropyl-; or a salt, particularly a pharmaceutically acceptable salt, thereof.

The invention is further directed to a compound according to Formula I, wherein:

E is —$((C_1-C_5)$alkyl$)C$(=O)— or —$((C_1-C_5)$alkyl$)NR^XC$(=O)—;

X is $NR^X$ or a bond, where $R^X$ is independently selected from H, $(C_1-C_4)$alkyl, or optionally substituted $(C_2-C_4)$alkyl, where the optionally substituted $(C_2-C_4)$alkyl is optionally substituted by hydroxyl, cyano, amino, $(C_1-C_4)$alkoxy, $(C_1-C_4)$alkyl)NH—, or $((C_1-C_4)$alkyl$)((C_1-C_4)$alkyl$)N$—;

B is a 4, 5, 6 or 7 membered heterocycloalkyl containing 1 or 2 nitrogen atoms, optionally substituted by 1 or 2 groups independently selected from $(C_1-C_2)$alkyl, halo$(C_1-C_2)$alkyl, halogen, cyano, aryl$(C_1-C_3)$alkyl-, $(C_3-C_6)$cycloalkyl$(C_1-C_3)$alkyl-, —$OR^Y$, —$(C_1-C_2)OR^Y$, —$NR^YR^Y$, —$(C_1-C_2)NR^YR^Y$, —$C$(=O)$OR^Y$, —$(C_1-C_2)C$(=O)$OR^Y$, —$C$(=O)$NR^YR^Y$, and —$(C_1-C_2)C$(=O)$NR^YR^Y$, where each $R^Y$ is independently selected from H and methyl;

L is a bond or $(C_1-C_3)$alkyl;

$R^2$ is —$N(CH_2CH_3)_2$, —C(=O)$NH_2$, —C(=O)NH$(CH_2CH_2CH_2CH_3)$, —C(=O)morpholinyl, —C(=O)pyrrolidinyl, phenyl, pyridyl, pyrazinyl, pyrimidinyl, thiazolyl, oxazolyl, 1,3-benzodioxolyl, thienopyrimidinyl, benzoisothiazolyl, 2,3-dihydro-1,4-benzodioxinyl, benzofuranyl, benzimidazolyl, benzimidazolonyl, tetrahydroisoquinolyl, indolinyl or isoindolinyl, where the pyrrolidinyl, phenyl, pyridyl, pyrazinyl, pyrimidinyl, thiazolyl, oxazolyl, 1,3-benzodioxolyl, thienopyrimidinyl, benzo-isothiazolyl, 2,3-dihydro-1,4-benzodioxinyl, benzofuranyl, benzimidazolyl, benzimidazolonyl, tetrahydroisoquinolyl, indolinyl or isoindolinyl moieties are optionally substituted with 1 or 2 groups independently selected from methyl, trifluoromethyl, chloro, fluoro, cyano, methoxy, methylthio-, nitro, phenyl, fluoro-phenyl, and morpholinylpropyl-; or a salt, particularly a pharmaceutically acceptable salt, thereof.

The invention is further directed to a compound according to Formula I, wherein:

E is -propyl-C(=O)— or -pentyl-C(=O)—;

X is $NR^X$ or a bond, where $R^X$ is H;

B is 1,4-diazepanyl, piperazinyl or piperidinyl, optionally substituted by 1 or 2 groups independently selected from methyl and —C(=O)OH;

L is a bond or is methyl (methylene), ethyl (ethylene) or propyl (propylene);

$R^2$ is —$N(CH_2CH_3)_2$, —C(=O)$NH_2$, —C(=O)NH$(CH_2CH_2CH_2CH_3)$, —C(=O)morpholinyl, —C(=O)pyrrolidinyl, phenyl, pyridyl, pyrazinyl, pyrimidinyl, thiazolyl, oxazolyl, 1,3-benzodioxolyl, thienopyrimidinyl, benzoisothiazolyl, benzimidazolyl, benzimidazolonyl, or indolinyl, where the phenyl, pyridyl, pyrazinyl, pyrimidinyl, thiazolyl, oxazolyl, and benzimidazolonyl are optionally substituted with 1 or 2 groups independently selected from methyl, trifluoromethyl, chloro, fluoro, cyano, methoxy, methylthio-, nitro, fluoro-phenyl, and morpholinylpropyl-;

or a salt, particularly a pharmaceutically acceptable salt, thereof.

The invention is still further directed to a compound according to Formula I, wherein:

Q is A-Z or E, wherein;

A is phenyl and Z is —C(=O)— or E is —$CH_2CH_2C(CH_3)_2$—C(=O)—;

X is a bond;

B is 1,4-diazepanyl, piperazinyl, piperidinyl, pyrrolidinyl, or azetidinyl, optionally substituted by 1 or 2 methyl groups;

L is a bond or is methyl (methylene);

$R^2$ is phenyl, pyridyl, pyrimidinyl, thiazolyl, or oxazolyl, where the phenyl, pyridyl, pyrimidinyl, thiazolyl, or oxazolyl is unsubstituted or is substituted by a group selected from methyl, cyano, phenyl or 4-fluorophenyl;

or a salt, particularly a pharmaceutically acceptable salt, thereof.

As used herein, the term "compound(s) of the invention" means a compound of formula (I) (as defined above) in any form, i.e., any salt or non-salt form (e.g., as a free acid or base form, or as a pharmaceutically acceptable salt thereof) and any physical form thereof (e.g., including non-solid forms (e.g., liquid or semi-solid forms), and solid forms (e.g., amorphous or crystalline forms, specific polymorphic forms, solvates, including hydrates (e.g., mono-, di- and hemi-hydrates)), and mixtures of various forms.

As used herein, the term "optionally substituted" means unsubstituted groups or rings (e.g., cycloalkyl, heterocycle, and heteroaryl rings) and groups or rings substituted with one or more specified substituents.

The compounds according to Formula I may contain one or more asymmetric center (also referred to as a chiral center) and may, therefore, exist as individual enantiomers, diastereomers, or other stereoisomeric forms, or as mixtures thereof. Chiral centers, such as chiral carbon atoms, may also be present in a substituent such as an alkyl group. Where the stereochemistry of a chiral center present in Formula I, or in any chemical structure illustrated herein, is not specified the structure is intended to encompass all individual stereoisomers and all mixtures thereof. Thus, compounds according to Formula I containing one or more chiral centers may be used as racemic mixtures, scalemic mixtures, or as diaseteromerically or enantiomerically pure materials.

Individual stereoisomers of a compound according to Formula I which contain one or more asymmetric center may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. The skilled artisan will appreciate that where the desired stereoisomer is converted into another chemical entity by one of the separation procedures described above, a further step is required to liberate the desired form. Alternatively, specific stereoisomers may be synthesized by asymmetric synthesis using optically active reagents, substrates, catalysts or solvents, or by converting one enantiomer to the other by asymmetric transformation.

When a disclosed compound or its salt is named or depicted by structure, it is to be understood that the compound or salt, including solvates (particularly, hydrates) thereof, may exist in crystalline forms, non-crystalline forms or a mixture thereof. The compound or salt, or solvates (particularly, hydrates) thereof, may also exhibit polymorphism (i.e. the capacity to occur in different crystalline forms). These different crystalline forms are typically known as "polymorphs." It is to be understood that when named or depicted by structure, the disclosed compound, or solvates (particularly, hydrates) thereof, also include all polymorphs thereof. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. One of ordinary skill in the art will appreciate that different polymorphs may be produced, for example, by changing or adjusting the conditions used in crystallizing/recrystallizing the compound.

Because of their potential use in medicine, the salts of the compounds of Formula I are preferably pharmaceutically acceptable salts. Suitable pharmaceutically acceptable salts include those described by Berge, Bighley and Monkhouse, J. Pharm. Sci (1977) 66, pp 1-19. Salts encompassed within the term "pharmaceutically acceptable salts" refer to non-toxic salts of the compounds of this invention.

Typically, a salt may be readily prepared by using a desired acid or base as appropriate. The salt may precipitate from solution and be collected by filtration or may be recovered by evaporation of the solvent.

When a compound of the invention is a base (contain a basic moiety), a desired salt form may be prepared by any suitable method known in the art, including treatment of the free base with an inorganic acid, such as hydrochloric acid, hydrobromic acid, sulfuric acid, nitric acid, phosphoric acid, and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, and the like, or with a pyranosidyl acid, such as glucuronic acid or galacturonic acid, or with an alpha-hydroxy acid, such as citric acid or tartaric acid, or with an amino acid, such as aspartic acid or glutamic acid, or with an aromatic acid, such as benzoic acid or cinnamic acid, or with a sulfonic acid, such as p-toluenesulfonic acid, methanesulfonic acid, ethanesulfonic acid or the like.

Suitable addition salts are formed from acids which form non-toxic salts and examples include acetate, p-aminobenzoate, ascorbate, aspartate, benzenesulfonate, benzoate, bicarbonate, bismethylenesalicylate, bisulfate, bitartrate, borate, calcium edetate, camsylate, carbonate, clavulanate, citrate, cyclohexylsulfamate, edetate, edisylate, estolate, esylate, ethanedisulfonate, ethanesulfonate, formate, fumarate, gluceptate, gluconate, glutamate, glycollate, glycollylarsanilate, hexylresorcinate, hydrabamine, hydrobromide, hydrochloride, dihydrochloride, hydrofumarate, hydrogen phosphate, hydroiodide, hydromaleate, hydrosuccinate, hydroxynaphthoate, isethionate, itaconate, lactate, lactobionate, laurate, malate, maleate, mandelate, mesylate, methylbromide, methylnitrate, methylsulfate, monopotassium maleate, mucate, napsylate, nitrate, N-methylglucamine, oxalate, oxaloacetate, pamoate (embonate), palmate, palmitate, pantothenate, phosphate/diphosphate, pyruvate, polygalacturonate, propionate, saccharate, salicylate, stearate, subacetate, succinate, sulfate, tannate, tartrate, teoclate, tosylate, triethiodide, trifluoroacetate and valerate.

Other exemplary acid addition salts include pyrosulfate, sulfite, bisulfite, decanoate, caprylate, acrylate, isobutyrate, caproate, heptanoate, propiolate, oxalate, malonate, suberate, sebacate, butyne-1,4-dioate, hexyne-1,6-dioate, chlorobenzoate, methylbenzoate, di nitrobenzoate, hydroxybenzoate, methoxybenzoate, phthalate, phenylacetate, phenylpropionate, phenylbutrate, lactate, γ-hydroxybutyrate, mandelate, and sulfonates, such as xylenesulfonate, propanesulfonate, naphthalene-1-sulfonate and naphthalene-2-sulfonate.

If an inventive basic compound is isolated as a salt, the corresponding free base form of that compound may be prepared by any suitable method known to the art, including treatment of the salt with an inorganic or organic base, suitably an inorganic or organic base having a higher $pK_a$ than the free base form of the compound.

When a compound of the invention is an acid (contains an acidic moiety), a desired salt may be prepared by any suitable method known to the art, including treatment of the free acid with an inorganic or organic base, such as an amine (primary, secondary, or tertiary), an alkali metal or alkaline earth metal hydroxide, or the like. Illustrative examples of suitable salts include organic salts derived from amino acids such as glycine and arginine, ammonia, primary, secondary, and tertiary amines, and cyclic amines, such as N-methyl-D-glucamine, diethylamine, isopropylamine, trimethylamine, ethylene diamine, dicyclohexylamine, ethanolamine, piperidine, morpholine, and piperazine, as well as inorganic salts derived from sodium, calcium, potassium, magnesium, manganese, iron, copper, zinc, aluminum, and lithium.

Certain of the compounds of this invention may form salts with one or more equivalents of an acid (if the compound contains a basic moiety) or a base (if the compound contains an acidic moiety). The present invention includes within its scope all possible stoichiometric and non-stoichiometric salt forms.

Compounds of the invention having both a basic and acidic moiety may be in the form of zwitterions, acid-addition salt of the basic moiety or base salts of the acidic moiety.

This invention also provides for the conversion of one pharmaceutically acceptable salt of a compound of this invention, e.g., a hydrochloride salt, into another pharmaceutically acceptable salt of a compound of this invention, e.g., a sodium salt.

For solvates of the compounds of Formula I, or salts thereof, which are in crystalline form, the skilled artisan will appreciate that pharmaceutically-acceptable solvates may be formed wherein solvent molecules are incorporated into the crystalline lattice during crystallization. Solvates may involve nonaqueous solvents such as ethanol, isopropanol, DMSO, acetic acid, ethanolamine, and ethyl acetate, or they may involve water as the solvent that is incorporated into the crystalline lattice. Solvates wherein water is the solvent that is incorporated into the crystalline lattice are typically referred to as "hydrates." Hydrates include stoichiometric hydrates as well as compositions containing variable amounts of water. The invention includes all such solvates.

The subject invention also includes isotopically-labeled compounds which are identical to those recited in formula (I) but for the fact that one or more atoms are replaced by an atom having an atomic mass or mass number different from the atomic mass or mass number most commonly found in nature. Examples of isotopes that can be incorporated into compounds of the invention include isotopes of hydrogen, carbon, nitrogen, oxygen, fluorine, iodine and chlorine such as $^3$H, $^{11}$C, $^{14}$C, $^{18}$F, $^{123}$I, or $^{125}$I.

Compounds of the present invention and pharmaceutically acceptable salts of said compounds that contain the aforementioned isotopes and/or other isotopes of other atoms are within the scope of the present invention. Isotopically labeled compounds of the present invention, for example those into which radioactive isotopes such as $^3$H or $^{14}$C have been incorporated, are useful in drug and/or substrate tissue distribution assays. Tritiated, ie. $^3$H, and carbon-14, ie. $^{14}$C isotopes are particularly preferred for their ease of preparation and detectability. $^{11}$C and $^{18}$F isotopes are particularly useful in PET (positron emission tomography).

Since the compounds of formula (I) are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions.

The compounds of Formula I may be obtained by using synthetic procedures illustrated in the Schemes below or by drawing on the knowledge of a skilled organic chemist. The synthesis provided in these Schemes are applicable for producing compounds of the invention having a variety of different R$^1$ and R$^2$ groups employing appropriate precursors, which are suitably protected if needed, to achieve compatibility with the reactions outlined herein. Subsequent deprotection, where needed, affords compounds of the nature generally disclosed. While the Schemes are shown with compounds only of Formula I, they are illustrative of processes that may be used to make the compounds of the invention.

Intermediates (compounds used in the preparation of the compounds of the invention) may also be present as salts. Thus, in reference to intermediates, the phrase "compound(s) of formula (number)" means a compound having that structural formula or a pharmaceutically acceptable salt thereof.

Specific compounds of this invention include the compounds of Examples 1-85.

Representative compounds of this invention include:
(3-(5-(trifluoromethyl)-1,2,4-oxadiazol-3-yl)phenyl)(4-(5-(trifluoromethyl)pyridin-2-yl)-1,4-diazepan-1-yl)methanone,
(4-(3,4-dimethyl phenyl)piperazin-1-yl)(3-(5-(trifluoromethyl)-1,2,4-oxadiazol-3-yl)phenyl)methanone,
(4-(3,4-dichlorophenyl)piperazin-1-yl)(3-(5-(trifluoromethyl)-1,2,4-oxadiazol-3-yl)phenyl)methanone,
(4-(pyrazin-2-yl)piperazin-1-yl)(3-(5-(trifluoromethyl)-1,2,4-oxadiazol-3-yl)phenyl)methanone,
1-(3-(5-(trifluoromethyl)-1,2,4-oxadiazol-3-yl)benzoyl)piperidine-2-carboxamide,
(4-(2-morpholinoethyl)piperazin-1-yl)(3-(5-(trifluoromethyl)-1,2,4-oxadiazol-3-yl)phenyl)methanone,
(4-(3-(dimethylamino)propyl)piperazin-1-yl)(3-(5-(trifluoromethyl)-1,2,4-oxadiazol-3-yl)phenyl)methanone,
2-(4-(3-(5-(trifluoromethyl)-1,2,4-oxadiazol-3-yl)benzoyl)piperazin-1-yl)benzonitrile,
(4-(2,4-dimethoxyphenyl)piperazin-1-yl)(3-(5-(trifluoromethyl)-1,2,4-oxadiazol-3-yl)phenyl)methanone,
1-morpholino-2-(4-(3-(5-(trifluoromethyl)-1,2,4-oxadiazol-3-yl)benzoyl)piperazin-1-yl)ethanone,
(4-phenethylpiperazin-1-yl)(3-(5-(trifluoromethyl)-1,2,4-oxadiazol-3-yl)phenyl)methanone,
N-butyl-4-(3-(5-(trifluoromethyl)-1,2,4-oxadiazol-3-yl)benzoyl)piperazine-1-carboxamide,
(4-(pyridin-2-yl)piperazin-1-yl)(3-(5-(trifluoromethyl)-1,2,4-oxadiazol-3-yl)phenyl)methanone,
1-(pyrrolidin-1-yl)-2-(4-(3-(5-(trifluoromethyl)-1,2,4-oxadiazol-3-yl)benzoyl)piperazin-1-yl)ethanone,
(4-benzylpiperazin-1-yl)(3-(5-(trifluoromethyl)-1,2,4-oxadiazol-3-yl)phenyl)methanone,
(4-(benzo[d][1,3]dioxol-5-ylmethyl)piperazin-1-yl)(3-(5-(trifluoromethyl)-1,2,4-oxadiazol-3-yl)phenyl)methanone,
3-(4-(3-(5-(trifluoromethyl)-1,2,4-oxadiazol-3-yl)benzoyl)piperazin-1-yl)pyrazine-2-carbonitrile,
(4-(pyridin-4-ylmethyl)piperazin-1-yl)(3-(5-(trifluoromethyl)-1,2,4-oxadiazol-3-yl)phenyl)methanone,
(4-(3-(diethylamino)propyl)piperazin-1-yl)(3-(5-(trifluoromethyl)-1,2,4-oxadiazol-3-yl)phenyl)methanone,
(4-(1H-indole-6-carbonyl)piperazin-1-yl)(3-(5-(trifluoromethyl)-1,2,4-oxadiazol-3-yl)phenyl)methanone,
(4-picolinoyl piperazin-1-yl)(3-(5-(trifluoromethyl)-1,2,4-oxadiazol-3-yl)phenyl)methanone,
(4-(thieno[3,2-d]pyrimidin-4-yl)piperazin-1-yl)(3-(5-(trifluoromethyl)-1,2,4-oxadiazol-3-yl)phenyl)methanone,
(4-(4-nitrobenzyl)piperazin-1-yl)(3-(5-(trifluoromethyl)-1,2,4-oxadiazol-3-yl)phenyl)methanone,
(4-(pyridin-4-yl)piperazin-1-yl)(3-(5-(trifluoromethyl)-1,2,4-oxadiazol-3-yl)phenyl)methanone, 6-(4-(3-(5-(trifluoromethyl)-1,2,4-oxadiazol-3-yl)benzoyl)piperazin-1-yl)nicotinonitrile,
(3-(5-(trifluoromethyl)-1,2,4-oxadiazol-3-yl)phenyl)(4-(3-(trifluoromethyl)pyridin-2-yl)piperazin-1-yl)methanone,
(4-(2-chlorophenyl)piperazin-1-yl)(3-(5-(trifluoromethyl)-1,2,4-oxadiazol-3-yl)phenyl)methanone,
(4-(3-fluorophenyl)piperazin-1-yl)(3-(5-(trifluoromethyl)-1,2,4-oxadiazol-3-yl)phenyl)methanone,
(4-(3-(methylthio)phenyl)piperazin-1-yl)(3-(5-(trifluoromethyl)-1,2,4-oxadiazol-3-yl)phenyl)methanone,
(4-(4-chlorobenzyl)piperazin-1-yl)(3-(5-(trifluoromethyl)-1,2,4-oxadiazol-3-yl)phenyl)methanone,
(4-(benzo[d]isothiazol-3-yl)piperazin-1-yl)(3-(5-(trifluoromethyl)-1,2,4-oxadiazol-3-yl)phenyl)methanone,
(4-(2-methoxybenzyl)piperazin-1-yl)(3-(5-(trifluoromethyl)-1,2,4-oxadiazol-3-yl)phenyl)methanone,
(4-(4-methoxyphenyl)piperazin-1-yl)(3-(5-(trifluoromethyl)-1,2,4-oxadiazol-3-yl)phenyl)methanone,
4-(4-(3-(5-(trifluoromethyl)-1,2,4-oxadiazol-3-yl)benzoyl)piperazin-1-yl)-1H-benzo[d]imidazol-2(3H)-one,
N-(4-((N-methylacetamido)methyl)phenyl)-3-(5-(trifluoromethyl)-1,2,4-oxadiazol-3-yl)benzamide,
N-(4-((1H-1,2,4-triazol-1-yl)methyl)phenyl)-3-(5-(trifluoromethyl)-1,2,4-oxadiazol-3-yl)benzamide,
(3-benzylpiperidin-1-yl)(3-(5-(trifluoromethyl)-1,2,4-oxadiazol-3-yl)phenyl)methanone,
4-(4-(3-(5-(trifluoromethyl)-1,2,4-oxadiazol-3-yl)benzoyl)piperazin-1-yl)benzonitrile,
6-(2-methyl-4-(3-(5-(trifluoromethyl)-1,2,4-oxadiazol-3-yl)benzoyl)piperazin-1-yl)nicotinonitrile,
6-(3-methyl-4-(3-(5-(trifluoromethyl)-1,2,4-oxadiazol-3-yl)benzoyl)piperazin-1-yl)nicotinonitrile,
6-(3,5-dimethyl-4-(3-(5-(trifluoromethyl)-1,2,4-oxadiazol-3-yl)benzoyl)piperazin-1-yl)nicotinonitrile,
methyl 4-(5-cyanopyridin-2-yl)-1-(3-(5-(trifluoromethyl)-1,2,4-oxadiazol-3-yl)benzoyl)piperazine-2-carboxylate,
4-(5-cyanopyridin-2-yl)-1-(3-(5-(trifluoromethyl)-1,2,4-oxadiazol-3-yl)benzoyl)piperazine-2-carboxylic acid,
6-(2,6-dimethyl-4-(3-(5-(trifluoromethyl)-1,2,4-oxadiazol-3-yl)benzoyl)piperazin-1-yl)nicotinonitrile,
1-(3-morpholinopropyl)-3-(1-(3-(5-(trifluoromethyl)-1,2,4-oxadiazol-3-yl)benzoyl)piperidin-4-yl)-1H-benzo[d]imidazol-2(3H)-one,
1-(1-(3-(5-(trifluoromethyl)-1,2,4-oxadiazol-3-yl)benzoyl)piperidin-4-yl)-1H-benzo[d]imidazol-2(3H)-one,
6-((3-methyl-4-(3-(5-(trifluoromethyl)-1,2,4-oxadiazol-3-yl)benzoyl)piperazin-1-yl)methyl)nicotinonitrile,
6-((3-methyl-4-(4-(5-(trifluoromethyl)-1,2,4-oxadiazol-3-yl)butanoyl)piperazin-1-yl)methyl)nicotinonitrile,
1-(4-phenylthiazol-2-yl)-N-(3-(5-(trifluoromethyl)-1,2,4-oxadiazol-3-yl)phenyl)pyrrolidine-3-carboxamide,
6-(1-(3-(5-(trifluoromethyl)-1,2,4-oxadiazol-3-yl)benzoyl)azetidin-3-yl)nicotinonitrile,
6-(1-(3-(5-(trifluoromethyl)-1,2,4-oxadiazol-3-yl)benzoyl)piperidin-4-yl)nicotinonitrile,
N-(1-(5-cyanopyridin-2-yl)piperidin-4-yl)-3-(5-(trifluoromethyl)-1,2,4-oxadiazol-3-yl)benzamide,
1-(5-cyanopyridin-2-yl)-N-(3-(5-(trifluoromethyl)-1,2,4-oxadiazol-3-yl)phenyl)pyrrolidine-3-carboxamide,
6-(3-methyl-4-(4-(5-(trifluoromethyl)-1,2,4-oxadiazol-3-yl)butanoyl)piperazin-1-yl)nicotinonitrile,
6-(2,2-dimethyl-4-(3-(5-(trifluoromethyl)-1,2,4-oxadiazol-3-yl)benzoyl)piperazin-1-yl)nicotinonitrile,
N-(1-(5-cyanopyridin-2-yl)piperidin-3-yl)-3-(5-(trifluoromethyl)-1,2,4-oxadiazol-3-yl)benzamide,
6-(3,3-dimethyl-4-(3-(5-(trifluoromethyl)-1,2,4-oxadiazol-3-yl)benzoyl)piperazin-1-yl)nicotinonitrile,
6-(4-(3-(5-(trifluoromethyl)-1,2,4-oxadiazol-3-yl)benzoyl)-1,4-diazepan-1-yl)nicotinonitrile,
1-(5-cyanopyridin-2-yl)-4-(3-(5-(trifluoromethyl)-1,2,4-oxadiazol-3-yl)benzoyl)piperazine-2-carboxylic acid,
(4-methyl-3-(4-phenylthiazol-2-yl)piperazin-1-yl)(3-(5-(trifluoromethyl)-1,2,4-oxadiazol-3-yl)phenyl)methanone,
6-(3-methyl-4-(3-(5-(2,2,2-trifluoroacetyl)thiophen-2-yl)benzoyl)piperazin-1-yl)nicotinonitrile,
6-(4-(3-(5-(2,2,2-trifluoroacetyl)thiophen-2-yl)benzoyl)piperazin-1-yl)nicotinonitrile,
6-(4-(2,2-dimethyl-4-(5-(trifluoromethyl)-1,2,4-oxadiazol-3-yl)butanoyl)-3-methylpiperazin-1-yl)nicotinonitrile,
(4-(5-methoxypyridin-2-yl)piperazin-1-yl)(3-(5-(trifluoromethyl)-1,2,4-oxadiazol-3-yl)phenyl)methanone,
(3-(4-(4-fluorophenyl)thiazol-2-yl)piperidin-1-yl)(3-(5-(trifluoromethyl)-1,2,4-oxadiazol-3-yl)phenyl)methanone,
6-(3-methyl-4-(4-(5-(2,2,2-trifluoroacetyl)thiophen-2-yl)butanoyl)piperazin-1-yl)nicotinonitrile,
(4-(2,3-dihydro-1H-inden-2-yl)piperazin-1-yl)(3-(5-(trifluoromethyl)-1,2,4-oxadiazol-3-yl)phenyl)methanone,
(4-(1H-benzo[d]imidazol-2-yl)piperazin-1-yl)(3-(5-(trifluoromethyl)-1,2,4-oxadiazol-3-yl)phenyl)methanone,
(3-(5-(4-fluorophenyl)oxazol-2-yl)piperidin-1-yl)(3-(5-(trifluoromethyl)-1,2,4-oxadiazol-3-yl)phenyl)methanone,
(4-(3-methoxyphenyl)piperazin-1-yl)(3-(5-(trifluoromethyl)-1,2,4-oxadiazol-3-yl)phenyl)methanone,
(4-(pyrimidin-5-yl)piperazin-1-yl)(3-(5-(trifluoromethyl)-1,2,4-oxadiazol-3-yl)phenyl)methanone,
2-(4-(3-(5-(trifluoromethyl)-1,2,4-oxadiazol-3-yl)benzoyl)piperazin-1-yl)nicotinonitrile
(4-(4-phenylpyrimidin-2-yl)piperazin-1-yl)(3-(5-(trifluoromethyl)-1,2,4-oxadiazol-3-yl)phenyl)methanone,
(4-(2-fluorophenyl)piperazin-1-yl)(3-(5-(trifluoromethyl)-1,2,4-oxadiazol-3-yl)phenyl)methanone,
(4-(2-methoxyphenyl)piperazin-1-yl)(3-(5-(trifluoromethyl)-1,2,4-oxadiazol-3-yl)phenyl)methanone,
(4-(pyridin-3-yl)piperazin-1-yl)(3-(5-(trifluoromethyl)-1,2,4-oxadiazol-3-yl)phenyl)methanone,
3-fluoro-4-(4-(3-(5-(trifluoromethyl)-1,2,4-oxadiazol-3-yl)benzoyl)piperazin-1-yl)benzonitrile,
(4-(pyrimidin-2-yl)piperazin-1-yl)(3-(5-(trifluoromethyl)-1,2,4-oxadiazol-3-yl)phenyl)methanone,
(4-([1,1'-biphenyl]-3-yl)piperazin-1-yl)(3-(5-(trifluoromethyl)-1,2,4-oxadiazol-3-yl)phenyl)methanone,
(3-((4-(4-fluorophenyl)thiazol-2-yl)methyl)azetidin-1-yl)(3-(5-(trifluoromethyl)-1,2,4-oxadiazol-3-yl)phenyl)methanone,
(4-(4-methylthiazol-2-yl)piperazin-1-yl)(3-(5-(trifluoromethyl)-1,2,4-oxadiazol-3-yl)phenyl)methanone,
(4-(benzo[d]oxazol-2-yl)piperazin-1-yl)(3-(5-(trifluoromethyl)-1,2,4-oxadiazol-3-yl)phenyl)methanone,
(4-((2-(4-fluorophenyl)thiazol-4-yl)methyl)piperazin-1-yl)(3-(5-(trifluoromethyl)-1,2,4-oxadiazol-3-yl)phenyl)methanone,
(4-((2-(4-fluorophenyl)oxazol-4-yl)methyl)piperazin-1-yl)(3-(5-(trifluoromethyl)-1,2,4-oxadiazol-3-yl)phenyl)methanone,
(2-phenylthiazol-4-yl)(4-(3-(5-(trifluoromethyl)-1,2,4-oxadiazol-3-yl)benzoyl)piperazin-1-yl)methanone,
((1S,4S)-5-(pyridin-2-yl)-2,5-diazabicyclo[2.2.1]heptan-2-yl)(3-(5-(trifluoromethyl)-1,2,4-oxadiazol-3-yl)phenyl)methanone,
or a salt, particularly a pharmaceutically acceptable salt, thereof.

Particular compounds of this invention include:

(3-((4-(4-fluorophenyl)thiazol-2-yl)methyl)azetidin-1-yl)(3-(5-(trifluoromethyl)-1,2,4-oxadiazol-3-yl)phenyl)methanone, 6-(4-(3-(5-(trifluoromethyl)-1,2,4-oxadiazol-3-yl)benzoyl)-1,4-diazepan-1-yl)nicotinonitrile, (4-methyl-3-(4-phenylthiazol-2-yl)piperazin-1-yl)(3-(5-(trifluoromethyl)-1,2,4-oxadiazol-3-yl)phenyl)methanone, (4-(pyrimidin-2-yl)piperazin-1-yl)(3-(5-(trifluoromethyl)-1,2,4-oxadiazol-3-yl)phenyl)methanone, 6-((3-methyl-4-(3-(5-(trifluoromethyl)-1,2,4-oxadiazol-3-yl)benzoyl)piperazin-1-yl)methyl)nicotinonitrile, 6-(4-(2,2-dimethyl-4-(5-(trifluoromethyl)-1,2,4-oxadiazol-3-yl)butanoyl)-3-methylpiperazin-1-yl)nicotinonitrile, 6-(4-(3-(5-(2,2,2-trifluoroacetyl)thiophen-2-yl)benzoyl)piperazin-1-yl)nicotinonitrile, (4-(4-methylthiazol-2-yl)piperazin-1-yl)(3-(5-(trifluoromethyl)-1,2,4-oxadiazol-3-yl)phenyl)methanone, (3-(5-(4-fluorophenyl)oxazol-2-yl)piperidin-1-yl)(3-(5-(trifluoromethyl)-1,2,4-oxadiazol-3-yl)phenyl)methanone, (3-(4-(4-fluorophenyl)thiazol-2-yl)piperidin-1-yl)(3-(5-(trifluoromethyl)-1,2,4-oxadiazol-3-yl)phenyl)methanone, 6-(4-(3-(5-(trifluoromethyl)-1,2,4-oxadiazol-3-yl)benzoyl)piperazin-1-yl)nicotinonitrile, or a salt, particularly a pharmaceutical salt thereof.

Compound names were generated using the software naming program ChemDraw 11.0 available from CambridgeSoft Corporation., 100 CambridgePark Drive, Cambridge, Mass. 02140, USA (http://www.cambridgesoft.com).

The compounds of Formula I can be prepared according to the methods outlined below.

Scheme 1

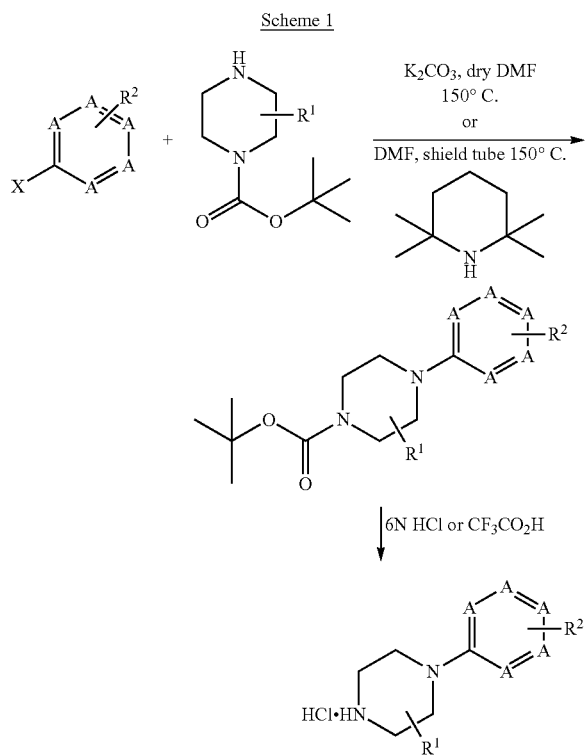

Scheme 2

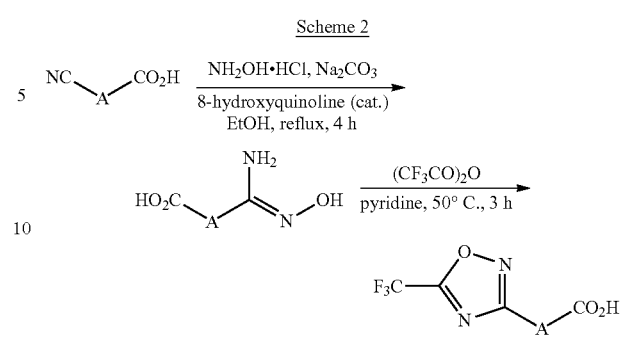

Scheme 3

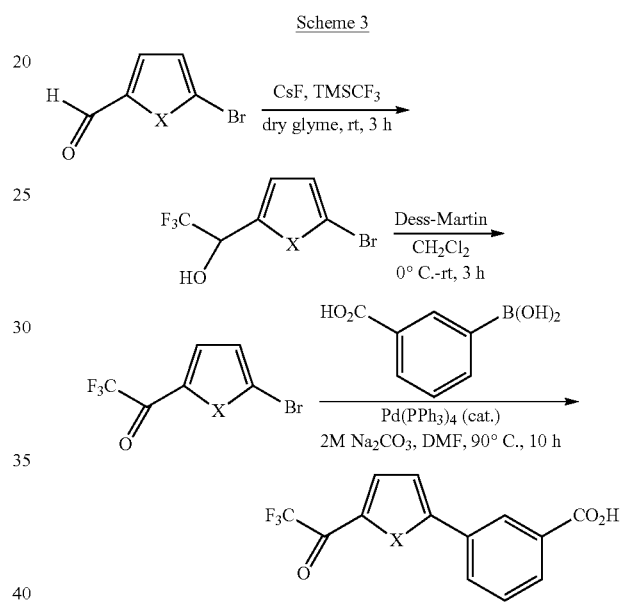

Scheme 4

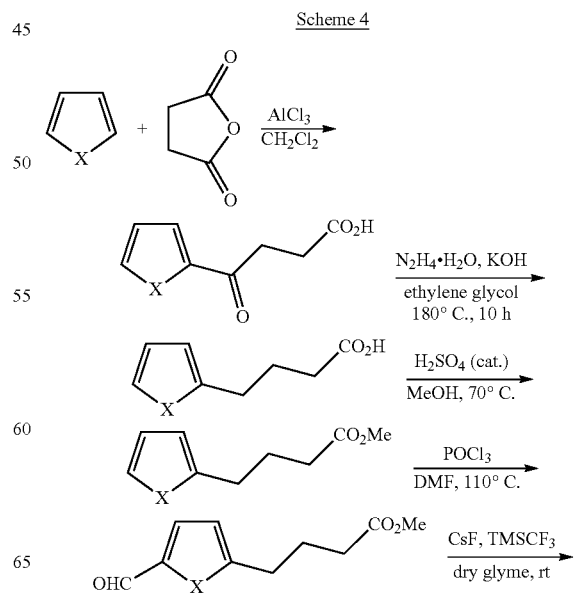

-continued

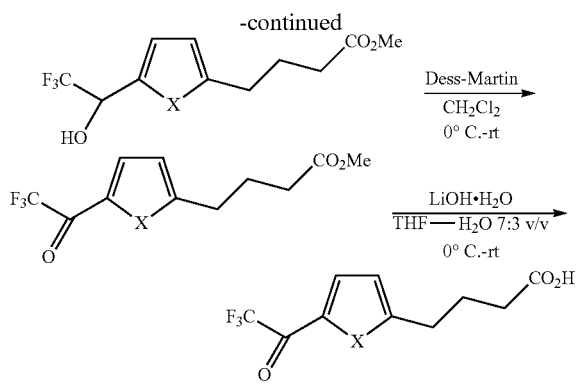

Scheme 5

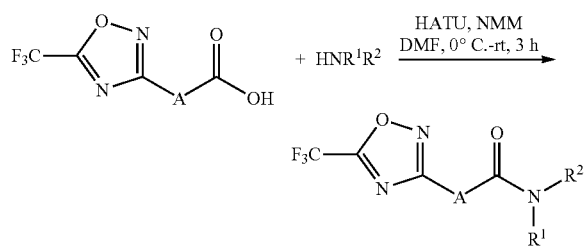

Scheme 6

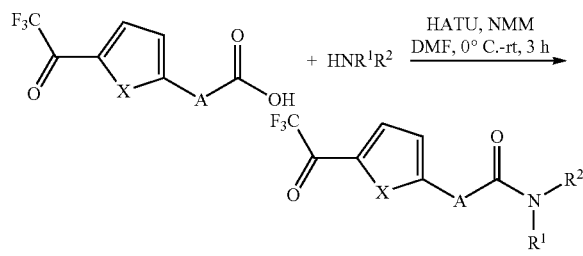

The invention also includes various deuterated forms of the compounds of Formula I. Each available hydrogen atom attached to a carbon atom may be independently replaced with a deuterium atom. A person of ordinary skill in the art will know how to synthesize deuterated forms of the compounds of Formula I. For example, deuterated alkyl groups (e.g., N-(deutero-methyl) amines) may be prepared by conventional techniques (see for example: methyl-$d_3$-amine available from Aldrich Chemical Co., Milwaukee, Wis., Cat. No. 489, 689-2). Employing such compounds will allow for the preparation of compounds of Formula I in which various hydrogen atoms of the N-methyl groups are replaced with a deuterium atom.

The present invention is directed to a method of inhibiting an HDAC which comprises contacting the acetylase with a compound of Formula I or a salt thereof, particularly a pharmaceutically acceptable salt thereof. This invention is also directed to a method of treatment of an HDAC-mediated disease or disorder comprising administering a therapeutically effective amount of the compound of Formula I or a salt thereof, particularly a pharmaceutically acceptable salt thereof, to a patient, specifically a human, in need thereof. As used herein, "patient" refers to a mammal, specifically, a human. A therapeutically "effective amount" is intended to mean that amount of a compound that, when administered to a patient in need of such treatment, is sufficient to effect treatment, as defined herein. Thus, e.g., a therapeutically effective amount of a compound of Formula I, or a pharmaceutically acceptable salt thereof, is a quantity of an inventive agent that, when administered to a human in need thereof, is sufficient to inhibit the activity of HDAC such that a disease condition which is mediated by that activity is reduced, alleviated or prevented. The amount of a given compound that will correspond to such an amount will vary depending upon factors such as the particular compound (e.g., the potency ($pXC_{50}$), efficacy ($EC_{50}$), and the biological half-life of the particular compound), disease condition and its severity, the identity (e.g., age, size and weight) of the patient in need of treatment, but can nevertheless be routinely determined by one skilled in the art. Likewise, the duration of treatment and the time period of administration (time period between dosages and the timing of the dosages, e.g., before/with/after meals) of the compound will vary according to the identity of the mammal in need of treatment (e.g., weight), the particular compound and its properties (e.g., pharmaceutical characteristics), disease or condition and its severity and the specific composition and method being used, but can nevertheless be determined by one of skill in the art.

"Treating" or "treatment" is intended to mean at least the mitigation of a disease condition in a patient, where the disease condition is caused or mediated by HDAC. The methods of treatment for mitigation of a disease condition include the use of the compounds in this invention in any conventionally acceptable manner, for example for prevention, retardation, prophylaxis, therapy or cure of a disease.

In one embodiment, this invention is directed to a method of treating, ameliorating, or preventing an autoimmune disorder, an immunological disease, an inflammatory disorder, transplant/graft rejection (e.g., allograft), lymphopenia, or graft-versus-host disease (GvHD) in a patient, specifically in a human, comprising administering to the patient a compound of this invention, in an amount sufficient to increase the level and/or activity of a Treg cell or a population of Treg cells in the patient, thereby treating, ameliorating, or preventing the autoimmune disorder, inflammatory disorder, transplant/graft rejection, lymphopenia, or GvHD in the patient.

Additional examples of diseases and conditions that may be treated by the compounds of this invention include but not limited to type II diabetes mellitus, coronary artery disease, allergies and allergic reactions, and sepsis/toxic shock.

Exemplary autoimmune disorders include, but are not limited to, multiple sclerosis, juvenile idiopathic arthritis, psoriatic arthritis, hepatitis C virus-associated mixed cryoglobulinemia, polymyositis, dermatomyositis, polyglandular syndrome type II, autoimmune liver disease, Kawasaki disease, myasthenia gravis, immunodysregulation polyendocrinopathy enteropathy X-linked syndrome (IPEX (syndrome)), type I diabetes, psoriasis, hypothyroidism, hemolytic anemia, autoimmune polyendocrinopathy-candidiasis-ectodermal dystrophy (APECED), thrombocytopenia, spondyloarthritis, Sjogren's syndrome, rheumatoid arthritis, inflammatory bowel disease (IBD), Crohn's disease, ulcerative colitis, eczema, gastritis, or thyroiditis. As part of a nonlimiting list, the inflammatory disorder can be contact hypersensitivity, atopic dermatitis or Still disease.

Additional examples of autoimmune diseases include but are not limited to autoimmune diseases include osteoarthritis, systemic sclerosis, sarcoidosis, insulin dependent diabetes mellitus (IDDM, type I diabetes), reactive arthritis, scleroderma, vasculitis, Wegener's granulomatosis, Hashimoto's disease, scleroderma, oophoritis, Lupus (SLE), Grave's disease, asthma, cryoglobulinemia, primary biliary sclerosis, pemphigus vulgaris, hemolytic anemia and pernicious anemia.

Examples of transplant/graft rejection (e.g., allograft), lymphopenia, or graft-versus-host disease (GvHD) are those arising from cell, tissue and organ transplantation procedures, such as therapeutic cell transplants such as stem cells, muscle cells such as cardiac cells, islet cells, liver cells, bone marrow transplants, skin grafts, bone grafts, lung transplants, kidney transplants, liver transplants, and heart transplants.

Other examples of diseases and conditions that may be treated by the compounds of this invention include but are not limited to cystic fibrosis, osteoporosis, obesity, epilepsy, depression, thalassemia, sickle cell anemia, amyotrophic lateral sclerosis (ALS) and hyperalgesia, cardiac disease (e.g., stroke, hypertension, atherothrombotic diseases, artherosclerosis or limitation of infarct size in acute coronary syndrome), diseases or disorders involving muscular atrophy, gentamicin-induced hearing loss, drug resistance (e.g., drug resistance in osteosarcoma and colon cancer cells), infectious diseases, and immune deficiency/immunocompromised patients. Examples of infectious diseases relate to various pathogen infections such as viral, fungal, bacterial, mycoplasm, and infections by unicellular and multicellular eukaryotic organisms. Common human pathogens include but are not limited to HIV, HSV, HPV, Hepatitis A, B and C viruses, influenza, denge, zostrella, rubella, RSV, rotavirus, gram positive, gram negative, *streptococcus*, tetanus, *staphalococcus*, tuberculosis, *listeria*, and malaria.

In another embodiment, this invention is directed to inhibitors of HDAC and their use to stop or reduce the growth of neoplastic cells, e.g., cancer cells and tumor cells.

The growth of cancer cells and/or tumor cells that are found in the following cancer types may be reduced by treatment with a compound of this invention: carcinoma (e.g., adenocarcinoma), heptaocellular carcinoma, sarcoma, myeloma (e.g., multiple myeloma), treating bone disease in multiple myeloma, leukemia, childhood acute lymphoblastic leukemia and lymphoma (e.g., cutaneous cell lymphoma), and mixed types of cancers, such as adenosquamous carcinoma, mixed mesodermal tumor, carcinosarcoma, and teratocarcinoma.

In one aspect of the invention, breast or prostate cancers or tumors are treated using the HDAC inhibitors of this invention.

Other cancers that may be treated using the compounds of this invention include, but are not limited to, bladder cancer, breast cancer, prostate cancer, stomach cancer, lung cancer, colon cancer, rectal cancer, colorectal cancer, liver cancer, endometrial cancer, pancreatic cancer, cervical cancer, ovarian cancer; head and neck cancer, and melanoma.

The inhibitors of the invention may be employed alone or in combination with standard anti-cancer regimens for neoplastic cell, e.g., tumor and cancer, treatments.

The compounds of the invention may be administered by any suitable route of administration, including both systemic administration and topical administration. Systemic administration includes oral administration, parenteral administration, transdermal administration, rectal administration, and administration by inhalation. Parenteral administration refers to routes of administration other than enteral, transdermal, or by inhalation, and is typically by injection or infusion. Parenteral administration includes intravenous, intramuscular, and subcutaneous injection or infusion. Inhalation refers to administration into the patient's lungs whether inhaled through the mouth or through the nasal passages. Topical administration includes application to the skin.

The compounds of the invention may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound of the invention depend on the pharmacokinetic properties of that compound, such as absorption, distribution, and half-life, which can be determined by the skilled artisan. In addition, suitable dosing regimens, including the duration such regimens are administered, for a compound of the invention depend on the condition being treated, the severity of the condition being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

Treatment of HDAC-mediated disease conditions may be achieved using the compounds of this invention as a monotherapy, or in dual or multiple combination therapy, such as in combination with other agents, for example, in combination with one or more of the following agents: DNA methyltransferase inhibitors, acetyl transferase enhancers, proteasome or HSP90 inhibitors, and one or more immunosuppressants that do not activate the T suppressor cells including but are not limited to corticosteroids, rapamycin, Azathioprine, Mycophenolate, Cyclosporine, Mercaptopurine (6-MP), basiliximab, daclizumab, sirolimus, tacrolimus, Muromonab-CD3, cyclophosphamide, and methotrexate, which are administered in effective amounts as is known in the art.

The compounds of the invention will normally, but not necessarily, be formulated into a pharmaceutical composition prior to administration to a patient. Accordingly, in another aspect the invention is directed to pharmaceutical compositions comprising a compound of the invention and a pharmaceutically-acceptable excipient.

The pharmaceutical compositions of the invention may be prepared and packaged in bulk form wherein an effective amount of a compound of the invention can be extracted and then given to the patient such as with powders, syrups, and solutions for injection. Alternatively, the pharmaceutical compositions of the invention may be prepared and packaged in unit dosage form. For oral application, for example, one or more tablets or capsules may be administered. A dose of the pharmaceutical composition contains at least a therapeutically effective amount of a compound of this invention (i.e., a compound of Formula I or a salt, particularly a pharmaceutically acceptable salt, thereof). When prepared in unit dosage form, the pharmaceutical compositions may contain from 1 mg to 1000 mg of a compound of this invention.

The pharmaceutical compositions of the invention typically contain one compound of the invention. However, in certain embodiments, the pharmaceutical compositions of the invention contain more than one compound of the invention. In addition, the pharmaceutical compositions of the invention may optionally further comprise one or more additional pharmaceutically active compounds.

As used herein, "pharmaceutically-acceptable excipient" means a material, composition or vehicle involved in giving form or consistency to the composition. Each excipient must be compatible with the other ingredients of the pharmaceutical composition when commingled such that interactions which would substantially reduce the efficacy of the compound of the invention when administered to a patient and interactions which would result in pharmaceutical compositions that are not pharmaceutically-acceptable are avoided. In addition, each excipient must of course be of sufficiently high purity to render it pharmaceutically-acceptable.

The compounds of the invention and the pharmaceutically-acceptable excipient or excipients will typically be formulated into a dosage form adapted for administration to the patient by the desired route of administration. Conventional dosage forms include those adapted for (1) oral administration such as tablets, capsules, caplets, pills, troches, powders, syrups, elixirs, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols and solutions; and (6) topical administration such as creams, ointments, lotions, solutions, pastes, sprays, foams, and gels.

Suitable pharmaceutically-acceptable excipients will vary depending upon the particular dosage form chosen. In addition, suitable pharmaceutically-acceptable excipients may be chosen for a particular function that they may serve in the composition. For example, certain pharmaceutically-acceptable excipients may be chosen for their ability to facilitate the production of uniform dosage forms. Certain pharmaceutically-acceptable excipients may be chosen for their ability to facilitate the production of stable dosage forms. Certain pharmaceutically-acceptable excipients may be chosen for their ability to facilitate the carrying or transporting the compound or compounds of the invention once administered to the patient from one organ, or portion of the body, to another organ, or portion of the body. Certain pharmaceutically-acceptable excipients may be chosen for their ability to enhance patient compliance.

Suitable pharmaceutically-acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anti-caking agents, humectants, chelating agents, plasticizers, viscosity increasing agents, antioxidants, preservatives, stabilizers, surfactants, and buffering agents. The skilled artisan will appreciate that certain pharmaceutically-acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in Remington's *Pharmaceutical Sciences* (Mack Publishing Company).

In one aspect, the invention is directed to a solid oral dosage form such as a tablet or capsule comprising an effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

EXAMPLES

The following examples illustrate the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention.

In the following experimental descriptions, the following abbreviations may be used:

| Abbreviation | Meaning |
| --- | --- |
| AcOH | acetic acid |
| aq | aqueous |
| brine | saturated aqueous NaCl |
| $CH_2Cl_2$ | methylene chloride |
| $CH_3CN$ or MeCN | acetonitrile |
| $CH_3NH_2$ | methylamine |
| d | day |
| DMF | N,N-dimethylformamide |
| DMSO | dimethylsulfoxide |
| equiv | equivalents |
| Et | ethyl |
| $Et_3N$ | triethylamine |
| $Et_2O$ | diethyl ether |
| EtOAc | ethyl acetate |
| h, hr | hour |
| HCl | hydrochloric acid |
| i-$Pr_2$NEt | N',N'-diisopropylethylamine |
| KOt-Bu | potassium tert-butoxide |
| LCMS | liquid chromatography-mass spectroscopy |
| Me | methyl |
| MeOH or $CH_3OH$ | methanol |
| $MgSO_4$ | magnesium sulfate |
| min | minute |
| MS | mass spectrum |
| μw | microwave |
| $NaBH_4$ | sodium borohydride |
| $Na_2CO_3$ | sodium carbonate |
| $NaHCO_3$ | sodium bicarbonate |
| NaOH | sodium hydroxide |
| $Na_2SO_4$ | sodium sulfate |
| $NH_4Cl$ | ammonium chloride |
| $NiCl_2 \cdot 6H_2O$ | nickel (II) chloride hexahydrate |
| NMP | N-methyl-2-pyrrolidone |
| Ph | phenyl |
| rt | room temperature |
| satd | saturated |

-continued

| Abbreviation | Meaning |
|---|---|
| SCX | strong cation exchange |
| SPE | solid phase extraction |
| TFA | trifluoroacetic acid |
| THF | tetrahydrofuran |
| $t_R$ | retention time |

Example 1

(3-(5-(Trifluoromethyl)-1,2,4-oxadiazol-3-yl)phenyl)(4-(5-(trifluoromethyl)pyridin-2-yl)-1,4-diazepan-1-yl)methanone

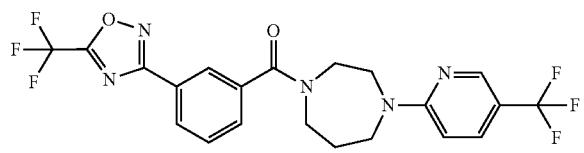 [SMILES: O=C(c1cccc(-c2noc(C(F)(F)F)n2)c1)N1CCCN(c2ccc(C(F)(F)F)cn2)CC1]

1-(5-(Trifluoromethyl)pyridin-2-yl)-1,4-diazepane (60 mg, 0.23 mmol), 3-(5-(trifluoromethyl)-1,2,4-oxadiazol-3-yl)benzoic acid (68 mg, 0.28 mmol), and N-(3-dimethylaminopropyl)-N'-ethylcarbodiimide hydrochloride (EDCl) (89 mg, 0.46 mmol) were dissolved in dichloromethane (3 mL) at room temperature. Diisopropylethylamine (DIEA) (0.085 mL, 0.93 mmol) was then introduced at room temperature and the reaction mixture was stirred at room temperature for 2 h. The reaction mixture was diluted with dichloromethane (60 mL) and washed with water (1×20 mL) and brine (1×20 mL). The organic layer was then dried over anhydrous sodium sulfate and concentrated under reduced pressure to give the crude product. The crude product was then purified on Prep TLC (30% Ethyl Acetate:Hexanes) to give (3-(5-(trifluoromethyl)-1,2,4-oxadiazol-3-yl)phenyl)(4-(5-(trifluoromethyl)pyridin-2-yl)-1,4-diazepan-1-yl)methanone (14 mg, 14% yield). $^1$H NMR (300 MHz, CDCl$_3$) δ 8.41 (s, 1H), 8.19-8.06 (m, 2H), 7.88 (s, 1H), 7.66-7.44 (m, 2H), 6.55 (bs, 1H), 3.98-3.64 (m, 8H), 1.74 (m, 2H). MS (ESI) m/z: Calculated for $C_{21}H_{17}F_6N_5O_2S$: 485.13. found: 486.1 (M+H)$^+$.

Examples 2-36 were synthesized from 3-(5-(trifluoromethyl)-1,2,4-oxadiazol-3-yl)benzoic acid and readily available amines in a similar manner as part of a screening collection and characterized by LCMS and $^1$H NMR.

| Example No. | Compound Structure | Compound Name |
|---|---|---|
| 2 | 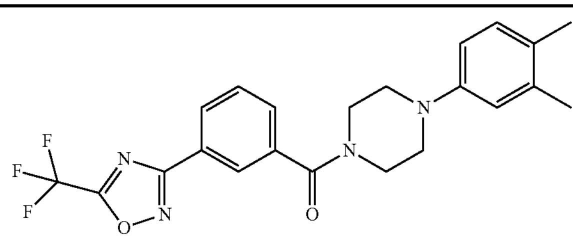 | (4-(3,4-dimethylphenyl)piperazin-1-yl)(3-(5-(trifluoromethyl)-1,2,4-oxadiazol-3-yl)phenyl)methanone |
| 3 | 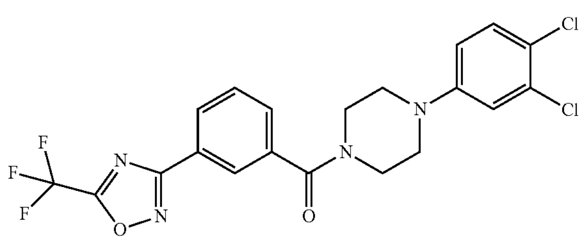 [SMILES: O=C(c1cccc(-c2noc(C(F)(F)F)n2)c1)N1CCN(c2ccc(Cl)c(Cl)c2)CC1] | (4-(3,4-dichlorophenyl)piperazin-1-yl)(3-(5-(trifluoromethyl)-1,2,4-oxadiazol-3-yl)phenyl)methanone |
| 4 | 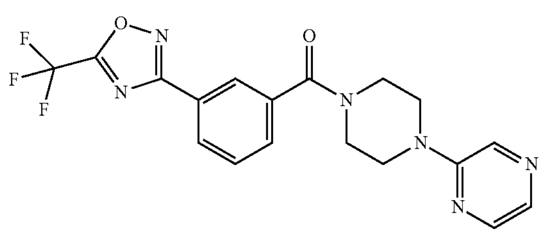 [SMILES: O=C(c1cccc(-c2noc(C(F)(F)F)n2)c1)N1CCN(c2cnccn2)CC1] | (4-(pyrazin-2-yl)piperazin-1-yl)(3-(5-(trifluoromethyl)-1,2,4-oxadiazol-3-yl)phenyl)methanone |
| 5 | 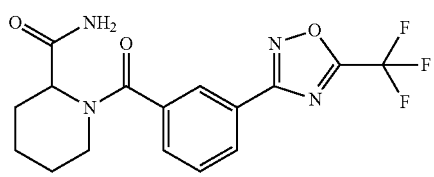 [SMILES: NC(=O)C1CCCCN1C(=O)c1cccc(-c2noc(C(F)(F)F)n2)c1] | 1-(3-(5-(trifluoromethyl)-1,2,4-oxadiazol-3-yl)benzoyl)piperidine-2-carboxamide |

| Example No. | Compound Structure | Compound Name |
|---|---|---|
| 6 | 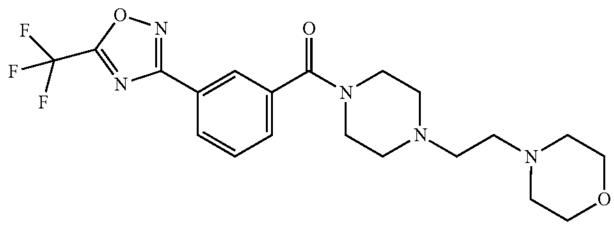 [SMILES: O=C(c1cccc(-c2noc(C(F)(F)F)n2)c1)N1CCN(CCN2CCOCC2)CC1] | (4-(2-morpholinoethyl)piperazin-1-yl)(3-(5-(trifluoromethyl)-1,2,4-oxadiazol-3-yl)phenyl)methanone |
| 7 | 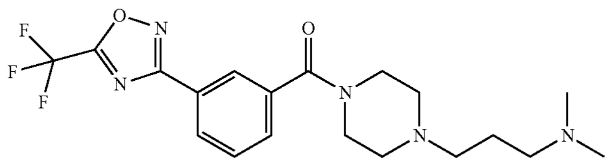 [SMILES: CN(C)CCCN1CCN(C(=O)c2cccc(-c3noc(C(F)(F)F)n3)c2)CC1] | (4-(3-(dimethylamino)propyl)piperazin-1-yl)(3-(5-(trifluoromethyl)-1,2,4-oxadiazol-3-yl)phenyl)methanone |
| 8 | 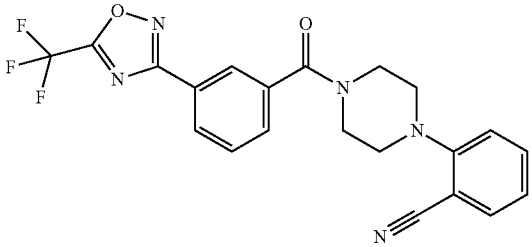 [SMILES: N#Cc1ccccc1N1CCN(C(=O)c2cccc(-c3noc(C(F)(F)F)n3)c2)CC1] | 2-(4-(3-(5-(trifluoromethyl)-1,2,4-oxadiazol-3-yl)benzoyl)piperazin-1-yl)benzonitrile |
| 9 | 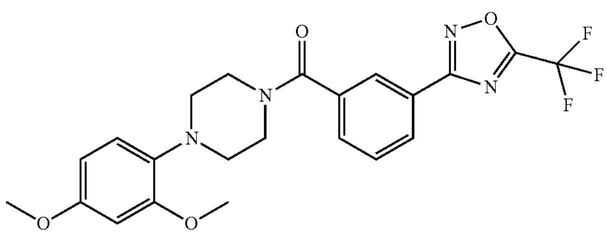 [SMILES: COc1ccc(N2CCN(C(=O)c3cccc(-c4noc(C(F)(F)F)n4)c3)CC2)c(OC)c1] | (4-(2,4-dimethoxyphenyl)piperazin-1-yl)(3-(5-(trifluoromethyl)-1,2,4-oxadiazol-3-yl)phenyl)methanone |
| 10 | 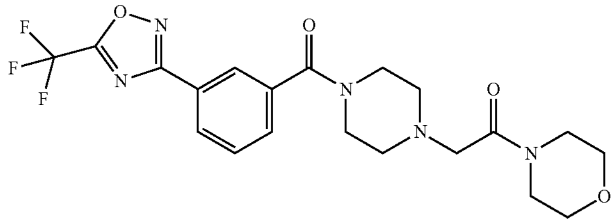 [SMILES: O=C(CN1CCN(C(=O)c2cccc(-c3noc(C(F)(F)F)n3)c2)CC1)N1CCOCC1] | 1-morpholino-2-(4-(3-(5-(trifluoromethyl)-1,2,4-oxadiazol-3-yl)benzoyl)piperazin-1-yl)ethanone |
| 11 | 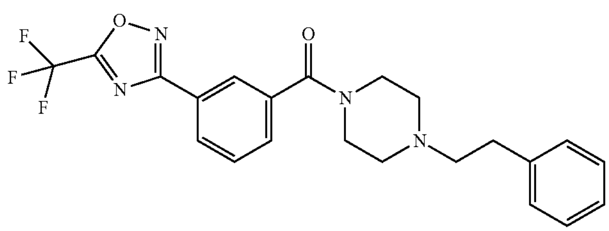 [SMILES: O=C(c1cccc(-c2noc(C(F)(F)F)n2)c1)N1CCN(CCc2ccccc2)CC1] | (4-phenethylpiperazin-1-yl)(3-(5-(trifluoromethyl)-1,2,4-oxadiazol-3-yl)phenyl)methanone |
| 12 | 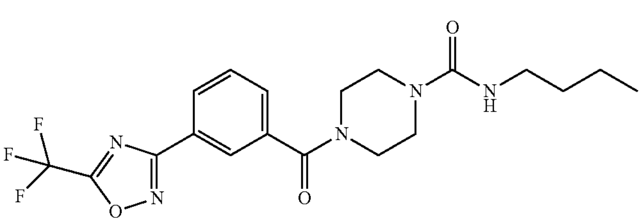 [SMILES: CCCCNC(=O)N1CCN(C(=O)c2cccc(-c3noc(C(F)(F)F)n3)c2)CC1] | N-butyl-4-(3-(5-(trifluoromethyl)-1,2,4-oxadiazol-3-yl)benzoyl)piperazine-1-carboxamide |

-continued

| Example No. | Compound Structure | Compound Name |
|---|---|---|
| 13 | 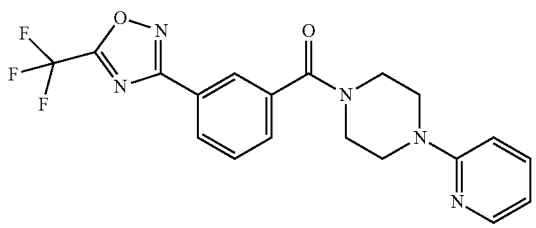 [SMILES: O=C(c1cccc(-c2noc(C(F)(F)F)n2)c1)N1CCN(c2ccccn2)CC1] | (4-(pyridin-2-yl)piperazin-1-yl)(3-(5-(trifluoromethyl)-1,2,4-oxadiazol-3-yl)phenyl)methanone |
| 14 | 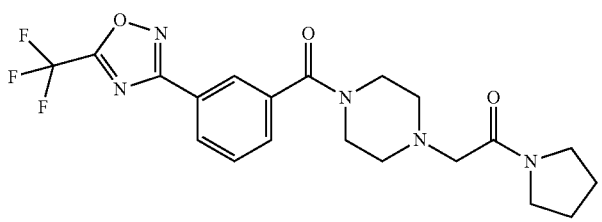 [SMILES: O=C(CN1CCN(C(=O)c2cccc(-c3noc(C(F)(F)F)n3)c2)CC1)N1CCCC1] | 1-(pyrrolidin-1-yl)-2-(4-(3-(5-(trifluoromethyl)-1,2,4-oxadiazol-3-yl)benzoyl)piperazin-1-yl)ethanone |
| 15 | 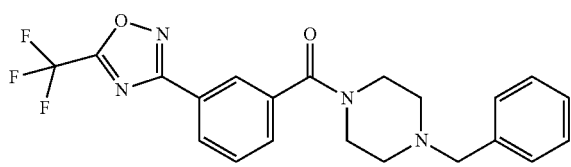 [SMILES: O=C(c1cccc(-c2noc(C(F)(F)F)n2)c1)N1CCN(Cc2ccccc2)CC1] | (4-benzylpiperazin-1-yl)(3-(5-(trifluoromethyl)-1,2,4-oxadiazol-3-yl)phenyl)methanone |
| 16 | 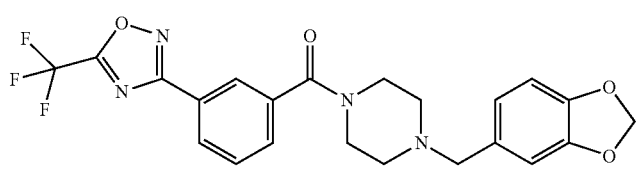 [SMILES: O=C(c1cccc(-c2noc(C(F)(F)F)n2)c1)N1CCN(Cc2ccc3c(c2)OCO3)CC1] | (4-(benzo[d][1,3]dioxol-5-ylmethyl)piperazin-1-yl)(3-(5-(trifluoromethyl)-1,2,4-oxadiazol-3-yl)phenyl)methanone |
| 17 | 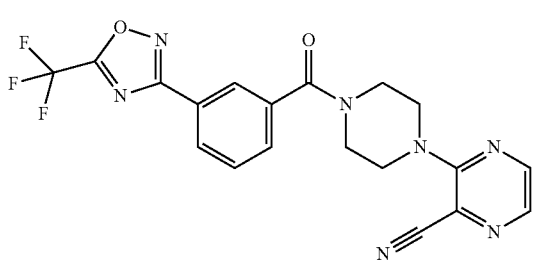 [SMILES: N#Cc1nccnc1N1CCN(C(=O)c2cccc(-c3noc(C(F)(F)F)n3)c2)CC1] | 3-(4-(3-(5-(trifluoromethyl)-1,2,4-oxadiazol-3-yl)benzoyl)piperazin-1-yl)pyrazine-2-carbonitrile |
| 18 | 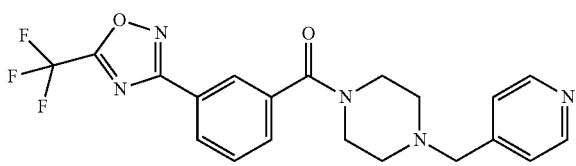 [SMILES: O=C(c1cccc(-c2noc(C(F)(F)F)n2)c1)N1CCN(Cc2ccncc2)CC1] | (4-(pyridin-4-ylmethyl)piperazin-1-yl)(3-(5-(trifluoromethyl)-1,2,4-oxadiazol-3-yl)phenyl)methanone |
| 19 | 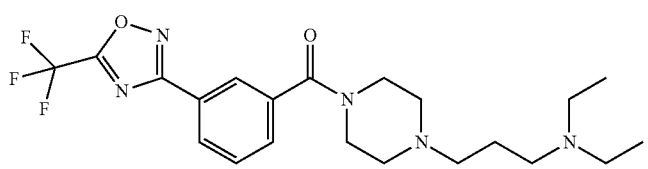 [SMILES: CCN(CC)CCCN1CCN(C(=O)c2cccc(-c3noc(C(F)(F)F)n3)c2)CC1] | (4-(3-(diethylamino)propyl)piperazin-1-yl)(3-(5-(trifluoromethyl)-1,2,4-oxadiazol-3-yl)phenyl)methanone |

-continued

| Example No. | Compound Structure | Compound Name |
|---|---|---|
| 20 | 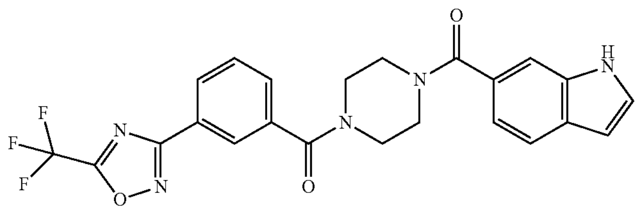 [SMILES: O=C(c1cccc(-c2noc(C(F)(F)F)n2)c1)N1CCN(C(=O)c2ccc3cc[nH]c3c2)CC1] | (4-(1H-indole-6-carbonyl)piperazin-1-yl)(3-(5-(trifluoromethyl)-1,2,4-oxadiazol-3-yl)phenyl)methanone |
| 21 | 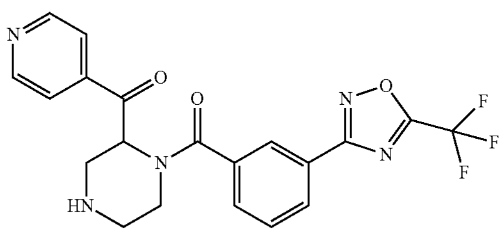 [SMILES: O=C(c1ccncc1)C1CNCCN1C(=O)c1cccc(-c2noc(C(F)(F)F)n2)c1] | (4-picolinoylpiperazin-1-yl)(3-(5-(trifluoromethyl)-1,2,4-oxadiazol-3-yl)phenyl)methanone |
| 22 | 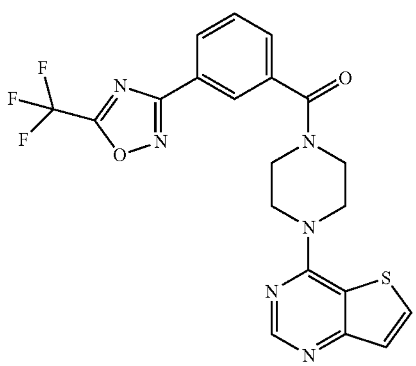 [SMILES: O=C(c1cccc(-c2noc(C(F)(F)F)n2)c1)N1CCN(c2ncnc3ccsc23)CC1] | (4-(thieno[3,2-d]pyrimidin-4-yl)piperazin-1-yl)(3-(5-(trifluoromethyl)-1,2,4-oxadiazol-3-yl)phenyl)methanone |
| 23 | 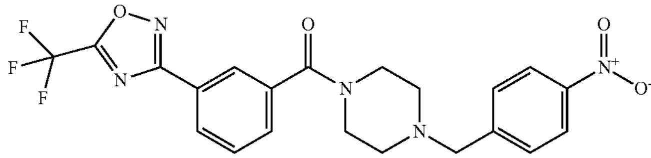 [SMILES: O=C(c1cccc(-c2noc(C(F)(F)F)n2)c1)N1CCN(Cc2ccc([N+](=O)[O-])cc2)CC1] | (4-(4-nitrobenzyl)piperazin-1-yl)(3-(5-(trifluoromethyl)-1,2,4-oxadiazol-3-yl)phenyl)methanone |
| 24 | 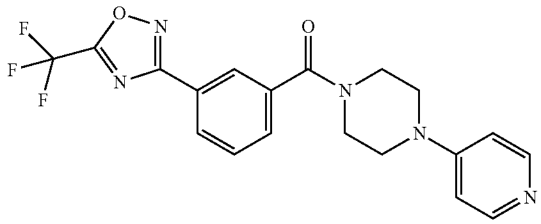 [SMILES: O=C(c1cccc(-c2noc(C(F)(F)F)n2)c1)N1CCN(c2ccncc2)CC1] | (4-(pyridin-4-yl)piperazin-1-yl)(3-(5-(trifluoromethyl)-1,2,4-oxadiazol-3-yl)phenyl)methanone |
| 25 | 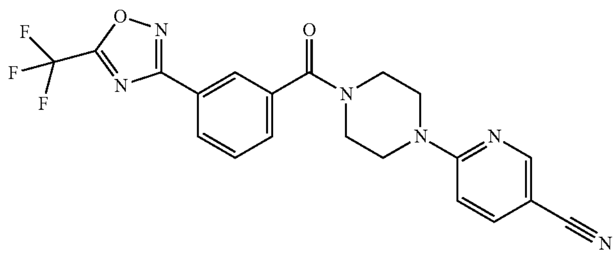 [SMILES: N#Cc1ccc(N2CCN(C(=O)c3cccc(-c4noc(C(F)(F)F)n4)c3)CC2)nc1] | 6-(4-(3-(5-(trifluoromethyl)-1,2,4-oxadiazol-3-yl)benzoyl)piperazin-1-yl)nicotinonitrile |

| Example No. | Compound Structure | Compound Name |
|---|---|---|
| 26 | 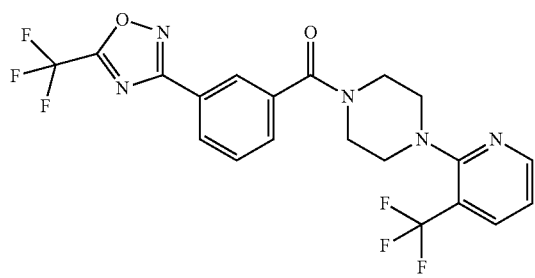 [SMILES: O=C(c1cccc(-c2noc(C(F)(F)F)n2)c1)N1CCN(c2ncccc2C(F)(F)F)CC1] | (3-(5-(trifluoromethyl)-1,2,4-oxadiazol-3-yl)phenyl)(4-(3-(trifluoromethyl)pyridin-2-yl)piperazin-1-yl)methanone |
| 27 | 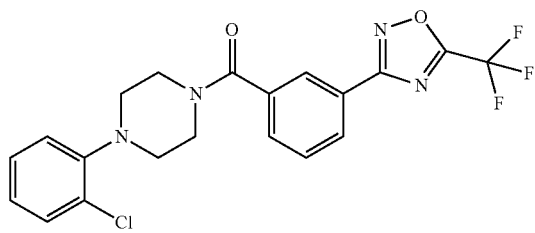 [SMILES: O=C(c1cccc(-c2noc(C(F)(F)F)n2)c1)N1CCN(c2ccccc2Cl)CC1] | (4-(2-chlorophenyl)piperazin-1-yl)(3-(5-(trifluoromethyl)-1,2,4-oxadiazol-3-yl)phenyl)methanone |
| 28 | 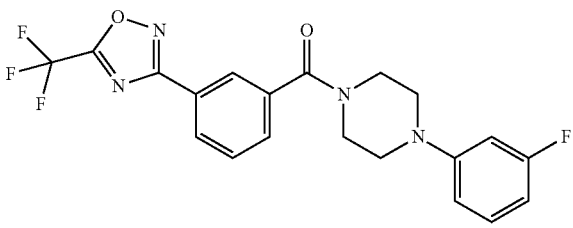 [SMILES: O=C(c1cccc(-c2noc(C(F)(F)F)n2)c1)N1CCN(c2cccc(F)c2)CC1] | (4-(3-fluorophenyl)piperazin-1-yl)(3-(5-(trifluoromethyl)-1,2,4-oxadiazol-3-yl)phenyl)methanone |
| 29 | 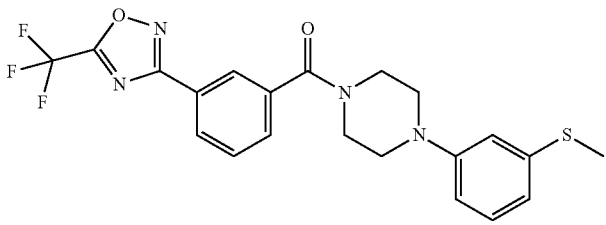 [SMILES: CSc1cccc(N2CCN(C(=O)c3cccc(-c4noc(C(F)(F)F)n4)c3)CC2)c1] | (4-(3-(methylthio)phenyl)piperazin-1-yl)(3-(5-(trifluoromethyl)-1,2,4-oxadiazol-3-yl)phenyl)methanone |
| 30 | 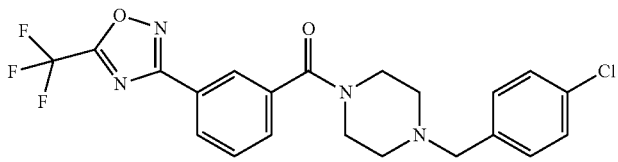 [SMILES: O=C(c1cccc(-c2noc(C(F)(F)F)n2)c1)N1CCN(Cc2ccc(Cl)cc2)CC1] | (4-(4-chlorobenzyl)piperazin-1-yl)(3-(5-(trifluoromethyl)-1,2,4-oxadiazol-3-yl)phenyl)methanone |

| Example No. | Compound Structure | Compound Name |
|---|---|---|
| 31 | 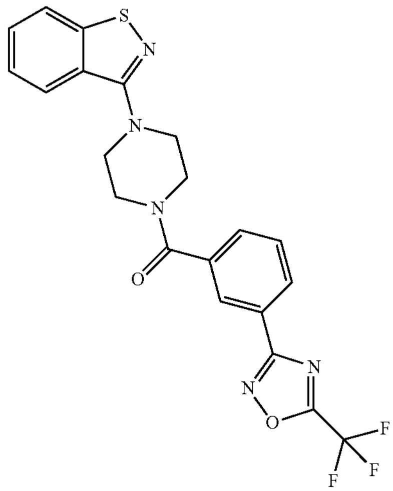 [SMILES: O=C(c1cccc(-c2noc(C(F)(F)F)n2)c1)N1CCN(c2nsc3ccccc23)CC1] | (4-(benzo[d]isothiazol-3-yl)piperazin-1-yl)(3-(5-(trifluoromethyl)-1,2,4-oxadiazol-3-yl)phenyl)methanone |
| 32 | 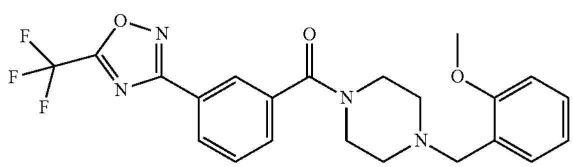 [SMILES: COc1ccccc1CN1CCN(C(=O)c2cccc(-c3noc(C(F)(F)F)n3)c2)CC1] | (4-(2-methoxybenzyl)piperazin-1-yl)(3-(5-(trifluoromethyl)-1,2,4-oxadiazol-3-yl)phenyl)methanone |
| 33 | 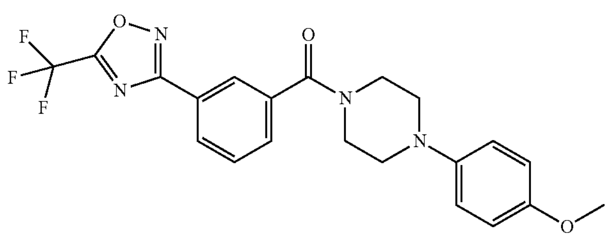 [SMILES: COc1ccc(N2CCN(C(=O)c3cccc(-c4noc(C(F)(F)F)n4)c3)CC2)cc1] | (4-(4-methoxyphenyl)piperazin-1-yl)(3-(5-(trifluoromethyl)-1,2,4-oxadiazol-3-yl)phenyl)methanone |
| 34 | 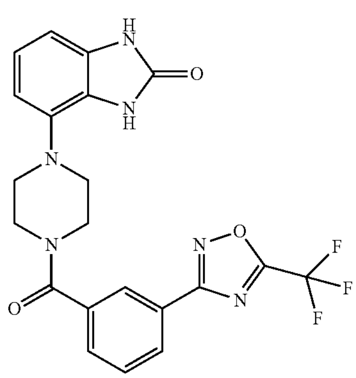 [SMILES: O=C(c1cccc(-c2noc(C(F)(F)F)n2)c1)N1CCN(c2cccc3[nH]c(=O)[nH]c23)CC1] | 4-(4-(3-(5-(trifluoromethyl)-1,2,4-oxadiazol-3-yl)benzoyl)piperazin-1-yl)-1H-benzo[d]imidazol-2(3H)-one |
| 35 | 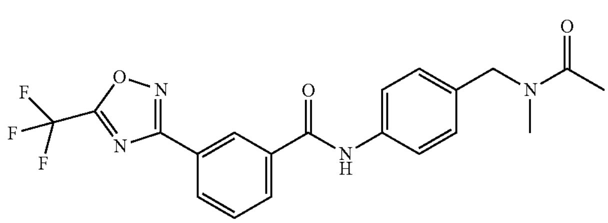 [SMILES: CC(=O)N(C)Cc1ccc(NC(=O)c2cccc(-c3noc(C(F)(F)F)n3)c2)cc1] | N-(4-((N-Methylacetamido)methyl)phenyl)-3-(5-(trifluoromethyl)-1,2,4-oxadiazol-3-yl)benzamide |

| Example No. | Compound Structure | Compound Name |
|---|---|---|
| 36 | 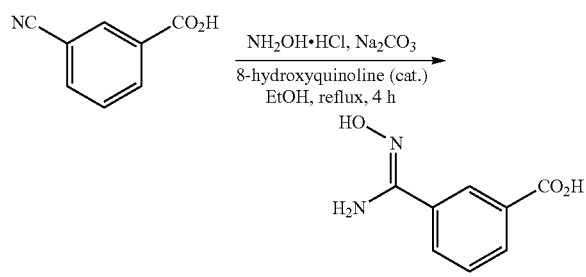 | N-(4-((1H-1,2,4-Triazol-1-yl)methyl)phenyl)-3-(5-(trifluoromethyl)-1,2,4-oxadiazol-3-yl)benzarnide |

Example 37

Step 1: 3-(N'-Hydroxycarbamimidoyl)benzoic acid

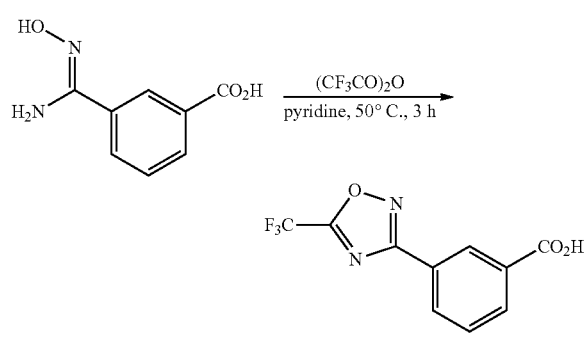

8-Hydroxyquinoline (5 mg, 0.03 mmol) was added to a solution of 3-cyanobenzoic acid (1 g, 6.8 mmol) in 50 mL ethanol. To this reaction mixture were added first hydroxylamine hydrochloric acid (950 mg, 13.6 mmol) in water (8 mL) followed by sodium carbonate (1.2 g, 10.9 mmol) in water (12 mL). The mixture was heated to reflux for 4 h. After removal of ethanol under reduced pressure, the residue was diluted with water, and the aqueous solution was acidified with 10% HCl to pH~3. The white precipitate was filtrated, washed with water and acetone and then dried under reduced pressure to afford compound 3-(N'-hydroxycarbamimidoyl)benzoic acid (1 g, yield 82%): $^1$H NMR (400 MHz, CDCl$_3$) δ 13.03 (br s, 1H), 9.76 (s, 1H), 8.27-8.26 (m, 1H), 7.95-7.89 (m, 2H), 7.53 (t, J=7.8 Hz, 1H), 5.94 (br s, 2H). MS (ESI) m/z: Calculated for C$_8$H$_8$N$_2$O$_3$: 180.05. found: 180.9 (M+H)$^+$.

Step 2: 3-(5-(Trifluoromethyl)-1,2,4-oxadiazol-3-yl)benzoic acid

A solution of 3-(N'-hydroxycarbamimidoyl)benzoic acid (1 g, 5.6 mmol) in anhydrous pyridine (15 mL) was cooled to 0° C. and trifluoroacetic anhydride (2.3 mL, 16.7 mmol) was added dropwise. The reaction mixture was slowly warmed to room temperature and further heated to 50° C. for 3 h. The reaction mixture was poured into ice-water and adjusted to pH~4 by addition of 1.5N HCl. The product was extracted with EtOAc and the solvent removed under reduced pressure. The crude product was purified by column chromatography [silica gel 60-120 mesh, eluent: 10% EtOAc in petroleum ether] to afford 3-(5-(trifluoromethyl)-1,2,4-oxadiazol-3-yl) benzoic acid (400 mg, yield 28%): $^1$H NMR (400 MHz, CDCl$_3$) δ 13.44 (br s, 1H), 8.56 (s, 1H), 8.30 (d, J=7.9 Hz, 1H), 8.21 (d, J=7.9 Hz, 1H), 7.78 (t, J=7.8 Hz, 1H). MS (ESI) m/z: Calculated for C$_{10}$H$_5$F$_3$N$_2$O$_3$: 258.03. found: 257 (M−H)$^-$.

Step 3: (3-Benzylpiperidin-1-yl)(3-(5-(trifluoromethyl)-1,2,4-oxadiazol-3-yl)phenyl)methanone

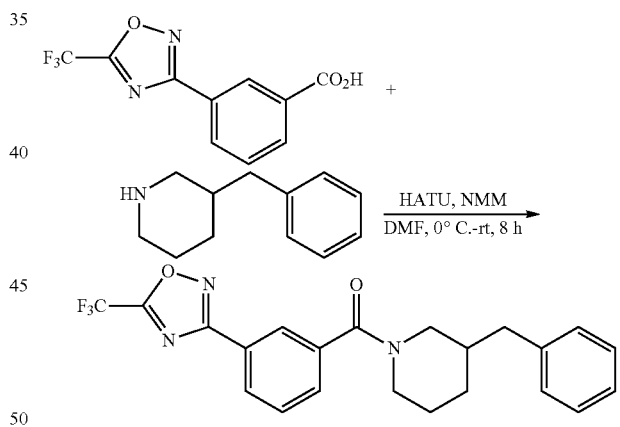

3-(5-(Trifluoromethyl)-1,2,4-oxadiazol-3-yl)benzoic acid (100 mg, 0.4 mmol) was dissolved in dry DMF (3 mL) and HATU (183 mg, 0.48 mmol) was added followed by 3-benzylpiperidine (75 mg, 0.42 mmol) and NMM (0.13 mL, 1.2 mmol) at 0° C. The reaction mixture was slowly warmed to room temperature and stirred for 8 h. The reaction mixture was then diluted with EtOAc and the organic layer was washed with water, 1.5N HCl solution and brine. The organic layer was dried over anhydrous sodium sulfate and concentrated under reduced pressure. The crude product was purified by column chromatography (silica 60-120 mesh, eluant 10% EtOAc in petroleum ether) to get (3-benzylpiperidin-1-yl)(3-(5-(trifluoromethyl)-1,2,4-oxadiazol-3-yl)phenyl)methanone (70 mg, yield 44%): $^1$H NMR (400 MHz, CDCl$_3$) δ 8.15-8.01 (m, 2H), 7.59-7.47 (m, 2H), 7.32-7.21 (m, 2H), 7.06-6.97 (m, 3H), 4.63 (m, 1H), 3.59-3.56 (m, 1H), 2.83-

2.51 (m, 4H), 1.93-1.84 (m, 3H), 1.26-1.22 (m, 2H). MS (ESI) m/z: Calculated for $C_{22}H_{20}F_3N_3O_2$: 415.41. found: 416.2 (M+H)$^+$.

Example 38

4-(4-(3-(5-(Trifluoromethyl)-1,2,4-oxadiazol-3-yl)benzoyl)piperazin-1-yl)benzonitrile

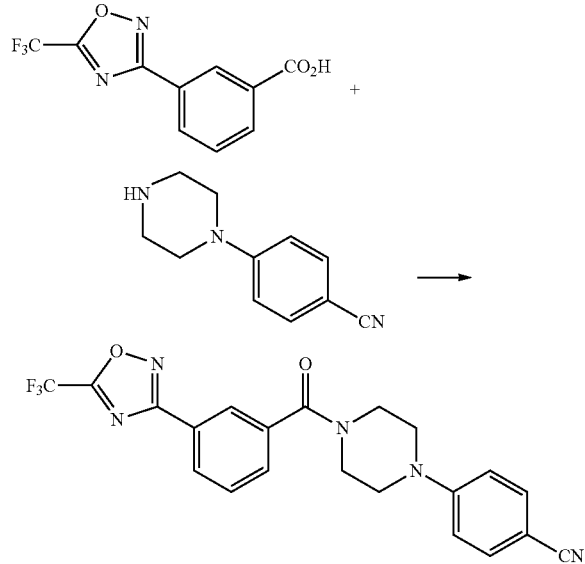

This compound was synthesized from 4-(piperazin-1-yl)benzonitrile and 3-(5-(trifluoromethyl)-1,2,4-oxadiazol-3-yl)benzoic acid as described in example 1 (13 mg, yield 19%): $^1$H NMR (400 MHz, CDCl$_3$) δ 8.23-8.18 (m, 2H), 7.67-7.60 (m, 2H), 7.53 (d, J=9 Hz, 2H), 6.87 (d, J=9 Hz, 2H), 4.05-3.85 (br s, 2H), 3.72-3.58 (br s, 2H), 3.48-3.28 (m, 4H). MS (ESI) m/z: Calculated for $C_{21}H_{16}F_3N_5O_2$: 427.13. found: 428.2 (M+H)$^+$.

Example 39

Step 1: tert-Butyl 4-(5-cyanopyridin-2-yl)-3-methylpiperazine-1-carboxylate

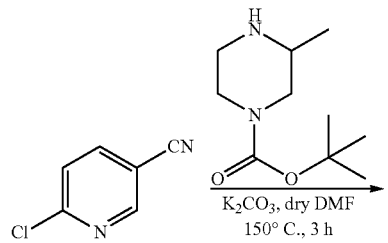

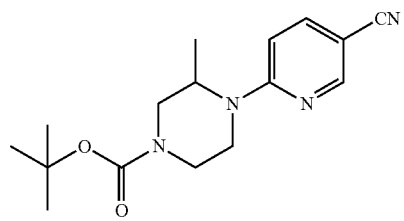

-continued

3-Methyl-piperazine-1-carboxylic acid tert-butyl ester (200 mg, 1.0 mmol) was dissolved in dry DMF (10 mL) taken in a shield tube. To the reaction mixture was added 6-chloronicotinonitrile (70 mg, 1.0 mmol) followed by potassium carbonate (140 mg, 1.0 mmol) and the mixture was heated to 150° C. for 3 h. The reaction mixture was cooled to room temperature and the solvent was evaporated under reduced pressure. The product was extracted with EtOAc and the organic layer was washed with H$_2$O and brine and dried over anhydrous sodium sulfate. Solvent was removed under reduced pressure and the crude product was purified by column chromatography (silica gel 60-120 mesh, eluent 30% EtOAc in petroleum ether) to afford compound tert-butyl 4-(5-cyanopyridin-2-yl)-3-methylpiperazine-1-carboxylate (120 mg, yield 40%) as yellow solid. $^1$H NMR (300 MHz, CDCl$_3$) δ 8.42 (d, J=2.2 Hz, 1H), 7.63 (dd, J=9.0 Hz, J=2.4 Hz, 1H), 6.56 (d, J=9.0 Hz, 1H), 4.53 (m, 1H), 4.13-3.91 (m, 3H), 3.29-3.16 (m, 2H), 3.02 (m, 1H), 1.49 (s, 9H), 1.20 (d, J=6.6 Hz, 3H).

6-(2-Methylpiperazin-1-yl)nicotinonitrile hydrochloride

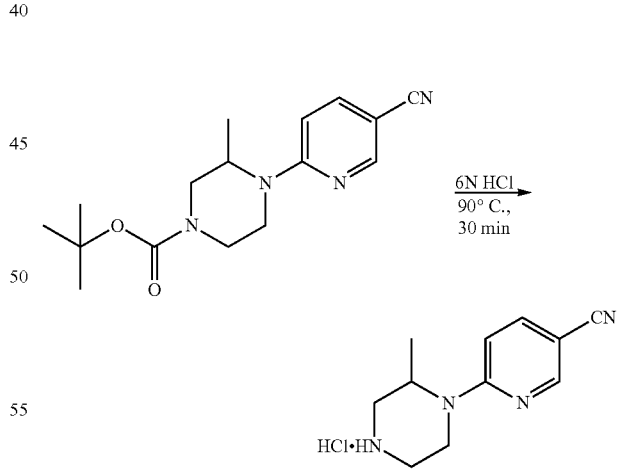

6N HCl (1 mL) was added to the compound tert-butyl 4-(5-cyanopyridin-2-yl)-3-methylpiperazine-1-carboxylate (120 mg, 0.39 mmol) and the reaction mixture was stirred at 90° C. for 30 min. The reaction mixture was cooled to room temperature, concentrated under reduced pressure and triturated with ether to afford 6-(2-methylpiperazin-1-yl)nicotinonitrile hydrochloride (90 mg, crude). $^1$H NMR (400 MHz, D$_2$O) δ 8.39 (d, J=2.0 Hz, 1H), 7.85 (dd, J=9.3 Hz, J=2.3 Hz, 1H), 6.95 (d, J=9.5 Hz, 1H), 4.74 (m, 2H), 4.32-4.27 (m, 1H), 3.48-3.41 (m, 1H), 3.35-3.28 (m, 2H), 3.17-3.10 (m, 1H), 1.27 (d, J=7.0 Hz, 3H)

6-(2-Methyl-4-(3-(5-(trifluoromethyl)-1,2,4-oxadiazol-3-yl)benzoyl)piperazin-1-yl)nicotinonitrile 6-(3-Methyl-4-(3-(5-(trifluoromethyl)-1,2,4-oxadiazol-3-yl)benzoyl)piperazin-1-yl)nicotinonitrile

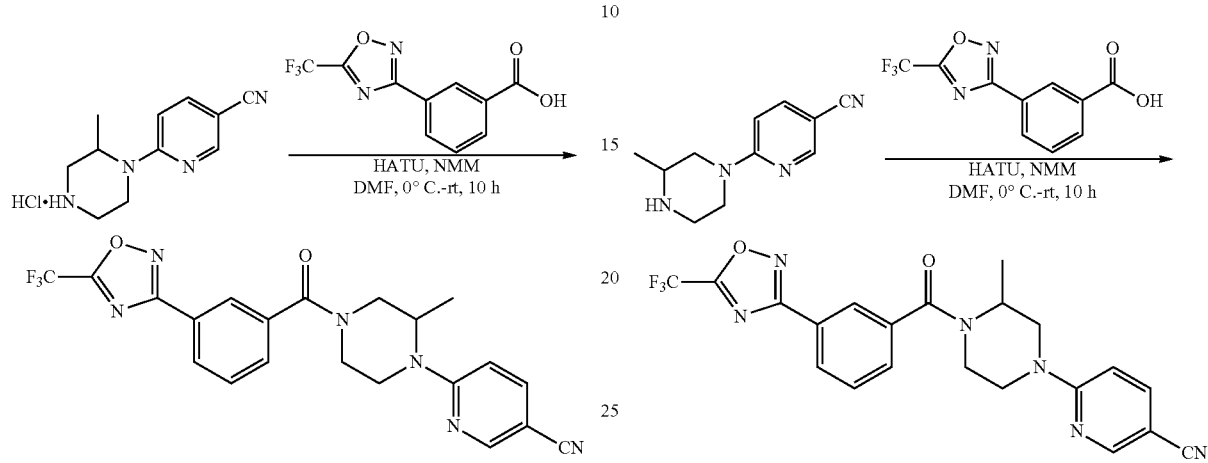

This compound was synthesized from 3-(5-(trifluoromethyl)-1,2,4-oxadiazol-3-yl)benzoic acid and 6-(2-methylpiperazin-1-yl)nicotinonitrile hydrochloride as described for example 37 step 3 (70 mg, yield 43%). ¹H NMR (400 MHz, MeOD) δ 8.43 (d, J=2.0 Hz, 1H), 8.27 (m, 1H), 8.22 (s, 1H), 7.78-7.73 (m, 3H), 6.86 (d, J=9.0 Hz, 1H), 4.66-4.56 (m, 2H), 4.34-4.29 (m, 1H), 3.85-3.83 (m, 1H), 3.65 (m, 1H), 3.49-3.40 (m, 1H), 3.26 (m, 1H), 1.29 (m, 3H). MS (ESI) m/z: Calculated for $C_{21}H_{17}F_3N_6O_2$: 442.14. found: 443.2 (M+H)⁺.

6.89 (d, J=9.2 Hz, 1H), 4.24 (t, J=10.2 Hz, 2H), 2.94-2.87 (m, 1H), 2.86-2.77 (m, 1H), 2.63-2.55 (m, 2H), 2.45-2.41 (m, 1H), 0.99 (d, J=6.1 Hz, 3H)

This compound was synthesized from 6-(3-methylpiperazin-1-yl)nicotinonitrile and 3-(5-(trifluoromethyl)-1,2,4-oxadiazol-3-yl)benzoic acid as described for example 37 step 3 (75 mg, yield 39%). ¹H NMR (400 MHz, MeOD) δ 8.41 (d, J=2.0 Hz, 1H), 8.27-8.25 (m, 1H), 8.18 (s, 1H), 7.77-7.72 (m, 3H), 6.89 (d, J=9.0 Hz, 1H), 4.39 (m, 3H), 3.48 (m, 2H), 3.22-3.15 (m, 1H), 1.29 (m, 3H). MS (ESI) m/z: Calculated for $C_{21}H_{17}F_3N_6O_2$: 442.14. found: 443.2 (M+H)⁺.

Example 40

6-(3-Methylpiperazin-1-yl)nicotinonitrile

Example 41

6-(3,5-Dimethylpiperazin-1-yl)nicotinonitrile

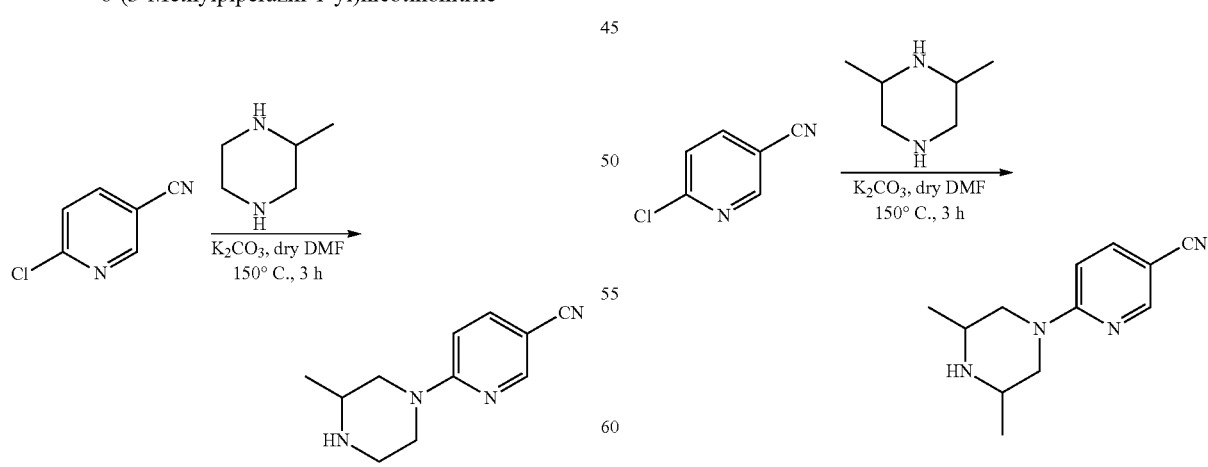

This compound was synthesized from 2-methyl-piperazine and 6-chloronicotinonitrile as described for example 39 step 1 (90 mg, yield 45%). ¹H NMR (400 MHz, CDCl₃) δ 8.44 (d, J=2.0 Hz, 1H), 7.79 (dd, J=9.2 Hz, J=2.4 Hz, 1H), This compound was synthesized from 2,6-dimethyl-piperazine and 6-chloronicotinonitrile as described for example 39 step 1 (90 mg, crude) and it was carried through without further purification. ¹H NMR (400 MHz, CDCl₃) δ 8.40 (d, J=2.0 Hz, 1H), 7.60 (dd, J=9.0 Hz, J=2.3 Hz, 1H), 6.60 (d, J=9.3 Hz, 1H), 4.27 (d, J=12.8 Hz, 2H), 2.96-2.88 (m, 2H), 2.52 (dd, J=12.4 Hz, J=10.9 Hz, 2H), 1.16 (d, J=6.3 Hz, 6H)

6-(3,5-Dimethyl-4-(3-(5-(trifluoromethyl)-1,2,4-oxadiazol-3-yl)benzoyl)piperazin-1-yl)nicotinonitrile

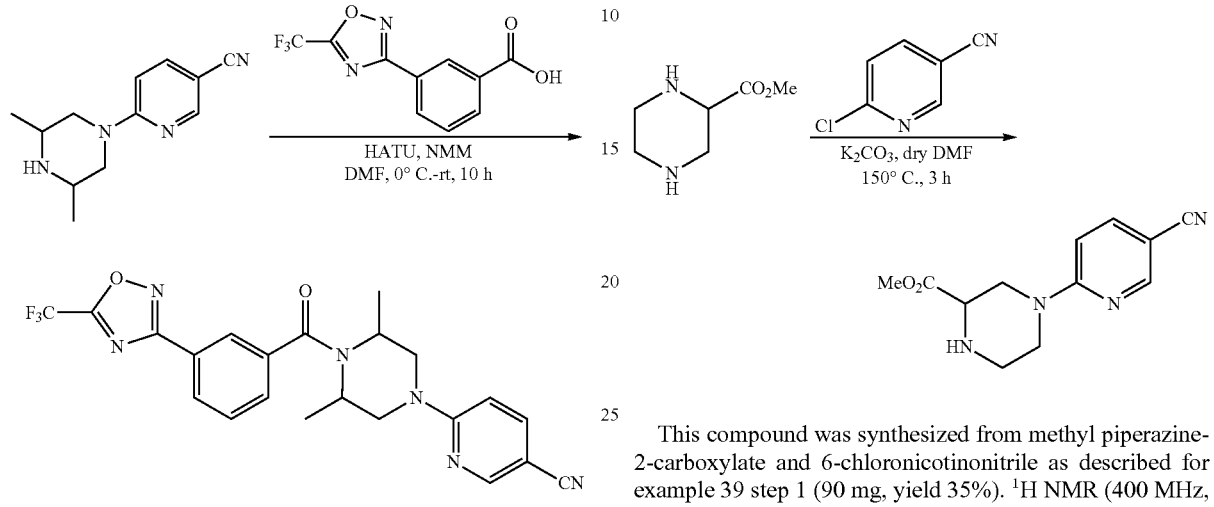

This compound was synthesized from 6-(3,5-dimethylpiperazin-1-yl)nicotinonitrile and 3-(5-(trifluoromethyl)-1,2,4-oxadiazol-3-yl)benzoic acid as described for example 37 step 3 (35 mg, yield 18%). $^1$H NMR (400 MHz, CDCl$_3$) δ 8.42 (d, J=1.8 Hz, 1H), 8.22 (dt, J=7.2 Hz, J=1.7 Hz, 1H), 8.16 (s, 1H), 7.68-7.62 (m, 3H), 6.66 (d, J=9.0 Hz, 1H), 4.46 (m, 2H), 4.29 (d, J=13.8 Hz, 1H), 3.36 (m, 2H), 1.16 (d, J=6.3 Hz, 6H). MS (ESI) m/z: Calculated for $C_{22}H_{19}F_3N_6O_2$: 456.15. found: 457.2 (M+H)$^+$.

Example 42

Methyl piperazine-2-carboxylate

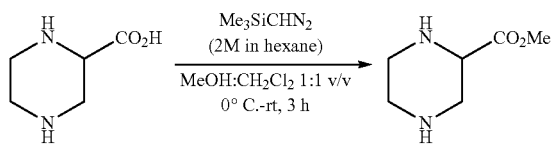 [SMILES: O=C(O)C1CNCCN1 ; COC(=O)C1CNCCN1]

piperazine-2-carboxylic acid dihydrochloride (750 mg, 3.7 mmol) was suspended in MeOH (15 mL) and sodium bicarbonate (620 mg, 7.4 mmol) was added and stirred for 4 h. The reaction mixture was diluted with CH$_2$Cl$_2$ (15 mL) and cooled to 0° C. (Trimethylsilyl)diazomethane (15 mL, 2M in hexane) was added dropwise until the yellow color persisted. The solution was stirred at room temperature for 3 h and concentrated under reduced pressure. The crude product was purified by column chromatography (neutral alumina, eluent 5-6% MeOH in CHCl$_3$) to get methyl piperazine-2-carboxylate (150 g, yield 28%). $^1$H NMR (300 MHz, CDCl$_3$) δ 3.74 (s, 3H), 3.51-3.47 (dd, J=8.0 Hz, 3.4 Hz, 1H), 3.24-3.19 (dd, J=12.1 Hz, 3.3 Hz, 1H), 3.04-2.99 (m, 1H), 2.96-2.86 (m, 3H), 2.83-2.77 (m, 1H)

Methyl 4-(5-cyanopyridin-2-yl)piperazine-2-carboxylate

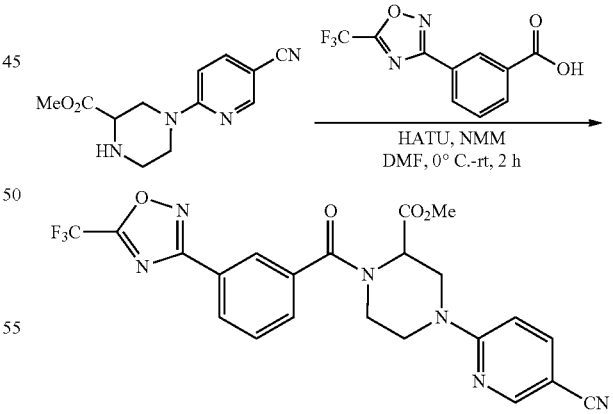

This compound was synthesized from methyl piperazine-2-carboxylate and 6-chloronicotinonitrile as described for example 39 step 1 (90 mg, yield 35%). $^1$H NMR (400 MHz, MeOD) δ 8.42 (dd, J=2.4 Hz, 0.6 Hz, 1H), 7.76 (dd, J=9.0 Hz, 2.3 Hz, 1H), 6.90 (m, 1H), 4.39-4.35 (dd, J=13.2 Hz, 2.6 Hz, 1H), 3.95-3.90 (m, 1H), 3.76 (s, 3H), 3.63-3.60 (dd, J=8.4 Hz, 3.4 Hz, 1H), 3.52-3.47 (dd, J=13.1 Hz, 8.4 Hz, 1H), 3.45-3.39 (ddd, J=13.1 Hz, 9.3 Hz, 3.4 Hz, 1H), 3.13-3.08 (m, 1H), 2.86-2.79 (ddd, J=12.5 Hz, 9.1 Hz, 3.5 Hz, 1H).

Methyl 4-(5-cyanopyridin-2-yl)-1-(3-(5-(trifluoromethyl)-1,2,4-oxadiazol-3-yl)benzoyl)piperazine-2-carboxylate This compound was synthesized from methyl 4-(5-cyanopyridin-2-yl)piperazine-2-carboxylate and 3-(5-(trifluoromethyl)-1,2,4-oxadiazol-3-yl)benzoic acid as described for example 37 step 3 (130 mg, yield 73%). $^1$H NMR (400 MHz, CDCl$_3$) δ 8.55-8.50 (m, 1H), 8.42 (br s, 1H), 8.24 (m, 1H), 7.73-7.64 (m, 3H), 6.71 (d, J=9.0 Hz, 1H), 4.94 (m, 1H), 4.52-4.41 (m, 1H), 3.78 (s, 3H), 3.75 (m, 2H), 3.69-3.59 (m, 1H), 3.51-3.48 (m, 1H), 3.11-3.04 (m, 1H). MS (ESI) m/z: Calculated for $C_{22}H_{17}F_3N_6O_4$: 486.13. found: 487.2 (M+H)$^+$.

4-(5-Cyanopyridin-2-yl)-1-(3-(5-(trifluoromethyl)-1,2,4-oxadiazol-3-yl)benzoyl)piperazine-2-carboxylic acid

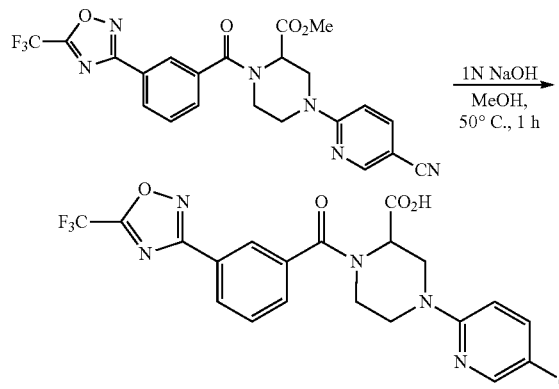

Methyl 4-(5-cyanopyridin-2-yl)-1-(3-(5-(trifluoromethyl)-1,2,4-oxadiazol-3-yl)benzoyl)piperazine-2-carboxylate (130 mg, 0.3 mmol) was dissolved in MeOH (4 mL) and cooled to 0° C. 1N NaOH solution (0.3 mL) was added and the reaction mixture was slowly warmed to room temperature and stirred at 50° C. for 1 h. The MeOH was removed under reduced pressure and the aqueous layer was washed with EtOAc. The aqueous layer was acidified to pH 2-3 using 1.5N HCl, extracted with EtOAc, dried over anhydrous sodium sulfate and concentrated over reduced pressure. The crude product was purified by preparative TLC (eluent petroleum ether/EtOAc/AcOH 4:6:0.1 v/v) to get 4-(5-cyanopyridin-2-yl)-1-(3-(5-(trifluoromethyl)-1,2,4-oxadiazol-3-yl)benzoyl) piperazine-2-carboxylic acid (30 mg, yield 24%). $^1$H NMR (400 MHz, DMSO-d$_6$) δ 8.49-8.47 (m, 1H), 8.20-8.12 (m, 1H), 8.07 (br s, 1H), 7.89-7.83 (m, 1H), 7.75-7.71 (m, 2H), 6.91 (d, J=7.6 Hz, 1H), 5.00-4.89 (m, 1H), 4.72-4.54 (m, 1H), 4.33-4.23 (m, 1H), 3.62-3.47 (m, 2H), 3.17-3.12 (m, 2H). MS (ESI) m/z: Calculated for $C_{21}H_{15}F_3N_6O_4$: 472.11. found: 473.2 (M+H)$^+$.

Example 43 tert-Butyl 4-(5-cyanopyridin-2-yl)-3,5-dimethylpiperazine-1-carboxylate

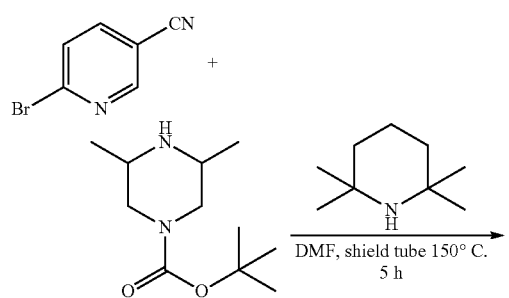

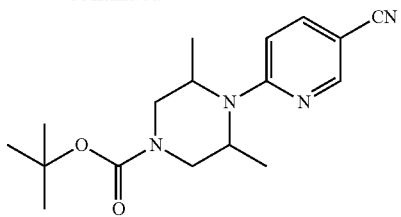

The compound 3,5-dimethyl-piperazine-1-carboxylic acid tert-butyl ester (250 mg, 1.1 mmol) was dissolved in dry DMF (1 mL) taken in a shield tube. To the reaction mixture was added 6-bromonicotinonitrile (210 mg, 1.1 mmol) followed by 2,2,6,6-tetramethyl piperidine (0.16 g, 1.1 mmol) and the mixture was heated to 150° C. for 5 h. Reaction mixture was cooled to room temperature. The product was extracted with EtOAc and the organic layer was washed with H$_2$O and brine. Solvent was removed under reduced pressure and the crude product was purified by column chromatography (silica gel 60-120 mesh, eluent 20-25% EtOAc in petroleum ether) to afford tert-butyl 4-(5-cyanopyridin-2-yl)-3,5-dimethylpiperazine-1-carboxylate (0.12 g, yield 33%). $^1$H NMR (400 MHz, CDCl$_3$) δ 8.45 (d, J=2.3 Hz, 1H), 7.64 (dd, J=9.0 Hz, J=2.3 Hz, 1H), 6.53 (d, J=9.0 Hz, 1H), 4.48 (m, 2H), 4.13-4.00 (m, 2H), 3.16-3.06 (m, 2H), 1.51 (s, 9H), 1.27 (s, 3H), 1.25 (s, 3H).

6-(2,6-Dimethylpiperazin-1-yl)nicotinonitrile

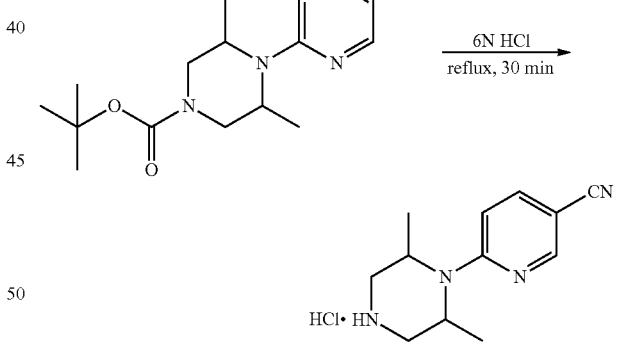

6N HCl (0.5 mL) was added to tert-butyl 4-(5-cyanopyridin-2-yl)-3,5-dimethylpiperazine-1-carboxylate (120 mg, 0.37 mmol) and the reaction mixture was stirred at 90° C. for 30 min. the reaction mixture was cooled to room temperature. The reaction mixture was concentrated under reduced pressure and triturated with ether to afford 6-(2,6-dimethylpiperazin-1-yl)nicotinonitrile (90 mg, crude), which was carried through without further purification. $^1$H NMR (300 MHz, D$_2$O) δ 8.51 (d, J=2.2 Hz, 1H), 7.93 (dd, J=9.1 Hz, J=2.3 Hz, 1H), 6.97 (d, J=9.2 Hz, 1H), 4.75 (m, 2H), 3.53-3.49 (m, 2H), 3.41-3.34 (m, 2H), 1.42 (s, 3H), 1.39 (s, 3H).

6-(2,6-Dimethyl-4-(3-(5-(trifluoromethyl)-1,2,4-oxadiazol-3-yl)benzoyl)piperazin-1-yl)nicotinonitrile

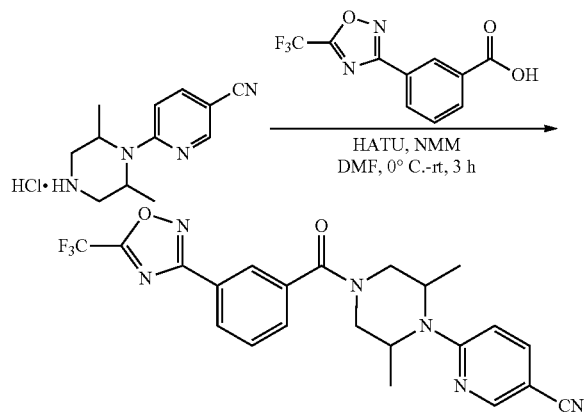

This compound was synthesized from 6-(2,6-dimethylpiperazin-1-yl)nicotinonitrile and 3-(5-(trifluoromethyl)-1,2,4-oxadiazol-3-yl)benzoic acid as described for example 37 step 3 (70 mg, yield 33%). $^1$H NMR (400 MHz, MeOD) δ 8.45 (d, J=2.0 Hz, 1H), 8.29-8.25 (m, 2H), 7.79-7.72 (m, 3H), 6.83 (d, J=9.0 Hz, 1H), 4.76-4.65 (m, 3H), 3.72-3.61 (m, 2H), 3.26 (m, 1H), 1.36 (m, 3H), 1.17 (m, 3H). MS (ESI) m/z: Calculated for $C_{22}H_{19}F_3N_6O_4$: 456.15. found: 457.2 (M+H)$^+$.

Examples 44-45 were synthesized from 3-(5-(trifluoromethyl)-1,2,4-oxadiazol-3-yl)benzoic acid and readily available amines in a similar manner as part of a screening collection and characterized by LCMS and $^1$H NMR.

| Example No. | Compound Structure | Compound Name |
| --- | --- | --- |
| 44 | 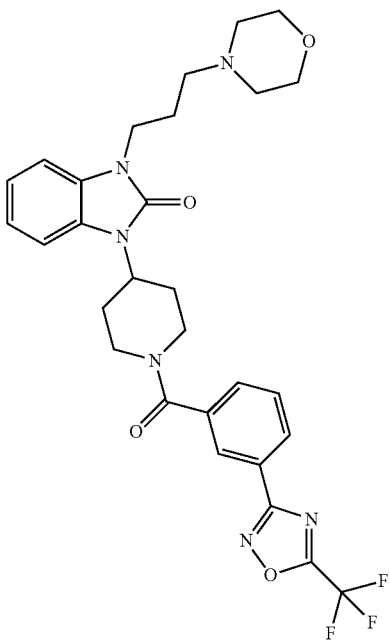 [SMILES: O=C(c1cccc(-c2noc(C(F)(F)F)n2)c1)N1CCC(n2c(=O)n(CCCN3CCOCC3)c3ccccc32)CC1] | 1-(3-morpholinopropyl)-3-(1-(3-(5-(trifluoromethyl)-1,2,4-oxadiazol-3-yl)benzoyl)piperidin-4-yl)-1H-benzo[d]imidazol-2(3H)-one |
| 45 | 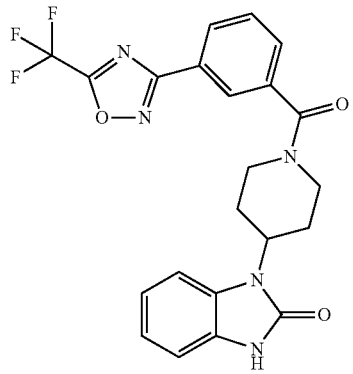 [SMILES: O=C(c1cccc(-c2noc(C(F)(F)F)n2)c1)N1CCC(n2c(=O)[nH]c3ccccc32)CC1] | 1-(1-(3-(5-(trifluoromethyl)-1,2,4-oxadiazol-3-yl)benzoyl)piperidin-4-yl)-1H-benzo[d]imidazol-2(3H)-one |

Example 46

4-Benzyl 1-tert-butyl 2-methylpiperazine-1,4-dicarboxylate

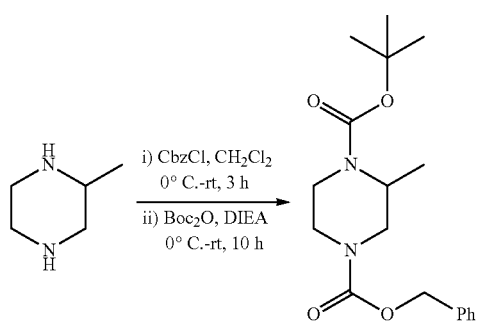

Benzylchloroformate (6 mL, 18 mmol, 50% in toluene) was added to a solution of 2-methylpiperazine (2.0 g, 20.0 mmol) in CH$_2$Cl$_2$ (20 mL) at 0° C. The reaction mixture was allowed to stir at 0° C. for 1 h and at room temperature for another 2 h. The reaction mixture was again cooled to 0° C. and N,N-diisopropylethyl amine (5.1 mL, 30.0 mmol) was added, followed by di-tert-butyl dicarbonate (5.1 mL, 22 mmol). The reaction mixture was allowed to warm up to room temperature and stirred for 10 h. The reaction mixture was concentrated under reduced pressure and the crude product was extracted with EtOAc. The combined extracts were washed with water and brine, dried over anhydrous sodium sulfate, and concentrated under reduced pressure. The crude product was purified by column chromatography (silica gel 60-120 mesh, eluent 15-20% EtOAc in petroleum ether) to afford 4-benzyl 1-tert-butyl 2-methylpiperazine-1,4-dicarboxylate (5.0 g, yield 76%) as a colorless viscous liquid. $^1$H NMR (400 MHz, CDCl$_3$) δ 7.36 (m, 5H), 5.16 (m, 2H), 4.25 (m, 1H), 4.03-4.02 (m, 1H), 3.89-3.79 (m, 2H), 3.07-3.01 (m, 3H), 1.47 (s, 9H), 1.14-1.13 (m, 3H). MS (ESI) m/z: Calculated for C$_{18}$H$_{28}$N$_2$O$_4$: 334.19. found: 235.0 (M+H-Boc)$^+$ tert-Butyl 2-methyl piperazine-1-carboxylate

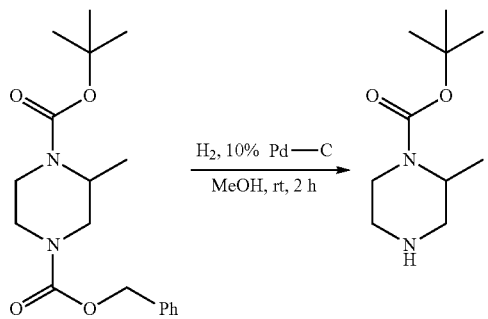

4-Benzyl 1-tert-butyl 2-methylpiperazine-1,4-dicarboxylate (3.0 g, 8.97 mmol) was dissolved in MeOH (30 mL) and purged with nitrogen for 5 min. 10% palladium on charcoal (300 mg) was added, and the reaction mixture was hydrogenated at room temperature for 2 h. The mixture was then filtered through Celite and the clear filtrate was concentrated under reduced pressure to obtain tert-butyl 2-methylpiperazine-1-carboxylate (2.1 g, crude), which was carried through without further purification. $^1$H NMR (400 MHz, CDCl$_3$) δ 4.23-4.15 (m, 1H), 3.82-3.77 (m, 1H), 3.01-2.88 (m, 3H), 2.78-2.75 (m, 1H), 2.71-2.63 (m, 1H), 1.47 (s, 9H), 1.22-1.21 (m, 3H). MS (ESI) m/z: Calculated for C$_{10}$H$_{20}$N$_2$O$_2$: 200.15. found: 201.0 (M+H)$^+$ tert-Butyl 4-((5-cyanopyridin-2-yl)methyl)-2-methylpiperazine-1-carboxylate

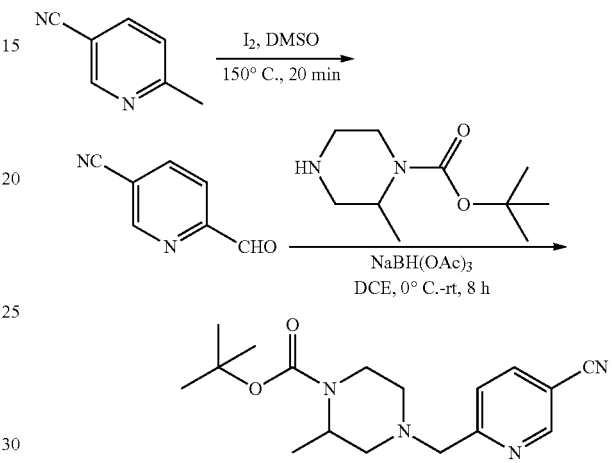

A mixture of 5-cyano-2-methylpyridine (400 mg, 3.38 mmol) and iodine (0.8 g, 3.15 mmol) in DMSO (2 mL) was heated to 150° C. under nitrogen for 20 min. The reaction mixture was cooled to room temperature and quenched with 10% aqueous NaHCO$_3$ solution. The organic product was extracted with EtOAc and the combined extracts were dried over anhydrous sodium sulfate, and concentrated under reduced pressure to get the crude 6-formylnicotinonitrile (400 mg), which was carried through without further purification. 6-Formylnicotinonitrile (400 mg, 3.03 mmol) was dissolved in 1,2-dichloroethane (5 mL) and cooled to 0° C. A solution of tert-butyl 2-methylpiperazine-1-carboxylate (606 mg, 3.03 mmol) in 1,2-dichloroethane (5 mL), followed by sodium triacetoxyborohydride (1.1 g, 5.4 mmol) were added and the reaction mixture was allowed to warm up to room temperature and further stirred for 8 h. The reaction mixture was quenched with 10% aqueous NaHCO$_3$ solution and the product was extracted with EtOAc.

The combined extracts were washed with brine, dried over anhydrous sodium sulfate, and concentrated under reduced pressure. The crude product was purified by column chromatography (silica gel 60-120 mesh, eluent 10-12% EtOAc in petroleum ether) to afford tert-butyl 4-((5-cyanopyridin-2-yl)methyl)-2-methylpiperazine-1-carboxylate (200 mg, yield 21%) as pale yellow solid. $^1$H NMR (300 MHz, CDCl$_3$) δ 8.82-8.81 (m, 1H), 7.97-7.93 (dd, J=8.2 Hz, 2.1 Hz, 1H), 7.70-7.68 (d, J=8.1 Hz, 1H), 4.25-4.21 (m, 1H), 3.88-3.83 (m, 1H), 3.79-3.62 (m, 2H), 3.20-3.10 (td, J=12.8 Hz, 3.4 Hz, 1H), 2.78-2.73 (dt, J=11.0 Hz, 1.5 Hz, 1H), 2.58-2.53 (dt, J=11.2 Hz, 1.8 Hz, 1H), 2.34-2.29 (dd, J=11.2 Hz, 3.9 Hz, 1H), 2.24-2.15 (m, 1H), 1.47 (s, 9H), 1.29-1.26 (d, J=6.6 Hz, 3H). MS (ESI) m/z: Calculated for C$_{17}$H$_{24}$N$_4$O$_2$: 316.19. found: 317.1 (M+H)$^+$

6-((3-Methylpiperazin-1-yl)methyl)nicotinonitrile TFA Salt

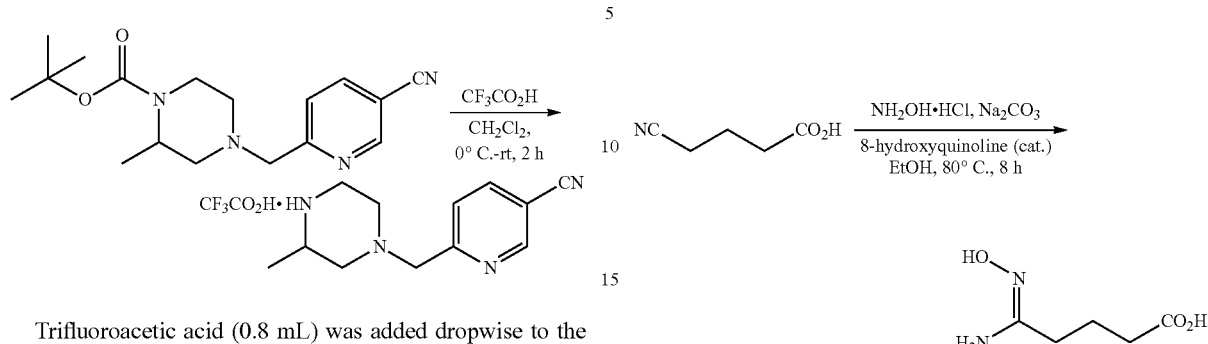

Trifluoroacetic acid (0.8 mL) was added dropwise to the cold solution of tert-butyl 4-((5-cyanopyridin-2-yl)methyl)-2-methylpiperazine-1-carboxylate (200 mg, 0.63 mmol) in $CH_2Cl_2$ (3 mL) at 0° C. and the reaction mixture was further stirred at room temperature for 2 h. The reaction mixture was concentrated under reduced pressure to afford 6-((3-methylpiperazin-1-yl)methyl)nicotinonitrile TFA salt (180 mg, crude), which was carried through without further purification. MS (ESI) m/z: Calculated for $C_{12}H_{16}N_4$: 216.14. found: 217.0 $(M+H)^+$

6-((3-Methyl-4-(3-(5-(trifluoromethyl)-1,2,4-oxadiazol-3-yl)benzoyl)piperazin-1-yl)methyl)nicotinonitrile

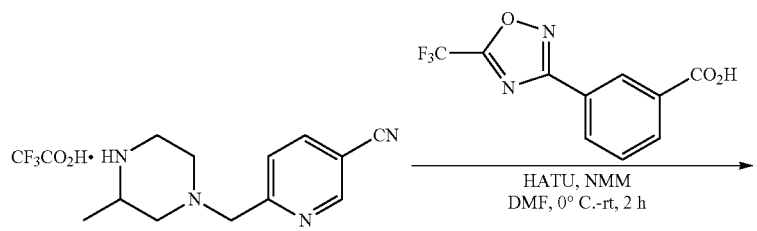

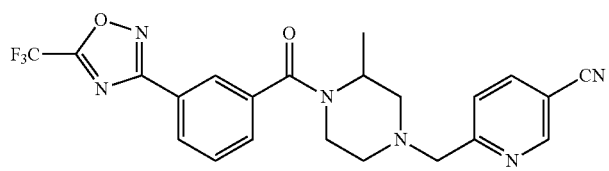

This compound was synthesized from 6-((3-methylpiperazin-1-yl)methyl)nicotinonitrile TFA salt and 3-(5-(trifluoromethyl)-1,2,4-oxadiazol-3-yl)benzoic acid as described for example 37 step 3 (60 mg, yield 21%) pale yellow viscous liquid. $^1$H NMR (400 MHz, MeOD) δ 8.85-8.84 (m, 1H), 8.25-8.22 (dt, J=7.4 Hz, 1.6 Hz, 1H), 8.19-8.16 (dd, J=8.2 Hz, 2.1 Hz, 1H), 8.13 (m, 1H), 7.82-7.80 (d, J=8.3 Hz, 1H), 7.72-7.66 (m, 2H), 3.82-3.70 (m, 3H), 3.50 (m, 2H), 2.89 (m, 1H), 2.74 (m, 1H), 2.43-2.41 (m, 1H), 2.31-2.25 (m, 1H), 1.46-1.44 (d, J=6.5 Hz, 3H). MS (ESI) m/z: Calculated for $C_{22}H_{16}F_3N_6O_2$: 456.15. found: 457.2 $(M+H)^+$

Example 47

5-Amino-5-(hydroxyimino)pentanoic acid

This compound was synthesized from 4-cyanobutyric acid as described for example 37 step 1 (5.3 g, crude) and it was carried through without further purification. $^1$H NMR (400 MHz, DMSO-$d_6$) δ 12.64 (br s, 1H), 10.94 (br s, 1H), 10.39 (br s, 2H), 2.42-2.38 (m, 2H), 2.26-2.23 (m, 2H), 1.86-1.79 (m, 2H). MS (ESI) m/z: Calculated for $C_6H_{10}N_2O_3$: 146.07. found: 147.0 $(M+H)^+$

4-(5-(Trifluoromethyl)-1,2,4-oxadiazol-3-yl)butanoic acid

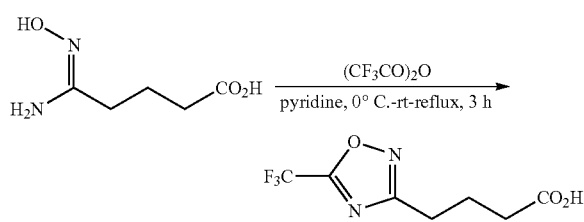

This compound was synthesized from 5-amino-5-(hydroxyimino)pentanoic acid as described for example 37 step 2 (2 g, yield 25%) as light yellow viscous liquid. $^1$H NMR (300 MHz, DMSO-$d_6$) δ 2.90-2.85 (t, J=7.5 Hz, 2H), 2.35-2.30 (t, J=7.3 Hz, 2H), 1.95-1.85 (m, 2H).

6((3-Methyl-4-(4-(5-(trifluoromethyl)-1,2,4-oxadiazol-3-yl)butanoyl)piperazin-1-yl)methyl)nicotinonitrile

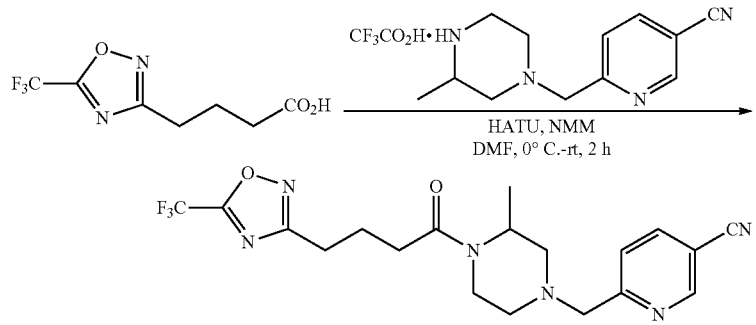

This compound was synthesized from 6-((3-methylpiperazin-1-yl)methyl)nicotinonitrile TFA salt and 4-(5-(trifluoromethyl)-1,2,4-oxadiazol-3-yl)butanoic acid as described for example 37 step 3 (16 mg, yield 16%) pale yellow viscous liquid. $^1$H NMR (400 MHz, MeOD) δ 8.82-8.81 (dd, J=2.0 Hz, 0.8 Hz, 1H), 8.15-8.12 (dd, J=8.2 Hz, 2.1 Hz, 1H), 7.77-7.75 (d, J=8.0 Hz, 1H), 3.78-3.66 (m, 2H), 2.96-2.92 (t, J=7.4 Hz, 2H), 2.89-2.85 (m, 1H), 2.73-2.69 (dt, J=11.5 Hz, 1.7 Hz, 1H), 2.51 (m, 2H), 2.34-2.30 (m, 1H), 2.22-2.17 (m, 1H), 2.14-2.06 (m, 2H), 1.35-1.32 (m, 3H), 1.30 (s, 3H). MS (ESI) m/z: Calculated for $C_{19}H_{21}F_3N_6O_2$: 422.17. found: 423.2 (M+H)$^+$ Example 48

4-Phenylthiazol-2(3H)-one

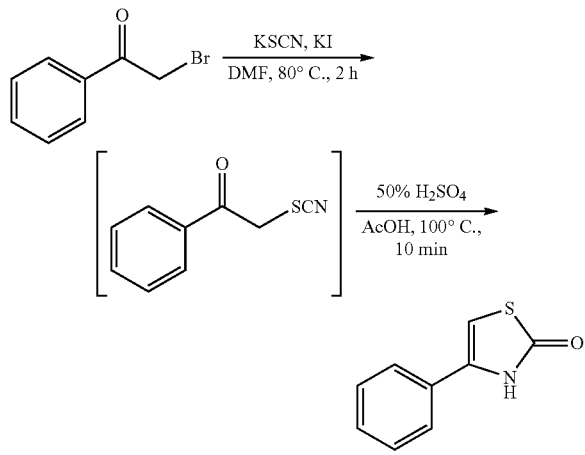

A suspension of 2-bromoacetophenone (5 g, 0.0251 mol), potassium thiocyanate (8.6 g, 0.088 mol) and potassium iodide (0.25 g, 0.0015 mol) in dry DMF (25 mL) was heated to 80° C. for 2 h. The reaction mixture was concentrated to dryness under reduced pressure and the residue was dissolved in glacial acetic acid (25 mL) and 50% aqueous $H_2SO_4$ was added to it. The reaction mixture was heated to 100° C. for 10 min. The reaction mixture was poured in ice water and the precipitate formed was filtered and dried under reduced pressure to get 4-phenylthiazol-2(3H)-one (3.3 g, yield 75%) as brown solid, which was carried through without further purification.

2-Bromo-4-phenylthiazole

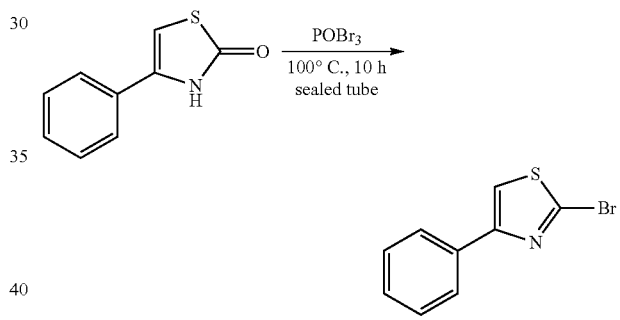

A mixture of 4-phenylthiazol-2(3H)-one (300 mg, 1.7 mmol) and POBr$_3$ (4.85 g, 17.0 mmol) was heated to 100° C. in a sealed tube for 10 h. The reaction mixture was poured in ice water and the organic product was extracted with EtOAc. The combined extracts were washed with brine, dried over anhydrous sodium sulfate, and concentrated under reduced pressure. The crude product was purified by column chromatography (silica 60-120 mesh, eluant 1% EtOAc in petroleum ether) to get 2-bromo-4-phenylthiazole (300 mg, yield 73%) as light brown colored liquid. $^1$H NMR (300 MHz, CDCl$_3$) δ 7.88-7.85 (m, 2H), 7.46-7.35 (m, 4H). MS (ESI) m/z: Calculated for $C_9H_6BrNS$: 240.94. found: 242.0 (M+H)$^+$ Methyl 1-(4-phenylthiazol-2-yl)pyrrolidine-3-carboxylate

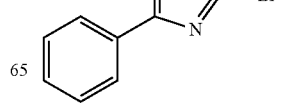

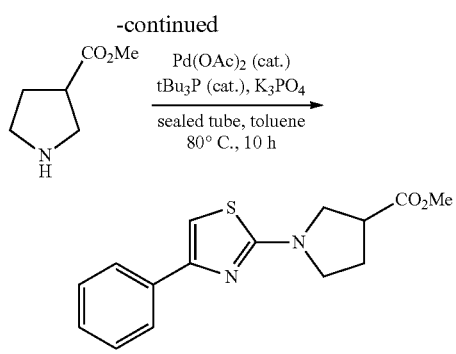

A mixture of 2-bromo-4-phenylthiazole (300 mg, 1.25 mmol) and pyrrolidine-3-carboxylic acid methyl ester (177 mg, 1.37 mmol) and potassium phosphate (290 mg, 1.37 mmol) in dry toluene (5 mL) were taken in a sealed tube and purged argon gas for 10 min. A catalytic amount of tri-tert-butylphosphine (12 mg, 0.06 mmol) was added, followed by palladium acetate (15 mg, 0.06 mmol), and the reaction mixture was heated to 80° C. for 10 h. The reaction mixture was then filtered through Celite and the clear filtrate was concentrated under reduced pressure to get the crude product which was purified by column chromatography (silica 60-120 mesh, eluant 15-18% EtOAc in petroleum ether) to get methyl 1-(4-phenylthiazol-2-yl)pyrrolidine-3-carboxylate (75 mg, yield 73%). $^1$H NMR (300 MHz, CDCl$_3$) δ 7.87-7.83 (m, 2H), 7.44-7.31 (m, 4H), 3.88-3.78 (m, 2H), 3.75 (s, 3H), 3.70-3.67 (m, 1H), 3.61-3.55 (m, 1H), 3.32-3.23 (m, 1H), 2.41-2.32 (m, 2H). MS (ESI) m/z: Calculated for $C_{16}H_{16}N_2O_2S$: 288.09. found: 289.2 (M+H)$^+$ 1-(4-Phenylthiazol-2-yl)pyrrolidine-3-carboxylic acid

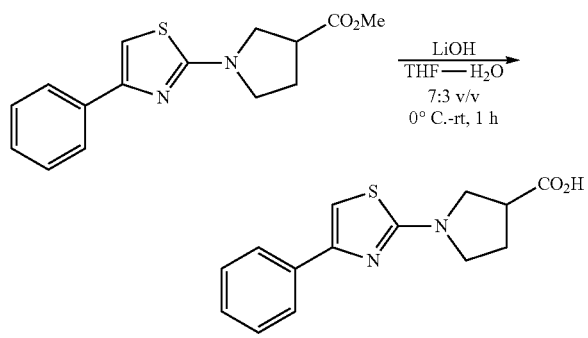

Lithium hydroxide (10 mg, 0.39 mmol) was added to a solution of methyl 1-(4-phenylthiazol-2-yl)pyrrolidine-3-carboxylate (75 mg, 0.26 mmol) in THF-H$_2$O (3 mL, 7:3 v/v) at 0° C. The reaction mixture was allowed to warm up to room temperature, stirred for 1 h, concentrated under reduced pressure, and then diluted with water. The aqueous layer was washed with EtOAc. The pH of the aqueous layer was adjusted to ~3 using 1.5N HCl and the organic product was extracted with EtOAc. The combined extracts were dried over anhydrous Na$_2$SO$_4$ and concentrated under reduced pressure to afford 1-(4-phenylthiazol-2-yl)pyrrolidine-3-carboxylic acid (40 mg, yield 56%) as off-white solid, which was carried through without further purification. MS (ESI) m/z: Calculated for $C_{14}H_{14}N_2O_2S$: 274.08. found: 275.0 (M+H)$^+$ 1-(4-Phenylthiazol-2-yl)-N-(3-(5-(trifluoromethyl)-1,2,4-oxadiazol-3-yl)phenyl)pyrrolidine-3-carboxamide

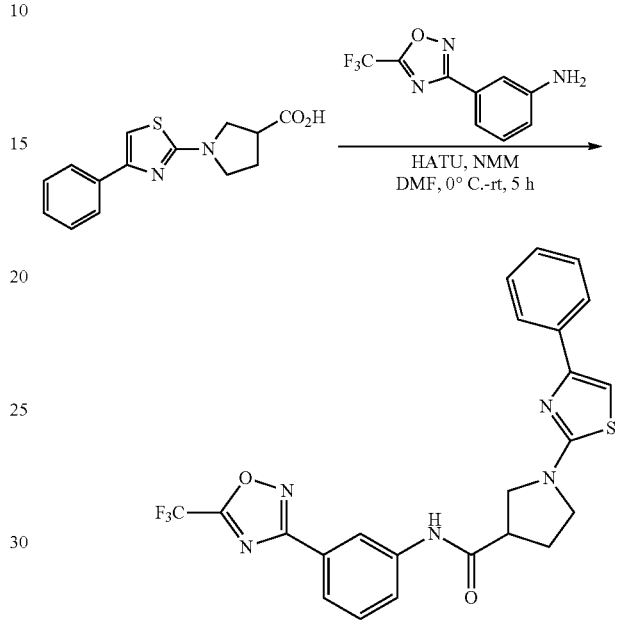

This compound was synthesized from 3-(5-(trifluoromethyl)-1,2,4-oxadiazol-3-yl)aniline and 1-(4-phenylthiazol-2-yl)pyrrolidine-3-carboxylic acid as described for example 37 step 3 (20 mg, yield 28%). $^1$H NMR (400 MHz, MeOD) δ 8.47 (t, J=1.8 Hz, 1H), 7.88-7.81 (m, 3H), 7.57-7.53 (t, J=7.9 Hz, 1H), 7.39-7.35 (m, 2H), 7.30-7.25 (m, 2H), 6.90 (s, 1H), 3.90-3.86 (m, 1H), 3.82-3.78 (m, 1H), 3.76-3.71 (m, 1H), 3.64-3.58 (m, 1H), 3.47-3.39 (m, 1H), 2.46-2.40 (m, 2H). MS (ESI) m/z: Calculated for $C_{23}H_{18}F_3N_5O_2S$: 485.11. found: 486.0 (M+H)$^+$ Example 49 tert-Butyl 3-(5-cyanopyridin-2-yl)azetidine-1-carboxylate

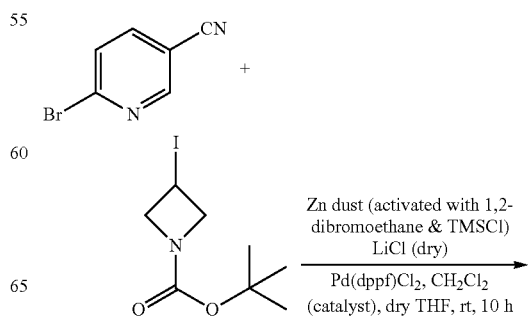

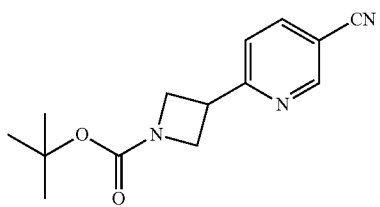

Zinc dust was purified by washing with HCl and dried thoroughly prior to use in this reaction. Zinc dust (325 mesh, 1.38 g, 21.2 mmol) and anhydrous lithium chloride (0.9 g, 21.2 mmol) were placed in a nitrogen-purged flask and freshly distilled THF (5.0 mL) was added, followed by 1,2-dibromoethane (0.2 mL). The reaction mixture was heated to 80° C. for 5 min and then cooled to room temperature. The process of heating and cooling was repeated for 2 times. Trimethylsilyl chloride (0.1 mL) was added to the reaction mixture and the suspension was stirred at room temperature for 20 min. A solution of N-Boc-3-iodo azetidine (2 g, 7.0 mmol) in dry THF (5 mL) was added dropwise to the activated zinc. The reaction mixture was stirred at room temperature for 2 h. In a separate dry flask were taken 6-bromonicotinonitrile (770 mg, 4.2 mmol) and Pd(dppf)Cl$_2$.CH$_2$Cl$_2$ (115 mg, 0.14 mmol) in dry THF (4 mL) and stirred for 5 min. The resulting reaction mixture was added dropwise to the organozinc compound. The reaction mixture was stirred at room temperature for 10 h, quenched with saturated ammonium chloride solution, and diluted with EtOAc. The product was extracted with EtOAc and the combined extracts were washed with H$_2$O and brine. Solvent was removed under reduced pressure and the crude product was purified by column chromatography (silica gel 60-120 mesh, eluent 20-25% EtOAc in petroleum ether) to afford tert-butyl 3-(5-cyanopyridin-2-yl)azetidine-1-carboxylate (180 mg, yield 17%). $^1$H NMR (300 MHz, DMSO-d6) δ 9.04-9.03 (m, 1H), 8.27-8.23 (dd, J=8.1 Hz, 2.2 Hz, 1H), 7.56-7.53 (m, 1H), 4.20-4.16 (m, 2H), 4.02-3.97 (m, 2H), 3.58-3.53 (m, 1H), 1.38 (s, 9H). MS (ESI) m/z: Calculated for C$_{14}$H$_{17}$N$_3$O$_2$: 259.13. found: 160.2 (M+H-Boc)$^+$ 6-(Azetidin-3-yl)nicotinonitrile TFA Salt

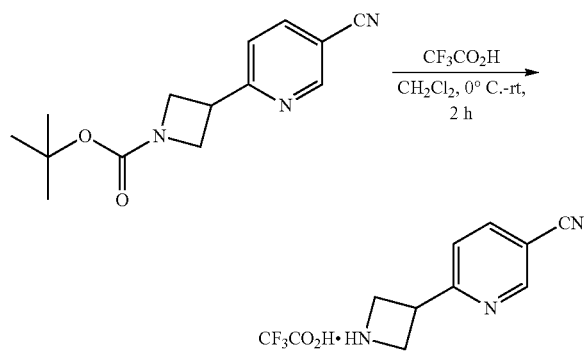

This compound was synthesized from tert-butyl 3-(5-cyanopyridin-2-yl)azetidine-1-carboxylate as described for example 46 step 4 (100 mg, crude), which was carried through without further purification. MS (ESI) m/z: Calculated for C$_9$H$_6$N$_3$: 159.08. found: 160.2 (M+H)$^+$ 6-(1-(3-(5-(Trifluoromethyl)-1,2,4-oxadiazol-3-yl)benzoyl)azetidin-3-yl)nicotinonitrile

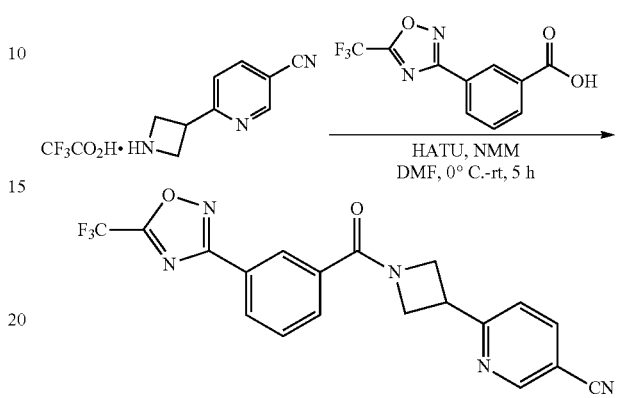

This compound was synthesized from 6-(azetidin-3-yl)nicotinonitrile TFA salt and 3-(5-(trifluoromethyl)-1,2,4-oxadiazol-3-yl)benzoic acid as described for example 37 step 3 (70 mg, yield 47%). $^1$H NMR (400 MHz, DMSO-d$_6$) δ 9.06 (m, 1H), 8.30-8.29 (m, 2H), 8.21-8.19 (d, J=7.8 Hz, 1H), 7.96-7.94 (d, J=7.8 Hz, 1H), 7.74-7.70 (t, J=7.7 Hz, 1H), 7.63-7.61 (d, J=8.1 Hz, 1H), 4.76-4.72 (m, 1H), 4.52-4.46 (m, 2H), 4.25-4.18 (m, 2H). MS (ESI) m/z: Calculated for C$_{19}$H$_{12}$F$_3$N$_5$O$_2$: 399.09. found: 400.2 (M+H)$^+$ Example 50 tert-Butyl 4-(5-cyanopyridin-2-yl)piperidine-1-carboxylate

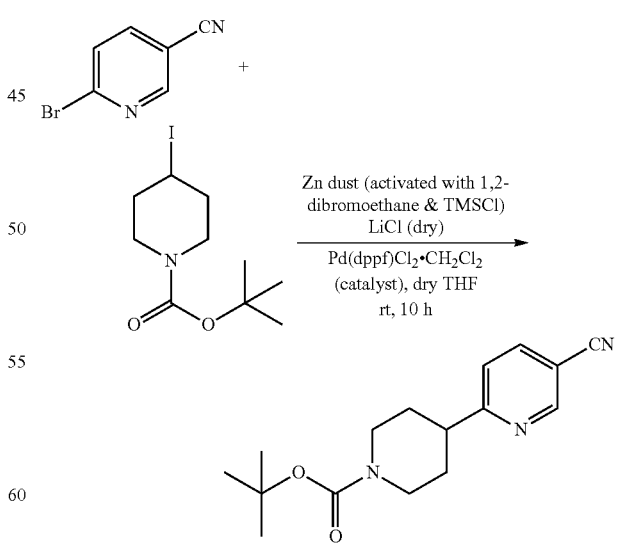

This compound was synthesized from 6-bromonicotinonitrile and tert-butyl 4-iodopiperidine-1-carboxylate as described for example 49 step 1 (150 mg, yield 27%). $^1$H NMR (400 MHz, CDCl$_3$) δ 8.82 (d, J=2.0 Hz, 1H), 7.91 (dd, J=8.2 Hz, 2.1 Hz, 1H), 7.30 (d, J=8.0 Hz, 1H), 4.28 (m, 2H), 2.97-2.81 (m, 3H), 1.91 (m, 2H), 1.78-1.67 (m, 2H), 1.48 (s, 9H). MS (ESI) m/z: Calculated for $C_{16}H_{21}N_3O_2$: 287.16. found: 188.2 (M+H-Boc)$^+$ 6-(Piperidin-4-yl)nicotinonitrile hydrochloride

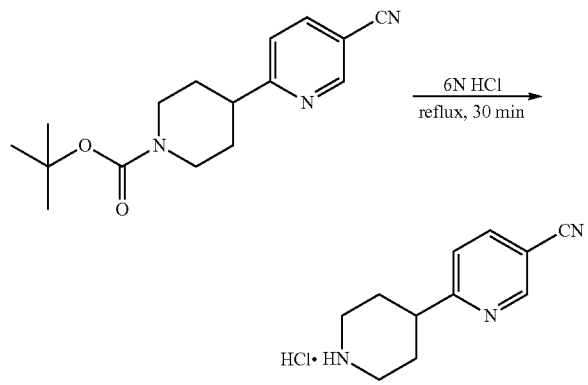

6N HCl (1.0 mL) was added to tert-butyl 4-(5-cyanopyridin-2-yl)piperidine-1-carboxylate (150 mg, 0.52 mmol) and the reaction mixture was stirred at 90° C. for 30 min, cooled to room temperature, and concentrated under reduced pressure. The crude residue was triturated with ether to afford 6-(piperidin-4-yl)nicotinonitrile hydrochloride (90 mg, crude). $^1$H NMR (300 MHz, D$_2$O) δ 8.90 (d, J=0.7 Hz, 1H), 8.30 (dd, J=8.2 Hz, 1.9 Hz, 1H), 7.66 (d, J=8.1 Hz, 1H), 3.60-3.55 (m, 2H), 3.27-3.13 (m, 3H), 2.20 (m, 2H), 2.07-1.97 (m, 2H). MS (ESI) m/z: Calculated for $C_{11}H_{13}N_3$: 187.11. found: 188.2 (M+H)$^+$ 6-(1-(3-(5-(Trifluoromethyl)-1,2,4-oxadiazol-3-yl)benzoyl)piperidin-4-yl)nicotinonitrile

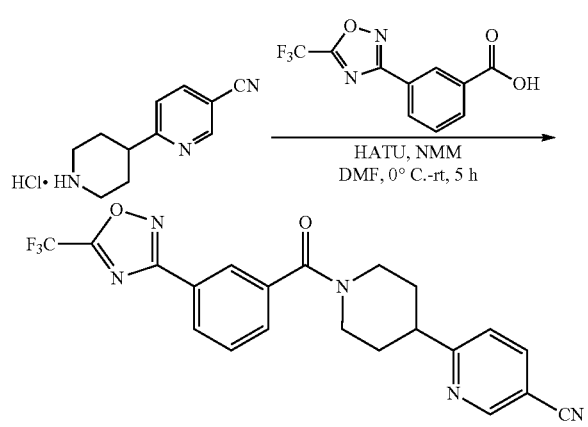

This compound was synthesized from 6-(piperidin-4-yl)nicotinonitrile hydrochloride and 3-(5-(trifluoromethyl)-1,2,4-oxadiazol-3-yl)benzoic acid as described for example 37 step 3 (50 mg, yield 30%). $^1$H NMR (400 MHz, CDCl$_3$) δ 8.84 (d, J=2.0 Hz, 1H), 8.20-8.19 (m, 2H), 7.95-7.92 (dd, J=8.2 Hz, 2.1 Hz, 1H), 7.67-7.59 (m, 2H), 7.33 (d, J=8.3 Hz, 1H), 4.92 (m, 1H), 3.91 (m, 1H), 3.24 (m, 1H), 3.09 (m, 1H), 2.97 (m, 1H), 2.09 (m, 1H), 1.94-1.83 (m, 3H). MS (ESI) m/z: Calculated for $C_{21}H_{16}F_3N_6O_2$: 427.13. found: 428.2 (M+H)$^+$ Example 51

N-(1-(5-Cyanopyridin-2-yl)piperidin-4-yl)acetamide

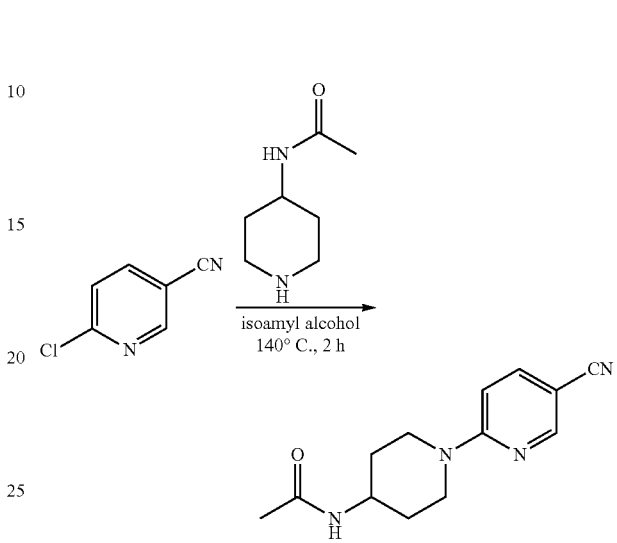

6-Chloronicotinonitrile (300 mg, 2.1 mmol) and 4-acetylaminopiperidine (610 mg, 4.33 mmol) were taken in isoamyl alcohol (15 mL) and the mixture was heated to 140° C. for 2 h. Reaction mixture was cooled to room temperature and the solvent was evaporated under reduced pressure. The crude product was purified by column chromatography (silica gel 60-120 mesh, eluent 5% MeOH in CHCl$_3$) to afford N-(1-(5-cyanopyridin-2-yl)piperidin-4-yl)acetamide (300 mg, yield 57%) as white solid. $^1$H NMR (400 MHz, DMSO-d$_6$) δ 8.47 (d, J=2.4 Hz, 1H), 7.83-7.80 (m, 2H), 6.95 (d, J=9.3 Hz, 1H), 4.32-4.28 (m, 2H), 3.89-3.80 (m, 1H), 3.14-3.07 (m, 2H), 1.80 (m, 2H), 1.78 (s, 3H), 1.33-1.24 (m, 2H). MS (ESI) m/z: Calculated for $C_{13}H_{16}N_4O$: 244.13. found: 245.2 (M+H)$^+$ 6-(4-Aminopiperidin-1-yl)nicotinonitrile

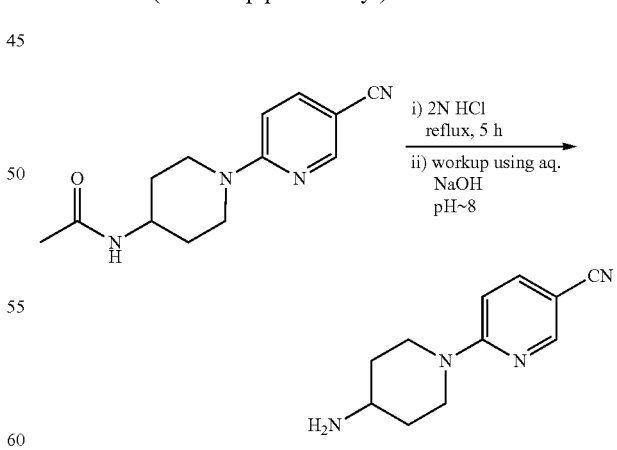

2N HCl (3 mL) was added to N-(1-(5-cyanopyridin-2-yl)piperidin-4-yl)acetamide (300 mg, 1.22 mmol) and the reaction mixture was stirred at 100° C. for 5 h. The reaction mixture was cooled to room temperature and the pH of the aqueous layer was adjusted to 8-9 using 10% NaOH solution. The product was extracted with CH$_2$Cl$_2$ and the combined extracts were washed with water and brine, dried over anhydrous sodium sulfate, and concentrated under reduced pressure to afford 6-(4-aminopiperidin-1-yl)nicotinonitrile (210 mg, crude), which was carried through without further purification. ¹H NMR (300 MHz, DMSO-d₆) δ 8.43 (d, J=2.3 Hz, 1H), 7.79-7.75 (dd, J=9.1 Hz, 2.3 Hz, 1H), 6.90 (d, J=9.2 Hz, 1H), 4.28-4.23 (m, 2H), 3.07-2.98 (m, 2H), 2.87-2.78 (m, 1H), 1.75-1.71 (m, 2H), 1.19-1.07 (m, 2H). MS (ESI) m/z: Calculated for $C_{11}H_{14}N_4$: 202.12. found: 203.2 (M+H)⁺

N-(1-(5-Cyanopyridin-2-yl)piperidin-4-yl)-3-(5-(trifluoromethyl)-1,2,4-oxadiazol-3-yl)benzamide

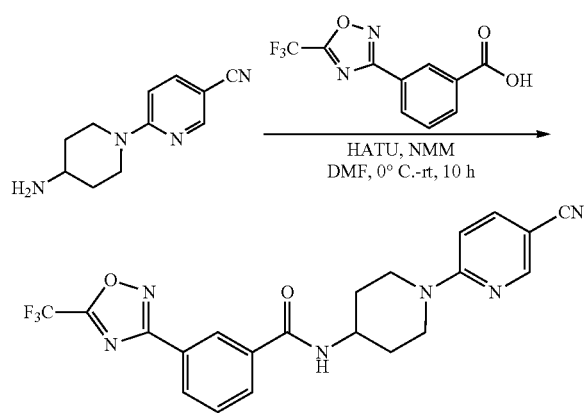

This compound was synthesized from 6-(4-aminopiperidin-1-yl)nicotinonitrile and 3-(5-(trifluoromethyl)-1,2,4-oxadiazol-3-yl)benzoic acid as described for example 37 step 3 (70 mg, yield 41%). ¹H NMR (400 MHz, CDCl₃) δ 8.42 (m, 2H), 8.27 (d, J=7.8 Hz, 1H), 8.04 (d, J=7.8 Hz, 1H), 7.66-7.61 (m, 2H), 6.67 (d, J=9.0 Hz, 1H), 6.14 (d, J=7.8 Hz, 1H), 4.51-4.48 (m, 2H), 4.39-4.29 (m, 1H), 3.20-3.13 (m, 2H), 2.24-2.20 (dd, J=12.3 Hz, 2.3 Hz, 2H), 1.62-1.52 (m, 2H). MS (ESI) m/z: Calculated for $C_{21}H_{17}F_3N_6O_2$: 442.14. found: 443.2 (M+H)⁺

Example 52

Methyl 1-(5-cyanopyridin-2-yl)pyrrolidine-3-carboxylate

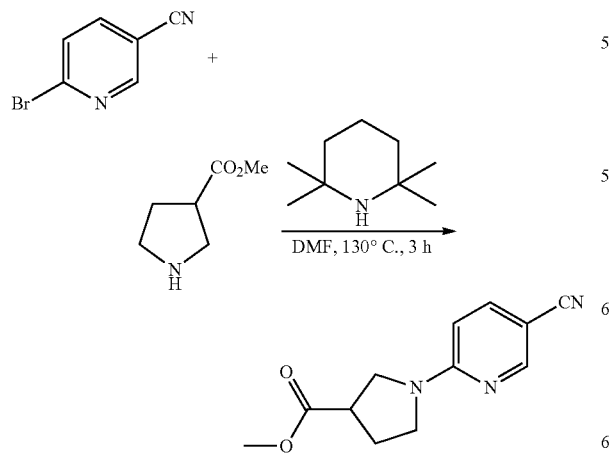

Pyrrolidine-3-carboxylic acid methyl ester (100 mg, 0.77 mmol) was dissolved in dry DMF (0.5 Ml) in a shield tube. 6-Bromonicotinonitrile (140 mg, 077 mmol) was added to the reaction mixture, followed by 2,2,6,6-tetramethylpiperadine (110 mg, 0.77 mmol) and the mixture was heated to 130° C. for 3 h, cooled to room temperature, and diluted with EtOAc. The organic layer was washed with H₂O and brine, dried over anhydrous sodium sulfate, and concentrated under reduced pressure. The crude product was purified by column chromatography (silica gel 60-120 mesh, eluent 15-18% EtOAc in petroleum ether) to afford methyl 1-(5-cyanopyridin-2-yl)pyrrolidine-3-carboxylate (90 mg, yield 70%). ¹H NMR (300 MHz, CDCl₃) δ 8.42 (d, J=2.2 Hz, 1H), 7.62-7.59 (dd, J=8.9 Hz, J=2.3 Hz, 1H), 6.36 (d, J=9.0 Hz, 1H), 3.78-3.77 (m, 2H), 3.75 (s, 3H), 3.67 (m, 1H), 3.56-3.52 (m, 1H), 3.28-3.23 (t, J=7.1 Hz, 1H), 2.37-2.30 (q, J=7.1 Hz, 2H). MS (ESI) m/z: Calculated for $C_{12}H_{13}N_3O_2$: 231.10. found: 232.2 (M+H)⁺

1-(5-Cyanopyridin-2-yl)pyrrolidine-3-carboxylic acid

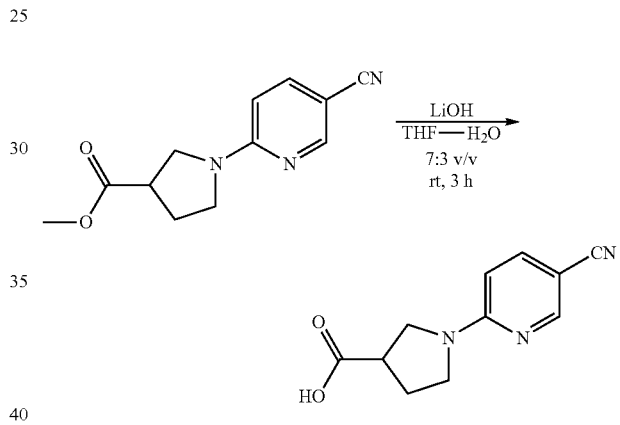

This compound was synthesized from methyl 1-(5-cyanopyridin-2-yl)pyrrolidine-3-carboxylate as described for example 48 step 4 (65 mg, yield 78%) as white solid. ¹H NMR (400 MHz, MeOD) δ 8.37 (d, J=2.3 Hz, 1H), 7.72-7.70 (dd, J=8.9 Hz, J=2.4 Hz, 1H), 6.57 (d, J=9.0 Hz, 1H), 3.76-3.75 (m, 2H), 3.61-3.55 (m, 2H), 3.29-3.26 (t, J=7.0 Hz, 1H), 2.36-2.30 (m, 2H). MS (ESI) m/z: Calculated for $C_{11}H_{12}N_3O_2$: 217.09. found: 218.2 (M+H)⁺

1-(5-Cyanopyridin-2-yl)-N-(3-(5-(trifluoromethyl)-1,2,4-oxadiazol-3-yl)phenyl)pyrrolidine-3-carboxamide

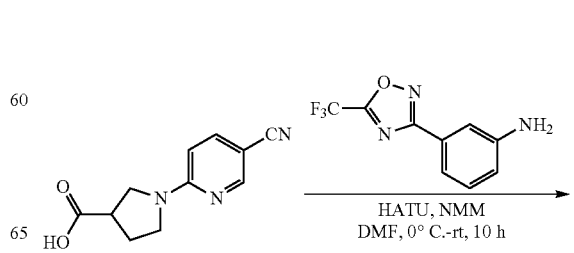

-continued

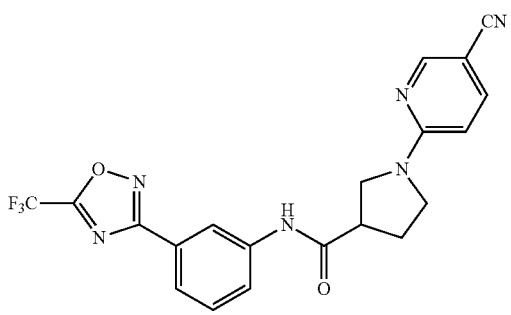

This compound was synthesized from 3-(5-(trifluoromethyl)-1,2,4-oxadiazol-3-yl)aniline and 1-(5-cyanopyridin-2-yl)pyrrolidine-3-carboxylic acid as described for example 37 step 3 (65 mg, yield 58%). $^1$H NMR (400 MHz, DMSO-$d_6$) δ 10.46 (s, 1H), 8.48-8.47 (m, 2H), 7.85-7.81 (m, 2H), 7.75 (d, J=7.8 Hz, 1H), 7.58-7.54 (m, 1H), 6.59 (d, J=8.9 Hz, 1H), 3.77-3.66 (m, 3H), 3.52 (m, 1H), 3.33 (m, 1H), 2.35-2.29 (m, 1H), 2.23 (m, 1H). MS (ESI) m/z: Calculated for $C_{20}H_{15}F_3N_6O_2$: 428.12. found: 429.0 (M+H)$^+$ Example 53

6-(4-(4-Cyanobutanoyl)-3-methylpiperazin-1-yl)nicotinonitrile

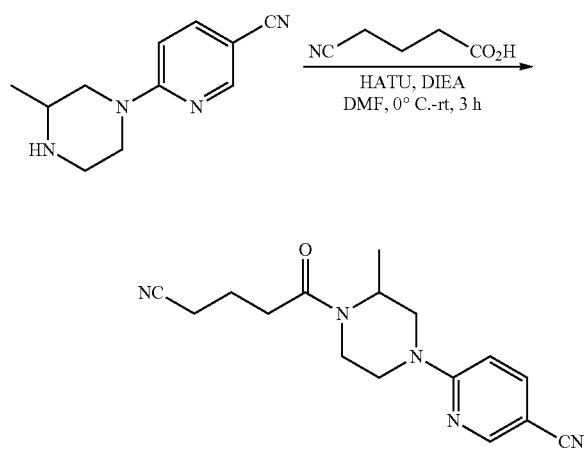 [SMILES: CC1CN(c2ccc(C#N)cn2)CCN1 ; N#CCCCC(=O)O ; CC1CN(c2ccc(C#N)cn2)CCN1C(=O)CCCC#N]

This compound was synthesized from 6-(3-methylpiperazin-1-yl)nicotinonitrile and 4-cyanobutyric acid as described for example 37 step 3 (900 mg, yield 85%) and it was carried through without further purification. $^1$H NMR (300 MHz, CDCl$_3$) δ 8.41-8.40 (dd, J=2.3 Hz, 0.5 Hz, 1H), 7.67-7.63 (dd, J=9.0 Hz, 2.2 Hz, 1H), 6.61-6.58 (d, J=9.0 Hz, 1H), 4.46-4.19 (m, 4H), 3.54-3.36 (m, 2H), 3.16-3.11 (m, 2H), 2.59-2.51 (m, 3H), 2.06-2.01 (m, 2H), 1.26 (m, 3H). MS (ESI) m/z: Calculated for $C_{16}H_{19}N_6O$: 297.16. found: 298.0 (M+H)$^+$ 5-(4-(5-Cyanopyridin-2-yl)-2-methylpiperazin-1-yl)-N'-hydroxy-5-oxopentanimidamide

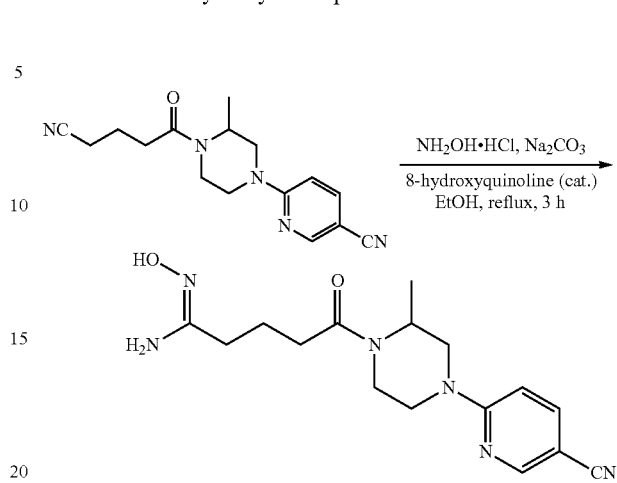

8-Hydroxyquinoline (14 mg) was added to a solution of 6-(4-(4-cyanobutanoyl)-3-methylpiperazin-1-yl)nicotinonitrile (0.9 g, 3.03 mmol) in ethanol (25 mL). Hydroxylamine hydrochloride (440 mg, 6.36 mmol) in water (4 mL), followed by sodium carbonate (510 mg, 4.81 mmol) in water (3 mL), were added to this solution and the reaction mixture was heated to reflux for 3 h. Ethanol was then removed under reduced pressure, and the product was extracted with EtOAc. The combined extracts were dried over anhydrous sodium sulfate, and concentrated under reduced pressure to afford 5-(4-(5-cyanopyridin-2-yl)-2-methylpiperazin-1-yl)-N'-hydroxy-5-oxopentanimidamide (400 mg, crude), which was carried through without further purification. MS (ESI) m/z: Calculated for $C_{16}H_{22}N_6O_2$: 330.18. found: 331.1 (M+H)$^+$ 6-(3-Methyl-4-(4-(5-(trifluoromethyl)-1,2,4-oxadiazol-3-yl)butanoyl)piperazin-1-yl)nicotinonitrile

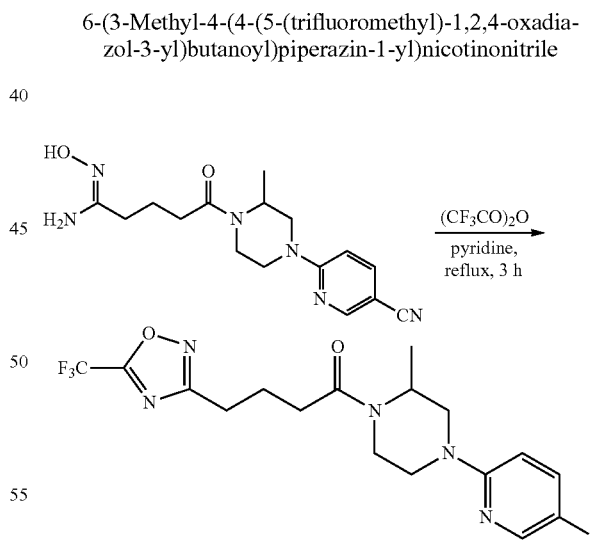

A solution of 5-(4-(5-cyanopyridin-2-yl)-2-methylpiperazin-1-yl)-N'-hydroxy-5-oxopentanimidamide (400 mg, 1.21 mmol) in anhydrous pyridine (4 mL) was cooled to 0° C. and trifluoroacetic anhydride (0.5 mL) was added dropwise. The reaction mixture was slowly warmed to room temperature and further heated to 110° C. for 3 h. The reaction mixture was concentrated under reduced pressure and diluted with EtOAc. The organic layer was washed with water and brine, concentrated under reduced pressure, and the crude product was purified by column chromatography (silica gel 60-120 mesh, eluant: 50% EtOAc in petroleum ether) followed by preparative TLC to afford 6-(3-methyl-4-(4-(5-(trifluoromethyl)-1,2,4-oxadiazol-3-yl)butanoyl)piperazin-1-yl)nicotinonitrile (28 mg, yield 6%) $^1$H NMR (400 MHz, DMSO-d$_6$, 70° C.) δ 8.74 (d, J=2.4 Hz, 1H), 8.09-8.06 (dd, J=8.8 Hz, 2.4 Hz, 1H), 6.99-6.97 (d, J=9.1 Hz, 1H), 4.47 (br s, 1H), 4.27-4.20 (m, 2H), 4.01 (br s, 1H), 3.39-3.35 (dd, J=13.4 Hz, 4.0 Hz, 1H), 3.30-3.12 (m, 2H), 2.55-2.53 (m, 2H), 2.49-2.43 (m, 2H), 1.89-1.82 (m, 2H), 1.15-1.13 (m, 3H). MS (ESI) m/z: Calculated for C$_{18}$H$_{19}$F$_3$N$_6$O$_2$: 408.15. found: 409.2 (M+H)$^+$ Example 54 tert-Butyl 4-(5-cyanopyridin-2-yl)-3,3-dimethylpiperazine-1-carboxylate

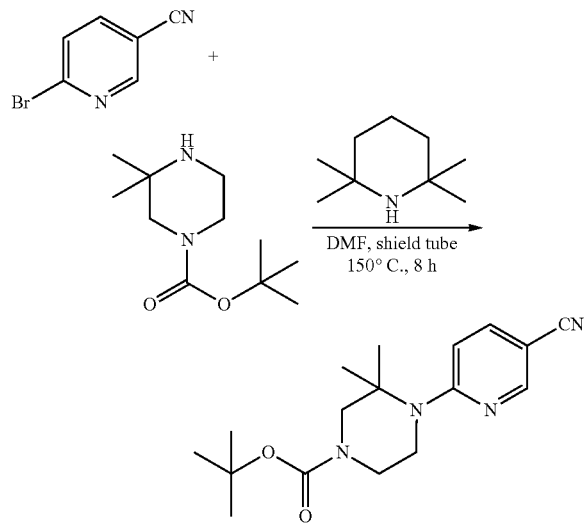

This compound was synthesized from 6-bromonicotinonitrile and tert-butyl 3,3-dimethylpiperazine-1-carboxylate as described for example 43 step 1 (0.12 g, yield 43%). $^1$H NMR (300 MHz, CDCl$_3$) δ 8.42 (d, J=1.5 Hz, 1H), 7.59 (dd, J=9.0 Hz, J=2.2 Hz, 1H), 6.64 (d, J=9.0 Hz, 1H), 3.89-3.82 (m, 2H), 3.58-3.51 (m, 4H), 1.52 (s, 6H), 1.49 (s, 9H). MS (ESI) m/z: Calculated for C$_{17}$H$_{24}$N$_4$O$_2$: 316.19. found: 217.2 (M+H-Boc)$^+$ 6-(2,2-Dimethylpiperazin-1-yl)nicotinonitrile hydrochloride

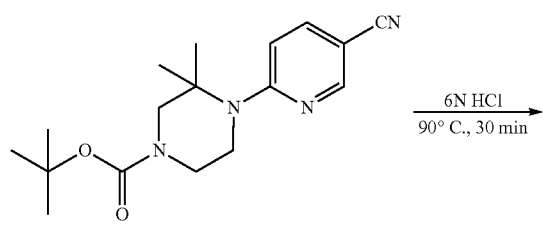

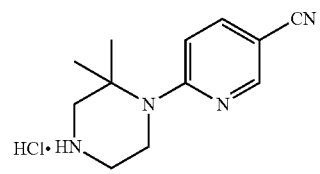

This compound was synthesized from tert-butyl 4-(5-cyanopyridin-2-yl)-3,3-dimethylpiperazine-1-carboxylate as described for example 50 step 2 (80 mg, crude). $^1$H NMR (300 MHz, D$_2$O) δ 8.57 (d, J=2.2 Hz, 1H), 7.98 (dd, J=9.0 Hz, J=2.3 Hz, 1H), 7.23 (d, J=9.0 Hz, 1H), 3.81-3.78 (m, 2H), 3.47-3.43 (m, 2H), 3.31-3.28 (m, 2H), 1.48 (s, 6H). MS (ESI) m/z: Calculated for C$_{12}$H$_{16}$N$_4$: 216.14. found: 217.2 (M+H)$^+$ 6-(2,2-Dimethyl-4-(3-(5-(trifluoromethyl)-1,2,4-oxadiazol-3-yl)benzoyl)piperazin-1-yl)nicotinonitrile

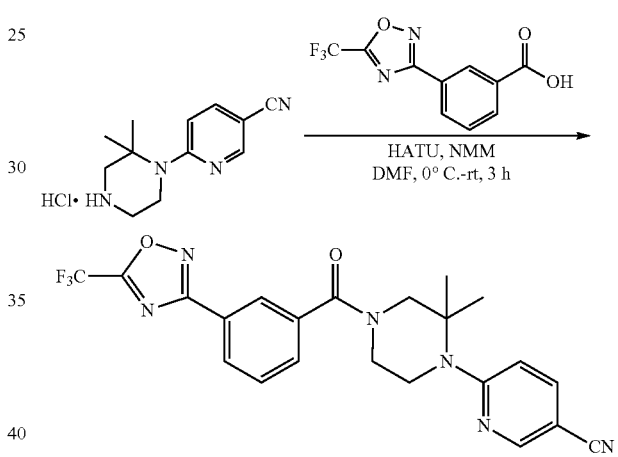

This compound was synthesized from 6-(2,2-dimethylpiperazin-1-yl)nicotinonitrile hydrochloride and 3-(5-(trifluoromethyl)-1,2,4-oxadiazol-3-yl)benzoic acid as described for example 37 step 3 (50 mg, yield 33%). $^1$H NMR (400 MHz, MeOD) δ 8.43 (d, J=1.8 Hz, 1H), 8.29-8.22 (m, 2H), 7.75-7.72 (m, 3H), 6.88 (d, J=9.0 Hz, 1H), 4.05-3.85 (m, 4H), 3.67 (m, 2H), 1.67-1.47 (m, 6H). MS (ESI) m/z: Calculated for C$_{22}$H$_{19}$F$_3$N$_6$O$_2$: 456.15. found: 457.2 (M+H)$^+$ Example 55

N-(1-(5-Cyanopyridin-2-yl)piperidin-3-yl)acetamide

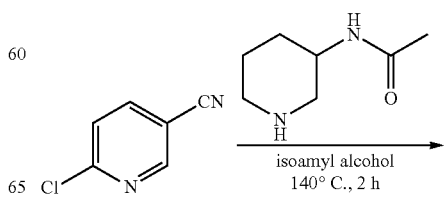

77

-continued

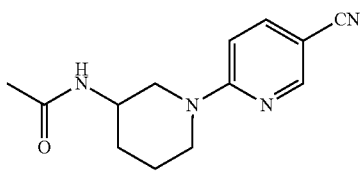

This compound was synthesized from 6-chloronicotinonitrile and 3-acetamidopiperidine as described for example 51 step 1 (850 mg, yield 96%) as white solid. $^1$H NMR (300 MHz, DMSO-d$_6$) δ 8.44 (d, J=2.2 Hz, 1H), 7.88 (d, J=7.5 Hz, 1H), 7.82-7.79 (dd, J=9.0 Hz, 2.4 Hz, 1H), 6.86 (d, J=9.2 Hz, 1H), 4.20-4.14 (dd, J=12.7 Hz, 3.1 Hz, 1H), 4.08-4.02 (dd, J=13.2 Hz, 3.9 Hz, 1H), 3.62 (m, 1H), 3.22-3.14 (m, 1H), 3.01-2.93 (dd, J=12.9 Hz, 9.2 Hz, 1H), 1.87-1.71 (m, 2H), 1.78 (s, 3H), 1.53-1.41 (m, 2H). MS (ESI) m/z: Calculated for C$_{13}$H$_{16}$N$_4$O: 244.13. found: 245.2 (M+H)$^+$ 6-(3-Aminopiperidin-1-yl)nicotinonitrile

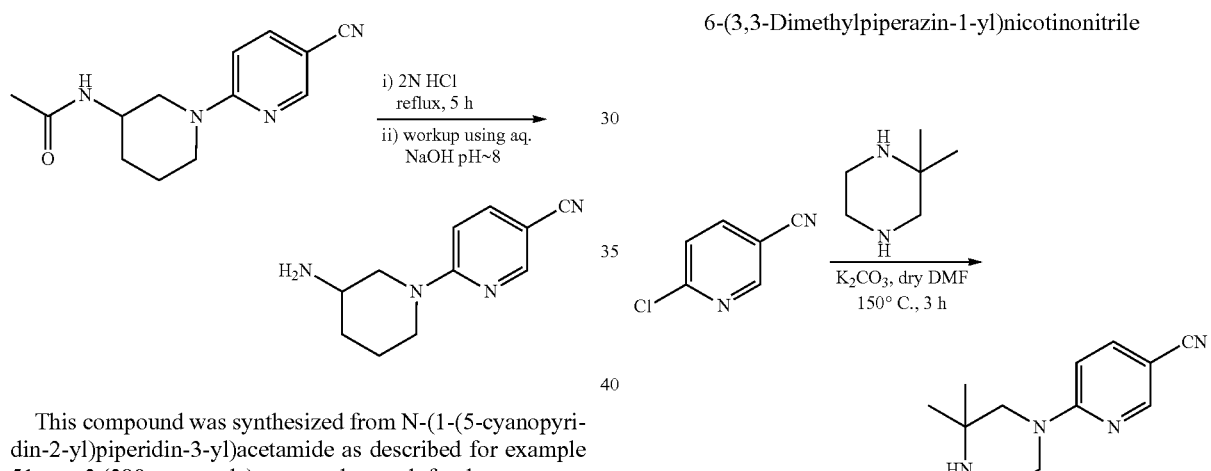

This compound was synthesized from N-(1-(5-cyanopyridin-2-yl)piperidin-3-yl)acetamide as described for example 51 step 2 (280 mg, crude) was used as such for the next step. $^1$H NMR (400 MHz, DMSO-d$_6$) δ 8.44 (d, J=2.1 Hz, 1H), 7.81-7.78 (dd, J=9.2 Hz, 2.1 Hz, 1H), 6.90 (d, J=9.2 Hz, 1H), 4.29-4.19 (m, 2H), 2.99-2.92 (m, 1H), 2.71-2.65 (m, 1H), 2.62-2.57 (m, 1H), 1.88-1.84 (m, 1H), 1.73-1.68 (dt, J=13.3 Hz, 3.3 Hz, 1H), 1.61 (m, 2H), 1.42-1.33 (m, 1H), 1.30-1.21 (m, 1H). MS (ESI) m/z: Calculated for C$_{11}$H$_{14}$N$_4$: 202.12. found: 203.2 (M+H)$^+$ N-(1-(5-Cyanopyridin-2-yl)piperidin-3-yl)-3-(5-(trifluoromethyl)-1,2,4-oxadiazol-3-yl)benzamide

78

-continued

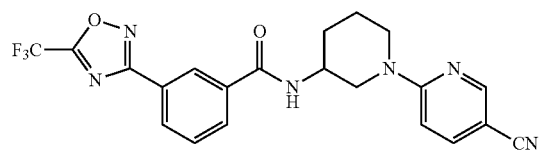

This compound was synthesized from 6-(3-aminopiperidin-1-yl)nicotinonitrile and 3-(5-(trifluoromethyl)-1,2,4-oxadiazol-3-yl)benzoic acid as described for example 37 step 3 (75 mg, yield 44%). $^1$H NMR (400 MHz, CDCl$_3$) δ 8.47 (d, J=2.1 Hz, 1H), 8.36 (s, 1H), 8.27 (d, J=7.6 Hz, 1H), 8.00-7.98 (dd, J=7.8 Hz, 1.1 Hz, 1H), 7.65-7.61 (m, 2H), 6.77 (d, J=9.2 Hz, 1H), 6.63 (d, J=6.1 Hz, 1H), 4.24-4.21 (dt, J=6.7 Hz, 3.4 Hz, 1H), 4.00-3.98 (m, 1H), 3.91-3.80 (m, 2H), 3.64-3.58 (m, 1H), 2.12-2.05 (ddd, J=13.0 Hz, 8.6 Hz, 4.3 Hz, 1H), 2.03-1.96 (m, 1H), 1.89-1.82 (m, 1H), 1.77-1.69 (m, 1H). MS (ESI) m/z: Calculated for C$_{21}$H$_{17}$F$_3$N$_6$O$_2$: 486.13. found: 487.2 (M+H)$^+$ Example 56

6-(3,3-Dimethylpiperazin-1-yl)nicotinonitrile

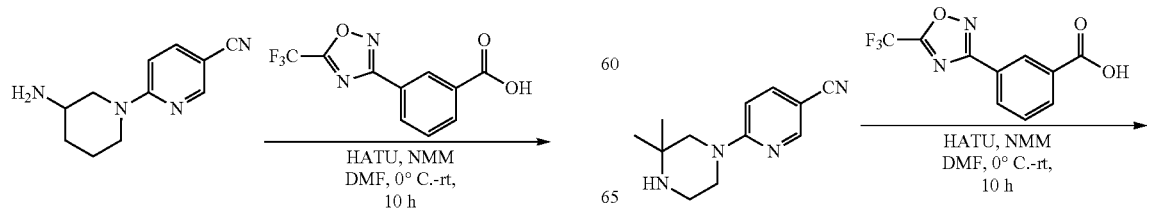

This compound was synthesized from 2,2-dimethylpiperazine and 6-chloronicotinonitrile as described for example 39 step 1 (270 mg, yield 73%). $^1$H NMR (400 MHz, MeOD) δ 8.38 (d, J=1.8 Hz, 1H), 7.71 (dd, J=9.2 Hz, J=2.4 Hz, 1H), 6.86 (d, J=9.2 Hz, 1H), 3.72-3.69 (m, 2H), 3.55 (s, 2H), 3.00-2.96 (m, 2H), 1.17 (s, 6H). MS (ESI) m/z: Calculated for C$_{12}$H$_{16}$N$_4$: 216.14. found: 217.2 (M+H)$^+$ 6-(3,3-Dimethyl-4-(3-(5-(trifluoromethyl)-1,2,4-oxadiazol-3-yl)benzoyl)piperazin-1-yl)nicotinonitrile -continued

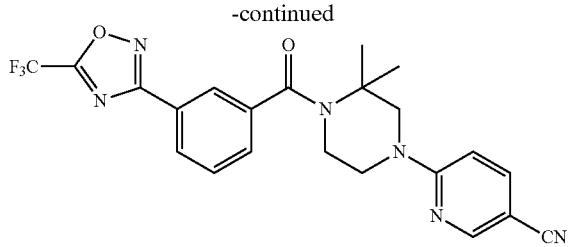

This compound was synthesized from 6-(3,3-dimethylpiperazin-1-yl)nicotinonitrile and 3-(5-(trifluoromethyl)-1,2,4-oxadiazol-3-yl)benzoic acid as described for example 37 step 3 (85 mg, yield 35%). $^1$H NMR (400 MHz, MeOD) δ 8.43 (m, 1H), 8.25-8.23 (m, 1H), 8.15 (s, 1H), 7.70-7.76 (dd, J=9.0 Hz, 2.5 Hz, 1H), 7.71-7.69 (m, 2H), 6.71 (d, J=9.0 Hz, 1H) 4.05 (s, 2H), 3.85 (t, J=5.6 Hz, 2H), 3.61 (t, J=5.6 Hz, 2H), 1.65 (m, 6H). MS (ESI) m/z: Calculated for $C_{22}H_{19}F_3N_6O_2$: 456.15. found: 457.2 (M+H)$^+$ Example 57

6-(4-(3-(5-(Trifluoromethyl)-1,2,4-oxadiazol-3-yl)benzoyl)-1,4-diazepan-1-yl)nicotinonitrile

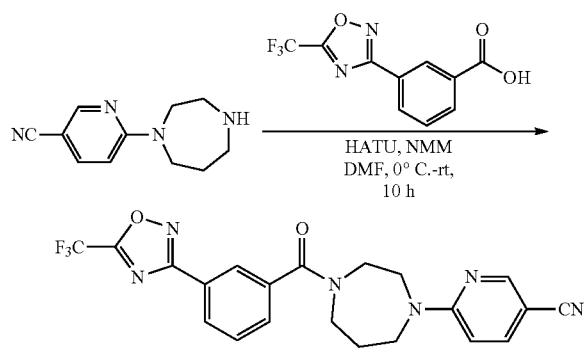

This compound was synthesized from 6-(1,4-diazepan-1-yl)nicotinonitrile and 3-(5-(trifluoromethyl)-1,2,4-oxadiazol-3-yl)benzoic acid as described for example 37 step 3 (80 mg, yield 34%). $^1$H NMR (400 MHz, MeOD) δ 8.20-8.18 (m, 1H), 8.02 (m, 1H), 7.69-7.65 (m, 1H), 7.60 (t, J=7.7 Hz, 1H), 7.55 (m, 1H), 7.38 (d, J=7.8 Hz, 1H), 6.78-6.76 (m, 1H), 4.01 (m, 1H), 3.93-3.90 (m, 2H), 3.83-3.79 (m, 2H), 3.75 (m, 2H), 3.48-3.46 (m, 1H), 2.07-2.02 (m, 2H). MS (ESI) m/z: Calculated for $C_{21}H_{17}F_3N_6O_2$: 442.14. found: 443.2 (M+H)$^+$ Example 58

4-(tert-Butoxycarbonyl)piperazine-2-carboxylic acid

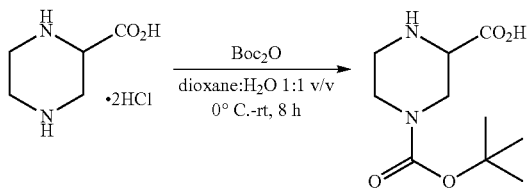 [SMILES: "Boc2O" ; O=C(O)C1CNCCN1 ; CC(C)(C)OC(=O)N1CCNC(C(=O)O)C1]

piperazine-2-carboxylic acid dihydrochloride (2.5 g, 12.3 mmol) was suspended in dioxane-H$_2$O (50 mL, 1:1 v/v) and sodium bicarbonate (1.95 g, 18.4 mmol) was added. The reaction mixture was cooled to 0° C. and di-tert-butyldicarbonate (4 g, 18.4 mmol) was added. The reaction mixture was allowed to warm up to room temperature and further stirred for 8 h. Solvent was removed under reduced pressure and crude reaction mixture was diluted with water. The aqueous layer was washed with EtOAc. The pH of the aqueous layer was adjusted to ~4 using 1.5N HCl. The organic product was extracted with n-BuOH. Solvent was removed under reduced pressure and 4-(tert-butoxycarbonyl)piperazine-2-carboxylic acid (2.6 g, crude) obtained as white solid, which was carried through without further purification. $^1$H NMR (300 MHz, DMSO-d$_6$) δ 4.01-3.97 (m, 2H), 3.81-3.76 (m, 1H), 3.24-3.17 (m, 3H), 2.98-2.92 (m, 1H), 1.40 (s, 9H).

1-tert-Butyl 3-methyl piperazine-1,3-dicarboxylate

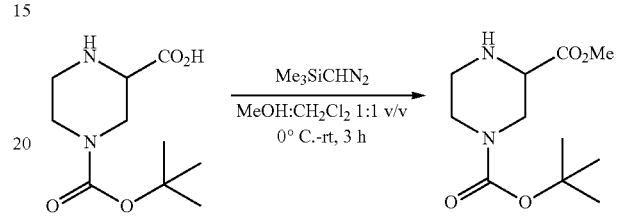

This compound was synthesized from 4-(tert-butoxycarbonyl)piperazine-2-carboxylic acid as described for example 42 step 1 (450 mg, yield 42%). $^1$H NMR (300 MHz, CDCl$_3$) δ 4.02 (m, 1H), 3.75 (s, 3H), 3.70-3.68 (m, 1H), 3.48-3.44 (m, 1H), 3.25-3.01 (m, 3H), 2.80-2.75 (m, 1H), 1.47 (s, 9H).

1-tert-Butyl 3-methyl 4-(5-cyanopyridin-2-yl)piperazine-1,3-dicarboxylate

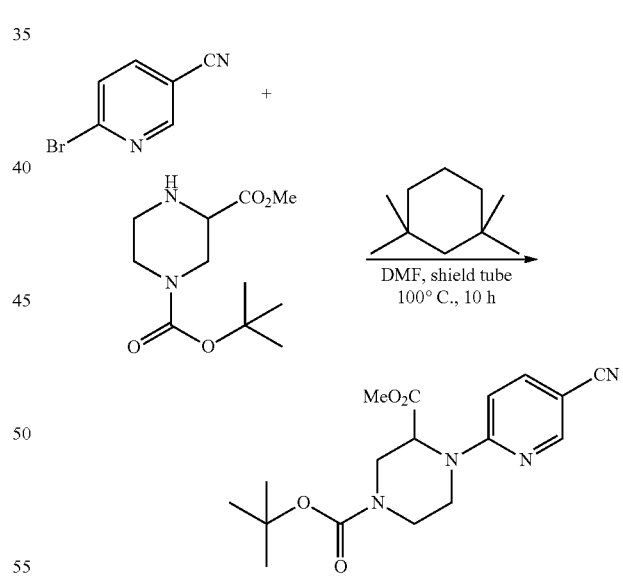

This compound was synthesized from 6-bromonicotinonitrile and 1-tert-butyl 3-methyl piperazine-1,3-dicarboxylate as described for example 43 step 1 (200 mg, yield 36%). $^1$H NMR (400 MHz, CDCl$_3$) δ 8.42 (d, J=2.3 Hz, 1H), 7.72-7.69 (dd, J=9.0 Hz, 2.3 Hz, 1H), 6.68 (d, J=9.0 Hz, 1H), 5.35 (m, 1H), 4.67-4.64 (d, J=13.6 Hz, 1H), 4.19 (m, 1H), 3.81-3.79 (d, J=9.8 Hz, 1H), 3.73 (s, 3H), 3.53-3.48 (m, 1H), 3.27-3.23 (m, 1H), 3.06 (m, 1H), 1.47 (s, 9H). MS (ESI) m/z: Calculated for $C_{17}H_{22}N_4O_4$: 346.16. found: 247.2 (M+H-Boc)$^+$

81

Methyl 1-(5-cyanopyridin-2-yl)piperazine-2-carboxylate TFA Salt

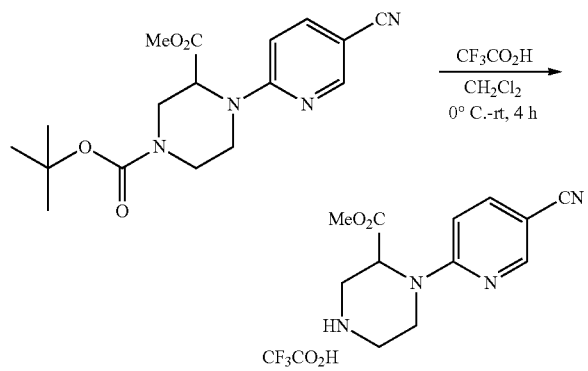

This compound was synthesized from 1-tert-butyl 3-methyl 4-(5-cyanopyridin-2-yl)piperazine-1,3-dicarboxylate as described for example 46 step 4 (50 mg, yield 36%) was pure enough to use for the next step. $^1$H NMR (300 MHz, CDCl$_3$) δ 8.41 (d, J=2.2 Hz, 1H), 7.71-7.67 (dd, J=9.0 Hz, 2.2 Hz, 1H), 6.67 (d, J=9.0 Hz, 1H), 5.38 (m, 1H), 3.84-3.78 (m, 1H), 3.75 (s, 3H), 3.70-3.66 (m, 1H), 3.44-3.34 (td, J=12.4 Hz, 3.8 Hz, 1H), 3.22-3.18 (m, 1H), 3.09-3.03 (dd, J=12.6 Hz, 4.3 Hz, 1H), 2.95-2.85 (m, 1H). MS (ESI) m/z: Calculated for C$_{12}$H$_{14}$N$_4$O$_2$: 246.27. found: 247.2 (M+H)$^+$

Methyl 1-(5-cyanopyridin-2-yl)-4-(3-(5-(trifluoromethyl)-1,2,4-oxadiazol-3-yl)benzoyl)piperazine-2-carboxylate

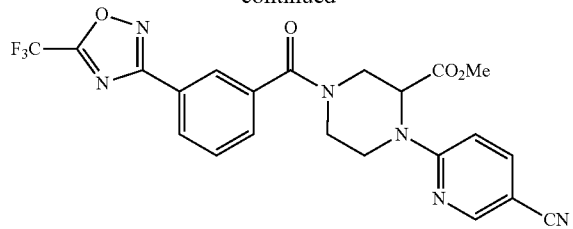

This compound was synthesized from methyl 1-(5-cyanopyridin-2-yl)piperazine-2-carboxylate TFA salt and 3-(5-(trifluoromethyl)-1,2,4-oxadiazol-3-yl)benzoic acid as described for example 37 step 3 (80 mg, yield 82%). $^1$H NMR (400 MHz, CDCl$_3$) δ 8.43 (d, J=1.0 Hz, 1H), 8.26-8.23 (m, 1H), 8.18 (s, 1H), 7.76-7.73 (dd, J=8.9 Hz, 2.1 Hz, 1H), 7.65-7.64 (m, 2H), 6.73-6.71 (m, 1H), 5.43 (m, 1H), 4.68 (m, 1H), 3.94-3.90 (m, 2H), 3.73-3.68 (m, 3H), 3.59 (m, 2H), 3.28 (m, 1H). MS (ESI) m/z: Calculated for C$_{22}$H$_{17}$F$_3$N$_6$O$_4$: 486.13. found: 487.2 (M+H)$^+$

1-(5-Cyanopyridin-2-yl)-4-(3-(5-(trifluoromethyl)-1,2,4-oxadiazol-3-yl)benzoyl)piperazine-2-carboxylic acid

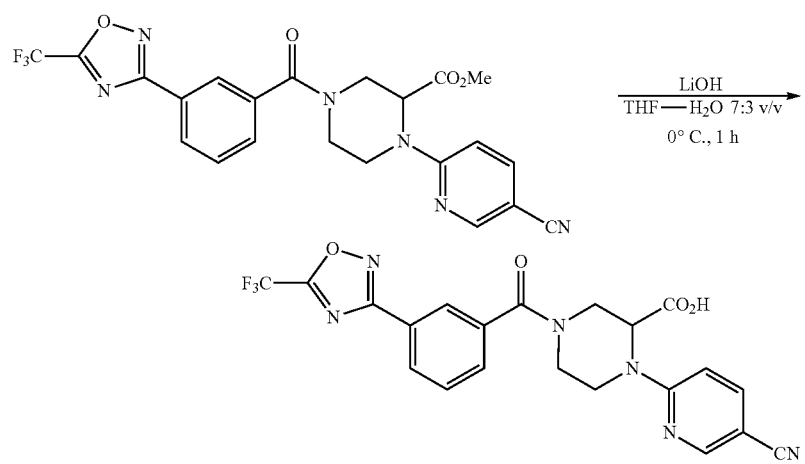

This compound was synthesized from methyl 1-(5-cyanopyridin-2-yl)-4-(3-(5-(trifluoromethyl)-1,2,4-oxadiazol-3-yl)benzoyl)piperazine-2-carboxylate as described for example 48 step 4 (30 mg, yield 40%). $^1$H NMR (400 MHz, MeOD) δ 8.40 (m, 1H), 8.24-8.22 (m, 2H), 7.79-7.70 (m, 3H), 6.80-6.78 (m, 1H), 5.13 (m, 1H), 4.53-4.50 (m, 1H), 4.36-4.26 (m, 2H), 3.89-3.73 (m, 2H), 3.37 (m, 1H). MS (ESI) m/z: Calculated for C$_{21}$H$_{15}$F$_3$N$_6$O$_4$: 472.11. found: 473.2 (M+H)$^+$

Example 59

1,4-Bis(tert-butoxycarbonyl)piperazine-2-carboxylic acid

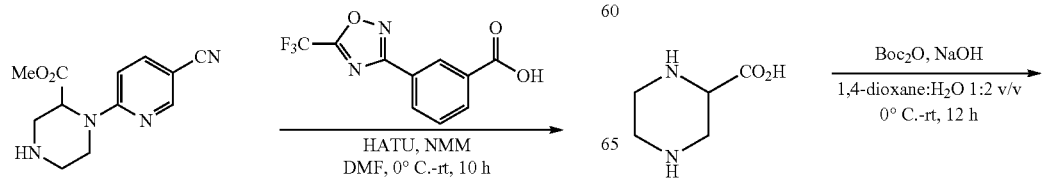

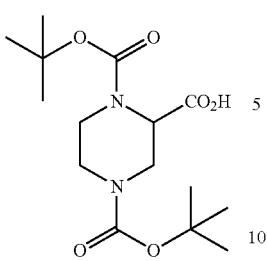

Piperazine-2-carboxylic acid dihydrochloride (5.0 g, 24.6 mmol) was added to a solution of sodium hydroxide (5.0 g, 0.125 mmol) in dioxane-H$_2$O (150 mL, 1:2 v/v). The reaction mixture was cooled to 0° C. and di-tert-butyldicarbonate (4.5 g, 66.47 mmol) was added. The reaction mixture was allowed to warm up to room temperature and stirred for 12 h. Solvent was removed under reduced pressure and crude reaction mixture was diluted with water. The aqueous layer was washed with EtOAc. The pH of the aqueous layer was adjusted to ~4 using 1.5N HCl. The organic product was extracted with EtOAc. Solvent was removed under reduced pressure and 1,4-bis(tert-butoxycarbonyl)piperazine-2-carboxylic acid (6.8 g, yield 84%) obtained as white solid was used as such for the next step. $^1$H NMR (400 MHz, DMSO-d$_6$) δ 12.94 (br s, 1H), 4.47-4.28 (m, 2H), 3.84 (m, 1H), 3.69-3.65 (m, 1H), 3.11-2.96 (m, 2H), 2.81 (m, 1H), 1.38 (s, 18H).

tert-Butyl 3-carbamoylpiperazine-1-carboxylate

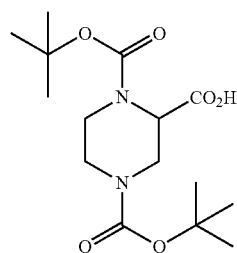

i) SOCl$_2$,
pyridine (cat.), DMF (cat.)
THF, 40° C., 4 h ii) NH$_3$ in dioxane
CH$_2$Cl$_2$,
40° C., 2 h & rt 12 h

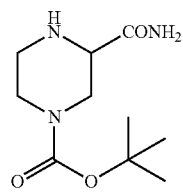

1,4-Bis(tert-butoxycarbonyl)piperazine-2-carboxylic acid (1.0 g, 3.03 mmol) was suspended in THF (5 mL) and pyridine (0.36 mL), DMF (0.1 mL) was added, followed by thionyl chloride (0.23 mL, 3.03 mmol). The reaction mixture was stirred at 40° C. for 4 h and then concentrated under reduced pressure. The crude product was dissolved in CH$_2$Cl$_2$ and transferred to a sealed tube. A saturated solution of ammonia in dioxane (10 mL) was added to the compound and the resulting reaction mixture was stirred at 40° C. for 2 h followed by room temperature stirring for 12 h. The reaction mixture was concentrated under reduced pressure and the residue was dissolved in 1.5 N HCl. The aqueous layer was washed with diethyl ether and then basified with 1N sodium hydroxide solution. The organic product was extracted with CH$_2$Cl$_2$. The combined extracts were dried over anhydrous sodium sulfate, and concentrated under reduced pressure to get tert-butyl 3-carbamoylpiperazine-1-carboxylate (340 mg, yield 49%), which was carried through without further purification. $^1$H NMR (400 MHz, CDCl$_3$) δ 6.70 (br s, 1H), 5.51 (br s, 1H), 4.06-4.03 (m, 1H), 3.77 (m, 1H), 3.37-3.33 (m, 1H), 3.11-2.95 (m, 3H), 2.81-2.76 (m, 1H), 1.47 (s, 9H).

tert-Butyl 3-carbamoyl-4-methylpiperazine-1-carboxylate

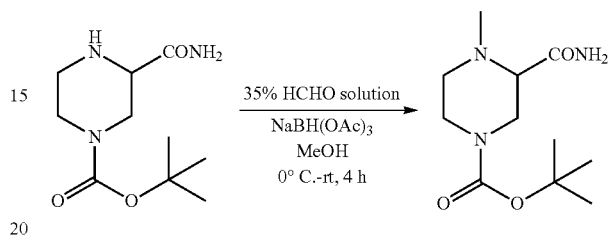

tert-Butyl 3-carbamoylpiperazine-1-carboxylate (340 mg, 1.48 mmol) was dissolved in methanol (10 mL) and cooled to 0° C. To the reaction mixture were added 35% formaline solution (185 mg) followed by sodium triacetoxyborohydride (0.95 g, 4.48 mmol). The reaction mixture was allowed to warm up to room temperature and further stirred for 4 h. The reaction mixture was quenched with 10% NaHCO$_3$ solution. The reaction mixture was diluted with EtOAc and the organic layer was separated in separatory funnel. The organic layer was dried over anhydrous Na$_2$SO$_4$ and concentrated in reduced pressure to afford tert-butyl 3-carbamoyl-4-methylpiperazine-1-carboxylate (310 mg, yield 86%). $^1$H NMR (300 MHz, CDCl$_3$) δ 6.51 (br s, 1H), 5.47 (br s, 1H), 4.21-4.15 (m, 1H), 4.03-3.97 (m, 1H), 2.93-2.81 (m, 3H), 2.64-2.59 (dd, J=10.6 Hz, 3.8 Hz, 1H), 2.31 (s, 3H), 2.24-2.19 (td, J=11.7 Hz, 3.3 Hz, 1H), 1.46 (s, 9H). MS (ESI) m/z: Calculated for C$_{11}$H$_{21}$N$_3$O$_3$: 243.16. found: 244.3 (M+H)$^+$ tert-Butyl 3-carbamothioyl-4-methylpiperazine-1-carboxylate

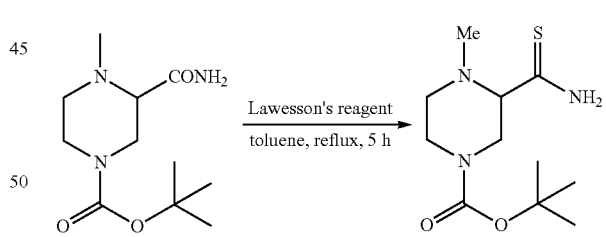

tert-Butyl 3-carbamoyl-4-methylpiperazine-1-carboxylate (400 mg, 1.64 mmol) was dissolved in toluene (20 mL) and Lawesson reagent (332 mg, 0.82 mmol) was added. The reaction mixture was heated to reflux for 5 h. Solvent was removed under reduced pressure and the crude product was purified by column chromatography (silica gel 60-120 mesh, eluent 10-15% MeOH in CHCl$_3$) to afford tert-butyl 3-carbamothioyl-4-methylpiperazine-1-carboxylate (0.17 g, yield 40%) as pale yellow liquid. $^1$H NMR (300 MHz, CDCl$_3$) δ 8.16 (br s, 1H), 7.47 (br s, 1H), 4.28-4.21 (m, 1H), 4.06-3.99 (m, 1H), 3.62 (m, 1H), 3.18-3.13 (dd, J=10.2 Hz, 4.1 Hz, 1H), 2.89-2.82 (m, 2H), 2.52-2.47 (dd, J=11.5 Hz, 3.4 Hz, 1H), 2.26 (s, 3H), 1.47 (s, 9H). MS (ESI) m/z: Calculated for C$_{11}$H$_{21}$N$_3$O$_2$S: 259.14. found: 260.2 (M+H)$^+$ tert-Butyl 4-methyl-3-(4-phenylthiazol-2-yl)piperazine-1-carboxylate

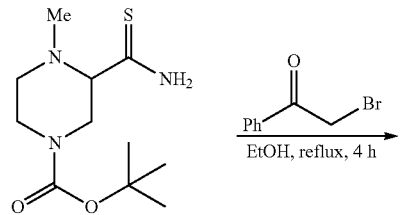

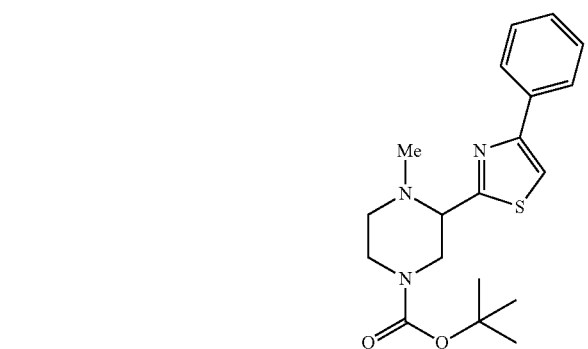

A mixture of 2-bromoacetophenone (130 mg, 0.65 mmol) and tert-butyl 3-carbamothioyl-4-methylpiperazine-1-carboxylate (170 mg, 0.65 mmol) in EtOH (15 mL) was heated to 70° C. for 4 h. The reaction mixture was cooled to room temperature and solvent was evaporated under reduced pressure. The residue was diluted with water and the organic product was extracted with EtOAc. The combined extracts were washed with H$_2$O and brine, and concentrated under reduced pressure. The crude product was purified by column chromatography (silica gel 60-120 mesh, eluent 20-25% EtOAc in petroleum ether) to afford tert-butyl 4-methyl-3-(4-phenylthiazol-2-yl)piperazine-1-carboxylate (150 mg, yield 64%). $^1$H NMR (300 MHz, CDCl$_3$) δ 7.92-7.90 (m, 2H), 7.49 (m, 1H), 7.46-7.41 (m, 2H), 7.37-7.34 (m, 1H), 4.03-3.98 (m, 1H), 3.67-3.64 (m, 2H), 3.23-3.15 (m, 2H), 2.97-2.93 (m, 2H), 2.26 (s, 3H), 1.46 (s, 9H). MS (ESI) m/z: Calculated for C$_{19}$H$_{25}$N$_3$O$_2$S: 359.17. found: 360.2 (M+H)$^+$

2-(1-Methylpiperazin-2-yl)-4-phenylthiazole

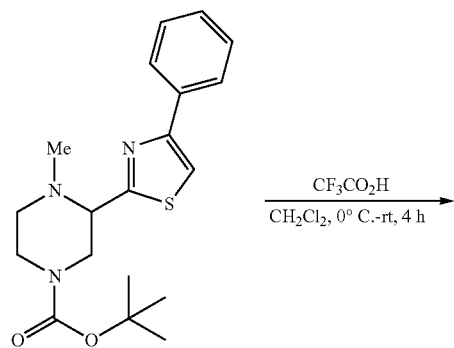

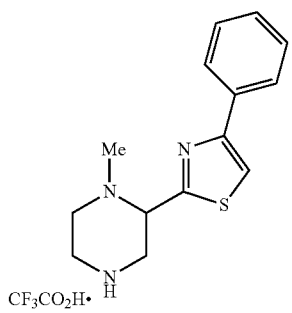

This compound was synthesized from tert-butyl 4-methyl-3-(4-phenylthiazol-2-yl)piperazine-1-carboxylate as described for example 46 step 4 (50 mg, crude) as a trifluoroacetate salt and it was taken as such for the next step. MS (ESI) m/z: Calculated for C$_{14}$H$_{17}$N$_3$S: 259.11. found: 260.2 (M+H)$^+$

(4-Methyl-3-(4-phenylthiazol-2-yl)piperazin-1-yl)(3-(5-(trifluoromethyl)-1,2,4-oxadiazol-3-yl)phenyl)methanone

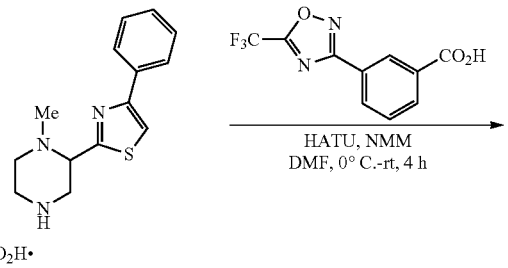

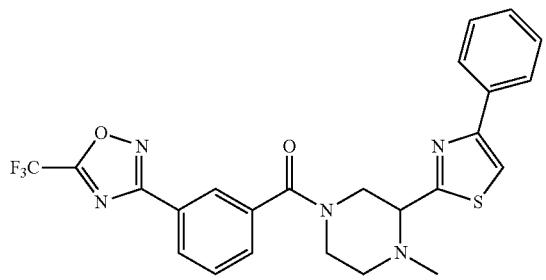

This compound was synthesized from 2-(1-methylpiperazin-2-yl)-4-phenylthiazole and 3-(5-(trifluoromethyl)-1,2,4-oxadiazol-3-yl)benzoic acid as described for example 37 step 3 (30 mg, yield 32%) as colorless viscous liquid. $^1$H NMR (400 MHz, CDCl$_3$) δ 8.17-8.16 (m, 2H), 7.93-7.79 (m, 2H), 7.64-7.62 (m, 2H), 7.48-7.32 (m, 4H), 4.78-4.53 (m, 1H), 3.85-3.69 (m, 2H), 3.49-3.30 (m, 2H), 3.17-2.98 (m, 1H), 2.53-2.40 (m, 1H), 2.32 (s, 3H). MS (ESI) m/z: Calculated for $C_{24}H_{20}F_3N_5O_2S$: 499.12. found: 500.2 (M+H)$^+$

Example 60

1-(5-Bromothiophen-2-yl)-2,2,2-trifluoroethanol

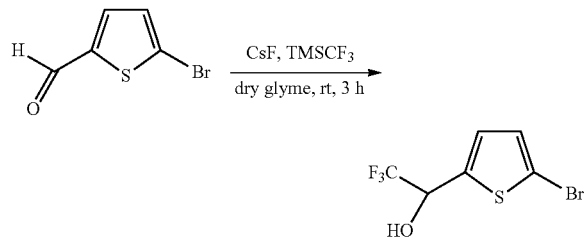

CsF (400 mg, 2.6 mmol) was added to a solution of 5-bromothiophene-2-carboxaldehyde (5.0 g, 26.17 mmol) in dry 1,2-dimethoxyethane (20 mL), followed by trifluoromethyl trimethylsilane (4.6 mL, 31.4 mmol) dropwise at 0° C. The reaction mixture was stirred at room temperature for 3 h, quenched with 1.5N HCl, and stirred for an additional 30 min. The crude product was extracted with $CH_2Cl_2$. The combined extracts were dried over anhydrous $Na_2SO_4$, and concentrated under reduced pressure. The crude product was purified by column chromatography (silica 60-120 mesh, eluant 5-10% EtOAc in petroleum ether) to get 1-(5-bromothiophen-2-yl)-2,2,2-trifluoroethanol (4 g, yield 59%). $^1$H NMR (400 MHz, CDCl$_3$) δ 7.01 (m, 1H), 6.95 (m, 1H), 5.23-5.18 (q, J=5.9 Hz, 1H), 3.07 (br s, 1H). MS (ESI) m/z: Calculated for $C_6H_4BrF_3OS$: 261.91. found: 260.7 (M−1)$^-$

1-(5-Bromothiophen-2-yl)-2.2.2-trifluoroethanone

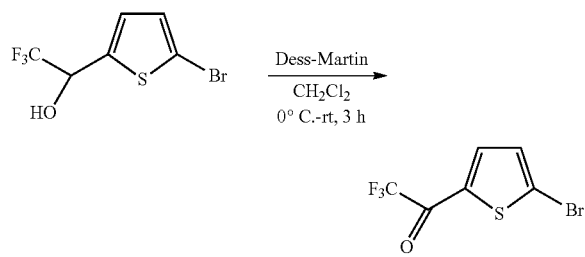

1-(5-Bromothiophen-2-yl)-2,2,2-trifluoroethanol (2 g, 7.66 mmol) was dissolved in dry $CH_2Cl_2$ (20 mL) and argon gas was purged for 10 min. Dess-Martin periodinane (3.56 g, 8.4 mmol) was added to the reaction mixture at 0° C. The reaction mixture was allowed to warm up to room temperature and further stirred for 3 h. The reaction mixture was then quenched with saturated $NaHCO_3$ solution and the organic product was extracted with EtOAc. Solvent was removed under reduced pressure and the crude product was purified by column chromatography (silica gel 60-120 mesh, eluent 10% EtOAc in petroleum ether) to afford 1-(5-bromothiophen-2-yl)-2,2,2-trifluoroethanone (0.8 g, yield 42%). $^1$H NMR (400 MHz, CDCl$_3$) δ 7.72-7.71 (m, 1H), 7.24-7.23 (d, J=4.3 Hz, 1H).

3-(5-(2,2,2-Trifluoroacetyl)thiophen-2-yl)benzoic acid

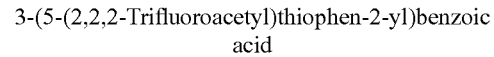

1-(5-Bromothiophen-2-yl)-2,2,2-trifluoroethanone (0.8 g, 3.09 mmol) and 3-carboxyphenylboronic acid (0.5 g, 3.01 mmol) were dissolved in DMF (10 mL) and the solution was purged with argon for 10 min. 2M aqueous solution of $Na_2CO_3$ (0.65 g, 6.17 mmol) and catalytic Pd(PPh$_3$)$_4$ (178 mg, 0.15 mmol) were added to the reaction mixture and heated to 90° C. for 10 h. The reaction mixture was cooled to room temperature, diluted with water and acidified to pH~6 with 1.5 N HCl. The crude product was extracted with EtOAc. The combined extracts were dried over anhydrous $Na_2SO_4$ and concentrated under reduced pressure. The crude product was triturated with diethyl ether to get 3-(5-(2,2,2-trifluoroacetyl)thiophen-2-yl)benzoic acid (700 mg, yield 79%). $^1$H NMR (400 MHz, DMSO-d$_6$) δ 13.35 (br s, 1H), 8.31-8.30 (m, 1H), 8.16-8.11 (m, 2H), 8.04-8.02 (d, J=7.6 Hz, 1H), 7.93-7.92 (d, J=4.3 Hz, 1H), 7.67-7.63 (t, J=7.8 Hz, 1H). MS (ESI) m/z: Calculated for $C_{13}H_7F_3O_3S$: 300.01. found: 299.0 (M−H)$^-$

6-(3-Methyl-4-(3-(5-(2,2,2-trifluoroacetyl)thiophen-2-yl)benzoyl)piperazin-1-yl)nicotinonitrile

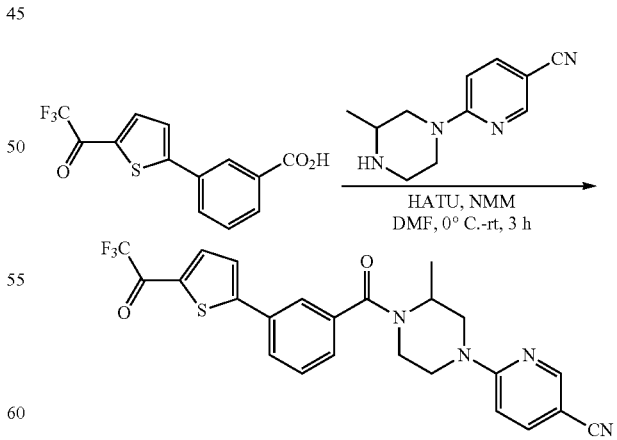

This compound was synthesized from 6-(3-methylpiperazin-1-yl)nicotinonitrile and 3-(5-(2,2,2-trifluoroacetyl) thiophen-2-yl)benzoic acid as described for example 37 step 3 (95 mg, yield 39%). $^1$H NMR (400 MHz, MeOD) δ 8.42 (d, J=1.9 Hz, 1H), 7.97-7.96 (m, 1H), 7.80-7.77 (dt, J=7.8 Hz, 1.4

Hz, 1H), 7.75-7.74 (t, J=1.5 Hz, 1H), 7.68-7.65 (dd, J=9.1 Hz, 2.4 Hz, 1H), 7.58-7.54 (t, J=7.6 Hz, 1H), 7.48-7.45 (m, 2H), 6.64-6.62 (d, J=9.1 Hz, 1H), 4.40-4.23 (m, 4H), 3.42-3.37 (m, 2H), 3.16-3.09 (m, 1H), 1.33-1.31 (m, 3H). MS (ESI) m/z: Calculated for $C_{24}H_{19}F_3N_4O_2S$: 484.12. found: 529.7 $(M+HCOOH)^-$ Example 61

6-(4-(3-(5-(2,2,2-Trifluoroacetyl)thiophen-2-yl)benzoyl)piperazin-1-yl)nicotinonitrile

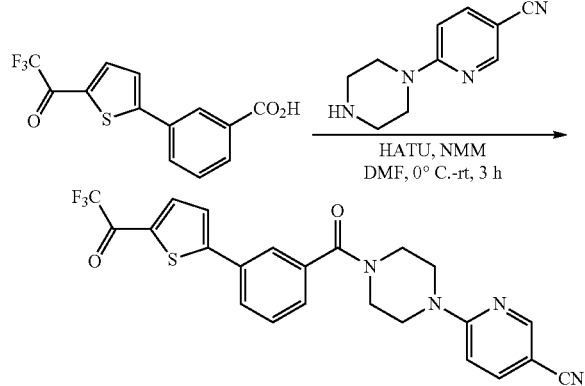

This compound was synthesized from 6-(piperazin-1-yl)nicotinonitrile and 3-(5-(2,2,2-trifluoroacetyl)thiophen-2-yl)benzoic acid as described for example 37 step 3 (60 mg, yield 32%). $^1$H NMR (400 MHz, DMSO-$d_6$) δ 8.52 (d, J=2.1 Hz, 1H), 8.19-8.17 (dd, J=4.0 Hz, J=1.5 Hz, 1H), 8.00-7.89 (m, 4H), 7.64-7.61 (m, 1H), 7.57-7.55 (m, 1H), 6.96-6.94 (t, J=9.2 Hz, 1H), 3.82-3.74 (m, 6H), 3.47 (m, 2H). MS (ESI) m/z: Calculated for $C_{23}H_{17}F_3N_4O_2S$: 470.10. found: 515.6 $(M+HCOOH)^-$ Example 62

4,4-Dimethyl-5-oxopentanenitrile

Isobutyraldehyde (12.7 mL, 138.6 mmol), a catalytic amount of hydroquinone (50 mg) and acrylonitrile (9.2 g, 173.4 mmol) were dissolved in 1,4-dioxane (50 mL), and 5% NaOH solution (9.2 mL) was added. The reaction was heated at 65° C. for 2.5 h and then stirred at room temperature for 16 h. The reaction mixture was concentrated under reduced pressure, and the organic product was extracted with $CH_2Cl_2$. The combined extracts were washed with $H_2O$ and brine, dried over anhydrous sodium sulfate, and concentrated under reduced pressure. The crude product was purified by column chromatography (silica gel 60-120 mesh, eluent 15-20% EtOAc in petroleum ether) to afford 4,4-dimethyl-5-oxopentanenitrile (11.0 g, yield 63%). $^1$H NMR (400 MHz, $CDCl_3$) δ 9.45 (s, 1H), 2.34-2.30 (m, 2H), 1.93-1.89 (m, 2H), 1.14 (s, 6H)

4-Cyano-2,2-dimethylbutanoic acid

A solution of 4,4-dimethyl-5-oxopentanenitrile (1.0 g, 7.98 mmol) in t-BuOH (2 mL) was cooled to 0° C. and 5% aqueous $NaH_2PO_4$ solution (11 mL) was added dropwise. 1M $KMnO_4$ solution (16 mL) was added dropwise to the reaction mixture at 0° C. followed by few drops of $CH_2Cl_2$ (0.5 mL). The reaction mixture was allowed to stir at 0° C. for 1 h, and quenched with sodium sulfite. 1.5N HCl was then added to adjust the pH of the solution to ~3. The organic product was extracted with EtOAc and dried over anhydrous sodium sulfate. Solvent was removed under reduced pressure to get 4-cyano-2,2-dimethylbutanoic acid (0.9 g, crude), which was carried through without further purification. $^1$H NMR (300 MHz, $CDCl_3$) δ 5.55 (br s, 1H), 2.43-2.37 (m, 2H), 1.99-1.94 (m, 2H), 1.28-1.27 (m, 6H).

6-(4-(4-Cyano-2,2-dimethylbutanoyl)-3-methylpiperazin-1-yl)nicotinonitrile

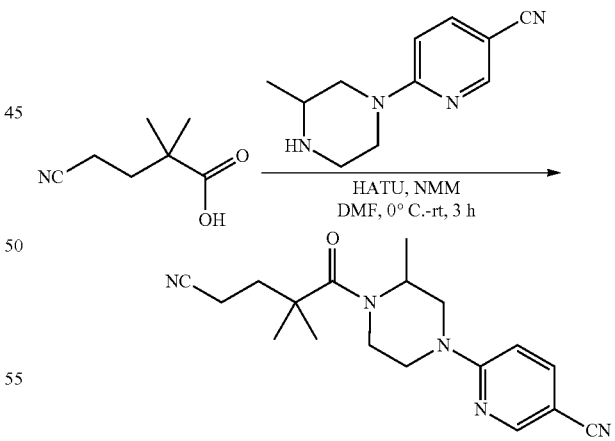

This compound was synthesized from 6-(3-methylpiperazin-1-yl)nicotinonitrile and 4-cyano-2,2-dimethylbutanoic acid as described for example 37 step 3 (400 mg, yield 17%) as yellow viscous liquid. $^1$H NMR (300 MHz, MeOD) δ 8.40-8.39 (dd, J=2.2 Hz, 0.7 Hz, 1H), 7.76-7.72 (dd, J=9.1 Hz, 2.3 Hz, 1H), 6.86-6.83 (d, J=9.0 Hz, 1H), 4.69-4.65 (m, 1H), 4.32-4.22 (m, 3H), 3.41-3.35 (m, 2H), 3.20-3.14 (m, 1H), 2.50-2.45 (m, 2H), 2.04-1.95 (m, 2H), 1.33 (s, 6H), 1.20-1.18 (m, 3H). MS (ESI) m/z: Calculated for $C_{18}H_{23}N_5O$: 325.19. found: 326.1 (M+H)$^+$ 5-(4-(5-Cyanopyridin-2-yl)-2-methylpiperazin-1-yl)-N'-hydroxy-4,4-dimethyl-5-oxopentanimidamide

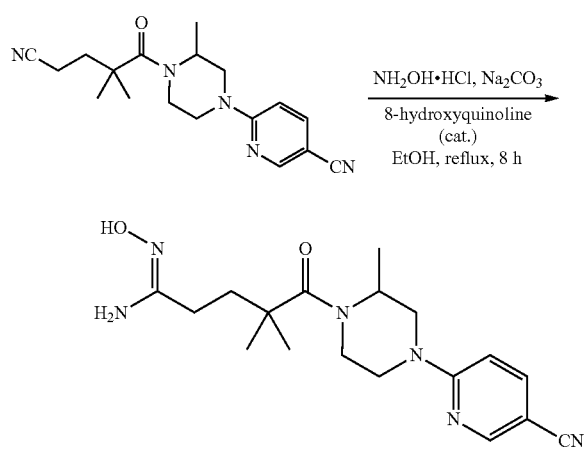

This compound was synthesized from 6-(4-(4-cyano-2,2-dimethylbutanoyl)-3-methylpiperazin-1-yl)nicotinonitrile as described in example 1 step 4 (400 mg, crude) and it was carried through without further purification. MS (ESI) m/z: Calculated for $C_{18}H_{26}N_6O_2$: 358.21. found: 359.3 (M+H)$^+$ 6-(4-(2,2-Dimethyl-4-(5-(trifluoromethyl)-1,2,4-oxadiazol-3-yl)butanoyl)-3-methylpiperazin-1-yl)nicotinonitrile

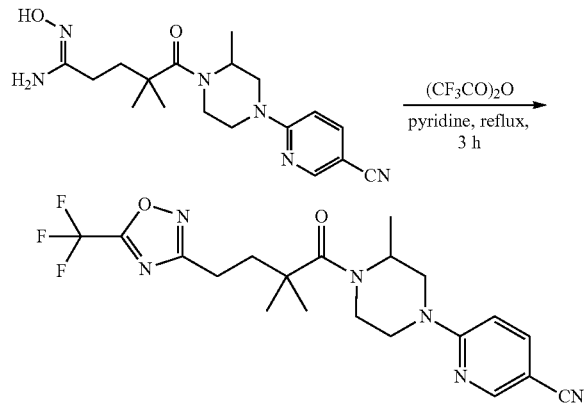

This compound was synthesized from 5-(4-(5-cyanopyridin-2-yl)-2-methylpiperazin-1-yl)-N'-hydroxy-4,4-dimethyl-5-oxopentanimidamide as described in example 1 step 5 (25 mg, yield 5%). $^1$H NMR (400 MHz, MeOD) δ 8.81 (m, 1H), 8.18-8.15 (dd, J=9.2 Hz, 2.4 Hz, 1H), 6.97-6.94 (d, J=9.0 Hz, 1H), 4.73-4.70 (m, 1H), 4.36-4.26 (m, 3H), 3.50-3.38 (m, 2H), 3.17-3.14 (m, 1H), 2.52-2.48 (m, 2H), 2.11-1.95 (m, 2H), 1.36 (m, 6H), 1.25 (m, 3H). MS (ESI) m/z: Calculated for $C_{20}H_{23}F_3N_6O_2$: 436.18. found: 437.2 (M+H)$^+$ Example 63

1-(5-Methoxypyridin-2-yl)piperazine

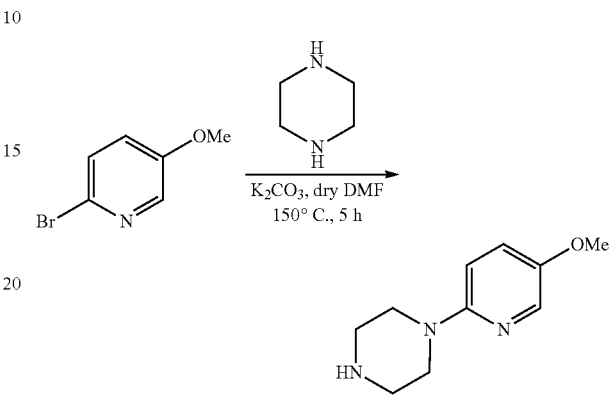

This compound was synthesized from piperazine and 2-bromo-5-methoxypyridine as described for example 39 step 1 (130 mg, yield 25%) as pale yellow liquid. $^1$H NMR (300 MHz, DMSO-d$_6$) δ 7.87-7.86 (d, J=2.9 Hz, 1H), 7.27-7.23 (dd, J=9.1 Hz, 3.2 Hz, 1H), 6.80-6.77 (d, J=9.2 Hz, 1H), 3.71 (s, 3H), 3.32-3.28 (m, 4H), 2.86-2.83 (m, 4H). MS (ESI) m/z: Calculated for $C_{10}H_{15}N_3O$: 193.12. found: 193.9 (M+H)$^+$ (4-(5-Methoxypyridin-2-yl)piperazin-1-yl)(3-(5-(trifluoromethyl)-1,2,4-oxadiazol-3-yl)phenyl)methanone

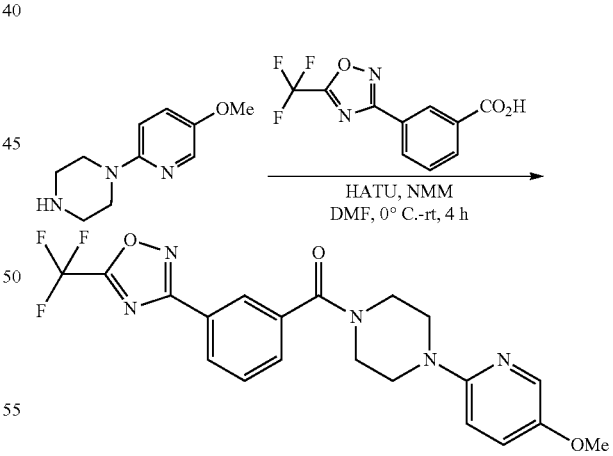

This compound was synthesized from 1-(5-methoxypyridin-2-yl)piperazine and 3-(5-(trifluoromethyl)-1,2,4-oxadiazol-3-yl)benzoic acid as described for example 37 step 3 (60 mg, yield 36%). $^1$H NMR (400 MHz, MeOD) δ 8.28-8.25 (m, 1H), 8.21-8.20 (m, 1H), 7.87-7.86 (m, 1H), 7.74-7.72 (m, 2H), 7.32-7.29 (dd, J=9.2 Hz, 3.1 Hz, 1H), 6.89-6.86 (d, J=9.3 Hz, 1H), 3.93 (m, 2H), 3.80 (s, 3H), 3.62 (m, 2H), 3.55 (m, 2H), 3.43 (m, 2H). MS (ESI) m/z: Calculated for $C_{20}H_{18}F_3N_6O_3$: 433.14. found: 434.0 (M+H)$^+$

Example 64 tert-Butyl 3-carbamoylpiperidine-1-carboxylate

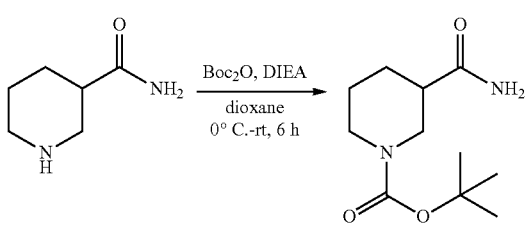 [SMILES: NC(=O)C1CCCNC1 ; CC(C)(C)OC(=O)N1CCCC(C(N)=O)C1]

This compound was synthesized from nipecotamide as described for example 59 step 1 (3.56 g, crude) and it was carried through without further purification. $^1$H NMR (400 MHz, CDCl$_3$) δ 6.27-6.55 (m, 2H), 3.86-3.57 (m, 2H), 3.31-3.20 (m, 2H), 2.37 (m, 1H), 1.88 (m, 2H), 1.46 (s, 9H).

tert-Butyl 3-carbamothioylpiperidine-1-carboxylate

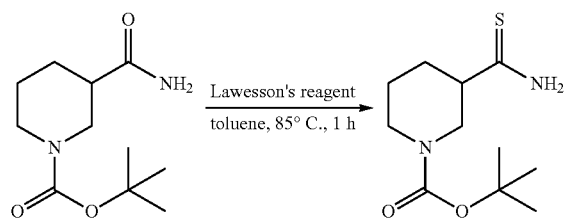 [SMILES: CC(C)(C)OC(=O)N1CCCC(C(N)=O)C1 ; CC(C)(C)OC(=O)N1CCCC(C(N)=S)C1]

This compound was synthesized from tert-butyl 3-carbamoylpiperidine-1-carboxylate as described for example 59 step 4 (890 mg, yield 33%). $^1$H NMR (300 MHz, CDCl$_3$) δ 3.94-3.87 (m, 1H), 3.76 (m, 1H), 3.36-3.30 (m, 1H), 3.06 (m, 1H), 2.73-2.67 (m, 1H), 2.14 (m, 1H), 1.98-1.95 (m, 1H), 1.66-1.65 (m, 1H), 1.53-1.52 (m, 1H), 1.46 (s, 9H). MS (ESI) m/z: Calculated for C$_{11}$H$_{20}$N$_2$O$_2$S: 244.12. found: 243.1 (M–H)$^-$ tert-Butyl 3-(4-(4-fluorophenyl)thiazol-2-yl)piperidine-1-carboxylate

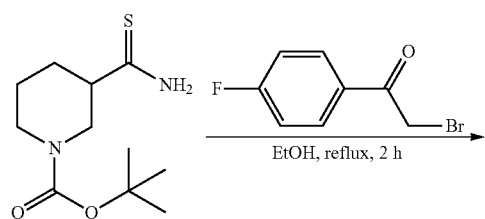

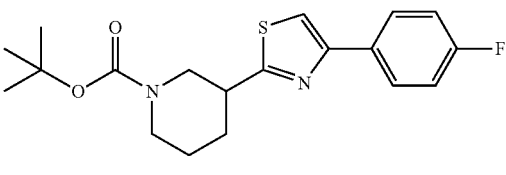

This compound was synthesized from 2-bromo-1-(4-fluorophenyl)ethanone and tert-butyl 3-carbamothioylpiperidine-1-carboxylate as described for example 59 step 5 (95 mg, yield 9%). $^1$H NMR (400 MHz, CDCl$_3$) δ 7.90-7.87 (dd, J=8.8 Hz, 5.3 Hz, 2H), 7.31 (s, 1H), 7.13-7.09 (t, J=8.8 Hz, 2H), 4.05-4.02 (m, 1H), 3.24-3.18 (m, 2H), 2.96-2.89 (m, 1H), 2.30-2.25 (m, 2H), 1.85-1.80 (m, 2H), 1.64 (m, 1H), 1.49 (s, 9H). MS (ESI) m/z: Calculated for C$_{19}$H$_{23}$FN$_2$O$_2$S: 362.15. found: 363.2 (M+H)$^+$

4-(4-Fluorophenyl)-2-(piperidin-3-yl)thiazole TFA Salt

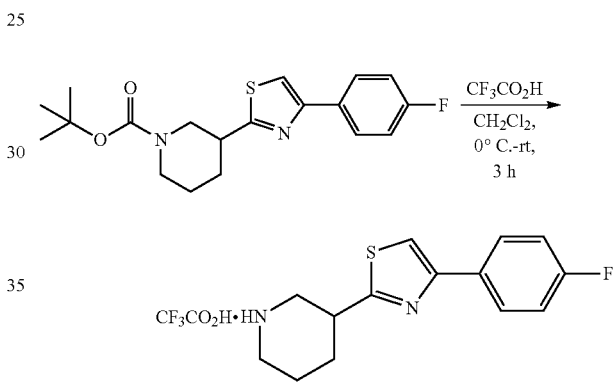

This compound was synthesized from tert-butyl 3-(4-(4-fluorophenyl)thiazol-2-yl)piperidine-1-carboxylate as described for example 46 step 4 (80 mg, crude) as a trifluoroacetate salt and it was carried through without further purification. MS (ESI) m/z: Calculated for C$_{14}$H$_{15}$FN$_2$S: 262.09. found: 263.0 (M+H)$^+$

(3-(4-(4-Fluorophenyl)thiazol-2-yl)piperidin-1-yl)(3-(5-(trifluoromethyl)-1,2,4-oxadiazol-3-yl)phenyl)methanone

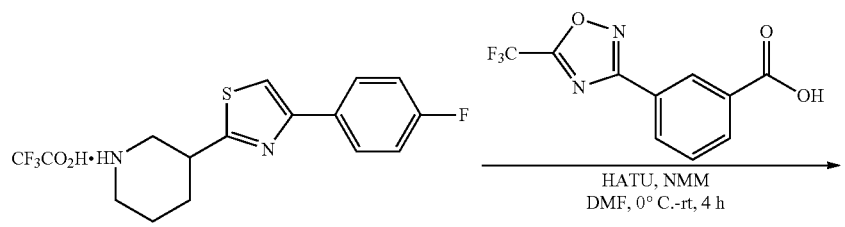

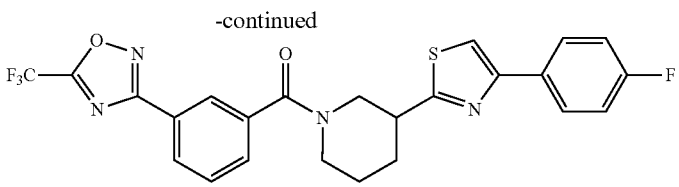

This compound was synthesized from 4-(4-fluorophenyl)-2-(piperidin-3-yl)thiazole TFA salt and 3-(5-(trifluoromethyl)-1,2,4-oxadiazol-3-yl)benzoic acid as described for example 37 step 3 (41 mg, yield 28%). $^1$H NMR (400 MHz, MeOD) δ 8.20-8.18 (m, 1H), 8.09 (m, 1H), 7.85 (m, 2H), 7.66-7.65 (d, J=4.3 Hz, 2H), 7.59 (m, 1H), 7.10-7.05 (t, J=8.4 Hz, 2H), 3.91 (m, 1H), 3.65 (m, 1H), 3.49-3.39 (m, 2H), 2.36-2.31 (m, 1H), 2.12-2.03 (m, 3H), 1.77-1.74 (m, 1H). MS (ESI) m/z: Calculated for $C_{24}H_{18}F_4N_4O_2S$: 502.11. found: 503.1 (M+H)$^+$ Example 65

4-Oxo-4-(thiophen-2-yl)butanoic acid

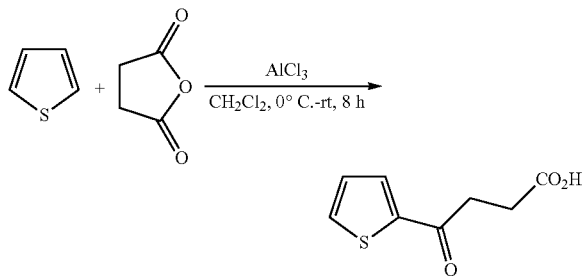

Anhydrous aluminium chloride (15.8 g, 0.12 mol) was added to a solution of succinic anhydride (11.9 g, 0.12 mol) in dry $CH_2Cl_2$ (50 Ml) and the reaction mixture was cooled to 0° C. A solution of thiophene (10.0 g, 0.12 mol) in $CH_2Cl_2$ (50 Ml) was then added dropwise maintaining the same temperature. The reaction mixture was allowed to warm up to room temperature and stirred for 8 h. The mixture was then cooled to 0° C. and the Ph was adjusted to ~3 using 6N HCl. The organic product was extracted with $CH_2Cl_2$. The combined extracts were washed with water and brine, dried over anhydrous sodium sulfate, and concentrated under reduced pressure. The crude product was purified by column chromatography (silica 60-120 mesh, eluant 5-10% MeOH in $CH_2Cl_2$), to get 4-oxo-4-(thiophen-2-yl)butanoic acid (8.3 g, yield 38%). $^1$H NMR (400 MHz, DMSO-d$_6$) δ 12.18 (s, 1H), 8.00-7.98 (m, 2H), 7.26-7.23 (m, 1H), 3.21-3.18 (m, 2H), 2.58-2.55 (m, 2H). MS (ESI) m/z: Calculated for $C_8H_8O_3S$: 184.02. found: 184.9 (M+H)$^+$ 4-(Thiophen-2-yl)butanoic acid

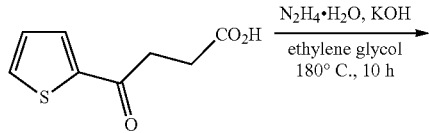

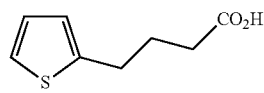

Hydrazine hydrate (99%) (2.2 Ml, 45.9 mmol) and KOH pellets (2.37 g, 42.4 mmol) were added to a solution of 4-oxo-4-(thiophen-2-yl)butanoic acid (2.3 g, 12.48 mmol) in ethylene glycol (30 Ml), and the reaction mixture was heated to 180° C. for 10 h. The reaction mixture was cooled to room temperature and diluted with water. The aqueous layer was washed with diethyl ether, acidified with 6N HCl and then extracted with diethyl ether. The organic layer was then dried over anhydrous sodium sulfate and concentrated under reduced pressure. The crude product was purified by column chromatography (silica 60-120 mesh, eluant 2% MeOH in $CH_2Cl_2$), to get 4-(thiophen-2-yl)butanoic acid (1.8 g, yield 85%). $^1$H NMR (300 MHz, DMSO-d$_6$) δ 12.06 (s, 1H), 7.31-7.29 (m, 1H), 6.94-6.91 (m, 1H), 6.84-6.82 (m, 1H), 2.82-2.77 (t, J=7.7 Hz, 2H), 2.27-2.22 (t, J=7.3 Hz, 2H), 1.86-1.76 (m, 2H). MS (ESI) m/z: Calculated for $C_8H_{10}O_2S$: 170.04. found: 170.8 (M+H)$^+$ Methyl 4-(thiophen-2-yl)butanoate

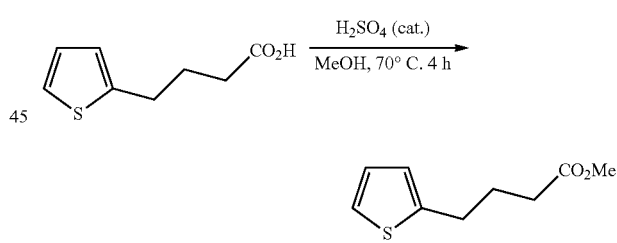

A catalytic amount of conc. $H_2SO_4$ (1 Ml) was added to a solution of 4-(thiophen-2-yl)butanoic acid (1.2 g, 7.05 mmol) in dry MeOH (30 Ml) at 0° C. The resulting reaction mixture was heated to 70° C. for 4 h, cooled to room temperature, and concentrated under reduced pressure. The mixture was then diluted with water and extracted with EtOAc. The combined extracts were washed with water and brine, dried over anhydrous sodium sulfate, and concentrated under reduced pressure. The crude product was purified by column chromatography (silica 60-120 mesh, eluant 5-10% EtOAc in petroleum ether) to get methyl 4-(thiophen-2-yl)butanoate (1.1 g, yield 89%). $^1$H NMR (300 MHz, CDCl$_3$) δ 7.14-7.12 (m, 1H), 6.94-6.91 (m, 1H), 6.81-6.80 (m, 1H), 3.68 (s, 3H), 2.91-2.86 (t, J=7.5 Hz, 2H), 2.41-2.36 (m, 2H), 2.07-1.97 (m, 2H).

Methyl 4-(5-formylthiophen-2-yl)butanoate

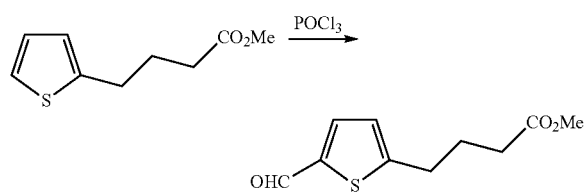

Freshly distilled POCl₃ (0.4 Ml, 4.12 mmol) was added to a solution of methyl 4-(thiophen-2-yl)butanoate (1.1 g, 5.97 mmol) in dry DMF (0.7 Ml) at 0° C. The reaction mixture was further heated to 110° C. for 1.5 h, then cooled to room temperature and quenched with ice water. The Ph of the reaction mixture was adjusted to ~7 using aqueous $Na_2CO_3$ solution. The organic product was extracted with diethyl ether and the combined extracts were washed with water and brine, dried over anhydrous sodium sulfate and concentrated under reduced pressure to get methyl 4-(5-formylthiophen-2-yl)butanoate (1.0 g, yield 83%), which was carried through without further purification. ¹H NMR (300 MHz, CDCl₃) δ 9.82 (s, 1H), 7.63-7.61 (d, J=3.7 Hz, 1H), 6.94-6.92 (m, 1H), 3.68 (s, 3H), 2.96-2.91 (t, J=7.5 Hz, 2H), 2.42-2.37 (m, 2H), 2.09-1.99 (m, 2H). MS (ESI) m/z: Calculated for $C_{10}H_{12}O_3S$: 212.05. found: 212.9 (M+H)⁺

4-(5-(2,2,2-Trifluoro-1-hydroxyethyl)thiophen-2-yl) butanoate

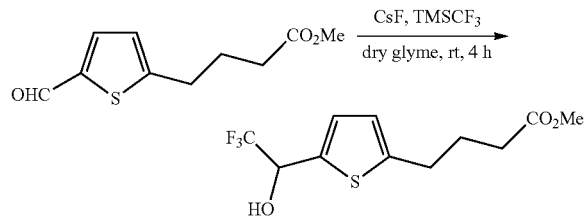

CsF (70 mg, 0.47 mmol) was added to a solution of methyl 4-(5-formylthiophen-2-yl)butanoate (1.0 g, 4.71 mmol) in dry 1,2-dimethoxyethane (5 Ml) at 0° C., followed by trifluoromethyl trimethylsilane (0.8 Ml, 5.65 mmol) dropwise. The reaction mixture was stirred at room temperature for 4 h, quenched with 3N HCl, and stirred for further 30 min. The crude product was extracted with EtOAc. The combined extracts were washed with brine, dried over anhydrous $Na_2SO_4$, and concentrated under reduced pressure. The crude product was purified by column chromatography (silica 60-120 mesh, eluant 10% EtOAc in petroleum ether) to get methyl 4-(5-(2,2,2-trifluoro-1-hydroxyethyl)thiophen-2-yl)butanoate (0.63 g, yield 47%) as yellow liquid. ¹H NMR (400 MHz, CDCl₃) δ 7.02-7.01 (d, J=3.5 Hz, 1H), 6.74-6.73 (m, 1H), 5.23-5.17 (m, 1H), 3.68 (s, 3H), 2.88-2.84 (t, J=7.5 Hz, 2H), 2.81-2.80 (d, J=5.3 Hz, 1H), 2.40-2.36 (t, J=7.5 Hz, 2H), 2.05-1.97 (m, 2H).

Methyl 4-(5-(2,2,2-trifluoroacetyl)thiophen-2-yl) butanoate

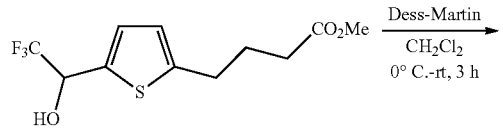

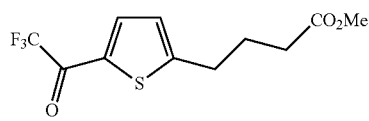

This compound was synthesized from methyl 4-(5-(2,2,2-trifluoro-1-hydroxyethyl)thiophen-2-yl)butanoate as described in example 9 step 4 (550 mg, yield 79%). ¹H NMR (300 MHz, CDCl₃) δ 7.83-7.81 (m, 1H), 6.98-6.97 (m, 1H), 3.70 (s, 3H), 3.00-2.95 (t, J=7.6 Hz, 2H), 2.43-2.39 (m, 2H), 2.12-2.02 (m, 2H). MS (ESI) m/z: Calculated for $C_{11}H_{11}F_3O_3S$: 280.04. found: 279.6 (M-H)⁻

4-(5-(2,2,2-Trifluoroacetyl)thiophen-2-yl)butanoic acid

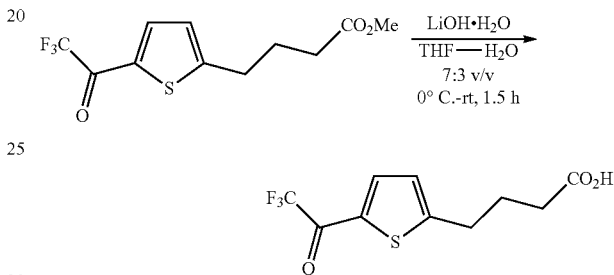

Methyl 4-(5-(2,2,2-trifluoroacetyl)thiophen-2-yl)butanoate (250 mg, 0.89 mmol) was dissolved in THF-H₂O (15 Ml, 2:1 v/v) and cooled to 0° C. LiOH.H₂O (35 mg, 0.89 mmol) was added and the reaction mixture was allowed to warm up to room temperature and stirred for 1.5 h. Solvent was removed under reduced pressure and the aqueous layer was washed with EtOAc. The Ph of the aqueous layer was adjusted to 2-3 using 1.5N HCl. The product was extracted with EtOAc. The combined extracts were dried over anhydrous sodium sulfate and concentrated under reduced pressure to get 4-(5-(2,2,2-trifluoroacetyl)thiophen-2-yl)butanoic acid (220 mg, crude), which was carried through without further purification. ¹H NMR (300 MHz, DMSO-d₆) δ 12.13 (br s, 1H), 8.00-7.98 (m, 1H), 7.21-7.19 (d, J=3.9 Hz, 1H), 2.98-2.93 (t, J=7.7 Hz, 2H), 2.31-2.26 (m, 2H), 1.93-1.83 (m, 2H). MS (ESI) m/z: Calculated for $C_{10}H_9F_3O_3S$: 266.02. found: 264.8 (M-H)⁻

6-(3-Methyl-4-(4-(5-(2,2,2-trifluoroacetyl)thiophen-2-yl)butanoyl)piperazin-1-yl)nicotinonitrile

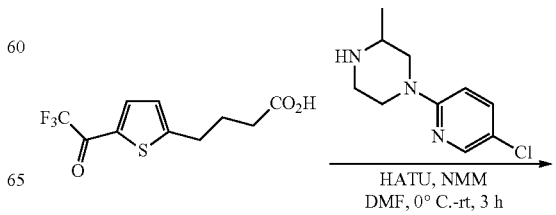

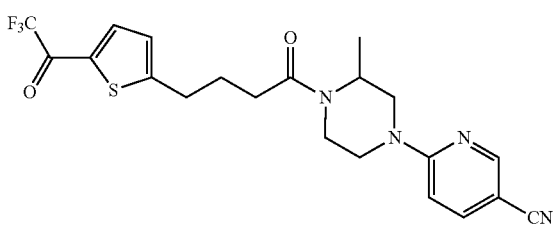

This compound was synthesized from 6-(3-methylpiperazin-1-yl)nicotinonitrile and 4-(5-(2,2,2-trifluoroacetyl)thiophen-2-yl)butanoic acid as described for example 37 step 3 (40 mg, yield 16%). $^1$H NMR (400 MHz, DMSO-d$_6$, 80° C.) δ 8.45-8.44 (m, 1H), 7.98-7.96 (m, 1H), 7.82-7.79 (dd, J=9.1 Hz, 2.4 Hz, 1H), 7.20-7.19 (d, J=4.0 Hz, 1H), 6.89-6.87 (d, J=9.1 Hz, 1H), 4.45 (m, 1H), 4.20-4.14 (m, 2H), 3.98 (m, 1H), 3.39-3.34 (dd, J=13.4 Hz, 4.0 Hz, 1H), 3.27 (m, 1H), 3.17-3.11 (m, 1H), 2.99 (m, 1H), 2.89 (m, 1H), 2.46-2.36 (m, 2H), 2.01-1.94 (m, 2H), 1.11-1.09 (d, J=6.7 Hz, 3H). MS (ESI) m/z: Calculated for C$_{21}$H$_{21}$F$_3$N$_4$O$_2$S: 450.13. found: 449.2 (M–H)$^-$

Example 66

(4-(2,3-Dihydro-1H-inden-2-yl)piperazin-1-yl)(3-(5-(trifluoromethyl)-1,2,4-oxadiazol-3-yl)phenyl)methanone

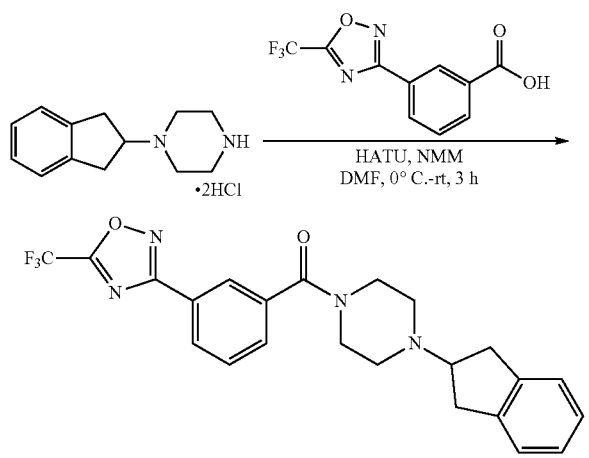

This compound was synthesized from 1-(2,3-dihydro-1H-inden-2-yl)piperazine dihydrochloride and 3-(5-(trifluoromethyl)-1,2,4-oxadiazol-3-yl)benzoic acid as described for example 37 step 3 (100 mg, yield 39%). $^1$H NMR (400 MHz, MeOD) δ 8.27-8.24 (m, 1H), 8.18 (m, 1H), 7.72-7.71 (m, 2H), 7.20-7.16 (m, 2H), 7.14-7.11 (m, 2H), 3.87 (m, 2H), 3.55 (m, 2H), 3.26-3.20 (m, 1H), 3.17-3.12 (m, 2H), 2.93-2.87 (dd, J=15.1 Hz, 8.5 Hz, 2H), 2.73 (m, 2H), 2.60 (m, 2H). MS (ESI) m/z: Calculated for C$_{23}$H$_{21}$F$_3$N$_4$O$_2$: 442.16. found: 443.2 (M+H)$^+$

Example 67

(4-(1H-Benzo[d]imidazol-2-yl)piperazin-1-yl)(3-(5-(trifluoromethyl)-1,2,4-oxadiazol-3-yl)phenyl)methanone

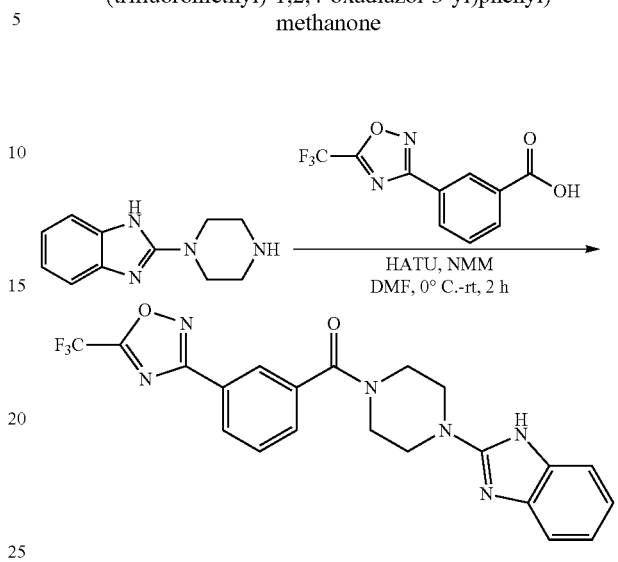

This compound was synthesized from 2-(piperazin-1-yl)-1H-benzo[d]imidazole and 3-(5-(trifluoromethyl)-1,2,4-oxadiazol-3-yl)benzoic acid as described for example 37 step 3 (100 mg, yield 23%). $^1$H NMR (400 MHz, DMSO-d$_6$) δ 11.49 (br s, 1H), 8.19-8.17 (d, J=8.5 Hz, 1H), 8.11 (s, 1H), 7.76-7.72 (m, 2H), 7.21 (m, 2H), 6.94 (m, 2H), 3.80 (m, 2H), 3.63-3.52 (m, 6H). MS (ESI) m/z: Calculated for C$_{21}$H$_{17}$F$_3$N$_6$O$_2$: 442.14. found: 441.4 (M–H)$^-$

Example 68

2-Amino-1-(4-fluorophenyl)ethanone hydrochloride

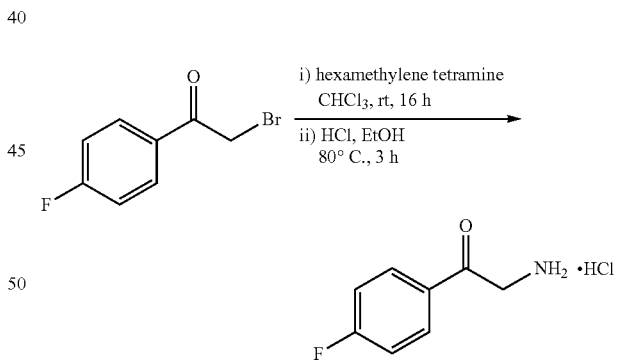

Hexamethylenetetramine (1.42 g, 10.1 mmol) was added dropwise over 30 min to a solution of 2-bromo-4-fluoroacetophenone (2.0 g, 9.2 mmol) in dry CHCl$_3$ (40 mL) at 0° C. The reaction mixture was allowed to warm up to room temperature and stirred for 16 h. After completion of the reaction the solid precipitate formed was collected by filtration and washed with CHCl$_3$. The solid obtained was suspended in EtOH (40 mL) and conc. HCl (4 mL) was added. The mixture was heated to 80° C. for 3 h, cooled to room temperature, and the solid formed was filtered off. The clear filtrate was concentrated to afford 2-amino-1-(4-fluorophenyl)ethanone hydrochloride (1.5 g, crude) as yellow solid. MS (ESI) m/z: Calculated for C$_8$H$_8$FNO: 153.06. found: 153.9 (M+H)$^+$

101 tert-Butyl 3-((2-(4-fluorophenyl)-2-oxoethyl)carbamoyl)piperidine-1-carboxylate

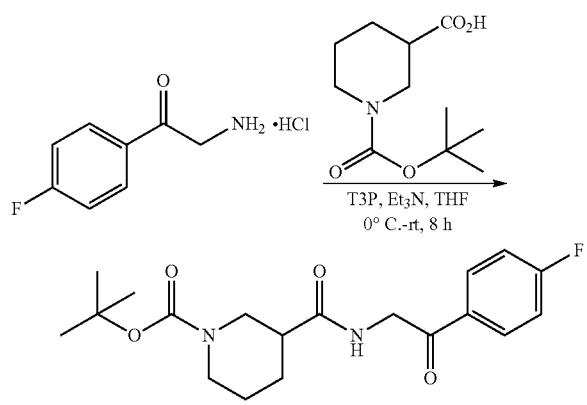

Triethyl amine (1.52 mL, 10.4 mmol) was added dropwise to a solution of piperidine-1,3-dicarboxylic acid 1-tert-butyl ester (600 mg, 2.6 mmol) and 2-amino-1-(4-fluorophenyl)ethanone hydrochloride (500 mg, 2.6 mmol) in THF (12 mL), followed by T3P (propylphosphonic anhydride) (1.7 mL, 2.6 mmol, 50% in EtOAc) at 0° C. The reaction mixture was stirred 30 min, allowed to warm up to room temperature and stirred for an additional 8 h. The reaction mixture was then concentrated under reduced pressure and diluted with EtOAc. The organic layer was washed with aqueous 10% NaHCO$_3$, water and brine, dried over anhydrous sodium sulfate, and concentrated under reduced pressure. The crude product was purified by purified by column chromatography (silica gel 60-120 mesh, eluent 20-25% EtOAc in petroleum ether) to afford tert-butyl 3-((2-(4-fluorophenyl)-2-oxoethyl)carbamoyl)piperidine-1-carboxylate (500 mg, yield 52%). $^1$H NMR (400 MHz, DMSO-d$_6$) δ 8.33-8.30 (t, J=5.6 Hz, 1H), 8.08-8.04 (dd, J=8.5 Hz, 5.8 Hz, 2H), 7.39-7.35 (t, J=8.7 Hz, 2H), 4.57-4.56 (m, 2H), 3.99-3.86 (m, 2H), 2.39-2.32 (m, 1H), 1.87-1.84 (m, 1H), 1.66-1.62 (m, 1H), 1.56-1.46 (m, 2H), 1.40 (s, 9H), 1.32-1.23 (m, 2H).

tert-Butyl 3-(5-(4-fluorophenyl)oxazol-2-yl)piperidine-1-carboxylate

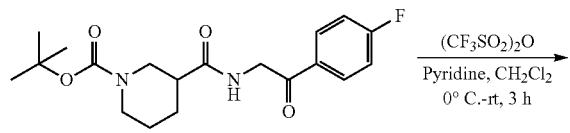

102

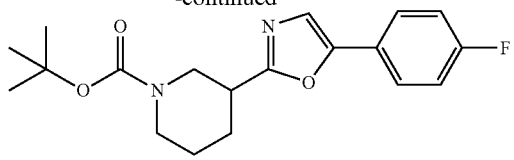

Dry pyridine (0.24 mL, 2.74 mmol) was added dropwise to a solution of tert-butyl 3-((2-(4-fluorophenyl)-2-oxoethyl)carbamoyl)piperidine-1-carboxylate (500 mg, 1.37 mmol) in dry CH$_2$Cl$_2$ (12 mL) at 0° C., followed by trifluoromethanesulfonic anhydride (0.5 mL, 2.74 mmol). The reaction mixture was allowed to warm up to room temperature and stirred for 3 h. The reaction mixture was diluted with CH$_2$Cl$_2$ and the organic layer was washed with water and brine, dried over anhydrous sodium sulfate, and concentrated under reduced pressure. The crude product was purified by purified by column chromatography (silica gel 60-120 mesh, eluent 12-15% EtOAc in petroleum ether) to afford tert-butyl 3-(5-(4-fluorophenyl)oxazol-2-yl)piperidine-1-carboxylate (150 mg, yield 32%). $^1$H NMR (400 MHz, DMSO-d$_6$) δ 7.75-7.72 (dd, J=9.0 Hz, 5.3 Hz, 2H), 7.55 (s, 1H), 7.33-7.29 (t, J=8.8 Hz, 2H), 3.99-3.90 (m, 1H), 3.69-3.60 (m, 1H), 3.02 (m, 1H), 2.12-2.07 (m, 1H), 1.82-1.76 (m, 2H), 1.64-1.57 (m, 1H), 1.51-1.42 (m, 2H), 1.35 (s, 9H). MS (ESI) m/z: Calculated for C$_{19}$H$_{23}$FN$_2$O$_3$: 346.17. found: 347.2 (M+H)$^+$ 5-(4-Fluorophenyl)-2-(piperidin-3-yl)oxazole TFA Salt

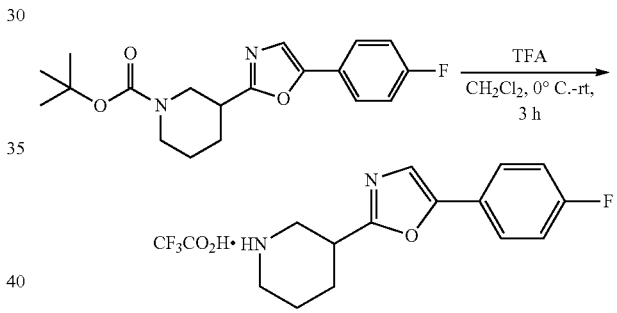

This compound was synthesized from tert-butyl 3-(5-(4-fluorophenyl)oxazol-2-yl)piperidine-1-carboxylate as described for example 46 step 4 (150 mg, crude) as a trifluoroacetate salt and it was carried through without further purification. MS (ESI) m/z: Calculated for C$_{14}$H$_{16}$FN$_2$O: 246.12. found: 247.0 (M+H)$^+$ (3-(5-(4-Fluorophenyl)oxazol-2-yl)piperidin-1-yl)(3-(5-(trifluoromethyl)-1,2,4-oxadiazol-3-yl)phenyl)methanone

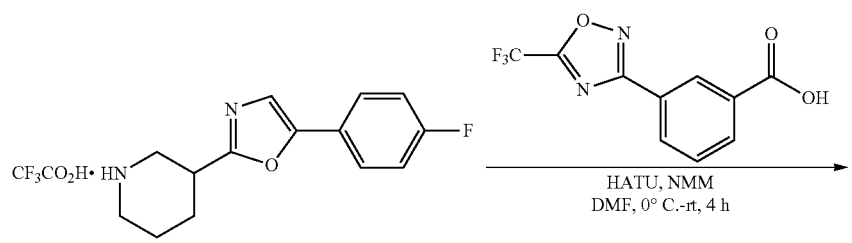

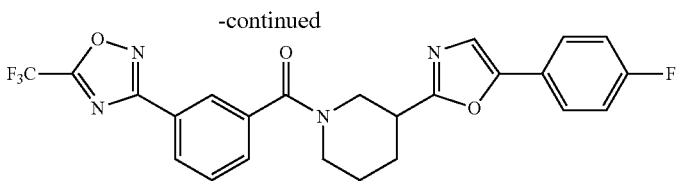

This compound was synthesized from 5-(4-fluorophenyl)-2-(piperidin-3-yl)oxazole TFA salt and 3-(5-(trifluoromethyl)-1,2,4-oxadiazol-3-yl)benzoic acid as described for example 37 step 3 (25 mg, yield 9%). $^1$H NMR (400 MHz, DMSO-$d_6$, 80° C.) δ 8.11-8.09 (m, 1H), 7.97 (s, 1H), 7.69-7.61 (m, 4H), 7.45 (s, 1H), 7.24-7.20 (t, J=8.8 Hz, 2H), 4.16 (m, 1H), 3.71-3.67 (m, 1H), 3.62-3.56 (dd, J=12.9 Hz, 8.4 Hz, 1H), 3.47-3.41 (m, 1H), 3.24-3.18 (m, 1H), 2.22-2.17 (m, 1H), 2.03-1.94 (m, 1H), 1.89-1.84 (m, 1H), 1.69-1.59 (m, 1H). MS (ESI) m/z: Calculated for $C_{24}H_{18}F_4N_4O_3$: 486.13. found: 487.3 (M+H)$^+$ Example 69

(4-(3-Methoxyphenyl)piperazin-1-yl)(3-(5-(trifluoromethyl)-1,2,4-oxadiazol-3-yl)phenyl)methanone

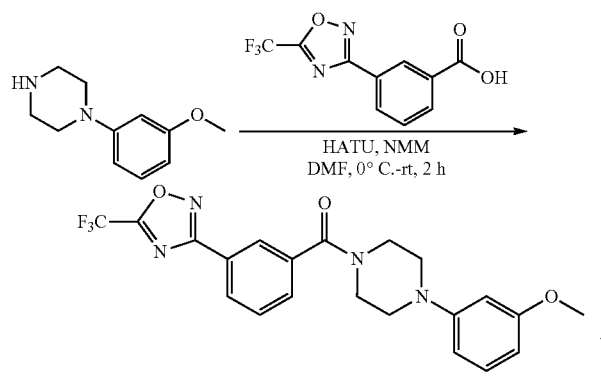

This compound was synthesized from 1-(3-methoxyphenyl)piperazine and 3-(5-(trifluoromethyl)-1,2,4-oxadiazol-3-yl)benzoic acid as described for example 37 step 3 (110 mg, yield 49%). $^1$H NMR (400 MHz, CDCl$_3$) δ 8.22-8.20 (m, 2H), 7.67-7.60 (m, 2H), 7.23-7.19 (m, 1H), 6.57-6.54 (m, 1H), 6.49-6.48 (m, 2H), 3.98 (m, 2H), 3.80 (s, 3H), 3.61 (m, 2H), 3.30-3.16 (m, 4H). MS (ESI) m/z: Calculated for $C_{21}H_{18}F_3N_4O_3$: 432.14. found: 433.2 (M+H)$^+$ Example 70 tert-Butyl 4-(pyrimidin-5-yl)piperazine-1-carboxylate

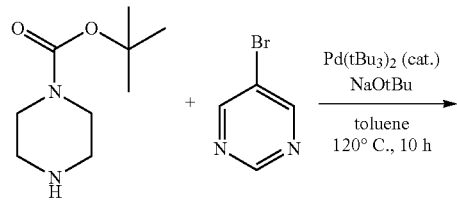

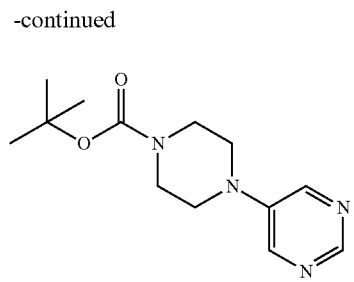

5-Bromo pyrimidine (1.0 g, 6.29 mmol) and 1-Boc-piperazine (1.17 g, 6.28 mmol) were dissolved in toluene (20 mL) and the solution was purged with argon for 10 min. Sodium tert-butoxide (816 mg, 8.49 mmol) and catalytic Pd(P$^t$Bu$_3$)$_2$ (320 mg, 0.63 mmol) were added and the reaction mixture was heated to 120° C. for 10 h. The reaction mixture was cooled to room temperature, diluted with EtOAc and filtered through Celite. The organic layer was washed with water and brine, dried over anhydrous Na$_2$SO$_4$, and concentrated under reduced pressure. The crude product was purified by column chromatography (silica 60-120 mesh, eluent 80% EtOAc in petroleum ether) to get tert-butyl 4-(pyrimidin-5-yl)piperazine-1-carboxylate (700 mg, yield 42%). $^1$H NMR (300 MHz, MeOD) δ 8.57 (s, 1H), 8.48 (m, 2H), 3.61-3.58 (m, 4H), 3.30-3.27 (m, 4H), 1.47 (s, 9H). MS (ESI) m/z: Calculated for $C_{13}H_{20}N_4O_2$: 264.16. found: 265.0 (M+H)$^+$ 5-(piperazin-1-yl)pyrimidine TFA Salt

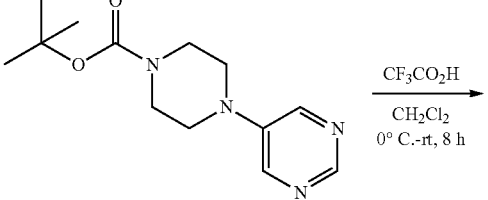

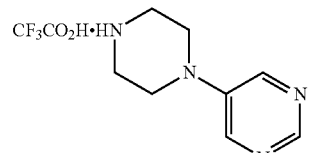

This compound was synthesized from tert-butyl 4-(pyrimidin-5-yl)piperazine-1-carboxylate as described for example 46 step 4 (500 mg, crude) as a trifluoroacetate salt and it was carried through without further purification. MS (ESI) m/z: Calculated for $C_8H_{12}N_4$: 164.11. found: 165.0 (M+H)$^+$ (4-(Pyrimidin-5-yl)piperazin-1-yl)(3-(5-(trifluoromethyl)-1,2,4-oxadiazol-3-yl)phenyl)methanone

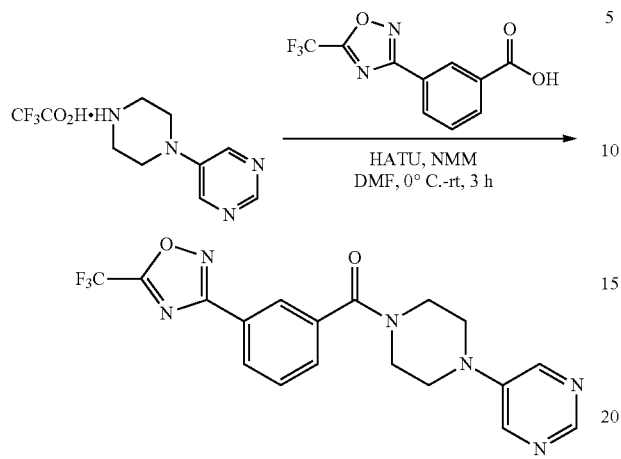

This compound was synthesized from 5-(piperazin-1-yl)pyrimidine TFA salt and 3-(5-(trifluoromethyl)-1,2,4-oxadiazol-3-yl)benzoic acid as described for example 37 step 3 (50 mg, yield 32%). $^1$H NMR (400 MHz, MeOD) δ 8.61 (s, 1H), 8.52 (s, 2H), 8.29-8.26 (dt, J=6.7 Hz, 1.9 Hz, 1H), 8.23 (m, 1H), 7.76-7.71 (m, 2H), 3.99-3.83 (m, 2H), 3.69 (m, 2H), 3.49 (m, 2H), 3.44-3.36 (m, 2H). MS (ESI) m/z: Calculated for $C_{18}H_{15}F_3N_6O_2$: 404.12. found: 405.2 (M+H)$^+$ Example 71

2-(4-(3-(5-(Trifluoromethyl)-1,2,4-oxadiazol-3-yl)benzoyl)piperazin-1-yl)nicotinonitrile

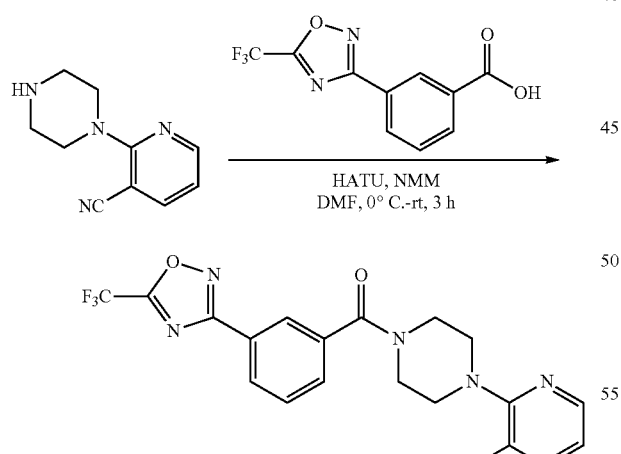

This compound was synthesized from 2-(piperazin-1-yl)nicotinonitrile and 3-(5-(trifluoromethyl)-1,2,4-oxadiazol-3-yl)benzoic acid as described for example 37 step 3 (135 mg, yield 81%). $^1$H NMR (400 MHz, DMSO-d$_6$) δ 8.45-8.43 (dd, J=4.8 Hz, 1.8 Hz, 1H), 8.18-8.15 (dd, J=7.3 Hz, 1.6 Hz, 1H), 8.13-8.10 (m, 2H), 7.78-7.71 (m, 2H), 6.99-6.96 (dd, J=7.5 Hz, 4.8 Hz, 1H), 3.81-3.75 (m, 4H), 3.63-3.54 (m, 4H). MS (ESI) m/z: Calculated for $C_{20}H_{15}F_3N_6O_2$: 428.12. found: 429.1 (M+H)$^+$ Example 72 tert-Butyl 4-(4-chloropyrimidin-2-yl)piperazine-1-carboxylate

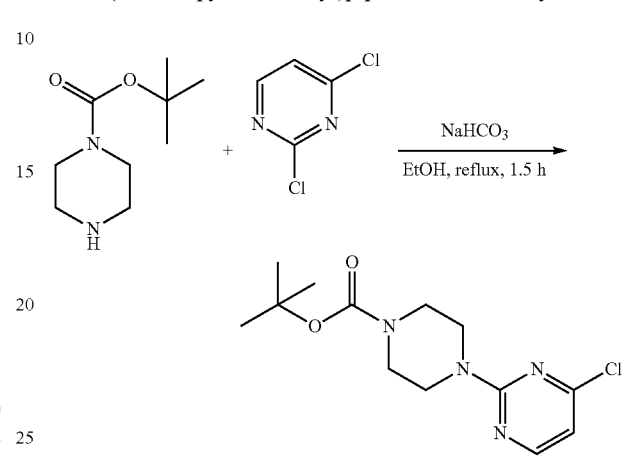

2,4-Dichloropyrimidine (5.0 g, 33.56 mmol) and 1-Boc-piperazine (6.25 g, 33.56 mmol) were dissolved in EtOH (40 mL). NaHCO$_3$ (5.07 g, 60.41 mmol) was added and the reaction mixture was heated to reflux for 1.5 h, cooled to room temperature, and concentrated under reduced pressure. The mixture was diluted with CH$_2$Cl$_2$ and the organic layer was washed with brine, dried over anhydrous sodium sulfate, and concentrated under reduced pressure. The crude product was purified by column chromatography (silica 60-120 mesh, eluent 5% MeOH in CH$_2$Cl$_2$) to get tert-butyl 4-(4-chloropyrimidin-2-yl)piperazine-1-carboxylate (3.5 g, yield 35%). $^1$H NMR (400 MHz, CDCl$_3$) δ 8.07-8.05 (d, J=6.0 Hz, 1H), 6.40-6.39 (d, J=6.3 Hz, 1H), 3.65 (m, 4H), 3.54-3.51 (m, 4H), 1.48 (s, 9H). MS (ESI) m/z: Calculated for $C_{13}H_{19}ClN_4O_2$: 298.12. found: 299.2 (M+H)$^+$ tert-Butyl 4-(4-phenylpyrimidin-2-yl)piperazine-1-carboxylate

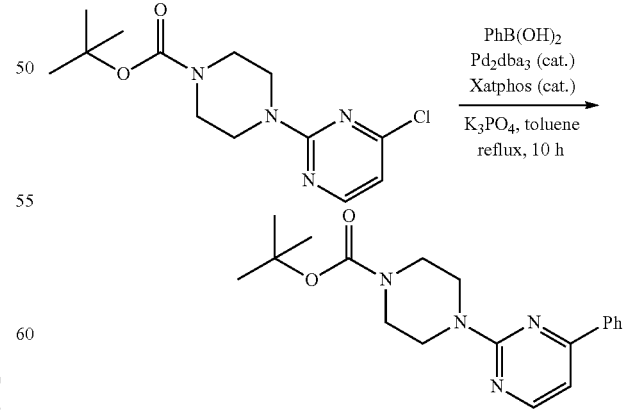

tert-Butyl 4-(4-chloropyrimidin-2-yl)piperazine-1-carboxylate (300 mg, 1.0 mmol) and phenylboronic acid (183 mg, 1.5 mmol) were dissolved in toluene (10 mL) and the solution was purged with argon for 10 min. Potassium phosphate (426 mg, 2.0 mmol) was added to the reaction mixture, followed by a catalytic amount of Pd$_2$(dba)$_3$ (9 mg, 0.01 mmol) and 4,5-bis(diphenylphosphino)-9,9-dimethylxanthene (23 mg, 0.04 mmol). The reaction mixture was then heated to 115° C. for 10 h, cooled to room temperature, diluted with EtOAc, and filtered through Celite. The organic layer was washed with water and brine, dried over anhydrous Na$_2$SO$_4$, and concentrated under reduced pressure. The crude product was purified by column chromatography (silica 60-120 mesh, eluent 30% EtOAc in petroleum ether) to get tert-butyl 4-(4-phenylpyrimidin-2-yl)piperazine-1-carboxylate (250 mg, yield 73%). $^1$H NMR (300 MHz, MeOD) δ 8.28-8.23 (m, 3H), 7.46-7.43 (m, 3H), 7.34 (m, 1H), 3.80-3.77 (m, 4H), 3.56-3.53 (m, 4H), 1.48 (s, 9H). MS (ESI) m/z: Calculated for C$_{19}$H$_{24}$N$_4$O$_2$: 340.19. found: 341.2 (M+H)$^+$ 4-Phenyl-2-(piperazin-1-yl)pyrimidine TFA Salt

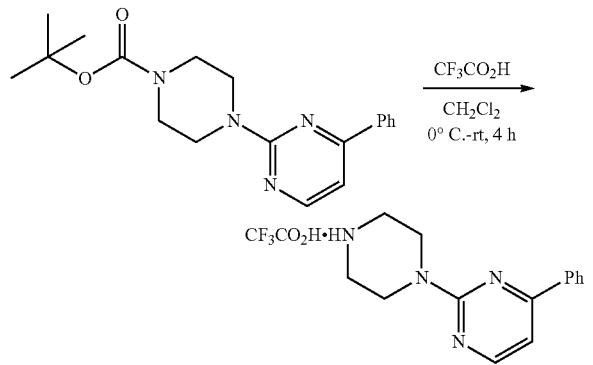

This compound was synthesized from tert-butyl 4-(4-phenylpyrimidin-2-yl)piperazine-1-carboxylate as described for example 46 step 4 (400 mg, crude) as a trifluoroacetate salt and it was carried through without further purification. MS (ESI) m/z: Calculated for C$_{14}$H$_{16}$N$_4$: 240.14. found: 241.0 (M+H)$^+$ (4-(4-Phenylpyrimidin-2-yl)piperazin-1-yl)(3-(5-(trifluoromethyl)-1,2,4-oxadiazol-3-yl)phenyl)methanone This compound was synthesized from 4-phenyl-2-(piperazin-1-yl)pyrimidine TFA salt and 3-(5-(trifluoromethyl)-1,2,4-oxadiazol-3-yl)benzoic acid as described for example 37 step 3 (100 mg, yield 53%). $^1$H NMR (400 MHz, MeOD) δ 8.31-8.25 (m, 5H), 7.78-7.72 (m, 2H), 7.47-7.45 (m, 3H), 6.77-6.75 (d, J=6.3 Hz, 1H), 3.99-3.87 (m, 6H), 3.66 (s, 2H). MS (ESI) m/z: Calculated for C$_{24}$H$_{19}$F$_3$N$_6$O$_2$: 480.15. found: 481.2 (M+H)$^+$ Example 73

1-(2-Fluorophenyl)piperazine

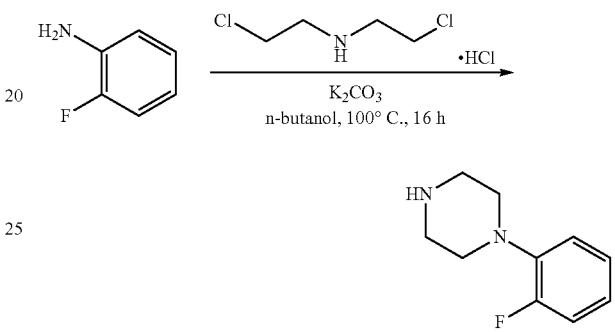

2-Fluoroaniline (4.0 g, 36.0 mmol) and bis-(2-chloroethyl)-amine hydrochloride (6.4 g, 36.0 mmol) were dissolved in n-butanol (40 mL) and potassium carbonate (12.0 g, 86.8 mmol) was added. The reaction mixture was heated to 100° C. for 16 h, cooled to room temperature, and concentrated under reduced pressure. The crude reaction mixture was diluted with 10% MeOH in CHCl$_3$ and filtered. The clear filtrate was concentrated under reduced pressure to get 1-(2-fluorophenyl)piperazine (2.0 g, yield 31%), which was carried through without further purification. $^1$H NMR (400 MHz, CDCl$_3$) δ 9.95 (br s, 1H), 7.12-6.95 (m, 4H), 3.43 (br s, 8H). MS (ESI) m/z: Calculated for C$_{10}$H$_{13}$FN$_2$: 180.11. found: 180.9 (M+H)$^+$

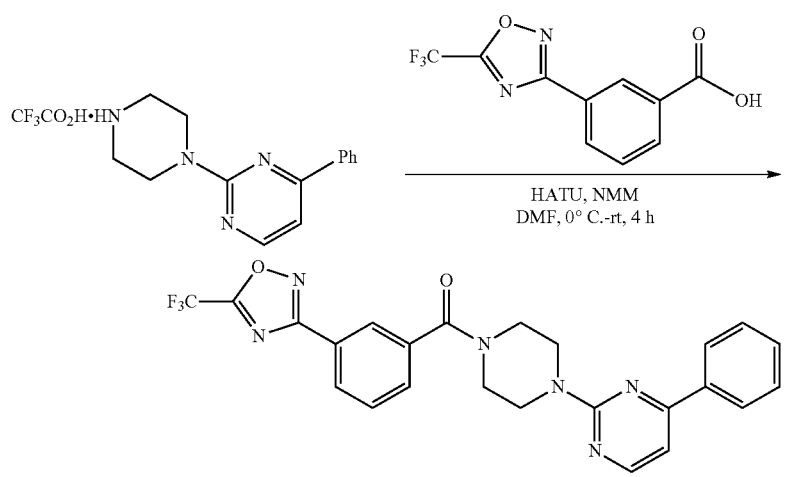

(4-(2-Fluorophenyl)piperazin-1-yl)(3-(5-(trifluoromethyl)-1,2,4-oxadiazol-3-yl)phenyl)methanone

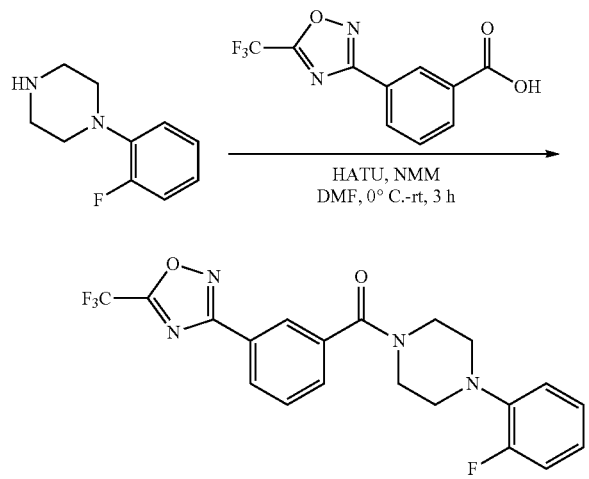

This compound was synthesized from 1-(2-fluorophenyl)piperazine and 3-(5-(trifluoromethyl)-1,2,4-oxadiazol-3-yl)benzoic acid as described for example 37 step 3 (45 mg, yield 28%). $^1$H NMR (400 MHz, CDCl$_3$) δ 8.21-8.20 (m, 2H), 7.68-7.60 (m, 2H), 7.11-6.94 (m, 4H), 4.01 (m, 2H), 3.63 (m, 2H), 3.20-3.06 (m, 4H). MS (ESI) m/z: Calculated for C$_{20}$H$_{16}$F$_4$N$_4$O$_2$: 420.12. found: 421.2 (M+H)$^+$ Example 74

(4-(2-Methoxyphenyl)piperazin-1-yl)(3-(5-(trifluoromethyl)-1,2,4-oxadiazol-3-yl)phenyl)methanone

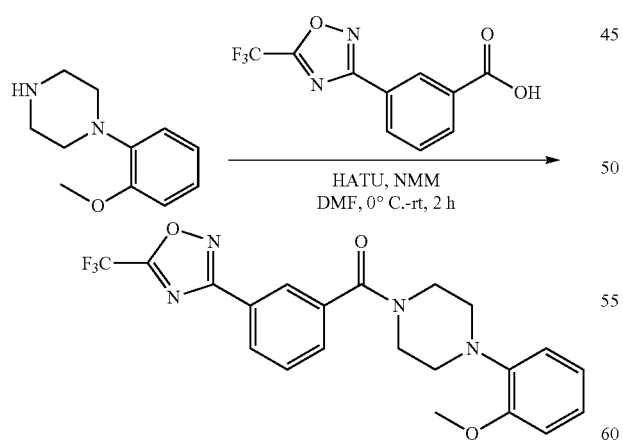

This compound was synthesized from 1-(2-methoxy-phenyl)-piperazine and 3-(5-(trifluoromethyl)-1,2,4-oxadiazol-3-yl)benzoic acid as described for example 37 step 3 (63 mg, yield 28%). $^1$H NMR (400 MHz, CDCl$_3$) δ 8.22-8.19 (m, 2H), 7.69-7.60 (m, 2H), 7.08-7.04 (m, 1H), 6.96-6.89 (m, 3H), 4.02 (m, 2H), 3.89 (s, 3H), 3.64 (m, 2H), 3.18 (m, 2H), 3.04 (m, 2H). MS (ESI) m/z: Calculated for C$_{21}$H$_{19}$F$_3$N$_4$O$_3$: 432.14. found: 433.2 (M+H)$^+$ Example 75

1-(Pyridin-3-yl)piperazine

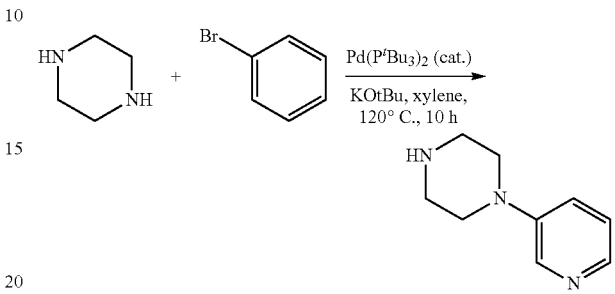

3-Bromopyridine (1.0 g, 6.32 mmol) and piperazine (3.2 g, 37.9 mmol) were dissolved in xylene (10 mL) and the solution was purged with argon for 10 min. Potassium tert-butoxide (0.99 g, 8.86 mmol) and catalytic Pd(P$^t$Bu$_3$)$_2$ (320 mg, 0.63 mmol) were added and the reaction mixture was heated to 120° C. for 10 h, cooled to room temperature, diluted with EtOAc and filtered through Celite. The filtrate was washed with water and brine, dried over anhydrous Na$_2$SO$_4$, and concentrated under reduced pressure. The crude product was purified by column chromatography (silica 60-120 mesh, eluent 10% MeOH in CH$_2$Cl$_2$) to get 1-(pyridin-3-yl)piperazine (350 mg, yield 35%). $^1$H NMR (400 MHz, DMSO-d$_6$) δ 8.26 (d, J=3.0 Hz, 1H), 7.97-7.95 (dd, J=4.6 Hz, 1.1 Hz, 1H), 7.29-7.26 (m, 1H), 7.20-7.16 (m, 1H), 3.08-3.06 (m, 4H), 2.83-2.81 (m, 4H). MS (ESI) m/z: Calculated for C$_9$H$_{13}$N$_3$: 163.11. found: 164.0 (M+H)$^+$ (4-(Pyridin-3-yl)piperazin-1-yl)(3-(5-(trifluoromethyl)-1,2,4-oxadiazol-3-yl)phenyl)methanone

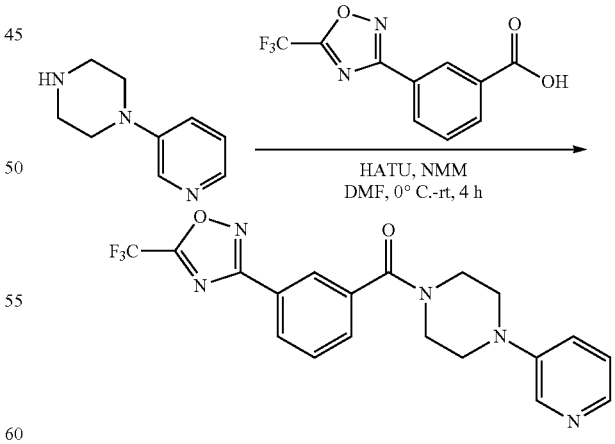

This compound was synthesized from 1-(pyridin-3-yl)piperazine and 3-(5-(trifluoromethyl)-1,2,4-oxadiazol-3-yl)benzoic acid as described for example 37 step 3 (110 mg, yield 47%). $^1$H NMR (400 MHz, DMSO-d$_6$) δ 8.32-8.31 (m, 1H), 8.18-8.15 (dt, J=6.7 Hz, 2.0 Hz, 1H), 8.08 (m, 1H), 8.03-8.02 (m, 1H), 7.76-7.71 (m, 2H), 7.36-7.33 (ddd, J=8.5

Hz, 3.0 Hz, 1.2 Hz, 1H), 7.25-7.22 (m, 1H), 3.81 (m, 2H), 3.50 (m, 2H), 3.21 (m, 4H). MS (ESI) m/z: Calculated for $C_{19}H_{16}F_3N_6O_2$: 403.13. found: 404.2 (M+H)$^+$

Example 76

3-Fluoro-4-(piperazin-1-yl)benzonitrile

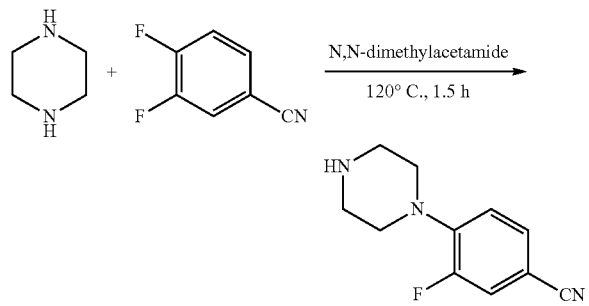

3,4-Difluorobenzonitrile (2.0 g, 14.3 mmol) and piperazine (6.19 g, 71.8 mmol) were dissolved in N,N-dimethylacetamide (10 mL) and the solution was heated to 120° C. for 1.5 h. The reaction mixture was cooled to room temperature, diluted with water, and extracted with EtOAc. The combined extracts were washed with water and brine, dried over anhydrous $Na_2SO_4$, and concentrated under reduced pressure to get 3-fluoro-4-(piperazin-1-yl)benzonitrile (2.8 g, yield 95%), which was carried through without further purification. $^1$H NMR (400 MHz, DMSO-$d_6$) δ 7.69-7.65 (dd, J=13.6 Hz, 2.0 Hz, 1H), 7.56-7.53 (dd, J=8.5 Hz, 1.8 Hz, 1H), 7.12-7.07 (d, J=8.7 Hz, 1H), 3.08-3.05 (m, 4H), 2.83-2.80 (m, 4H). MS (ESI) m/z: Calculated for $C_{11}H_{12}FN_3$: 205.10. found: 205.9 (M+H)$^+$

3-Fluoro-4-(4-(3-(5-(trifluoromethyl)-1,2,4-oxadiazol-3-yl)benzoyl)piperazin-1-yl)benzonitrile

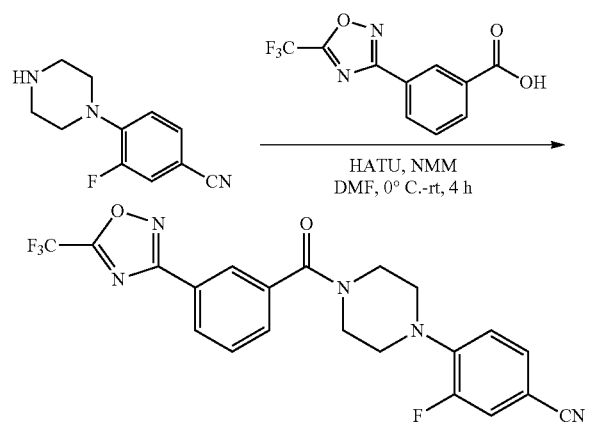

This compound was synthesized from 3-fluoro-4-(piperazin-1-yl)benzonitrile and 3-(5-(trifluoromethyl)-1,2,4-oxadiazol-3-yl)benzoic acid as described for example 37 step 3 (100 mg, yield 38%). $^1$H NMR (400 MHz, DMSO-$d_6$) δ 8.17-8.15 (dt, J=6.6 Hz, 1.7 Hz, 1H), 8.09 (s, 1H), 7.75-7.72 (m, 3H), 7.61-7.58 (dd, J=8.5 Hz, 1.5 Hz, 1H), 7.17-7.13 (t, J=8.7 Hz, 1H), 3.81 (m, 2H), 3.52 (m, 2H), 3.19 (m, 4H). MS (ESI) m/z: Calculated for $C_{21}H_{15}F_4N_5O_2$: 445.12. found: 446.2 (M+H)$^+$

Example 77

(4-(Pyrimidin-2-yl)piperazin-1-yl)(3-(5-(trifluoromethyl)-1,2,4-oxadiazol-3-yl)phenyl)methanone

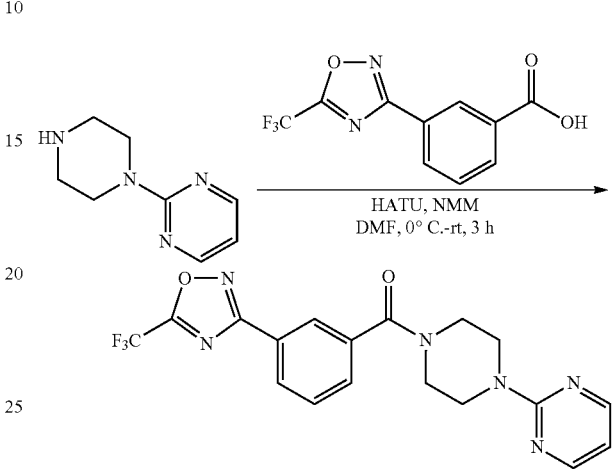

This compound was synthesized from 2-piperazin-1-yl-pyrimidine and 3-(5-(trifluoromethyl)-1,2,4-oxadiazol-3-yl)benzoic acid as described for example 37 step 3 (52 mg, yield 33%). $^1$H NMR (400 MHz, CDCl$_3$) δ 8.35 (d, J=4.7 Hz, 2H), 8.23-8.21 (m, 2H), 7.68-7.61 (m, 2H), 6.58-6.56 (t, J=4.7 Hz, 1H), 3.97-3.85 (m, 6H), 3.53 (m, 2H). MS (ESI) m/z: Calculated for $C_{18}H_{16}F_3N_6O_2$: 404.12. found: 405.1 (M+H)$^+$

Example 78

(4-([1,1'-Biphenyl]-3-yl)piperazin-1-yl)(3-(5-(trifluoromethyl)-1,2,4-oxadiazol-3-yl)phenyl)methanone

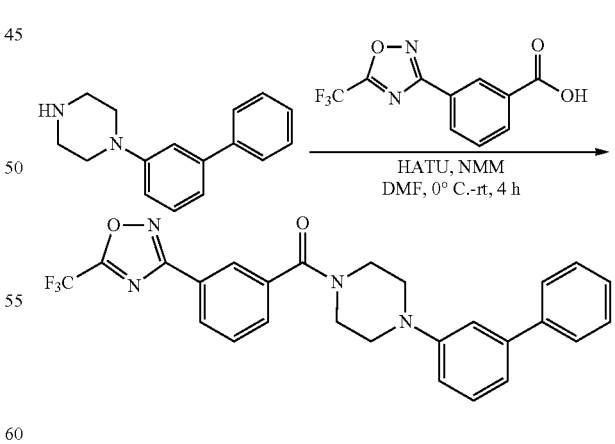

This compound was synthesized from 1-([1,1'-biphenyl]-3-yl)piperazine and 3-(5-(trifluoromethyl)-1,2,4-oxadiazol-3-yl)benzoic acid as described for example 37 step 3 (110 mg, yield 40%). $^1$H NMR (400 MHz, MeOD) δ 8.27-8.25 (m, 1H), 8.22-8.21 (m, 1H), 7.75-7.70 (m, 2H), 7.60-7.58 (m, 2H), 7.43-7.40 (m, 2H), 7.53-7.30 (m, 2H), 7.22-7.21 (m, 1H), 7.14-7.12 (m, 1H), 7.02-6.00 (m, 1H), 3.99 (m, 2H), 3.67

(m, 2H), 3.37 (m, 2H), 3.24 (m, 2H). MS (ESI) m/z: Calculated for $C_{26}H_{21}F_3N_4O_2$: 478.16. found: 479.1 (M+H)$^+$

Example 79

4-(4-Fluorophenyl)-2-methylthiazole

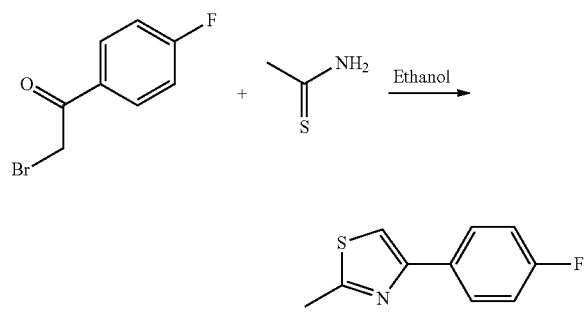

Thioacetamide (1.73 g, 23.03 mmol) was added to a solution of 2-bromo-1-(4-fluorophenyl)ethanone (5.0 g, 23.03 mmol) in ethanol (50 mL) and the reaction was refluxed at 70° C. for 4 h. The reaction mixture was then cooled to room temperature, neutralized to pH 7 with aqueous ammonia solution (20 ml), and extracted with ethyl acetate (200 mL). The combined extracts were washed with water (100 mL), dried over $Na_2SO_4$, and concentrated to provide 4-(4-fluorophenyl)-2-methylthiazole (4.0 g, 90%). $^1$H NMR (400 MHz, DMSO) δ 7.95-8.00 (m, 2H), 7.91 (s, 1H), 7.23-7.29 (m, 2H), 2.71 (s, 3H). MS (ESI) m/z: Calculated for $C_{10}H_8FNS$: 193.04. found: 194.0 (M+H)$^+$

2-(Bromomethyl)-4-(4-fluorophenyl)thiazole

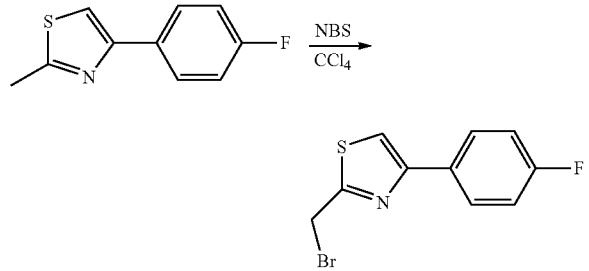

N-Bromosuccinimide (3.22 g, 18.13 mmol) was added to a solution of 4-(4-fluorophenyl)-2-methylthiazole (3.5 g, 18.13 mmol) in $CCl_4$ (30.0 mL) and the reaction was refluxed at 80° C. overnight. The reaction mixture was then diluted with $CH_2Cl_2$, washed with water and brine, dried over anhydrous $Na_2SO_4$, and concentrated under reduced pressure to yield crude 2-(bromomethyl)-4-(4-fluorophenyl)thiazole (5 g), which was carried through without further purification. $^1$H NMR (400 MHz, DMSO) δ 8.18 (s, 1H), 7.93-8.01 (m, 2H), 7.26-7.31 (m, 2H), 5.07 (s, 2H). MS (ESI) m/z: Calculated for $C_{10}H_7BrFNS$: 272.94. found: 273.9 (M+H)$^+$

4-(4-Fluorophenyl)-2-((tri phenyl phosphoranylidene)methyl)thiazole

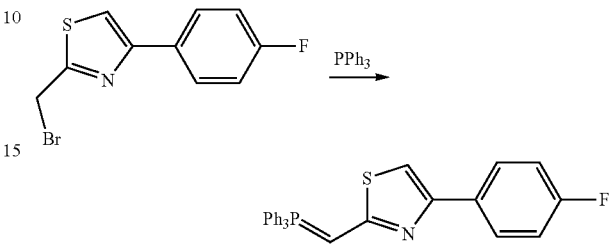

Triphenylphosphine (4.82 g, 18.38 mmol) was added to a solution of 2-(bromomethyl)-4-(4-fluorophenyl)thiazole (5 g, 18.38 mmol) in toluene (30.0 mL) and the reaction was refluxed at 60° C. for 2 h. A precipitate was formed which was filtered and washed with ether (10 mL) thrice to provide 4-(4-fluorophenyl)-2-((triphenylphosphoranylidene)methyl) thiazole (1.1 g, 10.89%), which was carried through without further purification. MS (ESI) m/z: Calculated for $C_{28}H_{21}FNPS$: 453.11. found: 454.0 (M+H)$^+$ tert-Butyl 3-((4-(4-fluorophenyl)thiazol-2-yl)methylene)azetidine-1-carboxylate

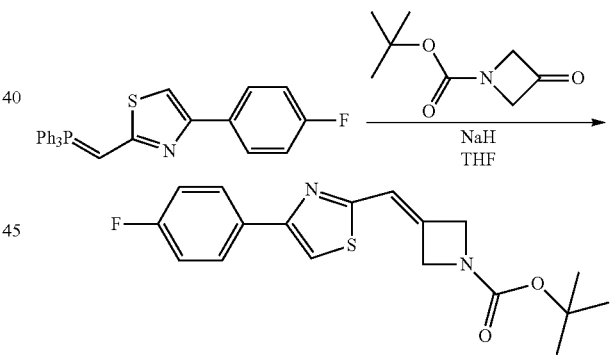

Sodium hydride (0.818 g, 20.4 mmol) was added to a solution of 4-(4-fluorophenyl)-2-((triphenylphosphoranylidene)methyl)thiazole (3.1 g, 5.84 mmol) in THF (15.0 mL) at 0° C. and the reaction mixture was stirred for 30 min. tert-Butyl 3-oxoazetidine-1-carboxylate (1.0 g, 5.84 mmol) was then added portionwise and the reaction mixture was allowed to warm up to room temperature and stirred overnight. The reaction mixture was then poured over crushed ice and then filtered through Celite. The filtrate was extracted with $CH_2Cl_2$. The combined extracts were dried over sodium sulphate and concentrated under reduced pressure to provide tert-butyl 3-((4-(4-fluorophenyl)thiazol-2-yl)methylene)azetidine-1-carboxylate (1.1 g, 10.89%). $^1$H NMR (400 MHz, CDCl3) δ 7.78-7.82 (m, 2H), 7.30 (s, 1H), 7.02-7.06 (m, 2H), 6.54-6.55 (t, 1H), 4.83-4.85 (t, 2H), 4.61-4.64 (q, 2H), 1.54 (s, 9H). MS (ESI) m/z: Calculated for $C_{18}H_{19}FN_2O_2S$: 346.12. found: 347.0 (M+H)$^+$ tert-Butyl 3-((4-(4-fluorophenyl)thiazol-2-yl)methyl)azetidine-1-carboxylate

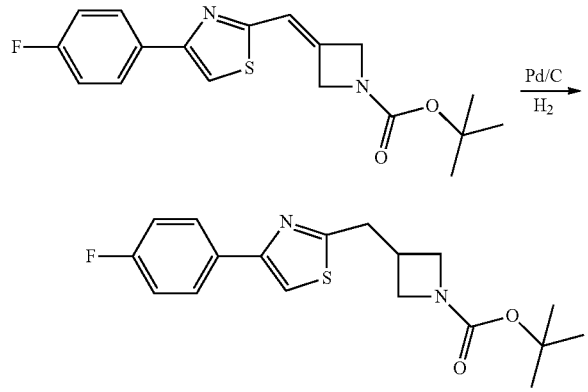

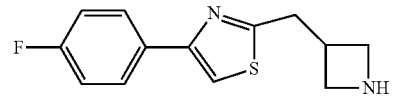

This compound was synthesized from tert-Butyl 3-((4-(4-fluorophenyl)thiazol-2-yl)methyl)azetidine-1-carboxylate as described for example 46 step 4 (0.170 g, 59.64%). $^1$H NMR (400 MHz, DMSO) δ 8.71 (br, 1H), 7.94-8.01 (m, 3H), 7.24-7.28 (t, 2H), 4.03-4.08 (t, 2H), 3.81-3.86 (t, 2H), 3.33-3.38 (m, 3H). MS (ESI) m/z: Calculated for $C_{13}H_{13}FN_2S$: 248.08. found: 249.0 (M+H)$^+$ (3-((4-(4-Fluorophenyl)thiazol-2-yl)methyl)azetidin-1-yl)(3-(5-(trifluoromethyl)-1,2,4-oxadiazol-3-yl)phenyl)methanone

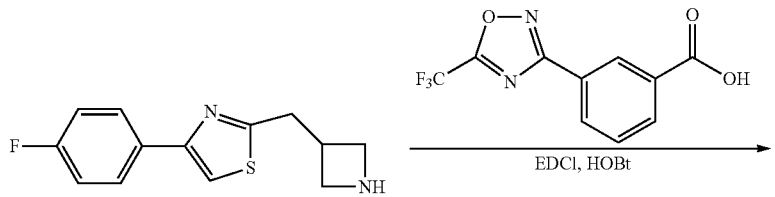

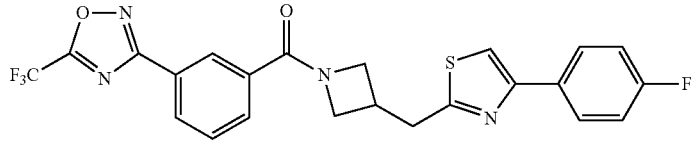

10% Palladium on Carbon (0.650 g) was added to a solution of tert-butyl 3-((4-(4-fluorophenyl)thiazol-2-yl)methylene)azetidine-1-carboxylate (1.3 g, 3.75 mmol) in methanol (175.0 mL) and the reaction mass was stirred with hydrogen bubbling for 1 h at room temperature. The reaction mixture was then filtered through Celite, washed with methanol and concentrated under reduced pressure to provide tert-butyl 3-((4-(4-fluorophenyl)thiazol-2-yl)methylene)azetidine-1-carboxylate (1.1 g, 84.6%). $^1$H NMR (400 MHz, CDCl3) δ 7.75-7.80 (m, 2H), 7.20 (s, 1H), 7.00-7.05 (m, 2H), 4.03-4.07 (t, 2H), 3.42-3.72 (m, 2H), 3.00-3.02 (m, 2H), 2.95-2.99 (m, 1H), 1.41 (s, 9H). MS (ESI) m/z: Calculated for $C_{18}H_{21}FN_2O_2S$: 348.13. found: 349.0 (M+H)$^+$ 2-(Azetidin-3-ylmethyl)-4-(4-fluorophenyl)thiazole

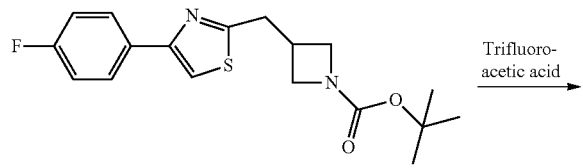

Dimethylaminopyridine (0.151 g, 1.24 mmol), EDCl (0.142 g, 0.744 mmol), and HOBt (0.095 g, 0.620 mmol) were added to a solution of 2-(azetidin-3-ylmethyl)-4-(4-fluorophenyl)thiazole (0.170 g, 0.682 mmol) in DMF (10.0 mL), followed by 3-(5-(trifluoromethyl)-1,2,4-oxadiazol-3-yl)benzoic acid (0.160 g, 0.62 mmol). The reaction was stirred at room temperature for 2 h and concentrated under reduced pressure. The residue was diluted with EtOAc, washed with water and brine, dried over anhydrous $Na_2SO_4$, and concentrated under reduced pressure to yield the crude product which was purified by preparative thin layer chromatography using (40% EtOAc/Hexane) to provide (3-((4-(4-fluorophenyl)thiazol-2-yl)methyl)azetidin-1-yl)(3-(5-(trifluoromethyl)-1,2,4-oxadiazol-3-yl)phenyl)methanone (0.140 g, 42.04%) $^1$H NMR (400 MHz, DMSO) δ 8.21 (s, 1H), 8.15-8.17 (d, 1H), 7.94-7.95 (d, 1H), 7.90-7.92 (m, 2H), 7.86-7.88 (d, 1H), 7.66-7.78 (t, 1H), 7.19-7.23 (t, 2H), 4.48-4.52 (t, 1H), 4.17-4.25 (m, 2H), 3.91-3.95 (m, 1H), 3.42-3.43 (m, 2H), 3.10-3.17 (m, 1H). MS (ESI) m/z: Calculated for $C_{23}H_{16}F_4N_4O_2S$: 488.09. found: 489.0 (M+H)$^+$

Example 80

(4-(4-Methylthiazol-2-yl)piperazin-1-yl)(3-(5-(trifluoromethyl)-1,2,4-oxadiazol-3-yl)phenyl)methanone

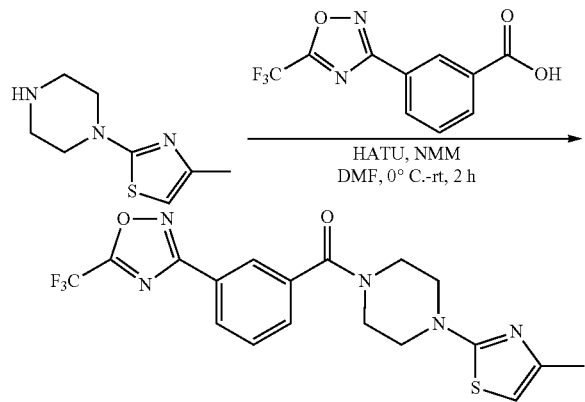

This compound was synthesized from 4-methyl-2-(piperazin-1-yl)thiazole and 3-(5-(trifluoromethyl)-1,2,4-oxadiazol-3-yl)benzoic acid as described for example 37 step 3 (90 mg, yield 39%) as yellow viscous liquid. $^1$H NMR (400 MHz, CDCl$_3$) δ 8.23-8.19 (m, 2H), 7.67-7.61 (m, 2H), 6.20 (m, 1H), 3.94 (m, 2H), 3.57 (m, 6H), 2.26 (m, 3H). MS (ESI) m/z: Calculated for C$_{18}$H$_{16}$F$_3$N$_5$O$_2$S: 423.10. found: 424.2 (M+H)$^+$.

Example 81

(4-(Benzo[d]oxazol-2-yl)piperazin-1-yl)(3-(5-(trifluoromethyl)-1,2,4-oxadiazol-3-yl)phenyl)methanone

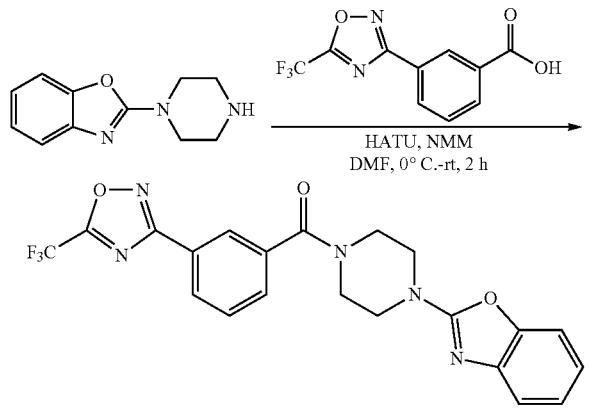

This compound was synthesized from 2-(piperazin-1-yl)benzo[d]oxazole and 3-(5-(trifluoromethyl)-1,2,4-oxadiazol-3-yl)benzoic acid as described for example 37 step 3 (20 mg, yield 12%). $^1$H NMR (400 MHz, CDCl$_3$) δ 8.26-8.22 (m, 2H), 7.69-7.63 (m, 2H), 7.40-7.39 (m, 1H), 7.31-7.29 (m, 1H), 7.23-7.19 (td, J=7.7 Hz, 1.1 Hz, 1H), 7.10-7.06 (m, 1H), 3.96-3.63 (m, 8H). MS (ESI) m/z: Calculated for C$_{21}$H$_{16}$F$_3$N$_5$O$_3$: 443.12. found: 444.2 (M+H)$^+$

Example 82

(2-(4-Fluorophenyl)thiazol-4-yl)methanol

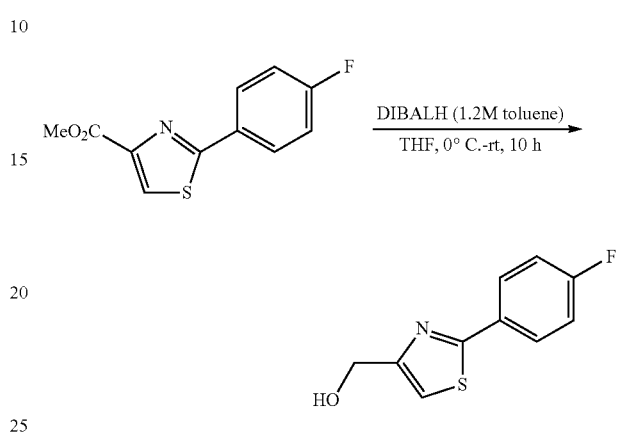

DIBAL-H (2.48 mL, 2.98 mmol, 1.2M in toluene) was added dropwise to a solution of methyl 2-(4-fluorophenyl)thiazole-4-carboxylate (300 mg, 1.26 mmol) in dry THF (6 mL) at −30° C. The reaction mixture was allowed to warm up to room temperature and stirred for 10 h. The reaction mixture was quenched carefully with saturated NH$_4$Cl solution, filtered through Celite and diluted with EtOAc. The organic layer was separated, washed with brine, dried over anhydrous Na$_2$SO$_4$, and concentrated under reduced pressure. The crude product was purified by column chromatography (silica gel 60-120 mesh, eluent 25% EtOAc in petroleum ether) to afford (2-(4-fluorophenyl)thiazol-4-yl)methanol (130 mg, yield 54%). $^1$H NMR (300 MHz, CDCl$_3$) δ 7.96-7.91 (dd, J=9.0 Hz, 5.3 Hz, 2H), 7.18-7.11 (m, 3H), 4.84-4.82 (d, J=5.3 Hz, 2H), 2.38-2.34 (t, J=6.2 Hz, 1H). MS (ESI) m/z: Calculated for C$_{10}$H$_8$FNOS: 209.03. found: 209.9 (M+H)$^+$ 2-(4-Fluorophenyl)thiazole-4-carbaldehyde

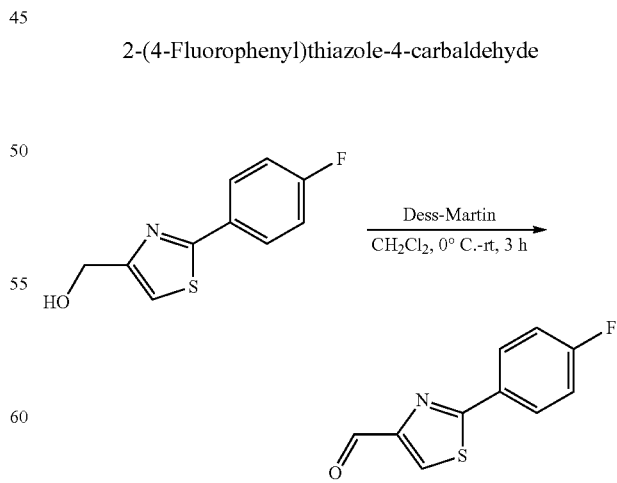

This compound was synthesized from (2-(4-fluorophenyl)thiazol-4-yl)methanol as described for example 61 step 2 (70 mg, yield 54%). $^1$H NMR (300 MHz, CDCl$_3$) δ 10.10 (s, 1H), 8.17 (s, 1H), 8.04-7.99 (dd, J=8.9 Hz, 5.2 Hz, 2H), 7.22-7.16 (t, J=8.6 Hz, 2H). MS (ESI) m/z: Calculated for $C_{10}H_6FNOS$: 207.02. found: 208.3 $(M+H)^+$ tert-Butyl 4((2-(4-fluorophenyl)thiazol-4-yl)methyl) piperazine-1-carboxylate

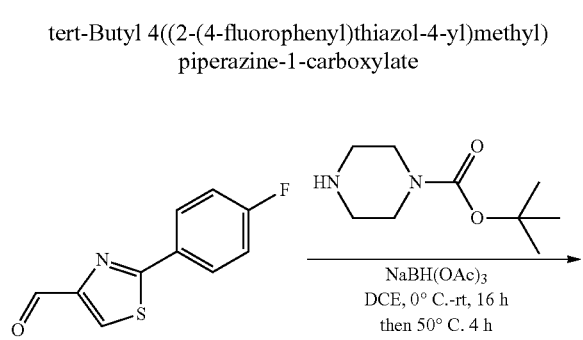

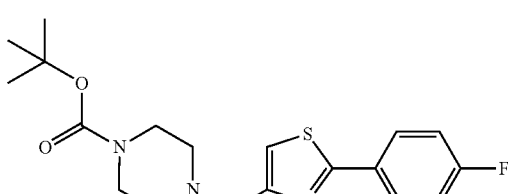

tert-Butyl piperazine-1-carboxylate (62 mg, 0.33 mmol) was added to a solution of 2-(4-fluorophenyl)thiazole-4-carbaldehyde (70 mg, 0.34 mmol) in 1,2-dichloroethane (3 mL) at 0° C., followed by sodium triacetoxyborohydride (85 mg, 0.4 mmol). The reaction mixture was allowed to warm up to room temperature, stirred for 16 h and further heated to 50° C. for another 4 h. The reaction mixture was quenched with 10% aqueous $NaHCO_3$ and extracted with EtOAc. The combined extracts were washed with brine, dried over anhydrous sodium sulfate, and concentrated under reduced pressure. The crude product was purified by column chromatography (silica gel 60-120 mesh, eluent 35% EtOAc in petroleum ether) to afford tert-butyl 4-((2-(4-fluorophenyl)thiazol-4-yl) methyl)piperazine-1-carboxylate (82 mg, yield 64%). $^1$H NMR (300 MHz, $CDCl_3$) δ 7.96-7.91 (dd, J=9.0 Hz, 5.3 Hz, 2H), 7.15-7.09 (m, 3H), 3.75 (s, 2H), 3.50-3.46 (m, 4H), 2.55-2.52 (m, 4H), 1.46 (s, 9H). MS (ESI) m/z: Calculated for $C_{19}H_{24}FN_3O_2S$: 377.16. found: 378.3 $(M+H)^+$ 2-(4-Fluorophenyl)-4-(piperazin-1-ylmethyl)thiazole TFA Salt

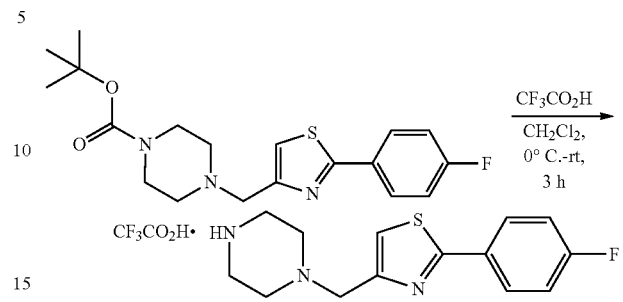

This compound was synthesized from tert-butyl 4-((2-(4-fluorophenyl)thiazol-4-yl)methyl)piperazine-1-carboxylate as described for example 46 step 4 (43 mg, crude) as a trifluoroacetate salt and it was carried through without further purification. MS (ESI) m/z: Calculated for $C_{14}H_{16}FN_3S$: 277.10. found: 278.1 $(M+H)^+$ (4-((2-(4-Fluorophenyl)thiazol-4-yl)methyl)piperazin-1-yl)(3-(5-(trifluoromethyl)-1,2,4-oxadiazol-3-yl)phenyl)methanone

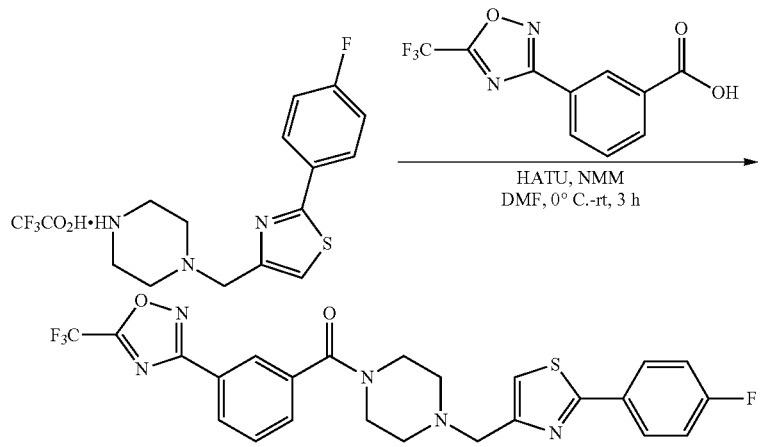

This compound was synthesized from 2-(4-fluorophenyl)-4-(piperazin-1-ylmethyl)thiazole TFA salt and 3-(5-(trifluoromethyl)-1,2,4-oxadiazol-3-yl)benzoic acid as described for example 37 step 3 (26 mg, yield 34%). $^1$H NMR (400 MHz, $CDCl_3$) δ 8.20-8.17 (m, 2H), 7.95-7.92 (dd, J=8.8 Hz, 5.1 Hz, 2H), 7.64-7.59 (m, 2H), 7.16-7.11 (m, 3H), 3.89 (m, 2H), 3.80 (s, 2H), 3.51 (m, 2H), 2.72 (m, 2H), 2.57 (m, 2H). MS (ESI) m/z: Calculated for $C_{24}H_{19}F_4N_5O_2S$: 517.12. found: 518.2 $(M+H)^+$ Example 83

Methyl 4-fluorobenzimidate hydrochloride

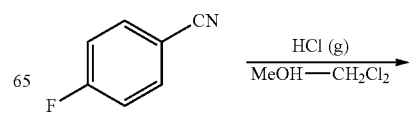

-continued

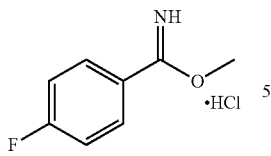

Dry HCl (g) was bubbled through a solution of 4-fluorobenzonitrile (5.0 g, 0.041 mol) in dry MeOH—CH$_2$Cl$_2$ (20 mL, 1:1 v/v) until saturation. The clear solution was kept at 0° C. for 2 days to crystallize methyl 4-fluorobenzimidate as hydrochloride salt, which was isolated by filtration (2.8 g, yield 36%). $^1$H NMR (400 MHz, DMSO-d$_6$) δ 7.95-7.92 (m, 2H), 7.38 (br s, 1H), 7.29-7.25 (m, 2H), 3.06 (s, 3H). MS (ESI) m/z: Calculated for C$_8$H$_8$FNO: 153.06. found: 154.2 (M+H)$^+$ Methyl 2-(4-fluorophenyl)-4,5-dihydrooxazole-4-carboxylate

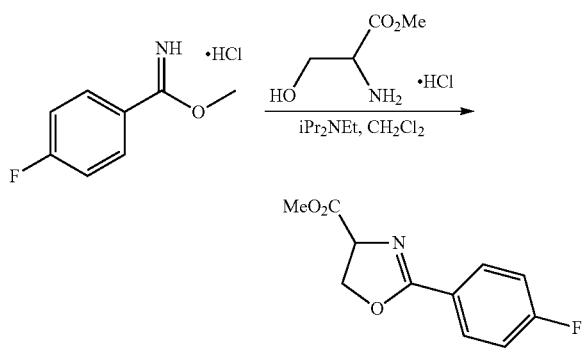

N,N-diisopropylethylamine (11 mL, 63.3 mmol) was added dropwise to a solution of methyl 4-fluorobenzimidate hydrochloride (10 g, 52.74 mmol) and DL-serine methyl ester HCl salt (9.9 g, 63.63 mmol) in dry CH$_2$Cl$_2$ (200 mL) at 0° C. The reaction mixture was stirred at room temperature for 24 h and then concentrated under reduced pressure. The reaction mixture was diluted with CH$_2$Cl$_2$ and the organic layer was washed with H$_2$O and brine, dried over anhydrous Na$_2$SO$_4$, and concentrated under reduced pressure to get methyl 2-(4-fluorophenyl)-4,5-dihydrooxazole-4-carboxylate (9.5 g, yield 81%) as an orange liquid. $^1$H NMR (300 MHz, CDCl$_3$) δ 8.02-7.97 (m, 2H), 7.13-7.07 (t, J=8.7 Hz, 2H), 4.98-4.92 (m, 1H), 4.73-4.57 (m, 2H), 3.83 (s, 3H). MS (ESI) m/z: Calculated for C$_{11}$H$_{10}$FNO$_3$: 223.06. found: 223.8 (M+H)$^+$ Methyl 2-(4-fluorophenyl)oxazole-4-carboxylate

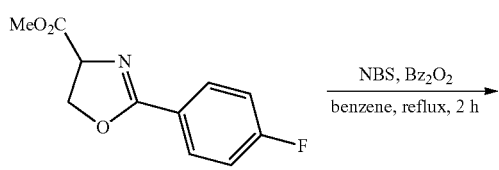

-continued

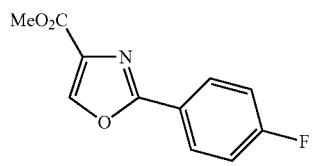

Benzoyl peroxide (0.49 g, 2.0 mmol) was added to a solution of methyl 2-(4-fluorophenyl)-4,5-dihydrooxazole-4-carboxylate (9.0 g, 40.3 mmol) in dry benzene (180 mL) and the mixture was refluxed for 15 min. N-bromosuccinimide (8.6 g, 48.3 mmol) was then added and the reaction mixture was refluxed for 2 h. The reaction mixture was quenched with ice-cold water and the crude product was extracted with EtOAc. The combined extracts were washed with 10% aqueous NaHCO$_3$ solution, H$_2$O and brine, dried over anhydrous Na$_2$SO$_4$, and concentrated under reduced pressure. The crude product was purified by column chromatography (silica 60-120 mesh, eluant 10-15% EtOAc in petroleum ether) to get methyl 2-(4-fluorophenyl)oxazole-4-carboxylate (6 g, 67%) as a white solid. $^1$H NMR (400 MHz, CDCl$_3$) δ 8.29 (s, 1H), 8.14-8.10 (m, 2H), 7.19-7.15 (t, J=8.5 Hz, 2H), 3.96 (s, 3H). MS (ESI) m/z: Calculated for C$_{11}$H$_8$FNO$_3$: 221.05. found: 221.8 (M+H)$^+$ (2-(4-Fluorophenyl)oxazol-4-yl)methanol

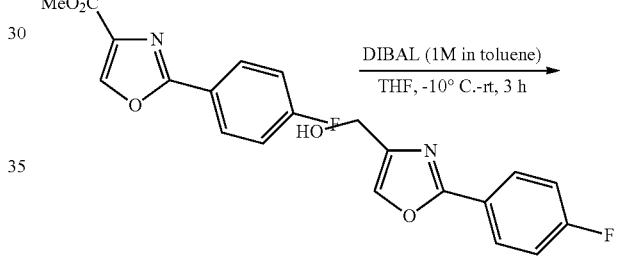

This compound was synthesized from methyl 2-(4-fluorophenyl)oxazole-4-carboxylate as described in example 82 step 1 (4.5 g, yield 86%) as a yellow solid. $^1$H NMR (300 MHz, CDCl$_3$) δ 8.06-8.01 (m, 2H), 7.65 (s, 1H), 7.18-7.12 (t, J=8.7 Hz, 2H), 4.68 (s, 2H). MS (ESI) m/z: Calculated for C$_{10}$H$_8$FNO$_2$: 193.05. found: 193.8 (M+H)$^+$ 2-(4-Fluorophenyl)oxazole-4-carbaldehyde

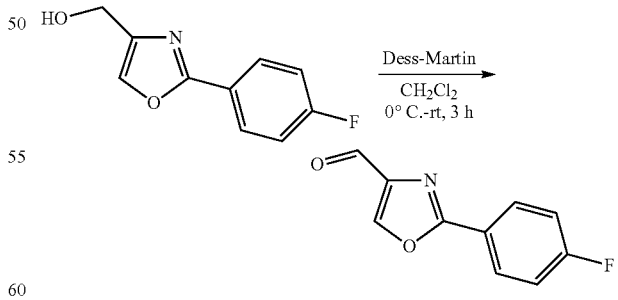

This compound was synthesized from (2-(4-fluorophenyl)oxazol-4-yl)methanol as described in example 61 step 2 (2.8 g, yield 63%) as a white solid. $^1$H NMR (300 MHz, CDCl$_3$) δ 10.01 (s, 1H), 8.32 (s, 1H), 8.14-8.10 (m, 2H), 7.23-7.17 (t, J=8.8 Hz, 2H). MS (ESI) m/z: Calculated for C$_{10}$H$_6$FNO$_2$: 191.04. found: 191.8 (M+H)$^+$

123 tert-Butyl 4-((2-(4-fluorophenyl)oxazol-4-yl)methyl)piperazine-1-carboxylate

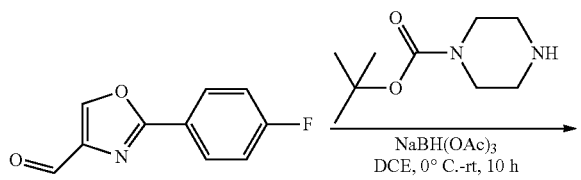

This compound was synthesized from tert-butyl piperazine-1-carboxylate and 2-(4-fluorophenyl)oxazole-4-carbaldehyde as described for example 82 step 3 (240 mg, yield 42%). $^1$H NMR (400 MHz, CDCl$_3$) δ 8.07-8.03 (dd, J=9.1 Hz, 5.3 Hz, 2H), 7.59 (s, 1H), 7.16-7.12 (t, J=8.8 Hz, 2H), 3.54 (s, 2H), 3.49-3.47 (m, 4H), 2.52-2.49 (m, 4H), 1.46 (s, 9H). MS (ESI) m/z: Calculated for C$_{19}$H$_{24}$FN$_3$O$_3$: 361.18. found: 362.2 (M+H)$^+$ 2-(4-Fluorophenyl)-4-(piperazin-1-ylmethyl)oxazole TFA Salt

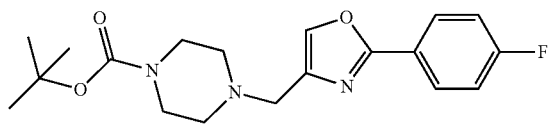

124

This compound was synthesized from tert-butyl 4-((2-(4-fluorophenyl)oxazol-4-yl)methyl)piperazine-1-carboxylate as described for example 46 step 4 (130 mg, crude) as a trifluoroacetate salt and it was carried through without further purification. $^1$H NMR (400 MHz, DMSO-d$_6$) δ 8.67 (br s, 2H), 8.21 (s, 1H), 8.04-8.01 (m, 2H), 7.42-7.38 (t, J=8.9 Hz, 2H), 3.80 (m, 2H), 3.18 (m, 4H), 2.88 (m, 4H). MS (ESI) m/z: Calculated for C$_{14}$H$_{16}$FN$_3$O: 261.13. found: 262.0 (M+H)$^+$ (4-((2-(4-Fluorophenyl)oxazol-4-yl)methyl)piperazin-1-yl)(3-(5-(trifluoromethyl)-1,2,4-oxadiazol-3-yl)phenyl)methanone

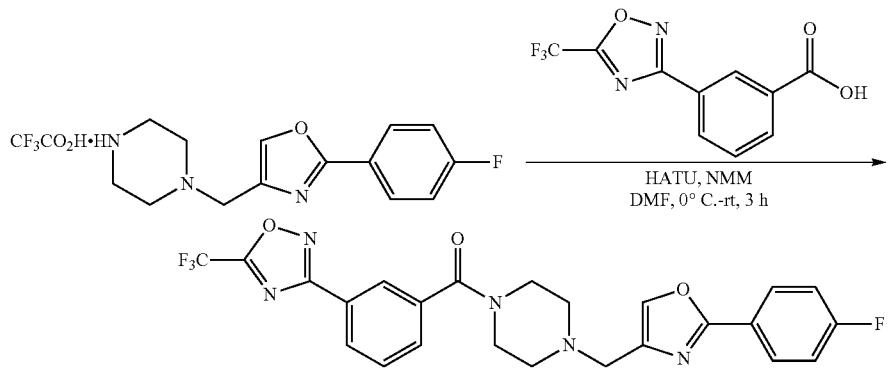

This compound was synthesized from 2-(4-fluorophenyl)-4-(piperazin-1-ylmethyl)oxazole TFA salt and 3-(5-(trifluoromethyl)-1,2,4-oxadiazol-3-yl)benzoic acid as described for example 37 step 3 (34 mg, yield 14%). $^1$H NMR (400 MHz, CDCl$_3$) δ 8.19-8.17 (m, 2H), 8.06-8.03 (dd, J=8.7 Hz, 5.1 Hz, 2H), 7.63-7.57 (m, 3H), 7.17-7.12 (t, J=8.7 Hz, 2H), 3.87 (m, 2H), 3.59 (s, 2H), 3.50 (m, 2H), 2.68 (m, 2H), 2.54 (m, 2H). MS (ESI) m/z: Calculated for C$_{24}$H$_{19}$F$_4$N$_6$O$_3$: 501.14. found: 502.1 (M+H)$^+$

Example 84 tert-Butyl 4-(2-phenylthiazole-4-carbonyl)piperazine-1-carboxylate

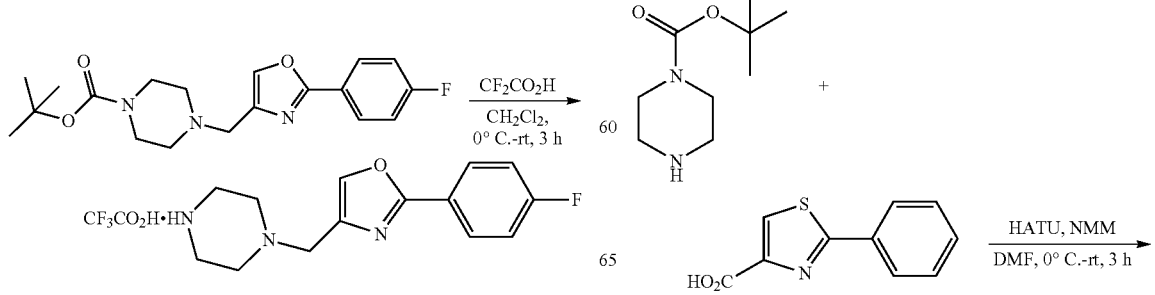

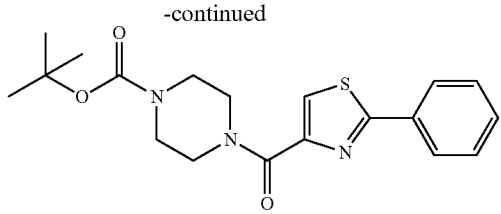

This compound was synthesized from tert-butyl piperazine-1-carboxylate and 2-phenylthiazole-4-carboxylic acid as described for example 37 step 3 (500 mg, yield 90%). $^1$H NMR (400 MHz, DMSO-$d_6$) δ 8.20 (s, 1H), 8.00-7.96 (m, 2H), 7.56-7.53 (m, 3H), 3.76-3.64 (m, 4H), 3.43 (m, 4H), 1.42 (s, 9H). MS (ESI) m/z: Calculated for $C_{19}H_{23}N_3O_3S$: 373.15. found: 374.2 (M+H)$^+$ (2-Phenylthiazol-4-yl)(piperazin-1-yl)methanone TFA Salt

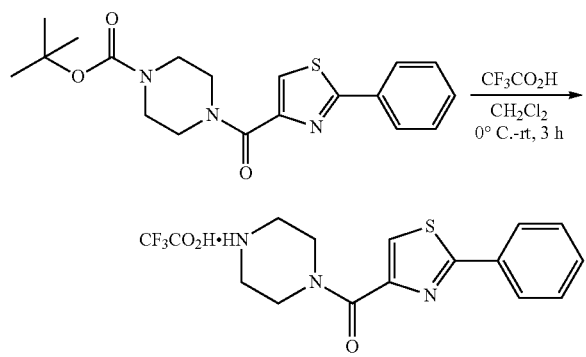

This compound was synthesized from tert-butyl 4-(2-phenylthiazole-4-carbonyl)piperazine-1-carboxylate as described for example 46 step 4 (300 mg, crude) as trifluoroacetate salt and it was taken as such for the next step. MS (ESI) m/z: Calculated for $C_{14}H_{15}N_3OS$: 273.09. found: 274.0 (M+H)$^+$ (2-Phenylthiazol-4-yl)(4-(3-(5-(trifluoromethyl)-1,2,4-oxadiazol-3-yl)benzoyl)piperazin-1-yl)methanone This compound was synthesized from (2-phenylthiazol-4-yl)(piperazin-1-yl)methanone TFA salt and 3-(5-(trifluoromethyl)-1,2,4-oxadiazol-3-yl)benzoic acid as described for example 37 step 3 (145 mg, yield 37%). $^1$H NMR (400 MHz, DMSO-$d_6$) δ 8.22 (s, 1H), 8.16-8.14 (m, 1H), 8.10 (s, 1H), 7.96 (m, 2H), 7.74-7.72 (m, 2H), 7.52 (m, 3H), 3.89-3.69 (m, 6H), 3.48 (s, 2H). MS (ESI) m/z: Calculated for $C_{24}H_{18}F_3N_5O_3S$: 513.11. found: 514.3 (M+H)$^+$ Example 85

(1S,4S)-tert-Butyl 5-(pyridin-2-yl)-2,5-diazabicyclo[2.2.1]heptane-2-carboxylate

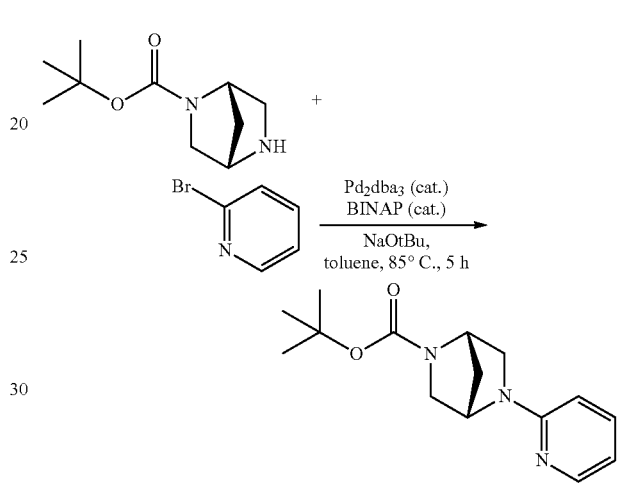

A mixture of BINAP (31 mg, 0.05 mmol) and Pd$_2$dba$_3$ (230 mg, 0.03 mmol) were taken in toluene and the solution was heated to 85° C. for 10 min under argon atmosphere. The solution was cooled to 40° C. and (1S,4S)-2-boc-2,5-diazabicyclo[2.2.1]heptane (250 mg, 1.26 mmol) was added, followed by 2-bromo pyridine (218 mg, 1.38 mmol) and sodium tert-butoxide (194 mg, 2.0 mmol). The reaction mixture was heated to 85° C. for 5 h, cooled to room temperature, diluted with EtOAc and filtered through Celite. The organic layer was washed with water and brine, dried over anhydrous Na$_2$SO$_4$, and concentrated under reduced pressure. The crude product was purified by column chromatography (silica 60-120 mesh,

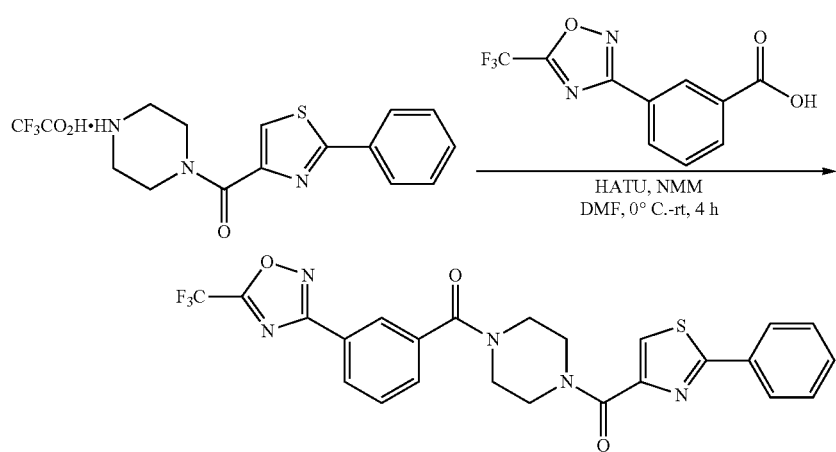

eluent 20-30% EtOAc in petroleum ether) to get (1S,4S)-tert-butyl 5-(pyridin-2-yl)-2,5-diazabicyclo[2.2.1]heptane-2-carboxylate (170 mg, yield 49%). $^1$H NMR (300 MHz, CDCl$_3$) δ 8.14 (d, J=4.6 Hz, 1H), 7.47-7.42 (t, J=7.7 Hz, 1H), 6.59-6.55 (m, 1H), 6.35-6.32 (d, J=8.6 Hz, 1H), 4.90-4.79 (m, 1H), 4.67-4.52 (m, 1H), 3.57-3.35 (m, 4H), 1.96-1.92 (m, 2H), 1.46-1.42 (m, 9H). MS (ESI) m/z: Calculated for C$_{15}$H$_{21}$N$_3$O$_2$: 275.16. found: 276.1 (M+H)$^+$ (1S,4S)-2-(Pyridin-2-yl)-2,5-diazabicyclo[2.2.1]heptane TFA Salt

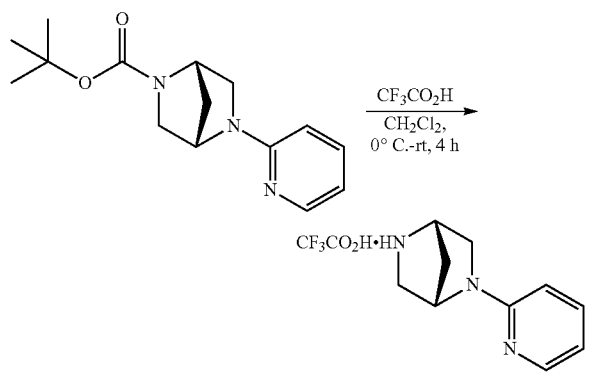

This compound was synthesized from (1S,4S)-tert-butyl 5-(pyridin-2-yl)-2,5-diazabicyclo[2.2.1]heptane-2-carboxylate as described for example 46 step 4 (50 mg, crude) as trifluoroacetate salt and it was taken as such for the next step. MS (ESI) m/z: Calculated for C$_{10}$H$_{13}$N$_3$: 175.11. found: 175.9 (M+H)$^+$ ((1S,4S)-5-(Pyridin-2-yl)-2,5-diazabicyclo[2.2.1]heptan-2-yl)(3-(5-(trifluoromethyl)-1,2,4-oxadiazol-3-yl)phenyl)methanone

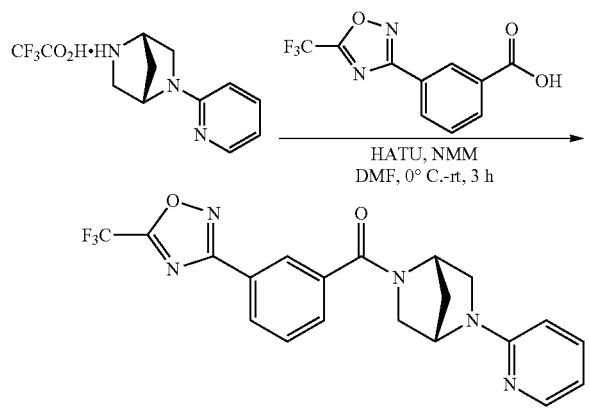

This compound was synthesized from (1S,4S)-2-(pyridin-2-yl)-2,5-diazabicyclo[2.2.1]heptane TFA salt and 3-(5-(trifluoromethyl)-1,2,4-oxadiazol-3-yl)benzoic acid as described for example 37 step 3 (30 mg, yield 27%). $^1$H NMR (400 MHz, CDCl$_3$) δ 8.28-8.07 (m, 3H), 7.74-7.71 (m, 1H), 7.65-7.43 (m, 2H), 6.66-6.55 (m, 1H), 6.45-6.33 (m, 1H), 5.16-4.94 (m, 2H), 3.82-3.49 (m, 4H), 2.10-2.05 (m, 2H). MS (ESI) m/z: Calculated for C$_{20}$H$_{16}$F$_3$N$_5$O$_2$: 415.13. found: 416.2 (M+H)$^+$ Pharmaceutical Compositions Example A Tablets are prepared using conventional methods and are formulated as follows:

| Ingredient | Amount per tablet |
| --- | --- |
| Compound of Example 1 | 5 mg |
| Microcrystalline cellulose | 100 mg |
| Lactose | 100 mg |
| Sodium starch glycollate | 30 mg |
| Magnesium stearate | 2 mg |
| Total | 237 mg |

Example B

Capsules are prepared using conventional methods and are formulated as follows:

| Ingredient | Amount per tablet |
| --- | --- |
| Compound of Example 3 | 15 mg |
| Dried starch | 178 mg |
| Magnesium stearate | 2 mg |
| Total | 195 mg |

Biological Assay(s)

Histone Deacetylase 9 (HDAC9) Inhibition Assay:

Novel histone deacetylase 9 (HDAC9) inhibitors were characterized in an in vitro biochemical functional assay. The assay measures the increased fluorescent signal due to deacetylation, by HDAC9, of a fluorogenic substrate. The commercial available substrate is Class IIa HDAC-specific and contains an acetylated lysine residue and would releases the fluorescent signal upon trypsin cleavage after deacetylation.

Specifically, test compounds diluted to various concentrations in 100% DMSO are first dispensed into 384-well assay plates. Recombinant HDAC9 isoform 4 (purchased from BPS Bioscience) in complete assay buffer (50 mM Tris-HCl, pH 8.0, 137 mM NaCl, 2.7 mM KCl, 1 mM MgCl2, 0.05% BSA & 0.005% Tween 20) were then added to each well (5 uL/well) using Multidrop Combi (Thermo Scientific), followed by 5 uL/well substrate (purchased from BPS Bioscience, 4.5 uM final). After 45 minutes incubation at room temperature, 10 uL 2× developer solution (assay buffer with 40 uM Trypsin and 20 uM Trichostatin A) was added. The plates were then incubated 1 hour at room temperature before reading in fluorescent intensity mode at 450 nm in an Envision (Perkin Elmer) plate reader. Percent Inhibition of HDAC9 activity by compounds in each test wells was calculated by normalizing to fluorescent signal in control wells containing DMSO only. The pIC50s value of test compounds were calculated from non-linear curve fitting, using ActivityBase5 data analysis tool (IDBS), from 11 point 3× dilution series starting from 100 uM final compound concentration.

For dose response experiments, normalized data were fit by ABASE/XC50 using the equation y=a+(b−a)/(1+(10^x/10^c)^d), where a is the minimum % activity, b is the maximum % activity, c is the pIC$_{50}$, d is the Hill slope.

The pIC$_{50}$s are averaged to determine a mean value, for a minimum of 2 experiments. As determined using the above method, the compounds of Examples 1-85 exhibited a pIC$_{50}$ greater than 4.0. For instance, the compounds of Examples 1, 38, 61 and 79 inhibited HDAC9 in the above method with a mean pIC$_{50}$ of >6.

REFERENCES

US 20060269559, U.S. Pat. No. 7,521,044, WO2007084775
"Deacetylase inhibition promotes the generation and function of regulatory T cells," R. Tao, E. F. de Zoeten, E. O'zkaynak, C. Chen, L. Wang, P. M. Porrett, B. Li, L. A. Turka, E. N. Olson, M. I. Greene, A. D. Wells, W. W. Hancock, Nature Medicine, 13 (11), 2007.
"Expression of HDAC9 by T Regulatory Cells Prevents Colitis in Mice," E. F. de Zoeten, L. Wang, H. Sai, W. H. Dillmann, W. W. Hancock, Gastroenterology. 2009 Oct. 28.
"Immunomodulatory effects of deacetylase inhibitors: therapeutic targeting of FOXP3+ regulatory T cells," L. Wang, E. F. de Zoeten, M. I. Greene and W. W. Hancock, Nature Review Drug Discovery. 8(12):969-81, 2009 and references therein.
"HDAC7 targeting enhances FOXP3+ Treg function and induces long-term allograft survival," L. Wang, et al., Am. J. Transplant 9, S621 (2009).
"Selective class II HDAC inhibitors impair myogenesis by modulating the stability and activity of HDAC-MEF2 complexes," A. Nebbioso, F. Manzo, M. Miceli, M. Conte, L. Manente, A. Baldi, A. De Luca, D. Rotili, S. Valente, A. Mai, A. Usiello, H. Gronemeyer, L. Altucci, EMBO reports 10 (7), 776-782, 2009. and references therein.
"Myocyte Enhancer Factor 2 and Class II Histone Deacetylases Control a Gender-Specific Pathway of Cardioprotection Mediated by the Estrogen Receptor," E. van Rooij, J. Fielitz, L. B. Sutherland, V. L. Thijssen, H. J. Crijns, M. J. Dimaio, J. Shelton, L. J. De Windt, J. A. Hill, E. N. Olson, Circulation Research, January 2010.

What is claimed is:

1. A compound having the formula:

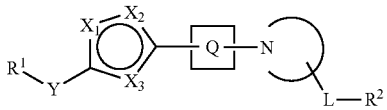

wherein:
R$^1$ is fluoro(C$_1$-C$_4$)alkyl containing at least 2 fluoro atoms;
Y is a bond X$_1$ is O, X$_2$ and X$_3$ are N;
Q is -phenyl-C(=O)— or —(C$_3$-C$_6$)cycloalkyl-C(=O)—, wherein the (C$_3$-C$_6$)cycloalkyl, or phenyl moiety is optionally substituted by 1, 2 or 3 groups independently selected from (C$_1$-C$_4$)alkyl, halogen, cyano, halo(C$_1$-C$_4$)alkyl, (C$_1$-C$_4$)alkoxy, and halo(C$_1$-C$_4$)alkoxy;

is an optionally substituted, saturated 4, 5, 6 or 7 membered heterocyclic ring, optionally containing one additional nitrogen atom, where said 4, 5, 6 or 7 membered heterocyclic ring is optionally substituted by 1 or 2 groups independently selected from (C$_1$-C$_4$)alkyl, halo(C$_1$-C$_4$)alkyl, halogen, cyano, —C(=O)OR$^Y$, and —(C$_1$-C$_2$)C(=O)OR$^Y$, where each R$^Y$ is independently selected from H and methyl;
L is a bond or methylene;
R$^2$ is 5-6 membered heteroaryl, phenyl, —C(O)-(5-6 membered heteroaryl), or —C(O)-phenyl,
wherein the 5-membered heteroaryl moiety of said 5-6 membered heteroaryl group or said —C(O)-(5-6 membered heteroaryl) group contains one oxygen or sulfur ring heteroatom, and optionally contains 1 additional nitrogen ring atom and the 6-membered heteroaryl moiety of said 5-6 membered heteroaryl group or said —C(O)-(5-6 membered heteroaryl) group contains 1 or 2 nitrogen ring heteroatoms,
wherein any of said 5-6 membered heteroaryl or phenyl moieties is optionally substituted by 1 or 2 groups independently selected from (C$_1$-C$_4$)alkyl, halo(C$_1$-C$_4$)alkyl, halogen, cyano and (C$_1$-C$_4$)alkoxy,
or said 5-6 membered heteroaryl group is optionally substituted by an optionally substituted phenyl group, wherein said optionally substituted phenyl group is optionally substituted by 1 or 2 groups independently selected from (C$_1$-C$_4$)alkyl, halogen, cyano, halo(C$_1$-C$_4$)alkyl, (C$_1$-C$_4$)alkoxy, halo(C$_1$-C$_4$)alkoxy, and hydroxyl;
or a salt thereof.

2. The compound or salt according to claim 1, wherein R$^1$ is CHF$_2$ or CF$_3$.

3. The compound or salt according to claim 1, wherein R$^1$ is CF$_3$.

4. The compound or salt according to claim 1, wherein A is a phenyl group optionally substituted by 1-2 groups independently selected from (C$_1$-C$_4$)alkyl, halogen, cyano, halo(C$_1$-C$_4$)alkyl, (C$_1$-C$_4$)alkoxy, and halo(C$_1$-C$_4$)alkoxy.

5. The compound or salt according to claim 1, wherein:
R$^1$ is —CF$_3$;
Q is -phenyl-C(=O)— or —(C$_3$-C$_6$)cycloalkyl-C(=O)—, wherein said phenyl or (C$_3$-C$_6$)cycloalkyl is optionally substituted by chloro, fluoro, cyano, methoxy, methyl, or trifluoromethyl;
L is a bond;
R$^2$ is phenyl, pyridyl, pyrimidinyl, thiazolyl, or oxazolyl, where said phenyl, pyridyl, pyrimidinyl, thiazolyl, or oxazolyl is optionally substituted with 1 or 2 groups independently selected from (C$_1$-C$_4$)alkyl, halo(C$_1$-C$_4$)alkyl, halogen, cyano and (C$_1$-C$_4$)alkoxy,
or is optionally substituted by an optionally substituted phenyl group, wherein said optionally substituted phenyl is optionally substituted by 1 or 2 groups independently selected from (C$_1$-C$_4$)alkyl, halogen, cyano, halo(C$_1$-C$_4$)alkyl, (C$_1$-C$_4$)alkoxy, and halo(C$_1$-C$_4$)alkoxy;

is an optionally substituted saturated 5 or 6-membered heterocyclic ring, optionally containing one additional nitrogen ring atom, where said 5 or 6-membered heterocyclic ring is optionally substituted by 1 or 2 groups independently selected from (C$_1$-C$_2$)alkyl, halo(C$_1$-C$_2$)alkyl, cyano, —C(=O)OR$^y$, and —(C$_1$-C$_2$)C(=O)OR$^y$, where each R$^y$ is independently selected from H and methyl.

6. The compound or salt according to claim 3, wherein
Q is unsubstituted phenyl-C(=O);
X is NR$^X$ or a bond, where R$^X$ is H;
B is 1,4-diazepanyl, piperazinyl or piperidinyl, optionally substituted by 1 or 2 groups independently selected from methyl and —C(=O)OH;
L is a bond;
R$^2$ is phenyl, pyridyl, pyrimidinyl, thiazolyl, or oxazolyl,
wherein the phenyl, pyridyl, pyrimidinyl, thiazolyl or oxazolyl is optionally substituted with 1 or 2 groups independently selected from methyl, trifluoromethyl, fluoro, cyano, and methoxy,
or wherein the phenyl, pyridyl, pyrimidinyl, thiazolyl or oxazolyl is optionally substituted by phenyl or fluorophenyl.

7. A compound which is:
(3-(5-(trifluoromethyl)-1,2,4-oxadiazol-3-yl)phenyl)(4-(5-(trifluoromethyl)pyridin-2-yl)-1,4-diazepan-1-yl)methanone,
6-(4-(3-(5-(trifluoromethyl)-1,2,4-oxadiazol-3-yl)benzoyl)piperazin-1-yl)nicotinonitrile,
4-(4-(3-(5-(trifluoromethyl)-1,2,4-oxadiazol-3-yl)benzoyl)piperazin-1-yl)benzonitrile,
6-(2-methyl-4-(3-(5-(trifluoromethyl)-1,2,4-oxadiazol-3-yl)benzoyl)piperazin-1-yl)nicotinonitrile,
6-(3-methyl-4-(3-(5-(trifluoromethyl)-1,2,4-oxadiazol-3-yl)benzoyl)piperazin-1-yl)nicotinonitrile,
6-(3,5-dimethyl-4-(3-(5-(trifluoromethyl)-1,2,4-oxadiazol-3-yl)benzoyl)piperazin-1-yl)nicotinonitrile,
4-(5-cyanopyridin-2-yl)-1-(3-(5-(trifluoromethyl)-1,2,4-oxadiazol-3-yl)benzoyl)piperazine-2-carboxylic acid,
6-(2,6-dimethyl-4-(3-(5-(trifluoromethyl)-1,2,4-oxadiazol-3-yl)benzoyl)piperazin-1-yl)nicotinonitrile,
6-(3,3-dimethyl-4-(3-(5-(trifluoromethyl)-1,2,4-oxadiazol-3-yl)benzoyl)piperazin-1-yl)nicotinonitrile,
6-(4-(3-(5-(trifluoromethyl)-1,2,4-oxadiazol-3-yl)benzoyl)-1,4-diazepan-1-yl)nicotinonitrile,
(4-methyl-3-(4-phenylthiazol-2-yl)piperazin-1-yl)(3-(5-(trifluoromethyl)-1,2,4-oxadiazol-3-yl)phenyl)methanone,
(4-(5-methoxypyridin-2-yl)piperazin-1-yl)(3-(5-(trifluoromethyl)-1,2,4-oxadiazol-3-yl)phenyl)methanone,
(3-(4-(4-fluorophenyl)thiazol-2-yl)piperidin-1-yl)(3-(5-(trifluoromethyl)-1,2,4-oxadiazol-3-yl)phenyl)methanone,
(3-(5-(4-fluorophenyl)oxazol-2-yl)piperidin-1-yl)(3-(5-(trifluoromethyl)-1,2,4-oxadiazol-3-yl)phenyl)methanone,
(4-(3-methoxyphenyl)piperazin-1-yl)(3-(5-(trifluoromethyl)-1,2,4-oxadiazol-3-yl)phenyl)methanone,
2-(4-(3-(5-(trifluoromethyl)-1,2,4-oxadiazol-3-yl)benzoyl)piperazin-1-yl)nicotinonitrile,
3-fluoro-4-(4-(3-(5-(trifluoromethyl)-1,2,4-oxadiazol-3-yl)benzoyl)piperazin-1-yl)benzonitrile,
(4-(pyrimidin-2-yl)piperazin-1-yl)(3-(5-(trifluoromethyl)-1,2,4-oxadiazol-3-yl)phenyl)methanone,
(3-((4-(4-fluorophenyl)thiazol-2-yl)methyl)azetidin-1-yl)(3-(5-(trifluoromethyl)-1,2,4-oxadiazol-3-yl)phenyl)methanone,
(4-(4-methylthiazol-2-yl)piperazin-1-yl)(3-(5-(trifluoromethyl)-1,2,4-oxadiazol-3-yl)phenyl)methanone,
(4-((2-(4-fluorophenyl)thiazol-4-yl)methyl)piperazin-1-yl)(3-(5-(trifluoromethyl)-1,2,4-oxadiazol-3-yl)phenyl)methanone,
(4-((2-(4-fluorophenyl)oxazol-4-yl)methyl)piperazin-1-yl)(3-(5-(trifluoromethyl)-1,2,4-oxadiazol-3-yl)phenyl)methanone,
(2-phenylthiazol-4-yl)(4-(3-(5-(trifluoromethyl)-1,2,4-oxadiazol-3-yl)benzoyl)piperazin-1-yl)methanone, or
((1S,4S)-5-(pyridin-2-yl)-2,5-diazabicyclo[2.2.1]heptan-2-yl)(3-(5-(trifluoromethyl)-1,2,4-oxadiazol-3-yl)phenyl)methanone,
or a pharmaceutically acceptable salt thereof.

* * * * *